US010829480B2

(12) United States Patent
Kuehnert et al.

(10) Patent No.: US 10,829,480 B2
(45) Date of Patent: *Nov. 10, 2020

(54) 3-((HETERO-)ARYL)-ALKYL-8-AMINO-2-OXO-L,3-DIAZA-SPIRO-[4.5]-DECANE DERIVATIVES

(71) Applicant: GRUENENTHAL GMBH, Aachen (DE)

(72) Inventors: Sven Kuehnert, Dueren (DE); Rene Michael Koenigs, Erkelenz (DE); Achim Kless, Aachen (DE); Anita Wegert, Aldenhoven (DE); Paul Ratcliffe, Aachen (DE); Ruth Jostock, Stolberg (DE); Thomas Koch, Stolberg (DE); Klaus Linz, Rheinbach (DE); Wolfgang Schroeder, Aachen (DE); Klaus Schiene, Juechen (DE); Ingo Konetzki, Aachen (DE)

(73) Assignee: GRUENENTHAL GMBH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/265,080

(22) Filed: Feb. 1, 2019

(65) Prior Publication Data

US 2020/0002319 A1 Jan. 2, 2020

Related U.S. Application Data

(63) Continuation of application No. 15/984,919, filed on May 21, 2018, now abandoned, which is a continuation of application No. 15/405,896, filed on Jan. 13, 2017, now abandoned.

(30) Foreign Application Priority Data

Jan. 13, 2016 (EP) .................................... 16151013

(51) Int. Cl.

| | |
|---|---|
| ***C07D 405/06*** | (2006.01) |
| ***C07D 235/02*** | (2006.01) |
| ***C07D 401/06*** | (2006.01) |
| ***C07D 403/06*** | (2006.01) |

(52) U.S. Cl.

CPC ......... *C07D 405/06* (2013.01); *C07D 235/02* (2013.01); *C07D 401/06* (2013.01); *C07D 403/06* (2013.01)

(58) Field of Classification Search

None

See application file for complete search history.

(56) References Cited

U.S. PATENT DOCUMENTS

| | | | |
|---|---|---|---|
| 5,698,567 | A | 12/1997 | Guillonneau et al. |
| 7,282,515 | B2 | 10/2007 | Meese et al. |
| 2004/0067930 | A1 | 4/2004 | Bhatti et al. |
| 2004/0192916 | A1 | 9/2004 | Buschmann et al. |
| 2006/0004034 | A1 | 1/2006 | Hinze et al. |
| 2007/0254904 | A1 | 11/2007 | Janssens et al. |
| 2008/0103183 | A1 | 5/2008 | Ackermann et al. |
| 2008/0249122 | A1 | 10/2008 | Bignan et al. |
| 2008/0287478 | A1 | 11/2008 | Hansen et al. |
| 2009/0247530 | A1 | 10/2009 | Nolte et al. |
| 2009/0253727 | A1 | 10/2009 | Goehring et al. |
| 2010/0331353 | A1 | 12/2010 | Schrimpf et al. |
| 2012/0029006 | A1 | 5/2012 | Linz et al. |
| 2017/0197919 | A1 | 7/2017 | Kuenert et al. |
| 2017/0197947 | A1 | 7/2017 | Kuehnert et al. |
| 2017/0197949 | A1 | 7/2017 | Kuehnert et al. |
| 2017/0197970 | A1 | 7/2017 | Kuehnert et al. |
| 2017/0197971 | A1 | 7/2017 | Kuehnert et al. |
| 2018/0201616 | A1 | 7/2018 | Kuehnert et al. |
| 2018/0282341 | A1 | 10/2018 | Kuehnert et al. |
| 2019/0016735 | A1 | 1/2019 | Smith, II et al. |
| 2019/0016768 | A1 | 1/2019 | Chien et al. |
| 2019/0100497 | A1 | 4/2019 | Kuehnert et al. |
| 2019/0100515 | A1 | 4/2019 | Kuehnert et al. |
| 2019/0106429 | A1 | 4/2019 | Kuehnert et al. |
| 2019/0106430 | A1 | 4/2019 | Kuehnert et al. |
| 2020/0002319 | A1 | 1/2020 | Kuehnert et al. |

FOREIGN PATENT DOCUMENTS

| | | | |
|---|---|---|---|
| CL | 2003-02246 | | 5/2004 |
| CL | 2009-00734 | | 5/2009 |
| CL | 2013-00266 | | 5/2013 |
| CL | 2018-01899 | | 11/2013 |
| CL | 2018-01868 | | 8/2018 |
| CL | 2018-01909 | | 10/2018 |
| CL | 2018-01910 | | 10/2018 |
| CL | 2018-01911 | | 10/2018 |
| CL | 2018-01912 | | 10/2018 |
| CL | 2018-01913 | | 10/2018 |
| EP | 1401841 | B1 | 8/2005 |
| EP | 2078718 | A1 | 7/2009 |

(Continued)

OTHER PUBLICATIONS

Schroeder et al., "Functional plasticity of the N/OFQ-NOP receptor system determines analgesic properties of NOP receptor agonists", British Journal of Pharmacology, Apr. 15, 2014, pp. 3777-3800.

Witkin et al., "The biology of Nociceptin/Orphanin FQ (N/OFQ) related to obesity, stress, anxiety, mood, and drug dependence", Pharmacology & Therapeutics 141, 2014, pp. 283-299, Elsevier.

Jenck et al., "Orphanin FQ acts as an anxiolytic to attenuate behavioral responses to stress", The National Academy of Sciences, Dec. 1997, pp. 14854-14858, vol. 94.

Mabrouk et al., "Stimulation of δ Opioid Receptor and Blockade of Nociceptin/Orphanin FQ Receptor Synergistically Attenuate Parkinsonism", The Journal of Neuroscience, Sep. 24, 2014, vol. 34, No. 19, pp. 12953-12962.

Pradhan et al., "The delta opioid receptor: an evolving target for the treatment of brain disorders", Trends in Pharmacological Sciences, CE Press, Oct. 2011, pp. 581-590, vol. 32, No. 10.

(Continued)

*Primary Examiner* — Po-Chih Chen

(74) *Attorney, Agent, or Firm* — Norris McLaughlin, P.A.

(57) ABSTRACT

The invention relates to 3-((hetero-)aryl)-alkyl-8-amino-2-oxo-1,3-diaza-spiro-[4.5]-decane derivatives, their preparation and their use in medicine, particularly in the treatment of pain.

27 Claims, No Drawings

(56) References Cited

FOREIGN PATENT DOCUMENTS

| | | | |
|---|---|---|---|
| WO | 2004/043967 | A1 | 5/2004 |
| WO | WO 2008/046758 | A2 | 4/2008 |
| WO | 2009/118168 | A1 | 10/2009 |
| WO | 2012/013343 | A1 | 2/2012 |
| WO | 2015/192039 | A1 | 12/2015 |

OTHER PUBLICATIONS

Gupta et al., "A Systematic Review of the Peripheral Analgesic Effects of Intraarticular Morphine", International Anesthesia Research Society, 2001, pp. 761-770, vol. 93.

Kalso et al., "No pain, no gain: clinical excellence and scientific rigour—lessons learned from IA morphine", International Association for the Study of Pain, 2002, pp. 269-275, vol. 98, Elsevier Science B.V.

Stein et al., "Attacking pain at its source: new perspectives on opioids", Nature Medicine, Aug. 2003, pp. 1003-1008, vol. 9, No. 8, Nature Publishing Group.

Zoellner et al., "Topical Fentanyl in a Randomized, Double-blind Study in Patients With Corneal Damage", Clin J Pain, Oct. 2008, pp. 690-696, vol. 24, No. 8, Lippincott Williams & Wilkins.

Bignan et al., "Recent advances towards the discovery of ORL-1 receptor agonists and antagonists", 2005, pp. 357-388, vol. 15, No. 4, Ashley Publications.

Chu et al., "Synthesis and DNA binding studies of bis-intercalators with a novel spiro-cyclic linker", Tetrahedron, 206, 62, 5536-5548.

U.S. Appl. No. 16/207,854, filed Dec. 3, 2018.

U.S. Appl. No. 16/207,916, filed Dec. 3, 2018.

U.S. Appl. No. 16/212,723, filed Dec. 7, 2018.

U.S. Appl. No. 16/207,676, filed Dec. 3, 2018.

AI.Mutairy, B. et. al., "Development and Characterization of a Floating Drug Delivery System prepared via Hot-Melt Extrusion Technology Coupled with Pressurized CO2 for a Thermo-Labile API," University of Mississippi, 2016, AAPS, Nov. 2016.

3-((HETERO-)ARYL)-ALKYL-8-AMINO-2-OXO-L,3-DIAZA-SPIRO-[4.5]-DECANE DERIVATIVES

This application is a continuation of U.S. Nonprovisional patent application Ser. No. 15/984,919, filed May 21, 2018, which is a continuation of U.S. Nonprovisional patent application Ser. No. 15/405,896, filed Jan. 13, 2017, which claims foreign priority benefit under 35 U.S.C. § 119 of European Patent Application No. 16 151 013.6, filed Jan. 13, 2016, the disclosures of which are incorporated herein by reference.

The invention relates to 3-((hetero-)aryl)-alkyl-8-amino-2-oxo-1,3-diaza-spiro-[4.5]-decane derivatives, their preparation and use in medicine, particularly in various neurological disorders, including but not limited to pain, neurodegenerative disorders, neuroinflammatory disorders, neuropsychiatric disorders, substance abuse/dependence.

Opioid receptors are a group of Gi/o protein-coupled receptors which are widely distributed in the human body. The opioid receptors are currently subdivided into four major classes, i.e. the three classical opioid receptors mu-opioid (MOP) receptor, kappa-opioid (KOP) receptor, and delta-opioid (DOP) receptor as well as the opioid receptor-like (ORL-1) receptor, which was more recently discovered based on its high homology with said classical opioid receptors. After identification of the endogenous ligand of the ORL-1 receptor, known as nociceptin/orphanin FQ, a highly basic 17 amino acid peptide isolated from tissue extracts in 1995, the ORL-1 receptor was renamed "nociceptin opioid peptide receptor" and abbreviated as "NOP-receptor".

The classical opioid receptors (MOP, KOP and DOP) as well as the NOP receptor are widely distributed/expressed in the human body, including in the brain, the spinal cord, on peripheral sensory neurons and the intestinal tract, wherein the distribution pattern differs between the different receptor classes.

Nociceptin acts at the molecular and cellular level in very much the same way as opioids. However, its pharmacological effects sometimes differ from, and even oppose those of opioids. NOP-receptor activation translates into a complex pharmacology of pain modulation, which, depending on route of administration, pain model and species involved, leads to either pronociceptive or antinociceptive activity. Furthermore, the NOP receptor system is upregulated under conditions of chronic pain. Systemic administration of selective NOP receptor agonists was found to exert a potent and efficacious analgesia in non-human primate models of acute and inflammatory pain in the absence of side effects. The activation of NOP receptors has been demonstrated to be devoid of reinforcing effects but to inhibit opioid-mediated reward in rodents and non-human primates (Review: Schroeder et al, Br J Pharmacol 2014; 171 (16): 3777-3800, and references therein).

Besides the involvement of the NOP receptor in nociception, results from preclinical experiments suggest that NOP receptor agonists might be useful inter alia in the treatment of neuropsychiatric disorders (Witkin et al, Pharmacology & Therapeutics, 141 (2014) 283-299; Jenck et al., Proc. Natl. Acad. Sci. USA 94, 1997, 14854-14858). Remarkably, the DOP receptor is also implicated to modulate not only pain but also neuropsychiatric disorders (Mabrouk et al, 2014; Pradhan et al., 2011).

Strong opioids acting at the MOP receptor site are widely used to treat moderate to severe acute and chronic pain. However, the therapeutic window of strong opioids is limited by severe side effects such as nausea and vomiting, constipation, dizziness, somnolence, respiratory depression, physical dependence and abuse. Furthermore, it is known that MOP receptor agonists show only reduced effectiveness under conditions of chronic and neuropathic pain.

It is known that some of the above mentioned side-effects of strong opioids are mediated by activation of classic opioid-receptors within the central nervous system. Furthermore, peripheral opioid receptors, when activated, can inhibit transmission of nociceptive signals shown in both, clinical and animal studies (Gupta et al., 2001; Kalso et al., 2002; Stein et al., 2003; Zollner et al., 2008).

Thus, to avoid CNS-mediated adverse effects after systemic administration, one approach has been to provide peripherally restricted opioid receptor ligands that do not easily cross the blood-brain barrier and therefore distribute poorly to the central nervous system (see for instance WO 2015/192039). Such peripherally acting compounds might combine effective analgesia with limited side-effects.

Another approach has been to provide compounds which interact with both the NOP receptor and the MOP receptor. Such compounds have for instance been described in WO 2004/043967, WO 2012/013343 and WO 2009/118168.

A further approach has been to provide multi-opioid receptor analgesics that modulate more than one of the opioid receptor subtypes to provide additive or synergistic analgesia and/or reduced side effects like abuse liability or tolerance.

On the one hand, it would be desirable to provide analgesics that selectively act on the NOP receptor system but less pronounced on the classic opioid receptor system, especially MOP receptor system, whereas it would be desirable to distinguish between central nervous activity and peripheral nervous activity. On the other hand, it would be desirable to provide analgesics that act on the NOP receptor system and also to a balanced degree on the MOP receptor system, whereas it would be desirable to distinguish between central nervous activity and peripheral nervous activity.

There is a need for medicaments which are effective in the treatment of pain and which have advantages compared to the compounds of the prior art. Where possible, such medicaments should contain such a small dose of active ingredient that satisfactory pain therapy can be ensured without the occurrence of intolerable treatment-emergent adverse events.

It is an object of the invention to provide pharmacologically active compounds, preferably analgesics that have advantages compared to the prior art.

This object has been achieved by the subject-matter of the patent claims.

A first aspect of the invention relates to 3-((hetero-)aryl)-alkyl-8-amino-2-oxo-1,3-diaza-spiro-[4.5]-decane derivatives according to general formula (I)

(I)

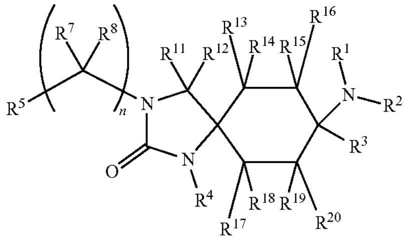

wherein n means 1, 2 or 3;

$R^1$ and $R^2$ independently of one another mean

—H;

—$C_1$-$C_6$-alkyl, linear or branched, saturated or unsaturated, unsubstituted or substituted with one, two, three or four substituents independently of one another selected from the group consisting of —F, —Cl, —Br, —I, —OH, —$OCH_3$, —CN and —$CO_2CH_3$;

a 3-12-membered cycloalkyl moiety, saturated or unsaturated, unsubstituted or substituted with one, two, three or four substituents independently of one another selected from the group consisting of —F, —Cl, —Br, —I, —OH, —$OCH_3$, —CN and —$CO_2CH_3$; wherein said 3-12-membered cycloalkyl moiety is optionally connected through —$C_1$-$C_6$-alkylene-, linear or branched, saturated or unsaturated, unsubstituted; or a 3-12-membered heterocycloalkyl moiety, saturated or unsaturated, unsubstituted or substituted with one, two, three or four substituents independently of one another selected from the group consisting of —F, —Cl, —Br, —I, —OH, —$OCH_3$, —CN and —$CO_2CH_3$; wherein said 3-12-membered heterocycloalkyl moiety is optionally connected through —$C_1$-$C_6$-alkylene-, linear or branched, saturated or unsaturated, unsubstituted;

or $R^1$ and $R^2$ together with the nitrogen atom to which they are attached form a ring and mean —$(CH_2)_{3-6}$—; —$(CH_2)_2$—O—$(CH_2)_2$—; or —$(CH_2)_2$—$NR^A$—$(CH_2)_2$—, wherein $R^A$ means —H or —$C_1$-$C_6$-alkyl, linear or branched, saturated or unsaturated, unsubstituted or substituted with one, two, three or four substituents independently of one another selected from the group consisting of —F, —Cl, —Br and —I;

preferably with the proviso that $R^1$ and $R^2$ do not simultaneously mean —H;

$R^3$ means

—$C_1$-$C_6$-alkyl, linear or branched, saturated or unsaturated, unsubstituted, mono- or polysubstituted;

a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted;

a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted;

$R^4$ means

—H;

—$C_1$-$C_6$-alkyl, linear or branched, saturated or unsaturated, unsubstituted, mono- or polysubstituted; wherein said —$C_1$-$C_6$-alkyl is optionally connected through —C(═O)—, —C(═O)O—, or —S(═O)$_2$—;

a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted; or wherein said 3-12-membered cycloalkyl moiety is optionally connected through —C(═O)—, —C(═O)O—, —C(═O)O—$CH_2$—, or —S(═O)$_2$—;

a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted; or wherein said 3-12-membered heterocycloalkyl moiety is optionally connected through —C(═O)—, —C(═O)O—, —C(═O)O—$CH_2$—, or —S(═O)$_2$—;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or wherein said 6-14-membered aryl moiety is optionally connected through —C(═O)—, —C(═O)O—, —C(═O)O—$CH_2$—, or —S(═O)$_2$—; or a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted; or wherein said 5-14-membered heteroaryl moiety is optionally connected through —C(═O)—, —C(═O)O—, —C(═O)O—$CH_2$—, or —S(═O)$_2$—;

$R^5$ means a 6-14-membered aryl moiety, unsubstituted, mono- or polysubstituted; or a 5-14-membered heteroaryl moiety, unsubstituted, mono- or polysubstituted;

$R^7$, $R^8$, $R^{11}$, $R^{12}$, $R^{13}$, $R^{14}$, $R^{15}$, $R^{16}$, $R^{17}$, $R^{18}$, $R^{19}$, and $R^{20}$ independently of one another mean —H, —F, —Cl, —Br, —I, —OH, or —$C_1$-$C_6$-alkyl, linear or branched, saturated or unsaturated, unsubstituted, mono- or polysubstituted;

or wherein $R^7$ and $R^8$ together with the carbon atom to which they are attached form a ring and mean —$(CH_2)_2$— or —$(CH_2)_3$—;

wherein "mono- or polysubstituted" means that one or more hydrogen atoms are replaced by a substituent independently of one another selected from the group consisting of —F, —Cl, —Br, —I, —CN, —$R^{21}$, —C(═O)$R^{21}$, —C(═O)$OR^{21}$, —C(═O)$NR^{21}R^{22}$, —O—$(CH_2CH_2$—$O)_{1-30}$—H, —O—$(CH_2CH_2$—$O)_{1-30}$—$CH_3$, ═O, —$OR^{21}$, —OC(═O)$R^{21}$, —OC(═O)$OR^{21}$, —OC(═O)$NR^{21}R^{22}$, —$NO_2$, —$NR^{21}R^{22}$, —$NR^{21}$—$(CH_2)_{1-6}$—C(═O)$R^{22}$, —$NR^{21}$—$(CH_2)_{1-6}$—C(═O)$OR^{22}$, —$NR^{23}$—$(CH_2)_{1-6}$—C(═O)$NR^{21}R^{22}$, —$NR^{21}$C(═O)$R^{22}$, —$NR^{21}$C(═O)—$OR^{22}$, —$NR^{23}$C(═O)$NR^{21}R^{22}$, —$NR^{21}$S(═O)$_2R^{22}$, —$SR^{21}$, —S(═O)$R^{21}$, —S(═O)$_2R^{21}$, —S(═O)$_2OR^{21}$, and —S(═O)$_2NR^{21}R^{22}$;

wherein $R^{21}$, $R^{22}$ and $R^{23}$ independently of one another mean

—H;

—$C_1$-$C_6$-alkyl, linear or branched, saturated or unsaturated, unsubstituted or substituted with one, two, three or four substituents independently of one another selected from the group consisting of —F, —Cl, —Br, —I, —CN, —OH, —$NH_2$, and —O—$C_1$-$C_6$-alkyl;

a 3-12-membered cycloalkyl moiety, saturated or unsaturated, unsubstituted; wherein said 3-12-membered cycloalkyl moiety is optionally connected through $—C_1-C_6$-alkylene-, linear or branched, saturated or unsaturated, unsubstituted or substituted with one, two, three or four substituents independently of one another selected from the group consisting of —F, —Cl, —Br, —I, —CN, —OH, $—NH_2$, $—C_1-C_6$-alkyl and $—O—C_1-C_6$-alkyl;

a 3-12-membered heterocycloalkyl moiety, saturated or unsaturated, unsubstituted; wherein said 3-12-membered heterocycloalkyl moiety is optionally connected through $—C_1-C_6$-alkylene-, linear or branched, saturated or unsaturated, unsubstituted or substituted with one, two, three or four substituents independently of one another selected from the group consisting of —F, —Cl, —Br, —I, —CN, —OH, $—NH_2$, $—C_1-C_6$-alkyl and $—O—C_1-C_6$-alkyl;

a 6-14-membered aryl moiety, unsubstituted, mono- or polysubstituted; wherein said 6-14-membered aryl moiety is optionally connected through $—C_1-C_6$-alkylene-, linear or branched, saturated or unsaturated, unsubstituted or substituted with one, two, three or four substituents independently of one another selected from the group consisting of —F, —Cl, —Br, —I, —CN, —OH, $—NH_2$, $—C_1-C_6$-alkyl and $—O—C_1-C_6$-alkyl;

a 5-14-membered heteroaryl moiety, unsubstituted, mono- or polysubstituted; wherein said 5-14-membered heteroaryl moiety is optionally connected through $—C_1-C_6$-alkylene-, linear or branched, saturated or unsaturated, unsubstituted or substituted with one, two, three or four substituents independently of one another selected from the group consisting of —F, —Cl, —Br, —I, —CN, —OH, $—NH_2$, $—C_1-C_6$-alkyl and $—O—C_1-C_6$-alkyl;

or $R^{21}$ and $R^{22}$ within $—C(=O)NR^{21}R^{22}$, $—OC(=O)NR^{21}R^{22}$, $—NR^{21}R^{22}$, $—NR^{23}—(CH_2)_{1-6}—C(=O)NR^{21}R^{22}$, $—NR^{23}C(=O)NR^{21}R^{22}$, or $—S(=O)_2NR^{21}R^{22}$ together with the nitrogen atom to which they are attached form a ring and mean $—(CH_2)_{3-6}—$; $—(CH_2)_2—O—(CH_2)_2—$; or $—(CH_2)_2—NR^B—(CH_2)_2—$, wherein $R^B$ means —H or $—C_1-C_6$-alkyl, linear or branched, saturated or unsaturated, unsubstituted or substituted with one, two, three or four substituents independently of one another selected from the group consisting of —F, —Cl, —Br and —I;

or a physiologically acceptable salt thereof.

Preferably, aryl includes but is not limited to phenyl and naphthyl. Preferably, heteroaryl includes but is not limited to -1,2-benzodioxole, -pyrazinyl, -pyridazinyl, -pyridinyl, -pyrimidinyl, -thienyl, -imidazolyl, -benzimidazolyl, -thiazolyl, -1,3,4-thiadiazolyl, -benzothiazolyl, -oxazolyl, -benzoxazolyl, -pyrazolyl, -quinolinyl, -isoquinolinyl, -quinazolinyl, -indolyl, -indolinyl, -benzo[c][1,2,5]oxadiazolyl, -imidazo[1,2-a]pyrazinyl, or -1H-pyrrolo[2,3-b]pyridinyl. Preferably, cycloalkyl includes but is not limited to -cyclopropyl, -cyclobutyl, -cyclopentyl and -cyclohexyl. Preferably, heterocycloalkyl includes but is not limited to -aziridinyl, -azetidinyl, -pyrrolidinyl, -piperidinyl, -piperazinyl, -morpholinyl, -sulfamorpholinyl, -oxiridinyl, -oxetanyl, -tetrahydropyranyl, and -pyranyl.

When a moiety is connected through an asymmetric group such as —C(=O)O— or $—C(=O)O—CH_2—$, said asymmetric group may be arranged in either direction. For example, when $R^4$ is connected to the core structure through —C(=O)O—, the arrangement may be either $R^4—C(=O)O—$ core or core-$C(=O)O—R^4$.

In preferred embodiments of the compound according to the invention, $R^7$, $R^8$, $R^{11}$, $R^{12}$, $R^{13}$, $R^{14}$, $R^{15}$, $R^{16}$, $R^{17}$, $R^{18}$, $R^{19}$, and $R^{20}$ independently of one another mean —H, —F, —OH, or $—C_1-C_6$-alkyl; preferably —H.

In preferred embodiments of the compound according to the invention, $R^1$ and $R^8$ together with the carbon atom to which they are attached form a ring and mean $—(CH_2)_2—$ (i.e. form a cyclopropyl ring) or $—(CH_2)_3—$ (i.e. form a cyclobutyl ring).

In a preferred embodiment of the compound according to the invention, $R^1$ means —H; and $R^2$ means $—C_1-C_6$-alkyl, linear or branched, saturated or unsaturated, unsubstituted, mono- or polysubstituted. Preferably, $R^1$ means —H and $R^2$ means $—CH_3$.

In another preferred embodiment of the compound according to the invention, $R^1$ means $—CH_3$; and $R^2$ means $—C_1-C_6$-alkyl, linear or branched, saturated or unsaturated, unsubstituted, mono- or polysubstituted. Preferably, $R^1$ means $—CH_3$ and $R^2$ means $—CH_3$.

In still another preferred embodiment of the compound according to the invention, $R^1$ and $R^2$ together with the nitrogen atom to which they are attached form a ring and mean $—(CH_2)_{3-6}—$. Preferably, $R^1$ and $R^2$ together with the nitrogen atom to which they are attached form a ring and mean $—(CH_2)_3—$.

In yet another preferred embodiment, $R^1$ means —H or $—CH_3$; and $R^2$ means a 3-12-membered cycloalkyl moiety, saturated or unsaturated, unsubstituted; wherein said 3-12-membered cycloalkyl moiety is connected through $—CH_2—$, unsubstituted; preferably $—CH_2$-cycloalkyl, $—CH_2$-cyclobutyl or $—CH_2$-cyclopentyl; or $R^2$ means a 3-12-membered heterocycloalkyl moiety, saturated or unsaturated, unsubstituted; wherein said 3-12-membered heterocycloalkyl moiety is connected through $—CH_2—$, unsubstituted; preferably $—CH_2$-oxetanyl or $—CH_2$-tetrahydrofuranyl.

In a preferred embodiment of the compound according to the invention, $R^3$ means $—C_1-C_6$-alkyl, linear or branched, saturated or unsaturated, unsubstituted, mono- or polysubstituted. Preferably, $R^3$ means $—C_1-C_6$-alkyl, linear or branched, saturated or unsaturated, unsubstituted or monosubstituted with $—OCH_3$.

In another preferred embodiment of the compound according to the invention, $R^3$ means a 6-14-membered aryl moiety, unsubstituted, mono- or polysubstituted, optionally connected through $—C_1-C_6$-alkylene-, linear or branched, saturated or unsaturated, unsubstituted. In a preferred embodiment, $R^3$ means -phenyl unsubstituted, mono- or polysubstituted. More preferably, $R^3$ means -phenyl unsubstituted, mono- or disubstituted with —F, —Cl, $—CH_3$, $—CF_3$, —OH, $—OCH_3$, $—OCF_3$ or $—OCH_2OCH_3$, preferably —F. In another preferred embodiment, $R^3$ means -benzyl unsubstituted, mono- or polysubstituted. More preferably, $R^3$ means -benzyl unsubstituted, mono- or disubstituted with —F, —Cl, $—CH_3$, $—CF_3$, —OH, $—OCH_3$, $—OCF_3$ or $—OCH_2OCH_3$, preferably —F.

In still another preferred embodiment of the compound according to the invention, $R^3$ means a 5-14-membered heteroaryl moiety, unsubstituted, mono- or polysubstituted. Preferably, $R^3$ means -thienyl or -pyridinyl, in each case unsubstituted, mono- or polysubstituted. More preferably, $R^3$ means -thienyl, -pyridinyl, -imidazolyl or benzimidazolyl, in each case unsubstituted or monosubstituted with —F, —Cl or $—CH_3$.

In a preferred embodiment of the compound according to the invention, $R^4$ means —H.

In another preferred embodiment of the compound according to the invention, $R^4$ means $—C_1-C_6$-alkyl, linear or branched, saturated or unsaturated, unsubstituted, mono- or polysubstituted. Preferably, $R^4$ means $—C_1-C_6$-alkyl, linear or branched, saturated or unsaturated, unsubstituted or monosubstituted with a substituent selected from the group consisting of —F, —Cl, —Br, —I, —CN, —$CF_3$, —OH, —O—$C_1$-$C_4$-alkyl, —$OCF_3$, —O—($CH_2CH_2$—O)$_{1-30}$—H, —O—($CH_2CH_2$—O)$_{1-30}$—$CH_3$, —OC(═O)$C_1$-$C_4$-alkyl, —C(═O)$C_1$-$C_4$-alkyl, —C(═O)OH, —C(═O)O—$C_1$-$C_4$-alkyl, —C(═O)$NH_2$, —C(═O)NH$C_1$-$C_4$-alkyl, —C(═O)NH$C_1$-$C_4$-alkylene-CN, —C(═O)NH$C_1$-$C_4$-alkylene-O—$C_1$-$C_4$-alkyl, —C(═O)N($C_1$-$C_4$-alkyl)$_2$; —S(═O)$C_1$-$C_4$-alkyl, and —S(═O)$_2C_1$-$C_4$-alkyl; or with —C(═O)$NR^{21}R^{22}$ wherein $R^{21}$ and $R^{22}$ together with the nitrogen atom to which they are attached form a ring and mean —($CH_2$)$_{3-6}$—, —($CH_2$)$_2$—O—($CH_2$)$_2$—, or —($CH_2$)$_2$—$NR^B$—($CH_2$)$_2$—, wherein $R^B$ means —H or —$C_1$-$C_6$-alkyl; or with —C(═O)NH-3-12-membered cycloalkyl, saturated or unsaturated, unsubstituted or monosubstituted with —F, —Cl, —Br, —I, —CN, or —OH; or with —C(═O)NH-3-12-membered heterocycloalkyl, saturated or unsaturated, unsubstituted or monosubstituted with —F, —Cl, —Br, —I, —CN, or —OH. More preferably, $R^4$ means —$C_1$-$C_6$-alkyl, linear or branched, saturated or unsaturated, unsubstituted or monosubstituted with —O—$C_1$-$C_4$-alkyl or —C(═O)N($C_1$-$C_4$-alkyl)$_2$.

In still another preferred embodiment of the compound according to the invention, $R^4$ means a 3-12-membered cycloalkyl moiety, saturated or unsaturated, unsubstituted, mono- or polysubstituted; wherein the 3-12-membered cycloalkyl moiety is connected through —$C_1$-$C_6$-alkylene-, linear or branched, saturated or unsaturated, unsubstituted, mono- or polysubstituted. Preferably, $R^4$ means a 3-12-membered cycloalkyl moiety, saturated or unsaturated, unsubstituted, mono- or polysubstituted; wherein said 3-12-membered cycloalkyl moiety is connected through —$CH_2$— or —$CH_2CH_2$—. More preferably, $R^4$ means a 3-12-membered cycloalkyl moiety, saturated or unsaturated, unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —C(═O)OH, —C(═O)O—$C_1$-$C_4$-alkyl, —C(═O)$NH_2$, —C(═O)NH$C_1$-$C_4$-alkyl, —C(═O)N($C_1$-$C_4$-alkyl)$_2$, —S(═O)$C_1$-$C_4$-alkyl and —S(═O)$_2C_1$-$C_4$-alkyl; wherein said 3-12-membered cycloalkyl moiety is connected through —$CH_2$— or —$CH_2CH_2$—.

In a preferred embodiment of the compound according to the invention, $R^4$ means a 3-12-membered heterocycloalkyl moiety, saturated or unsaturated, unsubstituted, mono- or polysubstituted; wherein said 3-12-membered heterocycloalkyl moiety is connected through —$C_1$-$C_6$-alkylene-, linear or branched, saturated or unsaturated, unsubstituted, mono- or polysubstituted. Preferably, $R^4$ means a 3-12-membered heterocycloalkyl moiety, saturated or unsaturated, unsubstituted, mono- or polysubstituted; wherein said 3-12-membered heterocycloalkyl moiety is connected through —$CH_2$— or —$CH_2CH_2$—. More preferably, $R^4$ means -oxetanyl, -tetrahydrofuranyl or -tetrahydropyranyl, in each case unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —C(═O)OH, —C(═O)O—$C_1$-$C_4$-alkyl, —C(═O)$NH_2$, —C(═O)NH$C_1$-$C_4$-alkyl, —C(═O)N($C_1$-$C_4$-alkyl)$_2$, —S(═O)$C_1$-$C_4$-alkyl and —S(═O)$_2C_1$-$C_4$-alkyl; wherein said -oxetanyl, -tetrahydrofuranyl or -tetrahydropyranyl is connected through —$CH_2$— or —$CH_2CH_2$—.

In yet another preferred embodiment of the compound according to the invention, $R^4$ means a 6-14-membered aryl moiety, unsubstituted, mono- or polysubstituted; wherein said 6-14-membered aryl moiety is connected through —$C_1$-$C_6$-alkylene-, linear or branched, saturated or unsaturated, unsubstituted, mono- or polysubstituted. Preferably, $R^4$ means -phenyl, unsubstituted, mono- or polysubstituted; wherein said -phenyl is connected through —$CH_2$— or —$CH_2CH_2$—. More preferably, $R^4$ means -phenyl, unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —C(═O)OH, —C(═O)O—$C_1$-$C_4$-alkyl, —C(═O)$NH_2$, —C(═O)NH$C_1$-$C_4$-alkyl, —C(═O)N($C_1$-$C_4$-alkyl)$_2$, —S(═O)$C_1$-$C_4$-alkyl and —S(═O)$_2C_1$-$C_4$-alkyl; wherein said -phenyl is connected through —$CH_2$— or —$CH_2CH_2$—.

In a further preferred embodiment of the compound according to the invention, $R^4$ means a 5-14-membered heteroaryl moiety, unsubstituted, mono- or polysubstituted; wherein said 5-14-membered heteroaryl moiety is connected through —$C_1$-$C_6$-alkylene-, linear or branched, saturated or unsaturated, unsubstituted, mono- or polysubstituted. Preferably, $R^4$ means a 5-14-membered heteroaryl moiety, unsubstituted, mono- or polysubstituted; wherein said -phenyl is connected through —$CH_2$— or —$CH_2CH_2$—. More preferably, $R^4$ means -pyridinyl, -pyrimidinyl, -pyrazinyl, or -pyrazolinyl, in each case unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —C(═O)OH, —C(═O)O—$C_1$-$C_4$-alkyl, —C(═O)$NH_2$, —C(═O)NH$C_1$-$C_4$-alkyl, —C(═O)N($C_1$-$C_4$-alkyl)$_2$, —S(═O)$C_1$-$C_4$-alkyl and —S(═O)$_2C_1$-$C_4$-alkyl; wherein said -pyridinyl, -pyrimidinyl, -pyrazinyl, or -pyrazolinyl is connected through —$CH_2$— or —$CH_2CH_2$—.

In a preferred embodiment of the compound according to the invention, n means 1 or 2. Preferably, n means 1.

In a preferred embodiment of the compound according to the invention, $R^5$ means -phenyl, unsubstituted, mono- or polysubstituted. Preferably, $R^5$ means -phenyl unsubstituted or substituted with one, two, three or four substituents independently of one another selected from the group consisting of —F; —Cl; —Br; —I; —CN; —OH; —$C_1$-$C_4$-alkyl; —$CF_3$; -3-12-membered cycloalkyl, saturated or unsaturated, unsubstituted, mono- or polysubstituted; preferably -cyclopropyl, saturated, unsubstituted; -3-12-membered heterocycloalkyl, saturated or unsaturated, unsubstituted, mono- or polysubstituted; preferably -pyrrolidinyl, -piperidinyl, -morpholinyl, -piperazinyl, -thiomorpholinyl, or -thiomorpholinyl dioxide, in each case saturated, unsubstituted or monosubstituted with —$C_1$-$C_4$-alkyl; —O—$CH_2$—O— (such that it is condensed with a dioxolanyl ring); —O—$C_1$-$C_4$-alkyl; —O—($CH_2CH_2$—O)$_{1-30}$—H; —O—($CH_2CH_2$—O)$_{1-30}$—$CH_3$; —C(═O)OH; —C(═O)O—$C_1$-$C_4$-alkyl; —C(═O)$NH_2$; —C(═O)NH$C_1$-$C_4$-alkyl; —C(═O)N($C_1$-$C_4$-alkyl)$_2$; —S(═O)$C_1$-$C_4$-alkyl and —S(═O)$_2C_1$-$C_4$-alkyl.

In another preferred embodiment of the compound according to the invention, $R^5$ means -pyrazinyl, -pyridazinyl, -pyridinyl, -pyrimidinyl, -thienyl, -imidazolyl, triazolyl, or -1,3-benzodioxolyl, in each case unsubstituted, mono- or polysubstituted. Preferably, $R^5$ means -pyrazinyl, -pyridazinyl, -pyridinyl, -pyrimidinyl, -thienyl, -imidazolyl, triazolyl, or -1,3-benzodioxolyl, in each case unsubstituted or substituted with one, two, three or four substituents independently of one another selected from the group consisting of —F; —Cl; —Br; —I; —CN; —OH; —$C_1$-$C_4$-alkyl; —$CF_3$; —$C_1$-$C_4$-alkyl-OH; —$C_1$-$C_4$-alkyl-C(═O)$NH_2$; -3-12-membered cycloalkyl, saturated or unsaturated, unsubstituted, mono- or polysubstituted; preferably -cyclopropyl, saturated, unsubstituted; -3-12-membered heterocycloalkyl, saturated or unsaturated, unsubstituted, mono- or polysubstituted; preferably -pyrrolidinyl, -piperidinyl, -morpholinyl, -piperazinyl, -thiomorpholinyl, or -thiomorpholinyl dioxide, in each case saturated, unsubstituted or monosubstituted with $—C_1$-$C_4$-alkyl; —O—$CH_2$—O— (such that it is condensed with a dioxolanyl ring); —O—$C_1$-$C_4$-alkyl; —O—$(CH_2CH_2—O)_{1-30}$—H; —O—$(CH_2CH_2—O)_{1-30}$—$CH_3$; —C(═O)OH; —C(═O)O$C_1$-$C_4$-alkyl; —C(═O)$NH_2$; —C(═O)NH$C_1$-$C_4$-alkyl; —C(═O)N($C_1$-$C_4$-alkyl)$_2$; —S$C_1$-$C_4$-alkyl; —S(═O)$C_1$-$C_4$-alkyl and —S(═O)$_2C_1$-$C_4$-alkyl.

In preferred embodiments, the compound according to the invention has a structure according to any of general formulas (II-A) to (VIII-C):

(II-A)

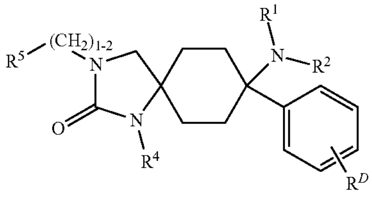

(II-B)

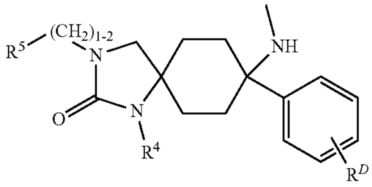

(II-C)

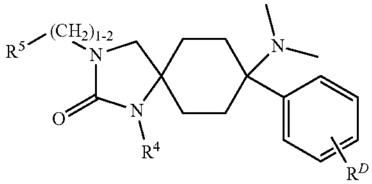

(III-A)

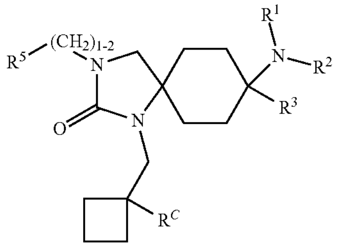

(III-B)

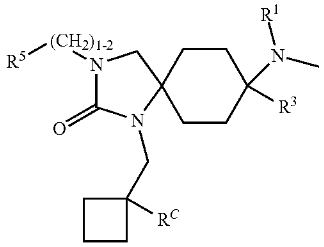

-continued (III-C)

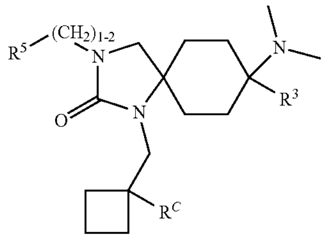

(IV-A)

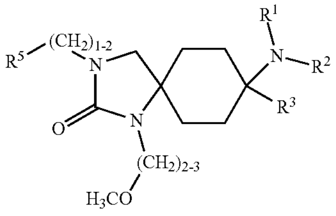

(IV-B)

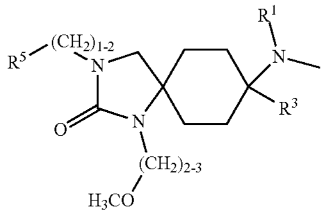

(IV-C)

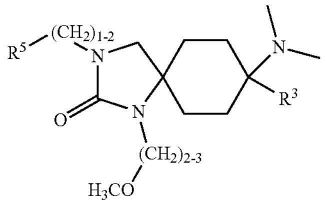

(V-A)

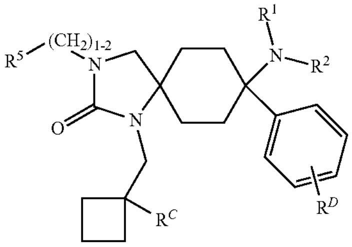

(V-B)

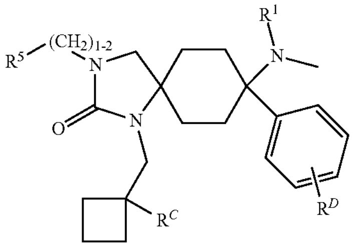

-continued (V-C)

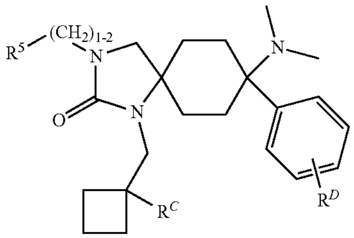

(VI-A)

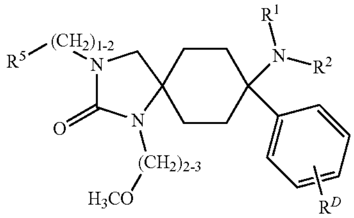

(VI-B)

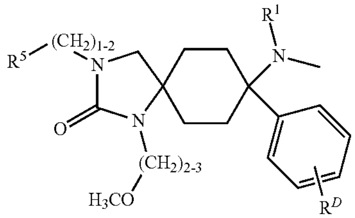

(VI-C)

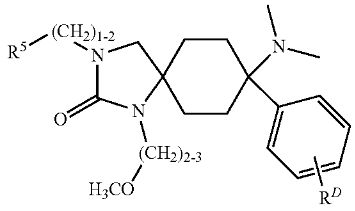

(VII-A)

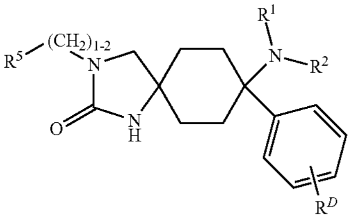

(VII-B)

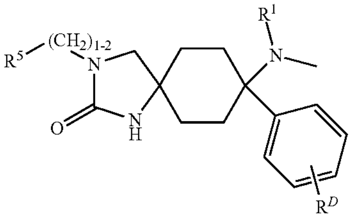

(VII-C)

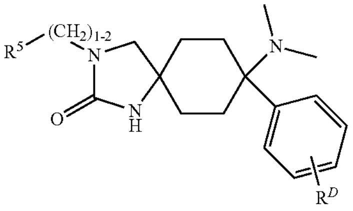

-continued (VIII-A)

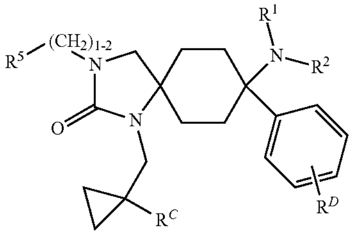

(VIII-B)

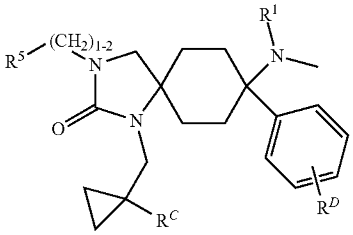

(VIII-C)

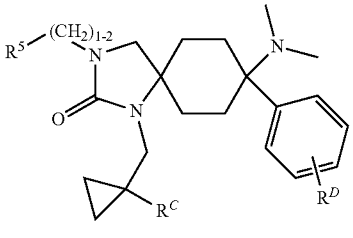

wherein in each case $R^1$, $R^2$, $R^3$, $R^4$, and $R^5$ are defined as above, $R^C$ means —H, —OH, —F, —CN or —$C_1$-$C_4$-alkyl; preferably —H or —OH;

$R^D$ means —H or —F;

or a physiologically acceptable salt thereof.

Preferably, in the compounds according to general formula (I) or any of the compounds according to general formulas (II-A) to (VIII-C), $R^5$ is selected from the group consisting of:

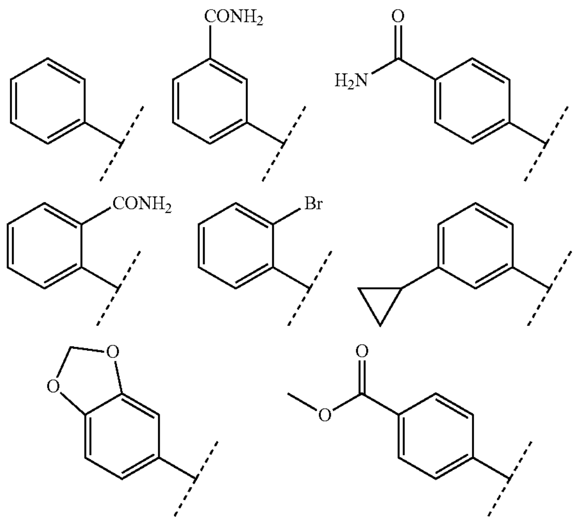

-continued

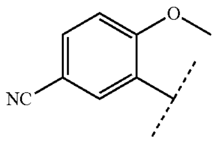
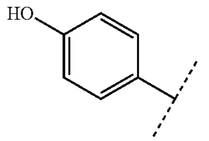
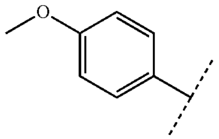
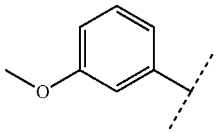
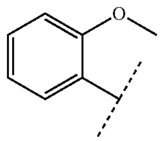
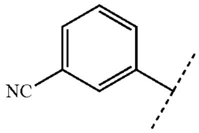
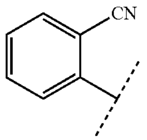
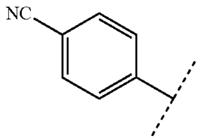
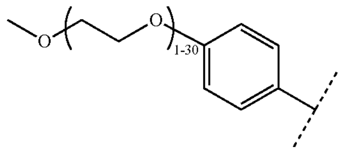
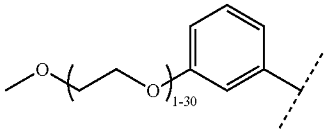
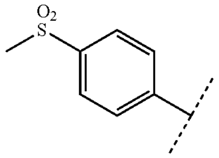
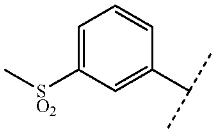
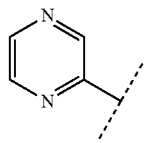
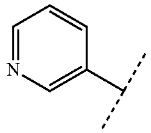
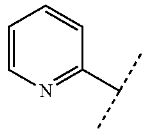
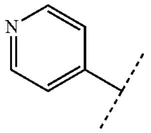
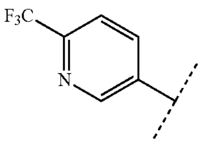
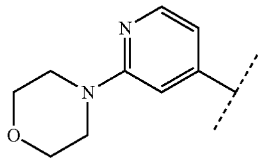
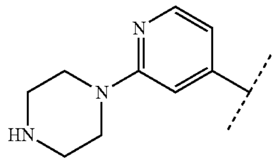
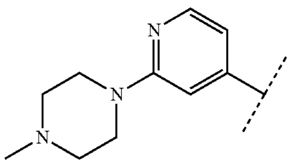
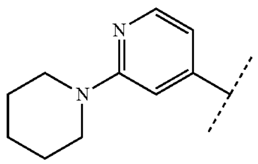
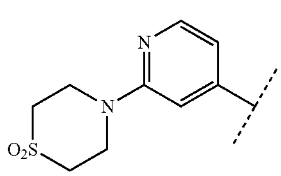
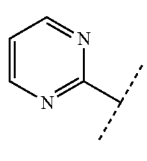

-continued

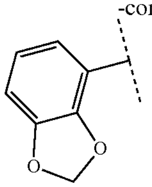
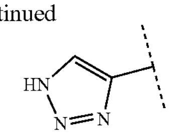
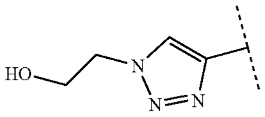
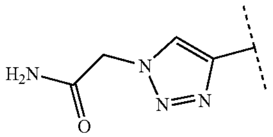
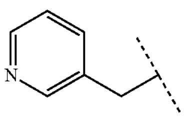
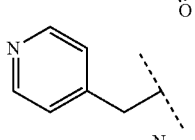
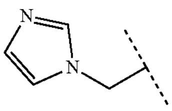
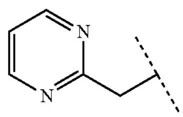
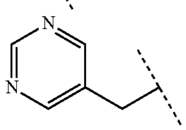
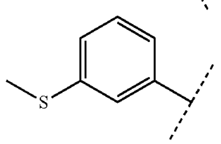
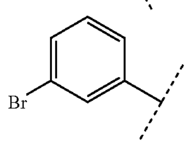
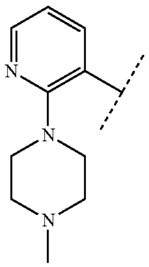
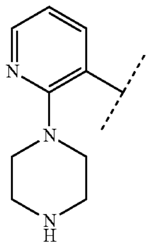
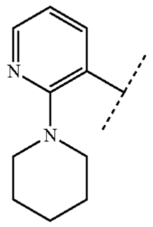
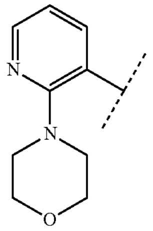
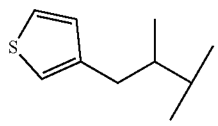

In a particularly preferred embodiment of the compound according to the invention, n means 1 or 2;

$R^1$ means —H or —$CH_3$;

$R^2$ means —H or —$C_1$-$C_6$-alkyl, linear or branched, saturated or unsaturated, unsubstituted or monosubstituted with —OH, —$OCH_3$, —C(═O)$OCH_3$, or —CN;

$R^3$ means

—$C_1$-$C_4$-alkyl, optionally monosubstituted with —$OCH_3$; -phenyl, -thienyl or -pyridinyl, in each case unsubstituted or substituted with one, two, three or four substituents independently of one another selected from the group consisting of —F, —Cl, —CN, —$CH_3$, —$CH_2CH_3$, —$CH_2F$, —$CHF_2$, —$CF_3$, —$OCF_3$, —OH, —$OCH_3$, —O—$CH_2$—O—$CH_3$, —C(═O)$NH_2$, C(═O)$NHCH_3$, —C(═O)N$(CH_3)_2$, —$NH_2$, —$NHCH_3$, —N$(CH_3)_2$, —NHC(═O)$CH_3$, —$CH_2OH$, $SOCH_3$ and $SO_2CH_3$; or $R^4$ means

—H;

—$C_1$-$C_6$-alkyl, linear or branched, saturated, unsubstituted or substituted with one, two, three or four substituents independently of one another selected from the group consisting of —F, —Cl, —Br, —I, —CN, =O, —OH, —O—$C_1$-$C_4$-alkyl, —$CO_2$H, —C(=O)O—$C_1$-$C_4$-alkyl, —C(=O)$NH_2$, —C(=O)NH—$C_1$-$C_4$-alkyl, —C(=O)N($C_1$-$C_4$-alkyl)$_2$, —C(=O)NH—$C_1$-$C_4$-alkyl-CN, —C(=O)$NCH_3$—$C_1$-$C_4$-alkyl-CN, —C(=O)NH-cyclopropyl-CN, —C(=O)$NCH_3$-cyclopropyl-CN, —C(=O)NH—$C_1$-$C_4$-alkyl-OH, —C(=O)$NCH_3$—$C_1$-$C_4$-alkyl-OH, —C(=O)NH—$C_1$-$C_4$-alkyl-$OCH_3$, —C(=O)$NCH_3$—$C_1$-$C_4$-alkyl-$OCH_3$, —C(=O)NRR' wherein R and R' together with the nitrogen atom to which they are attached form a ring and mean —$(CH_2)_{2-4}$—;

3-6-membered cycloalkyl, unsubstituted or substituted with one, two, three or four substituents independently of one another selected from the group consisting of —F, —Cl, —Br, —I, —CN, —OH, and —O—$C_1$-$C_4$-alkyl, wherein said 3-6-membered cycloalkyl is connected through —$C_1$-$C_6$-alkylene;

3-6-membered heterocycloalkyl, unsubstituted or substituted with one, two, three or four substituents independently of one another selected from the group consisting of —F, —Cl, —Br, —I, —CN, —$CO_2$H, —C(=O)O—$C_1$-$C_4$-alkyl, —OH, and —O—$C_1$-$C_4$-alkyl, wherein said 3-6-membered heterocycloalkyl is connected through —$C_1$-$C_6$-alkylene;

6-14-membered aryl, unsubstituted or substituted with one, two, three or four substituents independently of one another selected from the group consisting of —F, —Cl, —Br, —I, —CN, —$CO_2$H, —C(=O)O—$C_1$-$C_4$-alkyl, —OH, and —O—$C_1$-$C_4$-alkyl; wherein said 6-14-membered aryl is connected through —$C_1$-$C_6$-alkylene- or —S(=O)$_2$—;

5-14-membered heteroaryl, unsubstituted or substituted with one, two, three or four substituents independently of one another selected from the group consisting of —F, —Cl, —Br, —I, —CN, —$CO_2$H, —C(=O)O—$C_1$-$C_4$-alkyl, —OH, and —O—$C_1$-$C_4$-alkyl; wherein said 5-14-membered heteroaryl is connected through —$C_1$-$C_6$-alkylene- or —S(=O)$_2$—;

$R^5$ means -phenyl, -pyrazinyl, -pyridazinyl, -pyridinyl, -pyrimidinyl, -thienyl, -imidazolyl, triazolyl, or -1,3-benzodioxolyl, in each case unsubstituted or substituted with one, two, three or four substituents independently of one another selected from the group consisting of —F; —Cl; —Br; —I; —CN; —OH; —$C_1$-$C_4$-alkyl; —$CF_3$; —$C_1$-$C_4$-alkyl-OH; —$C_1$-$C_4$-alkyl-C(=O)$NH_2$; -3-12-membered cycloalkyl, saturated or unsaturated, unsubstituted, mono- or polysubstituted; preferably -cyclopropyl, saturated, unsubstituted; -3-12-membered heterocycloalkyl, saturated or unsaturated, unsubstituted, mono- or polysubstituted; —O—$CH_2$—O—; —O—$C_1$-$C_4$-alkyl; —O—$(CH_2CH_2$—O)$_{1-30}$—H; —O—$(CH_2CH_2$—O)$_{1-30}$—$CH_3$; —C(=O)OH; —C(=O)O—$C_1$-$C_4$-alkyl; —C(=O)$NH_2$; —C(=O)NH$C_1$-$C_4$-alkyl; —C(=O)N($C_1$-$C_4$-alkyl)$_2$; —S$C_1$-$C_4$-alkyl; —S(=O)$C_1$-$C_4$-alkyl and —S(=O)$_2C_1$-$C_4$-alkyl; and $R^7$, $R^8$, $R^{11}$, $R^{12}$, $R^{13}$, $R^{14}$, $R^{15}$, $R^{16}$, $R^{17}$, $R^{18}$, $R^{19}$, and $R^{20}$ mean —H.

In a particularly preferred embodiment of the compound according to the invention, n means 1 or 2; and/or $R^1$ means —H or —$CH_3$; and/or $R^2$ means —$C_1$-$C_6$-alkyl, linear or branched, saturated, unsubstituted; preferably, $R^2$ means —$CH_3$ or —$CH_2CH_3$; more preferably, $R^1$ and $R^2$ both mean —$CH_3$; and/or $R^3$ means -phenyl, -thienyl or -pyridinyl, in each case unsubstituted or substituted with one, two, three or four substituents independently of one another selected from the group consisting of —F, —Cl, —CN, —$CH_3$, —$CH_2CH_3$, —$CH_2$F, —$CHF_2$, —$CF_3$, —$OCF_3$, —OH, —$OCH_3$, —C(=O)$NH_2$, C(=O)$NHCH_3$, —C(=O)N$(CH_3)_2$, —$NH_2$, —$NHCH_3$, —N$(CH_3)_2$, —NHC(=O)$CH_3$, —$CH_2$OH, $SOCH_3$ and $SO_2CH_3$; preferably $R^3$ means -phenyl, -thienyl or -pyridinyl, in each case unsubstituted or substituted with —F; more preferably, $R^3$ means phenyl, unsubstituted; and/or $R^4$ means

—H;

—$C_1$-$C_6$-alkyl, linear or branched, saturated, unsubstituted or substituted with one, two, three or four substituents independently of one another selected from the group consisting of —F, —Cl, —Br, —I, —CN, —OH, and —O—$C_1$-$C_4$-alkyl; or 3-6-membered cycloalkyl, unsubstituted or substituted with one, two, three or four substituents independently of one another selected from the group consisting of —F, —Cl, —Br, —I, —CN, —OH, and —O—$C_1$-$C_4$-alkyl, wherein said 3-6-membered cycloalkyl is connected through —$C_1$-$C_6$-alkylene; preferably $R^4$ means 3-6-membered cycloalkyl, unsubstituted or substituted with one, two, three or four substituents independently of one another selected from the group consisting of —F, —Cl, —Br, —I, —CN, —OH, and —O—$C_1$-$C_4$-alkyl, wherein said 3-6-membered cycloalkyl is connected through —$CH_2$— or —$CH_2CH_2$—; more preferably, $R^4$ means -cyclobutyl, unsubstituted or monosubstituted with —OH, wherein said -cyclobutyl is connected through —$CH_2$—; and/or $R^5$ means -phenyl, -pyridazinyl, -pyridinyl, or -pyrimidinyl, in each case unsubstituted or substituted with one, two, three or four substituents independently of one another selected from the group consisting of —F; —$C_1$; —Br; —I; —CN; —OH; —$C_1$-$C_4$-alkyl; —$CF_3$; -3-12-membered cycloalkyl, saturated or unsaturated, unsubstituted, mono- or polysubstituted; preferably -cyclopropyl, saturated, unsubstituted; -3-12-membered heterocycloalkyl, saturated or unsaturated, unsubstituted, mono- or polysubstituted; preferably -pyrrolidinyl, -piperidinyl, -morpholinyl, -piperazinyl, -thiomorpholinyl, or -thiomorpholinyl dioxide, in each case saturated, unsubstituted or monosubstituted with —$C_1$-$C_4$-alkyl; —O—$CH_2$—O— (such that it is condensed with a dioxolanyl ring); —O—$C_1$-$C_4$-alkyl; —O—$(CH_2CH_2$—O)$_{1-30}$—H; —O—$(CH_2CH_2$—O)$_{1-30}$—$CH_3$; —C(=O)OH; —C(=O)O$C_1$-$C_4$-alkyl; —C(=O)$NH_2$; —C(=O)NH$C_1$-$C_4$-alkyl; —C(=O)N($C_1$-$C_4$-alkyl)$_2$; —S(=O)$C_1$-$C_4$-alkyl and —S(=O)$_2C_1$-$C_4$-alkyl; and/or $R^7$, $R^8$, $R^{11}$, $R^{12}$, $R^{13}$, $R^{14}$, $R^{15}$, $R^{16}$, $R^{17}$, $R^{18}$, $R^{19}$, and $R^{20}$ mean —H.

In preferred embodiments, the compound according to the invention is selected from the group consisting of

| | |
|---|---|
| SC_2001 | CIS-1-(Cyclobutyl-methyl)-8-dimethylamino-3-[(4-methylsulfonyl-phenyl)-methyl]-8-phenyl-1,3-diazaspiro[4.5]decan-2-one |
| SC_2002 | CIS-1-(Cyclobutyl-methyl)-8-dimethylamino-3-[(3-methoxyphenyl)-methyl]-8-phenyl-1,3-diazaspiro[4.5]decan-2-one |
| SC_2003 | CIS-8-Dimethylamino-1-isopropyl-3-[(4-methoxyphenyl)-methyl]-8-phenyl-1,3-diazaspiro[4.5]decan-2-one |

-continued

| | |
|---|---|
| SC_2004 | CIS-1-(Cyclopropyl-methyl)-8-dimethylamino-3-[(4-methoxyphenyl)-methyl]-8-phenyl-1,3-diazaspiro[4.5]decan-2-one |
| SC_2005 | CIS-1-(Cyclobutyl-methyl)-3-[(4-methoxyphenyl)-methyl]-8-[methyl-(2-methyl-propyl)-amino]-8-phenyl-1,3-diazaspiro[4.5]decan-2-one |
| SC_2006 | CIS-2-[[1-(Cyclobutyl-methyl)-8-dimethylamino-2-oxo-8-phenyl-1,3-diazaspiro[4.5]decan-3-yl]-methyl]-benzamide |
| SC_2007 | CIS-1-(Cyclobutyl-methyl)-8-dimethylamino-8-phenyl-3-(pyrazin-2-yl-methyl)-1,3-diazaspiro[4.5]decan-2-one |
| SC_2008 | CIS-8-(Allyl-methyl-amino)-1-(cyclobutyl-methyl)-3-[(4-methoxyphenyl)-methyl]-8-phenyl-1,3-diazaspiro[4.5]decan-2-one |
| SC_2009 | CIS-4-[[1-(Cyclobutyl-methyl)-8-dimethylamino-2-oxo-8-phenyl-1,3-diazaspiro[4.5]decan-3-yl]-methyl]-benzamide |
| SC_2010 | CIS-1-(Cyclobutyl-methyl)-8-dimethylamino-8-(3-fluorophenyl)-3-[(4-methoxyphenyl)-methyl]-1,3-diazaspiro[4.5]decan-2-one |
| SC_2011 | CIS-1-(Cyclobutyl-methyl)-8-dimethylamino-8-(4-fluorophenyl)-3-[(4-methoxyphenyl)-methyl]-1,3-diazaspiro[4.5]decan-2-one |
| SC_2012 | CIS-1-(Cyclobutyl-methyl)-8-dimethylamino-8-(3-methoxyphenyl)-3-[(4-methoxyphenyl)-methyl]-1,3-diazaspiro[4.5]decan-2-one |
| SC_2013 | CIS-1-(Cyclobutyl-methyl)-8-dimethylamino-8-(4-methoxyphenyl)-3-[(4-methoxyphenyl)-methyl]-1,3-diazaspiro[4.5]decan-2-one |
| SC_2014 | CIS-8-Dimethylamino-3-[(4-methoxyphenyl)-methyl]-1-(2-methyl-propyl)-8-phenyl-1,3-diazaspiro[4.5]decan-2-one |
| SC_2015 | CIS-1-Butyl-8-dimethylamino-3-[(4-methoxyphenyl)-methyl]-8-phenyl-1,3-diazaspiro[4.5]decan-2-one |
| SC_2016 | CIS-8-Dimethylamino-8-(4-fluorophenyl)-3-[(4-methoxyphenyl)-methyl]-1,3-diazaspiro[4.5]decan-2-one |
| SC_2017 | CIS-8-Dimethylamino-8-(3-fluorophenyl)-3-[(4-methoxyphenyl)-methyl]-1,3-diazaspiro[4.5]decan-2-one |
| SC_2018 | CIS-1-(Cyclobutyl-methyl)-8-dimethylamino-8-(3-hydroxyphenyl)-3-[(4-methoxyphenyl)-methyl]-1,3-diazaspiro[4.5]decan-2-one |
| SC_2019 | CIS-1-(Cyclobutyl-methyl)-8-dimethylamino-8-phenyl-3-(pyridin-3-yl-methyl)-1,3-diazaspiro[4.5]decan-2-one |
| SC_2020 | CIS-1-(Cyclobutyl-methyl)-8-dimethylamino-3-[[3-[2-[2-[2-[2-[2-(2-methoxy-ethoxy)-ethoxy]-ethoxy]-ethoxy]-ethoxy]-ethoxy]-phenyl]-methyl]-8-phenyl-1,3-diazaspiro[4.5]decan-2-one |
| SC_2021 | CIS-1-(Cyclobutyl-methyl)-8-dimethylamino-8-(4-hydroxyphenyl)-3-[(4-methoxyphenyl)-methyl]-1,3-diazaspiro[4.5]decan-2-one hydrochloride |
| SC_2022 | CIS-8-Dimethylamino-1-[(1-hydroxy-cyclobutyl)-methyl]-3-[(3-methoxyphenyl)-methyl]-8-phenyl-1,3-diazaspiro[4.5]decan-2-one |
| SC_2023 | CIS-1-(Cyclopentyl-methyl)-8-dimethylamino-3-[(4-methoxyphenyl)-methyl]-8-phenyl-1,3-diazaspiro[4.5]decan-2-one |
| SC_2024 | CIS-8-Dimethylamino-1-(2-hydroxy-2-methyl-propyl)-3-[(4-methoxyphenyl)-methyl]-8-phenyl-1,3-diazaspiro[4.5]decan-2-one |
| SC_2025 | CIS-8-Dimethylamino-1-(2-methoxy-2-methyl-propyl)-3-[(4-methoxyphenyl)-methyl]-8-phenyl-1,3-diazaspiro[4.5]decan-2-one |
| SC_2026 | CIS-1-(Cyclobutyl-methyl)-3-[(3-methoxyphenyl)-methyl]-8-methylamino-8-phenyl-1,3-diazaspiro[4.5]decan-2-one |
| SC_2027 | CIS-3-[[1-(Cyclobutyl-methyl)-8-(ethyl-methyl-amino)-2-oxo-8-phenyl-1,3-diazaspiro[4.5]decan-3-yl]-methyl]-benzonitrile |
| SC_2028 | CIS-1-(Cyclobutyl-methyl)-3-[(3-methoxyphenyl)-methyl]-8-(methyl-propyl-amino)-8-phenyl-1,3-diazaspiro[4.5]decan-2-one |
| SC_2029 | CIS-1-(Cyclobutyl-methyl)-8-(ethyl-methyl-amino)-3-[(3-methoxyphenyl)-methyl]-8-phenyl-1,3-diazaspiro[4.5]decan-2-one |
| SC_2030 | CIS-3-8-Dimethylamino-3-[(4-methoxyphenyl)-methyl]-2-oxo-8-phenyl-1,3-diazaspiro[4.5]decan-1-yl]-propionitrile |
| SC_2031 | CIS-1-(Cyclobutyl-methyl)-8-methylamino-8-phenyl-3-(pyridin-3-yl-methyl)-1,3-diazaspiro[4.5]decan-2-one |
| SC_2032 | CIS-8-Dimethylamino-3-[(4-methoxyphenyl)-methyl]-1-(oxetan-3-yl-methyl)-8-phenyl-1,3-diazaspiro[4.5]decan-2-one |
| SC_2033 | CIS-1-(Cyclobutyl-methyl)-8-(ethyl-methyl-amino)-8-phenyl-3-(pyridin-3-yl-methyl)-1,3-diazaspiro[4.5]decan-2-one |
| SC_2034 | CIS-8-Dimethylamino-1-(2-hydroxy-ethyl)-3-[(4-methoxyphenyl)-methyl]-8-phenyl-1,3-diazaspiro[4.5]decan-2-one |
| SC_2035 | CIS-8-Dimethylamino-1-(2,2-dimethyl-propyl)-3-[(4-methoxyphenyl)-methyl]-8-phenyl-1,3-diazaspiro[4.5]decan-2-one |
| SC_2036 | CIS-8-Dimethylamino-3-[(4-methoxyphenyl)-methyl]-1-(3-methyl-butyl)-8-phenyl-1,3-diazaspiro[4.5]decan-2-one |
| SC_2037 | CIS-8-Dimethylamino-3-[(4-methoxyphenyl)-methyl]-8-phenyl-1-[3-(trifluoromethyloxy)-propyl]-1,3-diazaspiro[4.5]decan-2-one |
| SC_2038 | CIS-1-(2-Cyclobutyl-ethyl)-8-dimethylamino-3-[(4-methoxyphenyl)-methyl]-8-phenyl-1,3-diazaspiro[4.5]decan-2-one |
| SC_2039 | CIS-1-(3,3-Difluoro-cyclobutyl)-methyl]-8-dimethylamino-3-[(4-methoxyphenyl)-methyl]-8-phenyl-1,3-diazaspiro[4.5]decan-2-one |
| SC_2040 | CIS-2-[[1-(Cyclobutyl-methyl)-3-[(4-methoxyphenyl)-methyl]-2-oxo-8-phenyl-1,3-diazaspiro[4.5]decan-8-yl]-methyl-amino]-acetonitrile |
| SC_2041 | CIS-1-(Cyclobutyl-methyl)-8-[(2-methoxy-ethyl)-methyl-amino]-3-[(4-methoxyphenyl)-methyl]-8-phenyl-1,3-diazaspiro[4.5]decan-2-one |
| SC_2042 | CIS-2-[8-Dimethylamino-3-[(4-methoxyphenyl)-methyl]-2-oxo-8-phenyl-1,3-diazaspiro[4.5]decan-1-yl]-acetic acid tert-butyl ester |

-continued

| | |
|---|---|
| SC_2043 | CIS-2-[8-Dimethylamino-3-[(4-methoxyphenyl)-methyl]-2-oxo-8-phenyl-1,3-diazaspiro[4.5]decan-1-yl]-acetic acid; 2,2,2-trifluoro-acetic acid salt |
| SC_2044 | CIS-1-(Cyclobutyl-methyl)-3-[(4-methoxyphenyl)-methyl]-8-methylamino-8-phenyl-1,3-diazaspiro[4.5]decan-2-one |
| SC_2045 | CIS-2-8-Dimethylamino-3-[(4-methoxyphenyl)-methyl]-2-oxo-8-phenyl-1,3-diazaspiro[4.5]decan-l-yl]-acetic acid methyl ester |
| SC_2046 | CIS-2-8-Dimethylamino-3-[(4-methoxyphenyl)-methyl]-2-oxo-8-phenyl-1,3-diazaspiro[4.5]decan-1-yl]-acetamide |
| SC_2047 | CIS-1-Benzyl-8-dimethylamino-3-[(4-methoxyphenyl)-methyl]-8-phenyl-1,3-diazaspiro[4.5]decan-2-one |
| SC_2048 | CIS-2-[8-Dimethylamino-3-[(4-methoxyphenyl)-methyl]-2-oxo-8-phenyl-1,3-diazaspiro[4.5]decan-1-yl]-N-methyl-acetamide |
| SC_2049 | CIS-2-[8-Dimethylamino-3-[(4-methoxyphenyl)-methyl]-2-oxo-8-phenyl-1,3-diazaspiro[4.5]decan-1-yl]-N-propyl-acetamide |
| SC_2050 | CIS-8-Dimethylamino-3-[(4-methoxyphenyl)-methyl]-1-(3-methoxy-propyl)-8-phenyl-1,3-diazaspiro[4.5]decan-2-one |
| SC_2051 | CIS-8-Dimethylamino-1-(1-hydroxy-cyclobutyl)-methyl]-3-[(4-methoxyphenyl)-methyl]-8-phenyl-1,3-diazaspiro[4.5]decan-2-one |
| SC_2052 | CIS-8-Dimethylamino-1-(2-methoxy-ethyl)-3-[(4-methoxyphenyl)-methyl]-8-phenyl-1,3-diazaspiro[4.5]decan-2-one |
| SC_2053 | CIS-2-8-Dimethylamino-3-[(4-methoxyphenyl)-methyl]-2-oxo-8-phenyl-1,3-diazaspiro[4.5]decan-1-yl]-acetonitrile |
| SC_2054 | CIS-8-Dimethylamino-1-hexyl-3-[(4-methoxyphenyl)-methyl]-8-phenyl-1,3-diazaspiro[4.5]decan-2-one |
| SC_2055 | CIS-8-Dimethylamino-3-[(4-methoxyphenyl)-methyl]-8-phenyl-1-(tetrahydro-pyran-4-yl-methyl)-1,3-diazaspiro[4.5]decan-2-one |
| SC_2056 | CIS-1-(Cyclohexyl-methyl)-8-dimethylamino-3-[(4-methoxyphenyl)-methyl]-8-phenyl-1,3-diazaspiro[4.5]decan-2-one |
| SC_2057 | CIS-N-(Cyano-methyl)-2-[8-dimethylamino-3-[(4-methoxyphenyl)-methyl]-2-oxo-8-phenyl-1,3-diazaspiro[4.5]decan-1-yl]-acetamide |
| SC_2058 | CIS-8-Dimethylamino-3-[(4-methoxyphenyl)-methyl]-8-phenyl-1-(pyridin-3-yl-methyl)-1,3-diazaspiro[4.5]decan-2-one |
| SC_2059 | CIS-8-Dimethylamino-3-[(4-methoxyphenyl)-methyl]-8-(3-methoxy-propyl)-1,3-diazaspiro[4.5]decan-2-one |
| SC_2060 | CIS-2-8-Dimethylamino-3-[(4-methoxyphenyl)-methyl]-2-oxo-8-phenyl-1,3-diazaspiro[4.5]decan-1-yl]-N-(2-methoxy-ethyl)-acetamide |
| SC_2062 | CIS-8-Dimethylamino-3-[(4-methoxyphenyl)-methyl]-1-(2-oxo-2-pyrrolidin-l-yl-ethyl)-8-phenyl-1,3-diazaspiro[4.5]decan-2-one |
| SC_2063 | CIS-2-[8-Dimethylamino-3-[(4-methoxyphenyl)-methyl]-2-oxo-8-phenyl-1,3-diazaspiro[4.5]decan-1-yl]-N,N-dimethyl-acetamide |
| SC_2064 | CIS-N-(1-Cyano-cyclopropyl)-2-[8-dimethylamino-3-[(4-methoxyphenyl)-methyl]-2-oxo-8-phenyl-1,3-diazaspiro[4.5]decan-1-yl]-acetamide |
| SC_2065 | CIS-2-8-Dimethylamino-3-[(4-methoxyphenyl)-methyl]-2-oxo-8-phenyl-1,3-diazaspiro[4.5]decan-1-yl]-N-methyl-N-propyl-acetamide |
| SC_2066 | CIS-1-(Cyclobutyl-methyl)-8-dimethylamino-3-[(4-methoxyphenyl)-methyl]-8-(3-methoxy-propyl)-1,3-diazaspiro[4.5]decan-2-one |
| SC_2067 | CIS-8-Dimethylamino-1-[3-hydroxy-propyl)-3-[(4-methoxyphenyl)-methyl]-8-phenyl-1,3-diazaspiro[4.5]decan-2-one |
| SC_2068 | CIS-8-Dimethylamino-1-(4-methoxy-butyl)-3-[(4-methoxyphenyl)-methyl]-8-phenyl-1,3-diazaspiro[4.5]decan-2-one |
| SC_2069 | CIS-8-Dimethylamino-3-[(4-methoxyphenyl)-methyl]-1-[(1-methyl-cyclobutyl)-methyl]-8-phenyl-1,3-diazaspiro[4.5]decan-2-one |
| SC_2070 | CIS-8-Dimethylamino-1-(1-hydroxy-cyclohexyl)-methyl]-3-[(4-methoxyphenyl)-methyl]-8-phenyl-1,3-diazaspiro[4.5]decan-2-one |
| SC_2071 | CIS-5-[8-Dimethylamino-3-[(4-methoxyphenyl)-methyl]-2-oxo-8-phenyl-1,3-diazaspiro[4.5]decan-l-yl]-pentanenitrile |
| SC_2072 | CIS-3-[8-Dimethylamino-3-[(4-methoxyphenyl)-methyl]-2-oxo-8-phenyl-1,3 -diazaspiro[4.5]decan-l-yl]-propionamide |
| SC_2073 | CIS-1-(Cyclobutyl-methyl)-8-[(2-hydroxy-ethyl)-methyl-amino]-3-[(4-methoxyphenyl)-methyl]-8-phenyl-1,3-diazaspiro[4.5]decan-2-one |
| SC_2074 | CIS-1-[[8-Dimethylamino-3-[(4-methoxyphenyl)-methyl]-2-oxo-8-phenyl-1,3-diazaspiro[4.5]decan-l-yl]-methyl-cyclobutane-1-carbonitrile |
| SC_2075 | CIS-8-Dimethylamino-1-[(1-hydroxy-cyclopentyl)-methyl]-3-[(4-methoxyphenyl)-methyl]-8-phenyl-1,3-diazaspiro[4.5]decan-2-one |
| SC_2076 | CIS-3-[(2-Bromophenyl)-methyl]-1-(cyclobutyl-methyl)-8-dimethylamino-8-phenyl-1,3-diazaspiro[4.5]decan-2-one |
| SC_2077 | CIS-3-[8-Dimethylamino-3-[(4-methoxyphenyl)-methyl]-2-oxo-8-phenyl-1,3-diazaspiro[4.5]decan-l-yl]-N-methyl-propionamide |
| SC_2078 | CIS-3-[8-Dimethylamino-3-[(4-methoxyphenyl)-methyl]-2-oxo-8-phenyl-1,3-diazaspiro[4.5]decan-l-yl]-N-propyl-propionamide |
| SC_2079 | CIS-8-Dimethylamino-1-(1-fluoro-cyclobutyl)-methyl]-3-[(4-methoxyphenyl)-methyl]-8-phenyl-1,3-diazaspiro[4.5]decan-2-one |
| SC_2080 | CIS-1-(2-Cyclohexyl-ethyl)-8-dimethylamino-3-[(4-methoxyphenyl)-methyl]-8-phenyl-1,3-diazaspiro[4.5]decan-2-one |
| SC_2081 | CIS-3-[[1-(Cyclobutyl-methyl)-8-dimethylamino-2-oxo-8-phenyl-1,3-diazaspiro[4.5]decan-3-yl]-methyl]-benzonitrile |
| SC_2082 | CIS-8-Dimethylamino-3-[(4-methoxyphenyl)-methyl]-1-methyl-8-phenyl-1,3-diazaspiro[4.5]decan-2-one |

-continued

| | |
|---|---|
| SC_2083 | CIS-8-Dimethylamino-1-[2-[2-[2-[2-[2-[2-[2-(2-methoxy-ethoxy)-ethoxy]-ethoxy]-ethoxy]-ethoxy]-ethoxy]-ethoxy]-ethyl]-3-[(4-methoxyphenyl)-methyl]-8-phenyl-1,3-diazaspiro[4.5]decan-2-one |
| SC_2084 | CIS-8-Dimethylamino-3-[(4-methoxyphenyl)-methyl]-8-phenyl-1-(2-tetrahydro-pyran-4-yl-ethyl)-1,3-diazaspiro[4.5]decan-2-one |
| SC_2085 | CIS-4-[[1-(Cyclobutyl-methyl)-8-dimethylamino-2-oxo-8-phenyl-1,3-diazaspiro[4.5]decan-3-yl]-methyl-benzonitrile |
| SC_2086 | CIS-1-(Cyclobutyl-methyl)-8-dimethylamino-8-phenyl-3-[[6-(trifluoromethyl)-pyridin-3-yl]-methyl]-1,3-diazaspiro[4.5]decan-2-one |
| SC_2087 | CIS-1-(Cyclobutyl-methyl)-8-dimethylamino-3-[[4-[2-[2-[2-[2-[2-[2-[2-(2-methoxy-ethoxy)-ethoxy]-ethoxy]-ethoxy]-ethoxy]-ethoxy]-ethoxy]-ethoxy]-phenyl]-methyl]-8-phenyl-1,3-diazaspiro[4.5]decan-2-one |
| SC_2088 | CIS-3-[[1-(Cyclobutyl-methyl)-8-dimethylamino-2-oxo-8-phenyl-1,3-diazaspiro[4.5]decan-3-yl]-methyl]-benzamide |
| SC_2089 | CIS-1-(Cyclobutyl-methyl)-8-dimethylamino-3-[(4-hydroxyphenyl)-methyl]-8-phenyl-1,3-diazaspiro[4.5]decan-2-one |
| SC_2090 | CIS-1-(Cyclobutyl-methyl)-8-(ethyl-methyl-amino)-3-[(4-methoxyphenyl)-methyl]-8-phenyl-1,3-diazaspiro[4.5]decan-2-one |
| SC_2091 | CIS-8-Dimethylamino-1-[(1-methoxy-cyclobutyl)-methyl]-3-[(4-methoxyphenyl)-methyl]-8-phenyl-1,3-diazaspiro[4.5]decan-2-one |
| SC_2092 | CIS-2-[[1-(Cyclobutyl-methyl)-8-dimethylamino-2-oxo-8-phenyl-1,3-diazaspiro[4.5]decan-3-yl]-methyl]-benzonitrile |
| SC_2093 | CIS-1-(Cyclobutyl-methyl)-8-dimethylamino-3-[(3-methylsulfonyl-phenyl)-methyl]-8-phenyl-1,3-diazaspiro[4.5]decan-2-one |
| SC_2094 | CIS-8-Dimethylamino-l-ethyl-3-[(4-methoxyphenyl)-methyl]-8-phenyl-1,3-diazaspiro[4.5]decan-2-one |
| SC_2095 | CIS-8-Dimethylamino-3-[(4-methoxyphenyl)-methyl]-8-phenyl-1-propyl-1,3-diazaspiro[4.5]decan-2-one |
| SC_2096 | CIS-3-Benzy1-1-(cyclobutyl-methyl)-8-dimethylamino-8-phenyl-1,3-diazaspiro[4.5]decan-2-one |
| SC_2097 | CIS-8-Dimethylamino-3-[(4-methoxyphenyl)-methyl]-8-phenyl-1,3-diazaspiro[4.5]decan-2-one |
| SC_2099 | CIS-8-Dimethylamino-3-[(4-methoxyphenyl)-methyl]-8-phenyl-1-(pyrimidin-4-yl-methyl)-1,3-diazaspiro[4.5]decan-2-one |
| SC_2100 | CIS-3-[8-Dimethylamino-3-[(4-methoxyphenyl)-methyl]-2-oxo-8-phenyl-1,3-diazaspiro[4.5]decan-1-yl]-2,2-dimethyl-propionitrile |
| SC_2101 | CIS-2-[[8-Dimethylamino-3-[(4-methoxyphenyl)-methyl]-2-oxo-8-phenyl-1,3-diazaspiro[4.5]decan-1-yl]-methyl]-benzoic acid methyl ester |
| SC_2102 | CIS-1-(Cyclobutyl-methyl)-8-dimethylamino-8-phenyl-3-(pyridin-2-yl-methyl)-1,3-diazaspiro[4.5]decan-2-one |
| SC_2103 | CIS-1-(Cyclobutyl-methyl)-8-dimethylamino-8-phenyl-3-(pyridin-4-yl-methyl)-1,3-diazaspiro[4.5]decan-2-one |
| SC_2104 | CIS-8-Dimethylamino-3-[(4-methoxyphenyl)-methyl]-8-phenyl-1-(tetrahydro-furan-3-yl-methyl)-1,3-diazaspiro[4.5]decan-2-one |
| SC_2105 | CIS-1-(Cyclobutyl-methyl)-8-dimethylamino-8-phenyl-3-(pyrimidin-2-yl-methyl)-1,3-diazaspiro[4.5]decan-2-one |
| SC_2106 | CIS-3-[[1-[(5-Cyano-2-methoxy-phenyl)-methyl]-8-dimethylamino-2-oxo-8-phenyl-1,3-diazaspiro[4.5]decan-3-yl]-methyl]-4-methoxy-benzonitrile |
| SC_2107 | CIS-8-Dimethylamino-1-(3-hydroxy-3-methyl-butyl)-3-[(4-methoxyphenyl)-methyl]-8-phenyl-1,3-diazaspiro[4.5]decan-2-one |
| SC_2108 | CIS-8-Dimethylamino-1-(3-methoxy-3-methyl-butyl)-3-[(4-methoxyphenyl)-methyl]-8-phenyl-1,3-diazaspiro[4.5]decan-2-one |
| SC_2109 | CIS-2-[[8-Dimethylamino-1-[(1-hydroxy-cyclobutyl)-methyl]-2-oxo-8-phenyl-1,3-diazaspiro[4.5]decan-3-yl]-methyl]-benzamide |
| SC_2110 | CIS-3-[[8-Dimethylamino-1-[(1-hydroxy-cyclobutyl)-methyl]-2-oxo-8-phenyl-1,3-diazaspiro[4.5]decan-3-yl]-methyl]-benzamide |
| SC_2111 | CIS-8-Dimethylamino-3-[(4-methoxyphenyl)-methyl]-1-(2-methylsulfonyl-ethyl)-8-phenyl-1,3-diazaspiro[4.5]decan-2-one |
| SC_2112 | CIS-1-[(1-Hydroxy-cyclobutyl)-methyl]-3-[(4-methoxyphenyl)-methyl]-8-methylamino-8-phenyl-1,3-diazaspiro[4.5]decan-2-one |
| SC_2113 | CIS-8-Dimethylamino-3-[(4-methoxyphenyl)-methyl]-8-phenyl-1-(tetrahydro-furan-2-yl-methyl)-1,3-diazaspiro[4.5]decan-2-one |
| SC_2114 | CIS-3-Benzyl-8-dimethylamino-8-phenyl-1,3-diazaspiro[4.5]decan-2-one |
| SC_2115 | CIS-3-Benzyl-8-dimethylamino-1-ethyl-8-phenyl-1,3-diazaspiro[4.5]decan-2-one |
| SC_2117 | CIS-8-Dimethylamino-3-[(4-methoxyphenyl)-methyl]-1-[2-(methylsulfinyl)-ethyl]-8-phenyl-1,3-diazaspiro[4.5]decan-2-one |
| SC_2118 | CIS-8-Dimethylamino-1-[(2R)-2-hydroxy-propyl]-3-[(4-methoxyphenyl)-methyl]-8-phenyl-1,3-diazaspiro[4.5]decan-2-one |
| SC_2119 | CIS-8-Dimethylamino-1-[(2S)-2-hydroxy-propyl]-3-[(4-methoxyphenyl)-methyl]-8-phenyl-1,3-diazaspiro[4.5]decan-2-one |
| SC_2120 | CIS-8-Dimethylamino-3-[(4-methoxyphenyl)-methyl]-8-phenyl-1-(tetrahydro-furan-3-yl-methyl)-1,3-diazaspiro[4.5]decan-2-one |
| SC_2122 | CIS-8-Dimethylamino-1-ethyl-3-[(4-methoxyphenyl)-methyl]-8-phenyl-1,3-diazaspiro[4.5]decan-2-one |
| SC_2123 | CIS-8-Amino-1-(1-hydroxy-cyclobutyl)-methyl]-3-[(4-methoxyphenyl)-methyl]-8-phenyl-1,3-diazaspiro[4.5]decan-2-one |
| SC_2124 | CIS-8-Dimethylamino-1-[(1-hydroxy-cyclobutyl)-methyl]-8-phenyl-3-(2-phenyl-ethyl)-1,3-diazaspiro[4.5]decan-2-one |

-continued

| | |
|---|---|
| SC_2125 | CIS-1-(Cyclobutyl-methyl)-8-dimethylamino-8-phenyl-3-[(4-methoxyphenyl)-methyl]-1,3-diazaspiro[4.5]decan-2-one |
| SC_2126 | CIS-3-[[8-Dimethylamino-1-[(1-hydroxy-cyclobutyl)-methyl]-2-oxo-8-phenyl-1,3-diazaspiro[4.5]decan-3-yl]-methyl]-4-methoxy-benzonitrile |
| SC_2127 | CIS-8-Dimethylamino-1-ethyl-8-phenyl-3-(pyridin-3-yl-methyl)-1,3-diazaspiro[4.5]decan-2-one |
| SC_2129 | CIS-8-Dimethylamino-1-[2-(1-methoxy-cyclobutyl)-ethyl]-3-[(4-methoxyphenyl)-methyl]-8-phenyl-1,3-diazaspiro[4.5]decan-2-one |
| SC_2130 | CIS-8-Dimethylamino-8-[3-(methoxymethyloxy)-phenyl]-3-[(4-methoxyphenyl)-methyl]-1,3-diazaspiro[4.5]decan-2-one |
| SC_2131 | CIS-8-Dimethylamino-8-[4-(methoxymethyloxy)-phenyl]-3-[(4-methoxyphenyl)-methyl]-1,3-diazaspiro[4.5]decan-2-one |
| SC_2132 | CIS-3-8-Dimethylamino-3-[(4-methoxyphenyl)-methyl]-2-oxo-8-phenyl-1,3-diazaspiro[4.5]decan-1-yl]-propionic acid |
| SC_2133 | CIS-3-[8-Dimethylamino-3-[(4-methoxyphenyl)-methyl]-2-oxo-8-phenyl-1,3-diazaspiro[4.5]decan-1-yl]-propionic acid tert-butyl ester |
| SC_2134 | CIS-2-[[1-(Cyclobutyl-methyl)-3-[(4-methoxyphenyl)-methyl]-2-oxo-8-phenyl-1,3-diazaspiro[4.5]decan-8-yl]-methyl-amino]-acetic acid methyl ester |
| SC_2135 | CIS-8-Dimethylamino-3-[(4-methoxyphenyl)-methyl]-1-(3-methyl-but-2-enyl)-8-phenyl-1,3-diazaspiro[4.5]decan-2-one |
| SC_2136 | CIS-1-(Cyclobutyl-methyl)-8-dimethylamino-3-[(3-methylsulfanyl-phenyl)-methyl]-8-phenyl-1,3-diazaspiro[4.5]decan-2-one |
| SC_2137 | CIS-3-[(3-Bromophenyl)-methyl]-1-(cyclobutyl-methyl)-8-dimethylamino-8-phenyl-1,3-diazaspiro[4.5]decan-2-one |
| SC_2138 | CIS-2-((8-(dimethylamino)-1-((1-hydroxycyclobutyl)methyl)-2-oxo-8-phenyl-1,3-diazaspiro[4.5]decan-3-yl)methyl)benzonitrile |
| SC_2139 | CIS-8-Dimethylamino-8-(3-methoxyphenyl)-3-[(4-methoxyphenyl)-methyl]-1,3-diazaspiro[4.5]decan-2-one |
| SC_2140 | CIS-8-Dimethylamino-8-(4-methoxyphenyl)-3-[(4-methoxyphenyl)-methyl]-1,3-diazaspiro[4.5]decan-2-one |
| SC_2141 | CIS-3-((8-(dimethylamino)-1-((1-hydroxycyclobutyl)methyl)-2-oxo-8-phenyl-1,3-diazaspiro[4.5]decan-3-yl)methyl)benzonitrile |
| SC_2142 | CIS-3-((8-(dimethylamino)-2-oxo-8-phenyl-1,3-diazaspiro[4.5]decan-3-yl)methyl)-4-methoxybenzonitrile |
| SC_2143 | CIS-8-Dimethylamino-8-phenyl-3-(1H-[1,2,3]triazol-4-yl-methyl)-1,3-diazaspiro[4.5]decan-2-one |
| SC_2144 | CIS-8-Dimethylamino-3-[[1-(2-hydroxy-ethyl)-1H-[1,2,3]triazol-4-yl]-methyl]-8-phenyl-1,3-diazaspiro[4.5]decan-2-one |
| SC_2145 | CIS-2-[4-[(8-Dimethylamino-2-oxo-8-phenyl-1,3-diazaspiro[4.5]decan-3-yl)-methyl]-1H-[1,2,3]triazol-1-yl]-acetamide |
| SC_2146 | CIS-8-Methylamino-8-phenyl-3-(1H-[1,2,3]triazol-4-yl-methyl)-1,3-diazaspiro[4.5]decan-2-one |
| SC_2147 | CIS-8-Dimethylamino-3-[(4-methoxyphenyl)-methyl]-8-phenyl-1-(p-tolylsulfonyl)-1,3-diazaspiro[4.5]decan-2-one |
| SC_2148 | CIS-2-[4-[(8-Methylamino-2-oxo-8-phenyl-1,3-diazaspiro[4.5]decan-3-yl)-methyl]-1H-[1,2,3]triazol-1-yl]-acetamide |
| SC_2149 | CIS-8-Dimethylamino-3-[(4-methoxyphenyl)-methyl]-2-oxo-8-phenyl-1,3-diazaspiro[4.5]decane-1-carboxylic acid benzyl ester |
| SC_2150 | CIS-3-1-(2-Hydroxy-ethyl)-1H-[1,2,3]triazol-4-yl]-methyl]-8-methylamino-8-phenyl-1,3-diazaspiro[4.5]decan-2-one |
| SC_2152 | CIS-8-Dimethylamino-8-phenyl-3-(2-pyridin-2-yl-ethyl)-1,3-diazaspiro[4.5]decan-2-one |
| SC_2153 | CIS-8-Dimethylamino-1-[(1-hydroxy-cyclobutyl)-methyl]-3-[[1-(2-hydroxy-ethyl)-1H-[1,2,3]triazol-4-yl]-methyl]-8-phenyl-1,3-diazaspiro[4.5]decan-2-one |
| SC_2155 | CIS-2-[4-[[8-Dimethylamino-1-[(1-hydroxy-cyclobutyl)-methyl]-2-oxo-8-phenyl-1,3-diazaspiro[4.5]decan-3-yl]-methyl-1H-[1,2,3]triazol-1-yl]-acetamide |
| SC_2156 | CIS-1-[(1-Hydroxy-cyclobutyl)-methyl]-3-[[1-(2-hydroxy-ethyl)-1H-[1,2,3]triazol-4-yl]-methyl]-8-methylamino-8-phenyl-1,3-diazaspiro[4.5]decan-2-one |
| SC_2159 | CIS-2-[4-[[1-(Cyclobutyl-methyl)-8-dimethylamino-2-oxo-8-phenyl-1,3-diazaspiro[4.5]decan-3-yl]-methyl]-1H-[1,2,3]triazol-1-yl]-acetamide |
| SC_2160 | CIS-1-(Cyclobutyl-methyl)-8-dimethylamino-3-[[1-(2-hydroxy-ethyl)-1H-[1,2,3]triazol-4-yl]-methyl]-8-phenyl-1,3-diazaspiro[4.5]decan-2-one |
| SC_2161 | CIS-2-[4-[[1-[(1-Hydroxy-cyclobutyl)-methyl]-8-methylamino-2-oxo-8-phenyl-1,3-diazaspiro[4.5]decan-3-yl]-methyl]-1H-[1,2,3]triazol-1-yl]-acetamide |
| SC_2162 | CIS-1-(Cyclobutyl-methyl)-3-[[1-(2-hydroxy-ethyl)-1H-[1,2,3]triazol-4-yl]-methyl]-8-methylamino-8-phenyl-1,3-diazaspiro[4.5]decan-2-one |
| SC_2163 | CIS-2-[4-[[1-(Cyclobutyl-methyl)-8-methylamino-2-oxo-8-phenyl-1,3-diazaspiro[4.5]decan-3-yl]-methyl]-1H-[1,2,3]triazol-1-yl]-acetamide |
| SC_2164 | CIS-8-Dimethylamino-8-phenyl-3-(2-pyridin-3-yl-ethyl)-1,3-diazaspiro[4.5]decan-2-one |
| SC_2165 | CIS-8-Dimethylamino-3-[2-(1H-imidazol-1-yl)-ethyl]-8-phenyl-1,3-diazaspiro[4.5]decan-2-one |
| SC_2166 | CIS-8-Dimethylamino-8-phenyl-3-(2-pyridin-4-yl-ethyl)-1,3-diazaspiro[4.5]decan-2-one |
| SC_2167 | CIS-8-Dimethylamino-8-phenyl-3-(2-pyrimidin-2-yl-ethyl)-1,3-diazaspiro[4.5]decan-2-one |
| SC_2168 | CIS-8-Dimethylamino-8-phenyl-3-(2-pyrimidin-5-yl-ethyl)-1,3-diazaspiro[4.5]decan-2-one |

-continued

| | |
|---|---|
| SC_2169 | CIS-8-Dimethylamino-1-ethyl-3-[(4-methylsulfonyl-phenyl)-methyl]-8-phenyl-1,3-diazaspiro[4.5]decan-2-one |
| SC_2170 | CIS-8-Dimethylamino-3-(1-methyl-1-phenyl-ethyl)-8-phenyl-1,3-diazaspiro[4.5]decan-2-one |
| SC_2171 | CIS-8-Dimethylamino-8-phenyl-3-(1-phenyl-cyclopropyl)-1,3-diazaspiro[4.5]decan-2-one |
| SC_2172 | CIS-8-Dimethylamino-1,3-bis[(2-methoxyphenyl)-methyl]-8-phenyl-1,3-diazaspiro[4.5]decan-2-one |
| SC_2173 | CIS-8-Dimethylamino-3-[(3-methylsulfonyl-phenyl)-methyl]-8-phenyl-1,3-diazaspiro[4.5]decan-2-one |
| SC_2174 | CIS-8-Dimethylamino-1-[(1-hydroxy-cyclobutyl)-methyl]-3-(1-methyl-l-phenyl-ethyl)-8-phenyl-1,3-diazaspiro[4.5]decan-2-one |
| SC_2175 | CIS-3-[(3-Cyclopropyl-phenyl)-methyl]-8-dimethylamino-8-phenyl-1,3-diazaspiro[4.5]decan-2-one |
| SC_2176 | CIS-3-(1,3-Benzodioxol-4-yl-methyl)-8-dimethylamino-8-phenyl-1,3-diazaspiro[4.5]decan-2-one |
| SC_2177 | CIS-8-Dimethylamino-1-[(1-hydroxy-cyclobutyl)-methyl]-8-phenyl-3-(1-phenyl-cyclopropyl)-1,3-diazaspiro[4.5]decan-2-one |
| SC_2178 | CIS-4-[[8-Dimethylamino-3-[(2-methoxyphenyl)-methyl]-2-oxo-8-phenyl-1,3-diazaspiro[4.5]decan-1-yl]-methyl]-benzonitrile |
| SC_2179 | CIS-8-Dimethylamino-3-[(2-methoxyphenyl)-methyl]-8-phenyl-1,3-diazaspiro[4.5]decan-2-one |
| SC_2180 | CIS-8-Dimethylamino-8-phenyl-3-(pyridin-4-yl-methyl)-1,3-diazaspiro[4.5]decan-2-one |
| SC_2181 | CIS-8-Dimethylamino-8-phenyl-3-(pyridin-2-yl-methyl)-1,3-diazaspiro[4.5]decan-2-one |
| SC_2182 | CIS-8-Dimethylamino-8-phenyl-3-(pyridin-3-yl-methyl)-1,3-diazaspiro[4.5]decan-2-one |
| SC_2183 | CIS-8-Dimethylamino-3-[[2-(4-methyl-piperazin-1-yl)-pyridin-4-yl]-methyl]-8-phenyl-1,3-diazaspiro[4.5]decan-2-one |
| SC_2184 | CIS-8-Dimethylamino-8-phenyl-3-[(2-piperidin-1-yl-pyridin-4-yl)-methyl]-1,3-diazaspiro[4.5]decan-2-one |
| SC_2185 | CIS-8-Dimethylamino-3-[(2-morpholin-4-yl-pyridin-4-yl)-methyl]-8-phenyl-1,3-diazaspiro[4.5]decan-2-one |
| SC_2186 | CIS-8-Dimethylamino-8-phenyl-3-[(2-piperazin-1-yl-pyridin-4-yl)-methyl]-1,3-diazaspiro[4.5]decan-2-one |

and the physiologically acceptable salts thereof.

According to the invention, unless expressly stated otherwise, "$—C_1$-$C_4$-alkyl", "$—C_1$-$C_6$-alkyl" and any other alkyl residues can be linear or branched, saturated or unsaturated. Linear saturated alkyl includes methyl, ethyl, n-propyl, n-butyl, n-pentyl and n-hexyl. Examples of branched saturated alkyl include but are not limited to iso-propyl, sec-butyl, and tert-butyl. Examples of linear unsaturated alkyl include but are not limited to vinyl, propenyl, allyl, and propargyl.

According to the invention, unless expressly stated otherwise, "$—C_1$-$C_4$-alkyl", "$—C_1$-$C_6$-alkyl" and any other alkyl residues can be unsubstituted, mono- or polysubstituted. Examples of substituted alkyl include but are not limited to $—CH_2CH_2OH$, $—CH_2CH_2OCH_3$, $—CH_2CH_2CH_2OCH_3$, $—CH_2CH_2S(=O)_2CH_3$, $—CH_2C(=O)NH_2$, $—C(CH_3)_2C(=O)NH_2$, $—CH_2C(CH_3)_2C(=O)NH_2$, and $—CH_2CH_2C(=O)N(CH_3)_2$.

According to the invention, unless expressly stated otherwise, "$—C_1$-$C_6$-alkylene-", "$—C_1$-$C_4$-alkylene" and any other alkylene residue can be unsubstituted, mono- or polysubstituted. Examples of saturated alkylene include but are not limited to $—CH_2—$, $—CH(CH_3)—$, $—C(CH_3)_2—$, $—CH_2CH_2—$, $—CH(CH_3)CH_2—$, $—CH_2CH(CH_3)—$, $—CH(CH_3)—CH(CH_3)—$, $—C(CH_3)_2CH_2—$, $—CH_2C(CH_3)_2—$, $—CH(CH_3)C(CH_3)_2—$, $—C(CH_3)_2CH(CH_3)—$, $C(CH_3)_2C(CH_3)_2—$, $—CH_2CH_2CH_2—$, and $—C(CH_3)_2CH_2CH_2—$. Examples of unsaturated alkylene include but are not limited to $—CH=CH—$, $—C≡C—$, $—C(CH_3)=CH—$, $—CH=C(CH_3)—$, $—C(CH_3)=C(CH_3)—$, $—CH_2CH=CH—$, $—CH=CHCH_2—$, $—CH=CH—CH=CH—$, and $—CH=CH—C≡C—$.

According to the invention, unless expressly stated otherwise, "$—C_1$-$C_6$-alkylene-", "$—C_1$-$C_4$-alkylene" and any other alkylene residue can be unsubstituted, mono- or polysubstituted. Examples of substituted $—C_1$-$C_6$-alkylene-include but are not limited to $—CHF—$, $—CF_2—$, $—CHOH—$ and $—C(=O)—$.

According to the invention, moieties may be connected through $—C_1$-$C_6$-alkylene-, i.e. the moieties may not be directly bound to the core structure of compound according to general formula (I), but may be connected to the core structure of compound according to general formula (I) or its periphery through a $—C_1$-$C_6$-alkylene-linker.

According to the invention, "3-12-membered cycloalkyl moiety" means a non-aromatic, monocyclic, bicyclic or tricyclic moiety comprising 3 to 12 ring carbon atoms but no heteroatoms in the ring. Examples of preferred saturated 3-12-membered cycloalkyl moieties according to the invention include but are not limited to cyclopropane, cyclobutane, cyclopentane, cyclohexane, cycloheptane, cyclooctane, hydrindane, and decaline. Examples of preferred unsaturated 3-12-membered cycloalkyl moiety moieties according to the invention include but are not limited to cyclopropene, cyclobutene, cyclopentene, cyclopentadiene, cyclohexene, 1,3-cyclohexadiene, and 1,4-cyclohexadiene. The 3-12-membered cycloalkyl moiety, which is bonded to the compound according to the invention, in its periphery may optionally be condensed with a 3-12-membered heterocycloalkyl moiety, saturated or unsaturated, unsubstituted, mono- or polysubstituted; and/or with a 6-14-membered aryl moiety, unsubstituted, mono- or polysubstituted; and/or with a 5-14-membered heteroaryl moiety, unsubstituted, mono- or polysubstituted. Under these circumstances, the ring atoms of the condensed moieties are not included in the 3 to 12 ring atoms of the 3-12-membered cycloalkyl moiety. Examples of 3-12-membered cycloalkyl moieties condensed with 3-12-membered heterocycloalkyl moieties include but are not limited to octahydro-1H-indol, decahydroquinoline, decahydroisoquinoline, octahydro-2H-benzo [b][1,4]oxazin, and decahydro-quinoxalin, which in each case are connected through the 3-12-membered cycloalkyl moiety. Examples of 3-12-membered cycloalkyl moieties condensed with 6-14-membered aryl moieties include but are not limited to 2,3-dihydro-1H-indene and tetraline, which in each case are connected through the 3-12-membered cycloalkyl moiety. Examples of 3-12-membered cycloalkyl moieties condensed with 5-14-membered heteroaryl moieties include but are not limited to 5,6,7,8-tetrahydroquinoline and 5,6,7,8-tetrahydroquinazoline, which in each case are connected through the 3-12-membered cycloalkyl moiety.

According to the invention, the 3-12-membered cycloalkyl moiety may optionally be connected through —$C_1$-$C_6$-alkylene-, i.e. the 3-12-membered cycloalkyl moiety may not be directly bound to the compound according to general formula (I) but may be connected thereto through a —$C_1$-$C_6$-alkylene-linker. Examples include but are not limited to —$CH_2$-cyclopropyl, —$CH_2$-cyclobutyl, —$CH_2$-cyclopentyl, —$CH_2$-cyclohexyl, —$CH_2CH_2$-cyclopropyl, —$CH_2CH_2$-cyclobutyl, —$CH_2CH_2$-cyclopentyl, and —$CH_2CH_2$-cyclohexyl.

According to the invention, unless expressly stated otherwise, the 3-12-membered cycloalkyl moiety can be unsubstituted, mono- or polysubstituted. Examples of substituted 3-12-membered cycloalkyl moieties include but are not limited to —$CH_2$-1-hydroxy-cyclobutyl.

According to the invention, "3-12-membered heterocycloalkyl moiety" means a non-aromatic, monocyclic, bicyclic or tricyclic moiety comprising 3 to 12 ring atoms, wherein each cycle comprises independently of one another 1, 2, 3, 4 or more heteroatoms independently of one another selected from the group consisting of nitrogen, oxygen and sulfur, whereas sulfur may be oxidized (S(═O) or (S(═O)$_2$), whereas the remaining ring atoms are carbon atoms, and whereas bicyclic or tricyclic systems may share common heteroatom(s). Examples of preferred saturated 3-12-membered heterocycloalkyl moieties according to the invention include but are not limited to aziridin, azetidine, pyrrolidine, imidazolidine, pyrazolidine, piperidine, piperazine, triazolidine, tetrazolidine, oxiran, oxetane, tetrahydrofurane, tetrahydropyrane, thiirane, thietane, tetra-hydrothiophene, diazepane, oxazolidine, isoxazolidine, thiazolidine, isothiazolidine, thiadiazoli-dine, morpholine, thiomorpholine. Examples of preferred unsaturated 3-12-membered heterocycloalkyl moiety moieties according to the invention include but are not limited to oxazoline, pyrazoline, imidazoline, isoxazoline, thiazoline, isothiazoline, and dihydropyran. The 3-12-membered heterocycloalkyl moiety, which is bonded to the compound according to the invention, in its periphery may optionally be condensed with a 3-12-membered cycloalkyl moiety, saturated or unsaturated, unsubstituted, mono- or polysubstituted; and/or with a 6-14-membered aryl moiety, unsubstituted, mono- or polysubstituted; and/or with a 5-14-membered heteroaryl moiety, unsubstituted, mono- or polysubstituted. Under these circumstances, the ring atoms of the condensed moieties are not included in the 3 to 12 ring atoms of the 3-12-membered heterocycloalkyl moieties. Examples of 3-12-membered heterocycloalkyl moieties condensed with 3-12-membered cycloalkyl moieties include but are not limited to octahydro-1H-indol, decahydroquinoline, decahydroisoquinoline, octahydro-2H-benzo[b][1,4]oxazin, and decahydro-quinoxalin, which in each case are connected through the 3-12-membered heterocycloalkyl moiety. An examples of a 3-12-membered heterocycloalkyl moiety condensed with a 6-14-membered aryl moiety includes but is not limited to 1,2,3,4-tetrahydroquinoline, which is connected through the 3-12-membered heterocycloalkyl moiety. An example of a 3-12-membered heterocycloalkyl moiety condensed with a 5-14-membered heteroaryl moieties includes but is not limited to 5,6,7,8-tetrahydro-[1,2,4]triazolo[1,5-a]pyrazine, which is connected through the 3-12-membered heterocycloalkyl moiety.

According to the invention, the 3-12-membered heterocycloalkyl moiety may optionally be connected through —$C_1$-$C_6$-alkylene-, i.e. the 3-12-membered heterocycloalkyl moiety may not be directly bound to the compound according to general formula (I) but may be connected thereto through a —$C_1$-$C_6$-alkylene-linker. Said linker may be connected to a carbon ring atom or to a hetero ring atom of the 3-12-membered heterocycloalkyl moiety. Examples include but are not limited to —$CH_2$-oxetane, —$CH_2$-pyrrolidine, —$CH_2$-piperidine, —$CH_2$-morpholine, —$CH_2CH_2$-oxetane, —$CH_2CH_2$-pyrrolidine, —$CH_2CH_2$-piperidine, and —$CH_2CH_2$-morpholine.

According to the invention, unless expressly stated otherwise, the 3-12-membered heterocycloalkyl moiety can be unsubstituted, mono- or polysubstituted. Examples of substituted 3-12-membered heterocycloalkyl moieties include but are not limited to 2-carboxamido-N-pyrrolidinyl-, 3,4-dihydroxy-N-pyrrolidinyl, 3-hydroxy-N-pyrimidinyl, 3,4-dihydroxy-N-pyrimidinyl, 3-oxo-N-piperazinyl, -tetrahydro-2H-thiopyranyl dioxide and thiomorpholinyl dioxide.

According to the invention, "6-14-membered aryl moiety" means an aromatic, monocyclic, bicyclic or tricyclic moiety comprising 6 to 14 ring carbon atoms but no heteroatoms in the ring. Examples of preferred 6-14-membered aryl moieties according to the invention include but are not limited to benzene, naphthalene, anthracen, and phenanthren. The 6-14-membered aryl moiety, which is bonded to the compound according to the invention, in its periphery may optionally be condensed with a 3-12-membered cycloalkyl moiety, saturated or unsaturated, unsubstituted, mono- or polysubstituted; and/or with a 3-12-membered heterocycloalkyl moiety, saturated or unsaturated, unsubstituted, mono- or polysubstituted; and/or with a 5-14-membered heteroaryl moiety, unsubstituted, mono- or polysubstituted. Under these circumstances, the ring atoms of the condensed moieties are not included in the 6 to 14 ring carbon atoms of the 6-14-membered heterocycloalkyl moieties. Examples of 6-14-membered aryl moieties condensed with 3-12-membered cycloalkyl moieties include but are not limited to 2,3-dihydro-1H-indene and tetraline, which in each case are connected through the 6-14-membered aryl moiety. An example of a 6-14-membered aryl moiety condensed with a 3-12-membered heterocycloalkyl moiety includes but is not limited to 1,2,3,4-tetrahydroquinoline, which is connected through the 6-14-membered aryl moiety. Examples of 6-14-membered aryl moieties condensed with 5-14-membered heteroaryl moieties include but are not limited to quinoline, isoquinoline, phenazine and phenoxacine, which in each case are connected through the 6-14-membered aryl moiety.

According to the invention, the 6-14-membered aryl moiety may optionally be connected through —$C_1$-$C_6$-alkylene-, i.e. the 6-14-membered aryl moiety may not be directly bound to the compound according to general formula (I) but may be connected thereto through a —$C_1$-$C_6$-alkylene-linker. Said linker may be connected to a carbon ring atom or to a hetero ring atom of the 6-14-membered aryl moiety. Examples include but are not limited to $—CH_2—C_6H_5$, $—CH_2CH_2—C_6H_5$ and $—CH{=}CH—C_6H_5$.

According to the invention, unless expressly stated otherwise, the 6-14-membered aryl moiety can be unsubstituted, mono- or polysubstituted. Examples of substituted 6-14-membered aryl moieties include but are not limited to 2-fluorophenyl, 3-fluorophenyl, 2-methoxyphenyl and 3-methoxyphenyl.

According to the invention, "5-14-membered heteroaryl moiety" means an aromatic, monocyclic, bicyclic or tricyclic moiety comprising 6 to 14 ring atoms, wherein each cycle comprises independently of one another 1, 2, 3, 4 or more heteroatoms independently of one another selected from the group consisting of nitrogen, oxygen and sulfur, whereas the remaining ring atoms are carbon atoms, and whereas bicyclic or tricyclic systems may share common heteroatom(s). Examples of preferred 5-14-membered heteroaryl moieties according to the invention include but are not limited to pyrrole, pyrazole, imidazole, triazole, tetrazole, furane, thiophene, oxazole, isoxazole, thiazole, isothiazole, pyridine, pyridazine, pyrimidine, pyrazine, indolicine, 9H-chinolicine, 1,8-naphthyridine, purine, imidazo[1,2-a]pyrazine, and pteridine. The 5-14-membered heteroaryl moiety, which is bonded to the compound according to the invention, in its periphery may optionally be condensed with a 3-12-membered cycloalkyl moiety, saturated or unsaturated, unsubstituted, mono- or polysubstituted; and/or with a 3-12-membered heterocycloalkyl moiety, saturated or unsaturated, unsubstituted, mono- or polysubstituted; and/or with a 6-14-membered aryl moiety, unsubstituted, mono- or polysubstituted. Under these circumstances, the ring atoms of the condensed moieties are not included in the 6 to 14 ring carbon atoms of the 6-14-membered heterocycloalkyl moieties. Examples of 5-14-membered heteroaryl moieties condensed with 3-12-membered cycloalkyl moieties include but are not limited to 5,6,7,8-tetrahydroquinoline and 5,6,7,8-tetrahydroquinazoline, which in each case are connected through the 5-14-membered heteroaryl moiety. An examples of a 5-14-membered heteroaryl moiety condensed with a 3-12-membered heterocycloalkyl moiety includes but is not limited to 5,6,7,8-tetrahydro-[1,2,4]triazolo[1,5-a]pyrazine, which is connected through the 5-14-membered heteroaryl moiety. Examples of 5-14-membered heteroaryl moieties condensed with 6-14-membered aryl moieties include but are not limited to quinoline, isoquinoline, phenazine and phenoxacine, which in each case are connected through the 5-14-membered heteroaryl moiety.

According to the invention, the 5-14-membered heteroaryl moiety may optionally be connected through $—C_1$-$C_6$-alkylene-, i.e. the 5-14-membered heteroaryl moiety may not be directly bound to the compound according to general formula (I) but may be connected thereto through a $—C_1$-$C_6$-alkylene-linker. Said linker may be connected to a carbon ring atom or to a hetero ring atom of the 5-14-membered heteroaryl moiety. Examples include but are not limited to $—CH_2$-oxazole, $—CH_2$-isoxazole, $—CH_2$-imidazole, $—CH_2$-pyridine, $—CH_2$-pyrimidine, $—CH_2$-pyridazine, $—CH_2CH_2$-oxazole, $—CH_2CH_2$-isoxazole, $—CH_2CH_2$-imidazole, $—CH_2CH_2$-pyridine, $—CH_2CH_2$-pyrimidine, and $—CH_2CH_2$-pyridazine.

According to the invention, unless expressly stated otherwise, the 5-14-membered heteroaryl moiety can be unsubstituted, mono- or polysubstituted. Examples of 5-14-membered heteroaryl moieties include but are not limited to 2-methoxy-4-pyridinyl, 2-methoxy-5-pyridinyl, 3-methoxy-4-pyridinyl, 3-methoxy-6-pyridinyl, 4-methoxy-2-pyridinyl, 2-methylsulfonyl-5-pyridinyl, 3-methylsulfonyl-6-pyridinyl, 3-methoxy-6-pyridazinyl, 2-nitrilo-5-pyrimidinyl, 4-hydroxy-2-pyrimidinyl, 4-methoxy-pyrimidinyl, and 2-methoxy-6-pyrazinyl.

Preferably, the compounds according to the invention have a structure according to general formula (I')

(I')

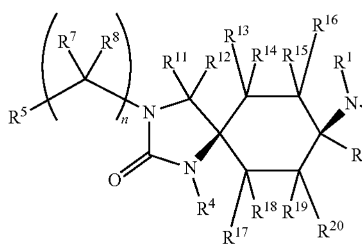

wherein $R^1$ to $R^5$, $R^7$, $R^8$, $R^{10}$ to $R^{20}$ and n are defined as above, or a physiologically acceptable salt thereof.

In one preferred embodiment, the excess of the cis-isomer so designated is at least 50% de, more preferably at least 75% de, yet more preferably at least 90% de, most preferably at least 95% de and in particular at least 99% de.

In a preferred embodiment, the compound according to the invention has a structure according to general formula (IX)

(IX)

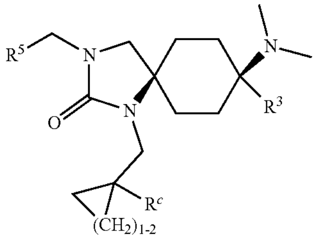

wherein $R^C$ means —H or —OH;

$R^3$ means -phenyl or -3-fluorophenyl; and $R^5$ means 6-14-membered aryl, unsubstituted, mono- or polysubstituted; or 5-14-membered heteroaryl, unsubstituted, mono- or polysubstituted;

or a physiologically acceptable salt thereof.

Preferably, $R^5$ is selected from -phenyl, -pyridyl, pyrimidinyl, or -triazolyl, in each case unsubstituted, mono- or polysubstituted.

In a preferred embodiment, the compounds according to the invention are in the form of the free bases.

In another preferred embodiment, the compounds according to the invention are in the form of the physiologically acceptable salts.

For the purposes of the description, a "salt" is to be understood as being any form of the compound in which it assumes an ionic form or is charged and is coupled with a counter-ion (a cation or anion) or is in solution. The term is also to be understood as meaning complexes of the compound with other molecules and ions, in particular complexes which are associated via ionic interactions. Preferred salts are physiologically acceptable, in particular physiologically acceptable salts with anions or acids or also a salt formed with a physiologically acceptable acid.

Physiologically acceptable salts with anions or acids are salts of the particular compound in question with inorganic or organic acids which are physiologically acceptable, in particular when used in humans and/or mammals. Examples of physiologically acceptable salts of particular acids include but are not limited to salts of hydrochloric acid, sulfuric acid, and acetic acid.

The invention also includes isotopic isomers of a compound according to the invention, wherein at least one atom of the compound is replaced by an isotope of the respective atom which is different from the naturally predominantly occurring isotope, as well as any mixtures of isotopic isomers of such a compound. Preferred isotopes are $^2$H (deuterium), $^3$H (tritium), $^{13}$C and $^{14}$C.

Certain compounds according to the invention are useful for modulating a pharmacodynamic response from one or more opioid receptors (mu, delta, kappa, NOP/ORL-1) either centrally or peripherally, or both. The pharmacodynamic response may be attributed to the compound either stimulating (agonizing) or inhibiting (antagonizing) the one or more receptors. Certain compounds according to the invention may antagonize one opioid receptor, while also agonizing one or more other receptors. Compounds according to the invention having agonist activity may be either full agonists or partial agonists.

As used herein, compounds that bind to receptors and mimic the regulatory effects of endogenous ligands are defined as "agonists". Compounds that bind to a receptor but produce no regulatory effect, but rather block the binding of ligands to the receptor, are defined as "antagonists".

In certain embodiments, the compounds according to the invention are agonists at the mu opioid (MOP) and/or kappa opioid (KOP) and/or delta opioid (DOP) and/or nociceptin opioid (NOP/ORL-1) receptors.

The compounds according to the invention potently bind to the MOP and/or KOP and/or DOP and/or NOP receptors.

The compounds according to the invention can be modulators at the MOP and/or KOP and/or DOP and/or NOP receptors, and therefore the compounds according to the invention can be used/administered to treat, ameliorate, or prevent pain.

In some embodiments, the compounds according to the invention are agonists of one or more opioid receptors. In some embodiments, the compounds according to the invention are agonists of the MOP and/or KOP and/or DOP and/or NOP receptors.

In some embodiments, the compounds according to the invention are antagonists of one or more opioid receptors. In some embodiments, the compounds according to the invention are antagonists of the MOP and/or KOP and/or DOP and/or NOP receptors.

In some embodiments, the compounds according to the invention have both, (i) agonist activity at the NOP receptor; and (ii) agonist activity at one or more of the MOP, KOP, and DOP receptors.

In some embodiments, the compounds according to the invention have both, (i) agonist activity at the NOP receptor; and (ii) antagonist activity at one or more of the MOP, KOP, and DOP receptors.

In some embodiments, the compounds according to the invention have both, (i) antagonist activity at the NOP receptor; and (ii) agonist activity at one or more of the MOP, KOP, and DOP receptors.

In some embodiments, the compounds according to the invention have both, (i) antagonist activity at the NOP receptor; and (ii) antagonist activity at one or more of the MOP, KOP, and DOP receptors.

In some embodiments, preferably with respect to receptors of the peripheral nervous system, the compounds according to the invention have selective agonist activity at the NOP receptor. In some embodiments, preferably with respect to receptors of the peripheral nervous system, the compounds according to the invention

- have agonist activity at the NOP receptor, but no significant activity at the MOP receptor;
- have agonist activity at the NOP receptor, but no significant activity at the KOP receptor;
- have agonist activity at the NOP receptor, but no significant activity at the DOP receptor;
- have agonist activity at the NOP receptor, but no significant activity at the MOP receptor as well as no significant activity at the KOP receptor;
- have agonist activity at the NOP receptor, but no significant activity at the MOP receptor as well as no significant activity at the DOP receptor; or
- have agonist activity at the NOP receptor, but no significant activity at the MOP receptor as well as no significant activity at the KOP receptor as well as no significant activity at the DOP receptor.

In some embodiments, preferably with respect to receptors of the peripheral nervous system, the compounds according to the invention have balanced agonist activity at the NOP receptor as well as at the MOP receptor. In some embodiments, preferably with respect to receptors of the peripheral nervous system, the compounds according to the invention

- have agonist activity at the NOP receptor as well as agonist activity at the MOP receptor;
- have agonist activity at the NOP receptor as well as agonist activity at the MOP receptor as well as agonist activity at the KOP receptor;
- have agonist activity at the NOP receptor as well as agonist activity at the MOP receptor as well as agonist activity at the DOP receptor;
- can be regarded as opioid pan agonists, i.e. have agonist activity at the NOP receptor as well as agonist activity at the MOP receptor as well as agonist activity at the KOP receptor as well as agonist activity at the DOP receptor;
- have agonist activity at the NOP receptor as well as agonist activity at the MOP receptor, but no significant activity at the KOP receptor;
- have agonist activity at the NOP receptor as well as agonist activity at the MOP receptor, but no significant activity at the DOP receptor; or
- have agonist activity at the NOP receptor as well as agonist activity at the MOP receptor, but no significant activity at the KOP receptor as well as no significant activity at the DOP receptor.

In some embodiments, preferably with respect to receptors of the peripheral nervous system, the compounds according to the invention have balanced agonist activity at the NOP receptor as well as at the KOP receptor. In some embodiments, preferably with respect to receptors of the peripheral nervous system, the compounds according to the invention

- have agonist activity at the NOP receptor as well as agonist activity at the KOP receptor;
- have agonist activity at the NOP receptor as well as agonist activity at the KOP receptor as well as agonist activity at the MOP receptor;

have agonist activity at the NOP receptor as well as agonist activity at the KOP receptor as well as agonist activity at the DOP receptor;

have agonist activity at the NOP receptor as well as agonist activity at the KOP receptor, but no significant activity at the MOP receptor;

have agonist activity at the NOP receptor as well as agonist activity at the KOP receptor, but no significant activity at the DOP receptor; or have agonist activity at the NOP receptor as well as agonist activity at the KOP receptor, but no significant activity at the MOP receptor as well as no significant activity at the DOP receptor.

In some embodiments, preferably with respect to receptors of the peripheral nervous system, the compounds according to the invention have balanced agonist activity at the NOP receptor as well as at the DOP receptor. In some embodiments, preferably with respect to receptors of the peripheral nervous system, the compounds according to the invention have agonist activity at the NOP receptor as well as agonist activity at the DOP receptor;

have agonist activity at the NOP receptor as well as agonist activity at the DOP receptor, but no significant activity at the MOP receptor;

have agonist activity at the NOP receptor as well as agonist activity at the DOP receptor, but no significant activity at the KOP receptor; or have agonist activity at the NOP receptor as well as agonist activity at the DOP receptor, but no significant activity at the MOP receptor as well as no significant activity at the KOP receptor.

In some embodiments, preferably with respect to receptors of the peripheral nervous system, the compounds according to the invention have selective agonist activity at the KOP receptor. In some embodiments, preferably with respect to receptors of the peripheral nervous system, the compounds according to the invention have agonist activity at the KOP receptor, but no significant activity at the MOP receptor;

have agonist activity at the KOP receptor, but no significant activity at the NOP receptor;

have agonist activity at the KOP receptor, but no significant activity at the DOP receptor;

have agonist activity at the KOP receptor, but no significant activity at the MOP receptor as well as no significant activity at the NOP receptor;

have agonist activity at the KOP receptor, but no significant activity at the MOP receptor as well as no significant activity at the DOP receptor; or have agonist activity at the KOP receptor, but no significant activity at the MOP receptor as well as no significant activity at the NOP receptor as well as no significant activity at the DOP receptor.

In some embodiments, preferably with respect to receptors of the peripheral nervous system, the compounds according to the invention have agonist activity at the MOP receptor, agonist activity at the KOP receptor, and antagonist activity at the DOP receptor. In some embodiments, preferably with respect to receptors of the peripheral nervous system, the compounds according to the invention have agonist activity at the MOP receptor as well as agonist activity at the KOP receptor as well as antagonist activity at the DOP receptor;

have agonist activity at the MOP receptor as well as agonist activity at the KOP receptor as well as antagonist activity at the DOP receptor as well as agonist activity at the NOP receptor;

have agonist activity at the MOP receptor as well as agonist activity at the KOP receptor as well as antagonist activity at the DOP receptor as well as antagonist activity at the NOP receptor; or have agonist activity at the MOP receptor as well as agonist activity at the KOP receptor as well as antagonist activity at the DOP receptor, no significant activity at the NOP receptor.

In some embodiments, preferably with respect to receptors of the central nervous system, the compounds according to the invention have selective agonist activity at the NOP receptor. In some embodiments, preferably with respect to receptors of the central nervous system, the compounds according to the invention have agonist activity at the NOP receptor, but no significant activity at the MOP receptor;

have agonist activity at the NOP receptor, but no significant activity at the KOP receptor;

have agonist activity at the NOP receptor, but no significant activity at the DOP receptor;

have agonist activity at the NOP receptor, but no significant activity at the MOP receptor as well as no significant activity at the KOP receptor;

have agonist activity at the NOP receptor, but no significant activity at the MOP receptor as well as no significant activity at the DOP receptor; or have agonist activity at the NOP receptor, but no significant activity at the MOP receptor as well as no significant activity at the KOP receptor as well as no significant activity at the DOP receptor.

In some embodiments, preferably with respect to receptors of the central nervous system, the compounds according to the invention have selective antagonist activity at the NOP receptor.

In some embodiments, preferably with respect to receptors of the central nervous system, the compounds according to the invention have antagonist activity at the NOP receptor, but no significant activity at the MOP receptor;

have antagonist activity at the NOP receptor, but no significant activity at the KOP receptor;

have antagonist activity at the NOP receptor, but no significant activity at the DOP receptor;

have antagonist activity at the NOP receptor, but no significant activity at the MOP receptor as well as no significant activity at the KOP receptor;

have antagonist activity at the NOP receptor, but no significant activity at the MOP receptor as well as no significant activity at the DOP receptor; or have antagonist activity at the NOP receptor, but no significant activity at the MOP receptor as well as no significant activity at the KOP receptor as well as no significant activity at the DOP receptor.

In some embodiments, preferably with respect to receptors of the central nervous system, the compounds according to the invention have antagonist activity at the NOP receptor as well as agonist activity at the DOP receptor. In some embodiments, preferably with respect to receptors of the central nervous system, the compounds according to the invention have antagonist activity at the NOP receptor as well as agonist activity at the DOP receptor;

have antagonist activity at the NOP receptor as well as agonist activity at the DOP receptor, but no significant activity at the MOP receptor;

have antagonist activity at the NOP receptor as well as agonist activity at the DOP receptor, but no significant activity at the KOP receptor; or have antagonist activity at the NOP receptor as well as agonist activity at the DOP receptor, but no significant activity at the MOP receptor as well as no significant activity at the KOP receptor.

For the purpose of the specification, "no significant activity" means that the activity (agonist/antagonist) of the given compound at this receptor is lower by a factor of 1000 or more compared to its activity (agonist/antagonist) at one or more of the other opioid receptors.

A further aspect of the invention relates to the compounds according to the invention as medicaments.

A further aspect of the invention relates to the compounds according to the invention for use in the treatment of pain. A further aspect of the invention relates to a method of treating pain comprising the administration of a pain alleviating amount of a compound according to the invention to a subject in need thereof, preferably to a human. The pain is preferably acute or chronic. The pain is preferably nociceptive or neuropathic.

A further aspect of the invention relates to the compounds according to the invention for use in the treatment of neurodegenerative disorders, neuroinflammatory disorders, neuropsychiatric disorders, and substance abuse/dependence. A further aspect of the invention relates to a method of treating any one of the aforementioned disorders, diseases or conditions comprising the administration of a therapeutically effective amount of a compound according to the invention to a subject in need thereof, preferably to a human.

Another aspect of the invention relates to a pharmaceutical composition which contains a physiologically acceptable carrier and at least one compound according to the invention.

Preferably, the composition according to the invention is solid, liquid or pasty; and/or contains the compound according to the invention in an amount of from 0.001 to 99 wt. %, preferably from 1.0 to 70 wt. %, based on the total weight of the composition.

The pharmaceutical composition according to the invention can optionally contain suitable additives and/or auxiliary substances and/or optionally further active ingredients.

Examples of suitable physiologically acceptable carriers, additives and/or auxiliary substances are fillers, solvents, diluents, colorings and/or binders. These substances are known to the person skilled in the art (see H. P. Fiedler, Lexikon der Hilfsstoffe fur Pharmazie, Kosmetik and angrenzende Gebiete, Editio Cantor Aulendoff).

The pharmaceutical composition according to the invention contains the compound according to the invention in an amount of preferably from 0.001 to 99 wt. %, more preferably from 0.1 to 90 wt. %, yet more preferably from 0.5 to 80 wt. %, most preferably from 1.0 to 70 wt. % and in particular from 2.5 to 60 wt. %, based on the total weight of the pharmaceutical composition.

The pharmaceutical composition according to the invention is preferably for systemic, topical or local administration, preferably for oral administration.

Another aspect of the invention relates to a pharmaceutical dosage form which contains the pharmaceutical composition according to the invention.

In one preferred embodiment, the pharmaceutical dosage form according to the invention is produced for administration twice daily, for administration once daily or for administration less frequently than once daily. Administration is preferably systemic, in particular oral.

The pharmaceutical dosage form according to the invention can be administered, for example, as a liquid dosage form in the form of injection solutions, drops or juices, or as a semi-solid dosage form in the form of granules, tablets, pellets, patches, capsules, plasters/spray-on plasters or aerosols. The choice of auxiliary substances etc. and the amounts thereof to be used depend on whether the form of administration is to be administered orally, perorally, parenterally, intravenously, intraperitoneally, intradermally, intramuscularly, intranasally, buccally, rectally or locally, for example to the skin, the mucosa or into the eyes.

Pharmaceutical dosage forms in the form of tablets, dragees, capsules, granules, drops, juices and syrups are suitable for oral administration, and solutions, suspensions, readily reconstitutable dry preparations and also sprays are suitable for parenteral, topical and inhalatory administration. Compounds according to the invention in a depot, in dissolved form or in a plaster, optionally with the addition of agents promoting penetration through the skin, are suitable percutaneous administration preparations.

The amount of the compounds according to the invention to be administered to the patient varies in dependence on the weight of the patient, on the type of administration, on the indication and on the severity of the disease. Usually, from 0.00005 mg/kg to 50 mg/kg, preferably from 0.001 mg/kg to 10 mg/kg, of at least one compound according to the invention is administered.

Another aspect of the invention relates to a process for the preparation of the compounds according to the invention. Suitable processes for the synthesis of the compounds according to the invention are known in principle to the person skilled in the art.

Preferred synthesis routes are described below:

The compounds according to the invention can be obtained via different synthesis routes. Depending on the synthesis route, different intermediates are prepared and subsequently further reacted.

In a preferred embodiment, the synthesis of the compounds according to the invention proceeds via a synthesis route which comprises the preparation of an intermediate according to general formula (IIIa):

(IIIa)

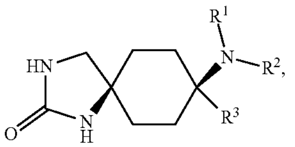

wherein $R^1$, $R^2$ and $R^3$ are defined as above.

In another preferred embodiment, the synthesis of the compounds according to the invention proceeds via a synthesis route which comprises the preparation of an intermediate according to general formula (IIIb):

(IIIb)

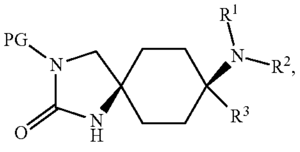

wherein $R^1$, $R^2$ and $R^3$ are defined as above and PG is a protecting group.

Preferably the protecting group is -p-methoxybenzyl. Therefore, in another preferred embodiment, the synthesis of the compounds according to the invention proceeds via a synthesis route which comprises the preparation of an intermediate according to general formula (IIIc):

(IIIc)

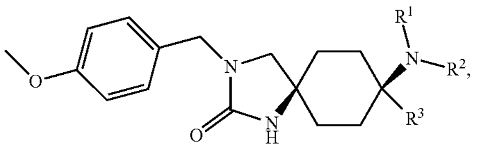

wherein $R^1$, $R^2$ and $R^3$ are defined as above.

As already indicated, in general formula (IIIc), the -p-methoxybenzyl moiety represents a protecting group which can be cleaved in the course of the synthesis route.

In yet another preferred embodiment, the synthesis of the compounds according to the invention proceeds via a synthesis route which comprises the preparation of

- an intermediate according to general formula (IIIa) and according to general formula (IIIb); or
- an intermediate according to general formula (IIIa) and according to general formula (IIIc); or
- an intermediate according to general formula (IIIb) and according to general formula (IIIc); or
- an intermediate according to general formula (IIIa), according to general formula (IIIb) and according to general formula (IIIc).

The following examples further illustrate the invention but are not to be construed as limiting its scope.

EXAMPLES

"RT" means room temperature (23±7° C.), "M" are indications of concentration in mol/l, "aq." means aqueous, "sat." means saturated, "sol." means solution, "conc." means concentrated.

Further abbreviations:

brine saturated aqueous sodium chloride solution
CC column chromatography
cHex cyclohexane
DCM dichloromethane
DIPEA N,N-diisopropylethylamine
DMF N,N-dimethylformamide
Et Ethyl
ether diethyl ether
EE ethyl acetate
EtOAc ethyl acetate
EtOH ethanol
h hour(s)
$H_2O$ water
HATU O-(7-aza-benzotriazol-1-yl)-N,N,N',N'-tetramethyl-uroniumhexafluorophosphate
LDA Lithium-di-isoproyl-amid
Me Methyl
m/z mass-to-charge ratio
MeOH methanol
MeCN acetonitrile
min minutes
MS mass spectrometry
NBS N-bromo-succinimide
$NEt_3$ triethylamine
PE Petrol Ether (60-80° C.)
RM reaction mixture
RT room temperature
T3P 2,4,6-Tripropyl-1,3,5,2,4,6-trioxatriphosphorinane-2,4,6-trioxide
tBME tert-.butyl methyl ether
THF tetrahydrofuran
v/v volume to volume
w/w weight to weight The yields of the compounds prepared were not optimised. All temperatures are uncorrected.

All starting materials, which are not explicitly described, were either commercially available (the details of suppliers such as for example Acros, Aldrich, Bachem, Butt park, Enamine, Fluka, Lancaster, Maybridge, Merck, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington D.C., US, respectively, for example) or can be prepared using the conventional methods known to the person skilled in the art.

The mixing ratios of solvents or eluents for chromatography are specified in v/v.

All the intermediate products and exemplary compounds were analytically characterised by mass spectrometry (MS, m/z for $[M+H]^+$). In addition $^1$H-NMR and $^{13}$C spectroscopy was carried out for all the exemplary compounds and selected intermediate products.

Remark Regarding Stereochemistry

CIS refers to the relative configuration of compounds described herein, in which both nitrogen atoms are drawn on the same face of the cyclohexane ring as described in the following exemplary structure. Two depictions are possible:

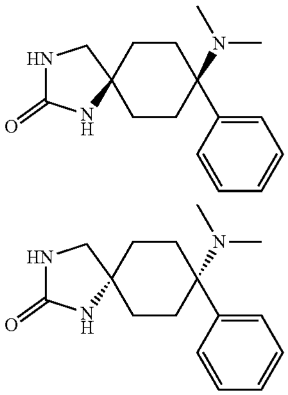

CIS configuration

TRANS refers to compounds, in which both nitrogen atoms are on opposite faces of the cyclohexane ring as described in the following exemplary structure. Two depictions are possible:

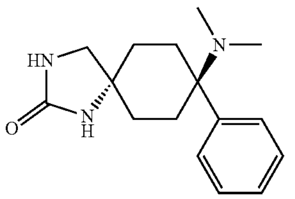

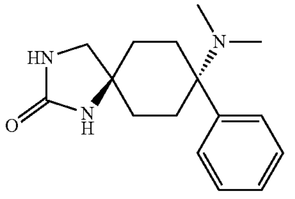

TRANS configuration

Synthesis of Intermediates

Synthesis of INT-795: CIS-8-Dimethylamino-8-phenyl-3-(2-phenyl-ethyl)-1,3-diazaspiro[4.5]decan-2-one

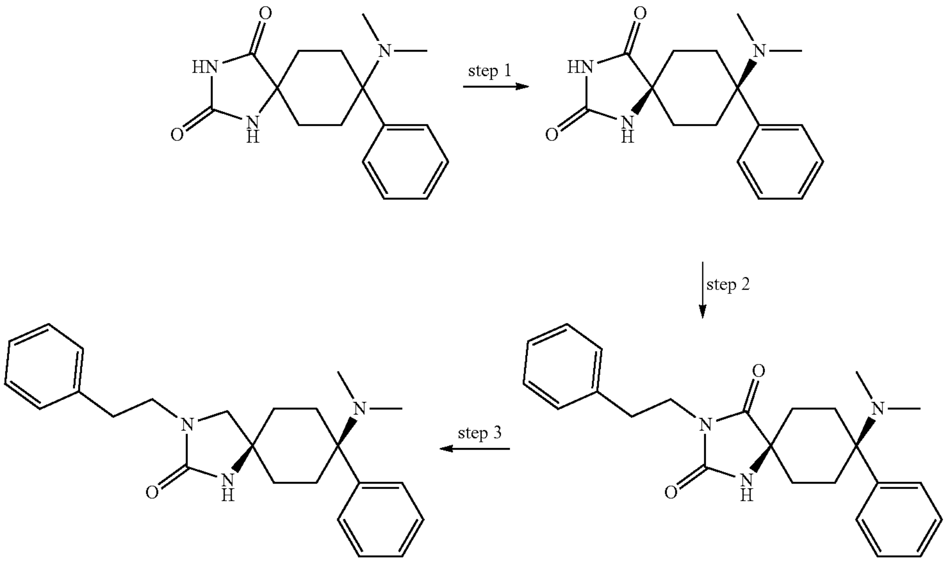

INT-795

Step 1: CIS-8-(dimethylamino)-8-phenyl-1,3-diazaspiro[4,5]decane-2,4-dione

A diastereomeric mixture of 8-(dimethylamino)-8-phenyl-1,3-diazaspiro[4.5]decane-2,4-dione (20 g) (INT-976 step 1) was suspended in methanol (200 mL) and was heated to 80° C. for 1 h. The resulting suspension was filtered hot and the precipitate was washed with methanol (100 mL). Solid obtained was dried under reduced pressure to afford major isomer CIS-8-(dimethylamino)-8-phenyl-1,3-diazaspiro[4,5]decane-2,4-dione (15 g) as an off-white solid. Chiral HPLC purity 98.93%, HPLC purity 98.61%.

Step 2: CIS-8-Dimethylamino-8-phenyl-3-(2-phenyl-ethyl)-1,3-diazaspiro[4.5]decane-2,4-dione $Cs_2CO_3$ (3.9 g, 10.98 mmol) was added to the solution of CIS-8-(dimethylamino)-8-phenyl-1,3-diazaspiro[4,5]decane-2,4-dione (1.5 g, 5.49 mmol) in MeCN (20 mL) under argon atmosphere and the reaction mixture was stirred for 30 min. (2-Bromoethyl)benzene (1.5 g, 8.24 mmol) was added and the reaction mixture was stirred under reflux for 16 h. The reaction completion was monitored by TLC. The reaction mixture was quenched with water (25 mL) and the organic product was extracted with DCM (2×150 mL). The combined organic layer was dried over anhydrous $Na_2SO_4$ and concentrated in vacuo. Purification of the residue by flash column chromatography on silica gel (230-400 mesh) (5-10% methanol in DCM) further by washing with pentane yielded 1.6 g (78%) of CIS-8-dimethylamino-8-phenyl-3-(2-phenyl-ethyl)-1,3-diazaspiro[4.5]decane-2,4-dione as white solid. (TLC system: 10% MeOH in DCM; Rf: 0.4).

Step 3: CIS-8-Dimethylamino-8-phenyl-3-(2-phenyl-ethyl)-1,3-diazaspiro[4.5]decan-2-one Anhydrous $AlCl_3$ (1.27 g, 9.59 mmol) was added to the solution of $LiAlH_4$ (1M in THF) (7.6 mL, 7.67 mmol) in THF at 0° C. under argon atmosphere. The reaction was stirred at RT for 1 h. CIS-8-(Dimethylamino)-3-phenethyl-8-phenyl-1,3-diazaspiro[4.5]decane-2,4-dione (1.5 g, 4.60 mmol) was added to the reaction mixture at 0° C. and stirred at RT for 16 h. The reaction completion was monitored by TLC. The mixture was cooled to 0° C.; quenched with sat. aq. $Na_2SO_4$ (10 mL) and filtered through celite. The filtrate was dried over anhydrous $Na_2SO_4$ and concentrated in vacuo. Purification of the residue by flash column chromatography on silica gel (230-400 mesh) (5-10% methanol in DCM) and further by washing with pentane yielded 1 g (69%) of CIS-8-dimethylamino-8-phenyl-3-(2-phenyl-ethyl)-1,3-diazaspiro[4.5]decan-2-one (INT-795) as a white solid. (TLC system: 10% MeOH in DCM; Rf: 0.3). $[M+H]^+$ 378.

Synthesis of INT-799: CIS-8-Dimethylamino-1-[(1-hydroxy-cyclobutyl)-methyl]-8-phenyl-1,3-diazaspiro[4.5]decan-2-one

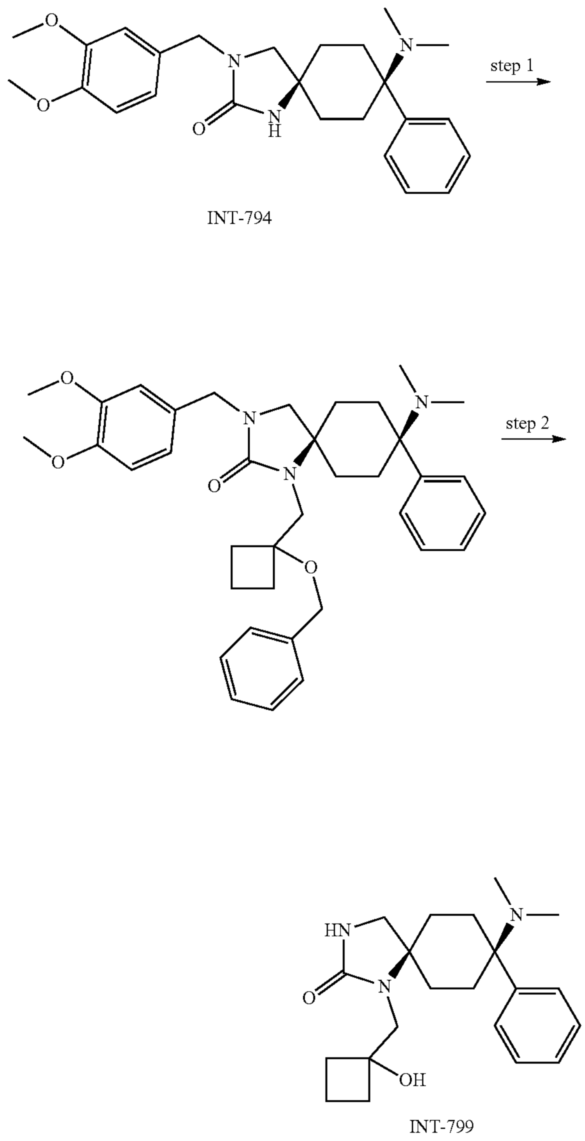

INT-794

INT-799

Step 1: CIS-1-((1-(benzyloxy)cyclobutyl)methyl)-3-(3,4-dimethoxybenzyl)-8-(dimethylamino)-8-phenyl-1,3-diazaspiro[4.5]decan-2-one NaOH (1.42 g, 35.5 mmol) was added to a solution of CIS-3-(3,4-dimethoxybenzyl)-8-(dimethylamino)-8-phenyl-1,3-diazaspiro[4.5]decan-2-one (INT-794) (3 g, 7.09 mmol) in DMSO (90 mL) under argon atmosphere and the reaction mixture was stirred at 80° C. for 30 min. ((1-(Bromomethyl)cyclobutoxy)methyl)benzene (5.4 g, 21.3 mmol) was added and stirring was continued for 2 days at 80° C. The reaction completion was monitored by TLC. The reaction mixture was diluted with water (500 mL) and extracted with diethyl ether (4×300 mL). The combined organic extracts were dried over anhydrous $Na_2SO_4$ and concentrated under reduced pressure. The residue was purified by column chromatography (230-400 mesh silica gel; 65-70% EtOAc in petroleum ether as eluent) to afford 2.5 g (59%) of CIS-1-((1-(benzyloxy)cyclobutyl)methyl)-3-(3,4-dimethoxybenzyl)-8-(dimethylamino)-8-phenyl-1,3-diazaspiro[4.5]decan-2-one (TLC system: 10% MeOH in DCM; Rf: 0.8).

Step 2: CIS-8-Dimethylamino-1-[(1-hydroxy-cyclobutyl)-methyl]-8-phenyl-1,3-diazaspiro[4.5]decan-2-one TFA (12 mL) was added to CIS-1-((1-(benzyloxy)cyclobutyl)methyl)-3-(3,4-dimethoxybenzyl)-8-(dimethylamino)-8-phenyl-1,3-diazaspiro[4.5]decan-2-one (2.5 g, 4.18 mmol) at 0° C. and the resulting mixture was stirred at 70° C. for 6 h. The reaction completion was monitored by LCMS. The reaction mixture was concentrated under reduced pressure. To the residue sat. aq. $NaHCO_3$ was added (until pH 10) and the organic product was extracted with DCM (3×150 mL). The combined organic extracts were dried over anhydrous $Na_2SO_4$ and concentrated under reduced pressure. The residue was purified by column chromatography (230-400 mesh silica gel; 5% MeOH in DCM as eluent) to afford 500 mg (33%) of CIS-8-dimethylamino-1-[(1-hydroxy-cyclobutyl)-methyl]-8-phenyl-1,3-diazaspiro[4.5]decan-2-one (INT-799) (TLC system: 10% MeOH in DCM; Rf: 0.5). $[M+H]^+$ 358.2

Synthesis of INT-951: CIS-1-[(8-Dimethylamino-2-oxo-8-phenyl-1,3-diazaspiro[4.5]decan-1-yl)-methyl]-cyclobutane-1-carbonitrile

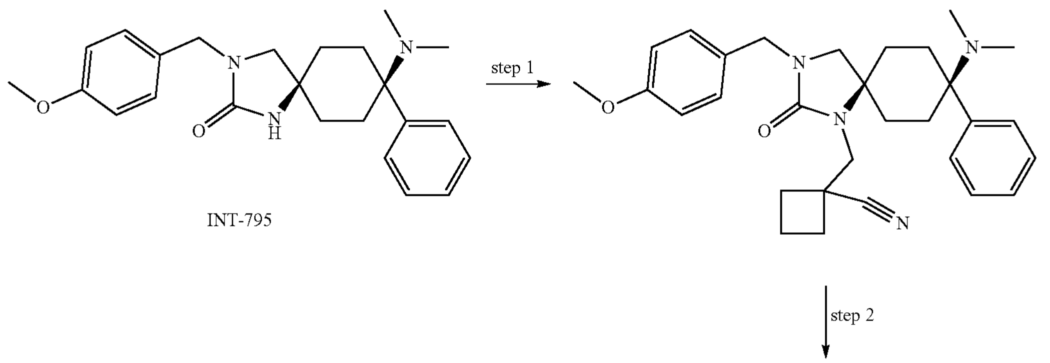

INT-795

-continued

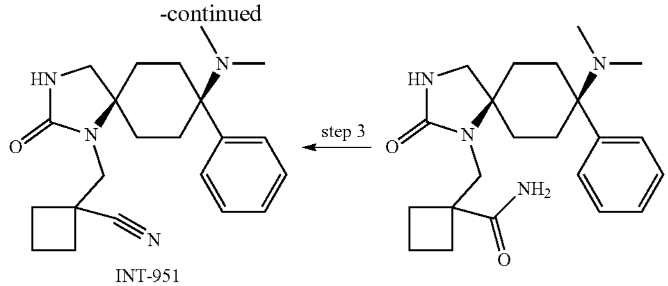

INT-951

Step 1: 1-((CIS-8-(dimethylamino)-3-(4-methoxybenzyl)-2-oxo-8-phenyl-1,3-diazaspiro[4.5]decan-1-yl)methyl)cyclobutanecarbonitrile NaH (50% in mineral oil) (2.44 g, 50.89 mmol) was added to a solution of CIS-8-dimethylamino-3-[(4-methoxyphenyl)-methyl]-8-phenyl-1,3-diazaspiro[4.5]decan-2-one (INT-975) (5 g, 12.72 mmol) in DMF (100 mL) at 0° C. portionwise over 10 min. 1-(Bromomethyl)cyclobutanecarbonitrile (4.4 g, 25.44 mmol) was added dropwise over 10 minutes at 0° C. The reaction mixture was allowed to stir at RT for 3 h, then quenched with water and the organic product was extracted with ethyl acetate (3×200 mL). The combined organic extracts were dried over anhydrous $Na_2SO_4$ and concentrated under reduced pressure to afford 5 g (crude) of 1-((CIS-8-(dimethylamino)-3-(4-methoxybenzyl)-2-oxo-8-phenyl-1,3-diazaspiro[4.5]decan-1-yl)methyl) cyclobutane-carbonitrile as gummy brown liquid. The material was used for the next step without further purification.

Step 2: 1-((CIS-8-(dimethylamino)-2-oxo-8-phenyl-1,3-diazaspiro[4.5]decan-1-yl)methyl)cyclobutanecarboxamide TFA (100 mL) was added to 1-((CIS-8-(dimethylamino)-3-(4-methoxybenzyl)-2-oxo-8-phenyl-1,3-diazaspiro[4.5]decan-1-yl)methyl)cyclobutanecarbonitrile (5 g, 10.28 mmol) at 0° C. and the reaction mixture at mixture was stirred at RT for 2 days. The reaction mixture was concentrated in vacuo. To the residue sat. aq. $NaHCO_3$ was added (until pH 10) and the organic product was extracted with dichloromethane (3×150 mL). The combined organic extracts were dried over anhydrous $Na_2SO_4$ and concentrated under reduced pressure to afford 3.5 g (crude) of 1-((CIS-8-(dimethylamino)-2-oxo-8-phenyl-1,3-diazaspiro[4.5]decan-1-yl)methyl)cyclobutanecarboxamide. The material was used for the next step without further purification.

Step 3: 1-((cis-8-(dimethylamino)-2-oxo-8-phenyl-1,3-diazaspiro[4.5]decan-1-yl)methyl)cyclobutane Carbonitrile Thionyl chloride (35 mL) was added to 1-((cis-8-(dimethylamino)-2-oxo-8-phenyl-1,3-diazaspiro[4.5]decan-1-yl) methyl)cyclobutanecarboxamide (3.5 g, 9.11 mmol) at RT and the resulting mixture was stirred at reflux for 2 h. The reaction mixture was concentrated in vacuo. To the residue sat. aq. $NaHCO_3$ was added (until pH 10) and the organic product was extracted with dichloromethane (3×150 mL). The combined organic layer was dried over anhydrous $Na_2SO_4$ and concentrated in vacuo. The residue was purified by column chromatography to afford 1.3 g (34% after three steps) of CIS-1-[(8-dimethylamino-2-oxo-8-phenyl-1,3-diazaspiro[4.5]decan-1-yl)-methyl]-cyclobutane-1-carbonitrile (INT-951). $[M+H]^+$ 367.2.

Synthesis of INT-953: CIS-1-(Cyclobutyl-methyl)-8-(methyl-(2-methyl-propyl)-amino)-8-phenyl-1,3-diazaspiro[4.5]decan-2-one

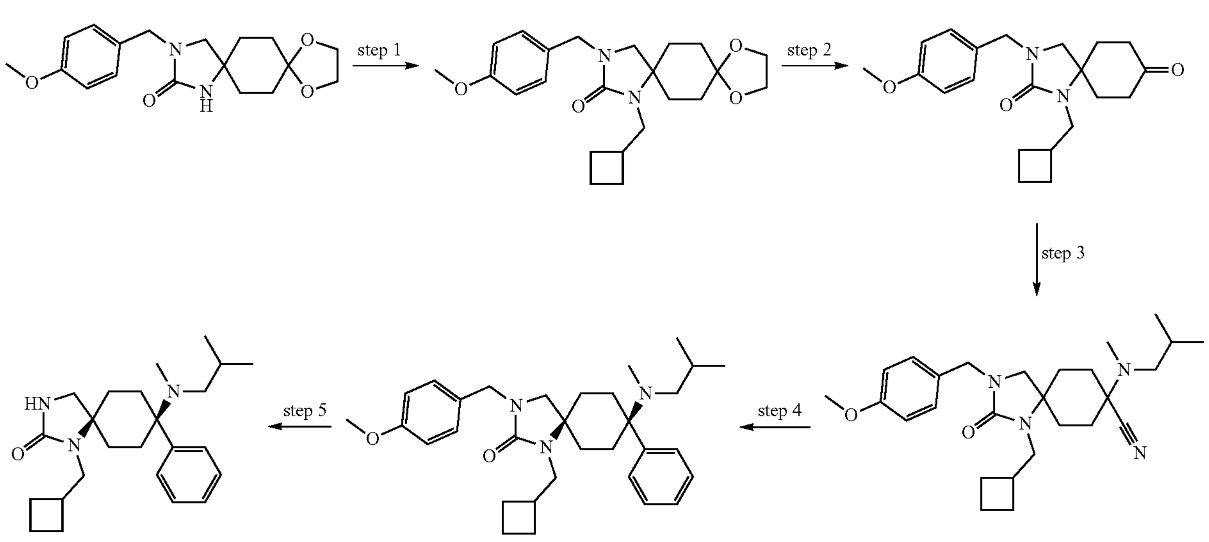

Step 1: 1-Cyclobutylmethyl-3-(4-methoxy-benzyl)-9,12-dioxa-1,3-diazadispiro[4.2.4.2]tetradecan-2-one To a stirred solution of 3-(4-methoxy-benzyl)-9,12-dioxa-1,3-diazadispiro[4.2.4.2]tetradecan-2-one (4 g, 12.04 mmol) in anhydrous DMF (60 ml) was added NaH (1.38 g, 60% dispersion in oil, 36.14 mmol) at RT. The reaction mixture was stirred for 10 min, bromomethylcyclobutane (3 ml, 26.5 mmol) was added dropwise and stirring was continued for 50 h. TLC analysis showed complete consumption of the starting material. The reaction mixture was quenched with sat. aq. $NH_4Cl$ (50 ml) and extracted with EtOAc (3×200 ml). The combined organic phase was dried over $Na_2SO_4$ and concentrated under reduced pressure. The resulting residue was purified column chromatography (neutral aluminum oxide, EtOAc-petroleum ether (2:8)) to give 1-cyclobutylmethyl-3-(4-methoxy-benzyl)-9,12-dioxa-1,3-diazadispiro[4.2.4.2]tetradecan-2-one (2.4 g, 50%, white solid). TLC system: EtOAc—pet ether (6:4); $R_f$=0.48.

Step 2: 1-Cyclobutylmethyl-3-(4-methoxy-benzyl)-1,3-diaza-spiro[4.5]decane-2,8-dione To a stirred solution of 1-cyclobutylmethyl-3-(4-methoxy-benzyl)-9,12-dioxa-1,3-diazadispiro[4.2.4.2]tetradecan-2-one (1 g, 2.5 mmol) in MeOH (7 ml) was added 10% aq. HCl (8 ml) at 0° C. The reaction mixture was warmed up to RT and stirred for 16 h. TLC analysis showed complete consumption of the starting material. The reaction mixture was quenched with sat. aq. $NaHCO_3$ (30 ml) and extracted with EtOAc (3×50 ml). The combined organic phase was dried over $Na_2SO_4$ and concentrated under reduced pressure. The resulting residue was purified by column chromatography (silica gel, 230-400 mesh, EtOAc—pet ether (1:3)→(3:7)) to give 1-cyclobutylmethyl-3-(4-methoxy-benzyl)-1,3-diaza-spiro[4.5]decane-2,8-dione (650 mg, 73%, colorless viscous oil). TLC system: EtOAc—pet ether (6:4); $R_f$=0.40.

Step 3: 1-(cyclobutylmethyl)-8-(isobutyl(methyl)amino)-3-(4-methoxybenzyl)-2-oxo-1,3-diazaspiro[4.5]decane-8-carbonitrile To a stirred solution of N-isobutyl-N-methylamine (1.34 ml, 11.23 mmol) and $MeOH/H_2O$ (8 ml, 1:1, v/v) was added 4N aq. HCl (1.5 ml) and the reaction mixture was stirred for 10 min at 0° C. (ice bath). A solution of 1-cyclobutylmethyl-3-(4-methoxy-benzyl)-1,3-diaza-spiro[4.5]decane-2,8-dione (1 g, 2.80 mmol) in MeOH (7 ml) and KCN (548 mg, 8.42 mmol) were added and the reaction mixture was stirred at 45° C. for 20 h. TLC analysis showed complete consumption of the starting material. The reaction mixture was diluted with water (30 ml), extracted with EtOAc (3×30 ml), the combined organic phase was dried over $Na_2SO_4$ and concentrated under reduced pressure to give 1-(cyclobutylmethyl)-8-(isobutyl(methyl)amino)-3-(4-methoxybenzyl)-2-oxo-1,3-diazaspiro[4.5]decane-8-carbonitrile (1.3 g, viscous yellow oil). TLC system: EtOAc—pet ether (1:1); $R_f$=0.45. The product was used for the next step without additional purification.

Step 4: CIS-1-(cyclobutylmethyl)-8-(isobutyl(methyl)amino)-3-(4-methoxybenzyl)-8-phenyl-1,3-diazaspiro[4.5]decan-2-one A round bottom flask containing 1-(cyclobutylmethyl)-8-(isobutyl(methyl)amino)-3-(4-methoxybenzyl)-2-oxo-1,3-diazaspiro[4.5]decane-8-carbonitrile (1.3 g, 2.81 mmol) was cooled in an ice bath (~0° C.) and a solution of phenylmagnesium bromide (26 ml, -2M in THF) was added slowly at 0° C.-5° C. The ice bath was removed and the reaction mixture was stirred for 30 min, then diluted with sat. aq. $NH_4Cl$ (25 ml) and extracted with EtOAc (4×30 ml). The combined organic phase was dried over $Na_2SO_4$ and concentrated under reduced pressure to give pale yellow viscous oil. This residue was purified by column chromatography (silica gel, 230-400 mesh, eluent: EtOAc—pet ether (15:85)→(2:4)) to give CIS-1-(cyclobutylmethyl)-8-(isobutyl(methyl)amino)-3-(4-methoxybenzyl)-8-phenyl-1,3-diazaspiro[4.5]decan-2-one (135 mg, 10%, white solid). TLC system: EtOAc—pet ether (1:1); $R_f$=0.6

Step 5: CIS-1-(cyclobutyl-methyl)-8-(methyl-(2-methyl-propyl)-amino)-8-phenyl-1,3-diazaspiro[4.5]decan-2-one A round bottom flask containing CIS-1-(cyclobutylmethyl)-8-(isobutyl(methyl)amino)-3-(4-methoxybenzyl)-8-phenyl-1,3-diazaspiro[4.5]decan-2-one (130 mg, 0.25 mmol) was cooled in an ice bath and a mixture of TFA/$CH_2Cl_2$ (2.6 ml, 1:1, v/v) was added slowly at 0° C.-5° C. The reaction mixture was warmed to RT and stirred for 20 h, then quenched with methanolic $NH_3$ (10 ml, ~10% in MeOH) and concentrated under reduced pressure to give pale yellow viscous oil. This residue was purified twice by column chromatography (silica gel, 230-400 mesh, eluent: MeOH—$CHCl_3$ (1:99)→(2:98)) to give CIS-1-(cyclobutylmethyl)-8-(methyl-(2-methyl-propyl)-amino)-8-phenyl-1,3-diazaspiro[4.5]decan-2-one (INT-953) (65 mg, 66%, white solid). TLC system: MeOH—$CHCl_3$ (5:95); $R_f$=0.25; $[M+H]^+$ 384.3

Synthesis of INT-958: 4-oxo-1-pyridin-2-yl-cyclohexane-1-carbonitrile

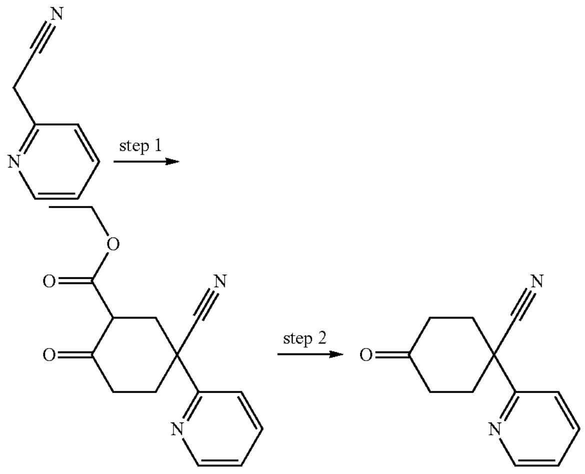

INT-958

Step 1: Ethyl 5-cyano-2-oxo-5-(pyridin-2-yl)cyclohexanecarboxylate

KOtBu (57.0 g, 508.4 mmol) was added to the solution of 2-(pyridin-2-yl)acetonitrile (50.0 g, 423.7 mmol) and ethyl acrylate (89.0 g, 889.8 mmol) in THF (500 mL) at 0° C. and stirred for 16 h at RT. The reaction mixture was quenched with sat. aq. $NH_4Cl$ and extracted with EtOAc (2×500 mL). The combined organic layer was washed with brine, dried over $Na_2SO_4$ and concentrated under reduced pressure to afford 68.0 g (60%; crude) of ethyl 5-cyano-2-oxo-5-(pyridin-2-yl)cyclohexanecarboxylate as a brown liquid (TLC system: 50% ethyl acetate in petroleum ether; $R_f$: 0.65).

Step 2: 4-Oxo-1-pyridin-2-yl-cyclohexane-1-carbonitrile

A solution of ethyl 5-cyano-2-oxo-5-(pyridin-2-yl)cyclohexanecarboxylate (68.0 g, 250.0 mmol) was added to a mixture of conc. aq. HCl and glacial acetic acid (170 mL/510 mL) at 0° C. The reaction mixture was heated to 100° C. for 16 h. All volatiles were evaporated under reduced pressure. The residue was diluted with sat. aq. $NaHCO_3$ and extracted with ethyl acetate (3×300 mL). The combined organic layer was washed with brine, dried over $Na_2SO_4$ and concentrated under reduced pressure to afford 44.0 g (88%) of 4-oxo-1-pyridin-2-yl-cyclohexane-1-carbonitrile INT-958 as a brown solid (TLC system: 50% ethyl acetate in pet ether; Rf: 0.45). $[M+H]^+$ 201.1

Synthesis of INT-961: 4-Dimethylamino-4-pyridin-2-yl-cyclohexan-1-one

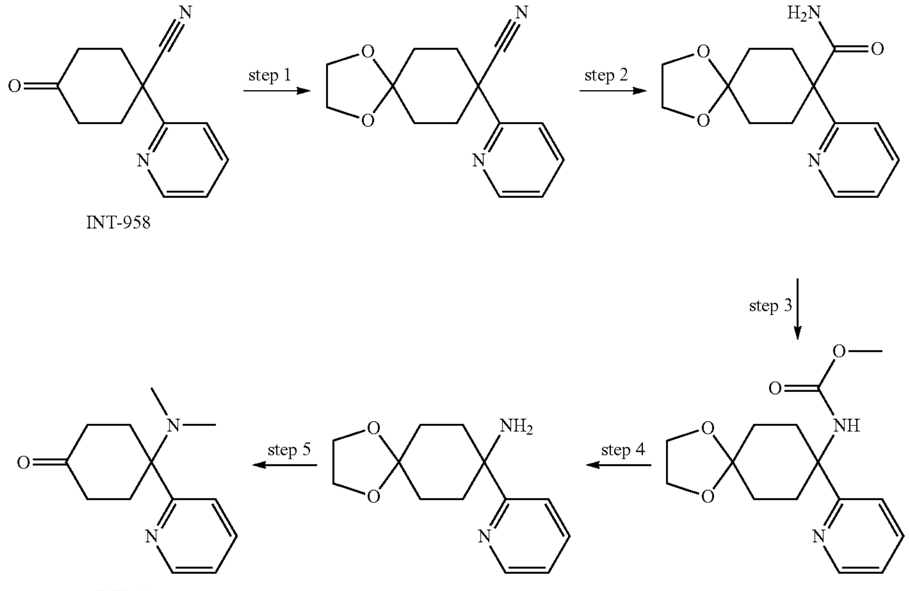

INT-958
INT-961

Step 1: 8-(pyridin-2-yl)-1,4-dioxaspiro[4.5]decane-8-carbonitrile

A solution of 4-oxo-1-pyridin-2-yl-cyclohexane-1-carbonitrile (INT-958) (44.0 g, 220.0 mmol), ethylene glycol (27.0 g, 440.0 mmol) and PTSA (4.2 g, 22.0 mmol) in toluene (450 mL) was heated to 120° C. for 16 h using Dean Stark apparatus. All volatiles were evaporated under reduced pressure. The residue was diluted with sat. aq. $NaHCO_3$ and extracted with ethyl acetate (3×300 mL). The combined organic layer was washed with brine, dried over $Na_2SO_4$ and concentrated under reduced pressure to afford 45.0 g (85%) of 8-(pyridin-2-yl)-1,4-dioxaspiro[4.5]decane-8-carbonitrile as a light brown solid (TLC system: 50% ethyl acetate in petroleum ether; Rf: 0.55).

Step 2: 8-(pyridin-2-yl)-1,4-dioxaspiro[4.5]decane-8-carboxamide

Potassium carbonate (50.0 g, 368.84 mmol) and 30% aq. $H_2O_2$ (210.0 mL, 1844.2 mmol) were added to the solution of 8-(pyridin-2-yl)-1,4-dioxaspiro[4.5]decane-8-carbonitrile (45.0 g, 184.42 mmol) in DMSO (450 mL) at 0° C. and the resulting mixture was stirred at RT for 14 h. The reaction mixture was diluted with water (1.5 L) and stirred for 1 h. The precipitated solid was separated by filtration, washed with water, petroleum ether and dried under reduced pressure to get 32.0 g (66%) of 8-(pyridin-2-yl)-1,4-dioxaspiro[4.5]decane-8-carboxamide as a white solid. (TLC system: 10% MeOH in DCM $R_f$: 0.35).

Step 3: methyl 8-(pyridin-2-yl)-1,4-dioxaspiro[4.5]decan-8-ylcarbamate

A mixture of 8-(pyridin-2-yl)-1,4-dioxaspiro[4.5]decane-8-carboxamide (25.0 g, 95.41 mmol), sodium hypochlorite (5 wt % aq. solution, 700 mL, 477.09 mmol) and $KF-Al_2O_3$ (125.0 g) in methanol (500 mL) was heated to 80° C. for 16 h. The reaction mixture was filtered through celite and the solid residue was washed with methanol. The combined filtrate was concentrated under reduced pressure. The residue was diluted with water and extracted with ethyl acetate (3×500 mL). The combined organic layer was washed with brine, dried over $Na_2SO_4$ and concentrated under reduced pressure to afford 18.0 g (66%) of methyl 8-(pyridin-2-yl)-1,4-dioxaspiro[4.5]decan-8-ylcarbamate as a light brown solid. (TLC system: 5% MeOH in DCM $R_f$: 0.52.)

Step 4: 8-(pyridin-2-yl)-1,4-dioxaspiro[4.5]decan-8-amine

A suspension of methyl 8-(pyridin-2-yl)-1,4-dioxaspiro[4.5]decan-8-ylcarbamate (18.0 g, 61.64 mmol) in 10 wt % aq. NaOH (200 mL) was heated to 100° C. for 24 h. The reaction mixture was filtered through celite pad, the solid residue was washed with water and the combined filtrate was extracted with EtOAc (4×200 mL). The combined organic layer washed with brine, dried over $Na_2SO_4$ and concentrated under reduced pressure to afford 12.5 g (88%) of 8-(pyridin-2-yl)-1,4-dioxaspiro[4.5]decan-8-amine as a light brown semi-solid. (TLC system: 5% MeOH in DCM $R_f$: 0.22.).

Step 5: 4-Dimethylamino-4-pyridin-2-yl-cyclohexan-1-one

Sodium cyanoborohydride (13.7 g, 0.213 mol) was added portionwise to a solution of 8-(pyridin-2-yl)-1,4-dioxaspiro [4.5]decan-8-amine (12.5 g, 53.418 mmol) and 35 wt % aq. formaldehyde (45 mL, 0.534 mol) in acetonitrile (130 mL) at 0° C. The reaction mixture was warmed up to room temperature and stirred for 16 h. The reaction mixture was quenched with sat. aq. $NH_4Cl$ and concentrated under reduced pressure. The residue was dissolved in water and extracted with EtOAc (3×200 mL). The combined organic layer was washed with brine, dried over $Na_2SO_4$ and concentrated under reduced pressure to afford 10.5 g (72%) of 4-dimethylamino-4-pyridin-2-yl-cyclohexan-1-one (INT-961) as a light brown solid. (TLC system: 5% MeOH in DCM $R_f$: 0.32.). $[M+H]^+$ 219.1

Synthesis of INT-965: 4-Dimethylamino-4-phenyl-cyclohexan-1-one

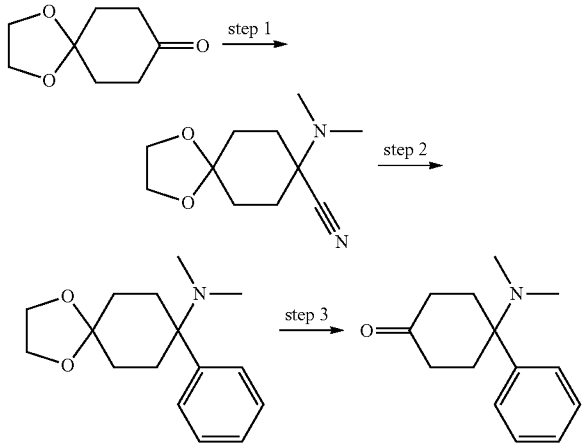

INT-965

Step 1: 8-(Dimethylamino)-1,4-dioxaspiro[4.5]decane-8-carbonitrile

Dimethylamine hydrochloride (52 g, 0.645 mol) was added to the solution of 1,4-dioxaspiro-[4.5]-decan-8-one (35 g, 0.224 mmol) in MeOH (35 mL) at RT under argon atmosphere. The solution was stirred for 10 min and 40 wt % aq. dimethylamine (280 mL, 2.5 mol) and KCN (32 g, 0.492 mol) were sequentially added. The reaction mixture was stirred for 48 h at RT, then diluted with water (100 mL) and extracted with EtOAc (2×200 mL). The combined organic layer was dried over anhydrous $Na_2SO_4$ and concentrated under reduced pressure to afford 44 g of 8-(dimethylamino)-1,4-dioxaspiro-[4.5]-decane-8-carbonitrile (93%) as a white solid.

Step 2: N,N-dimethyl-8-phenyl-1,4-dioxaspiro[4.5] decan-8-amine 8-(Dimethylamino)-1,4-dioxaspiro[4.5]decane-8-carbonitrile (35 g, 0.167 mol) in THF (350 mL) was added to the solution of 3M phenylmagnesium bromide in diethyl ether (556 mL, 1.67 mol) dropwise at ~10° C. under argon atmosphere. The reaction mixture was stirred for 4 h at −10° C. to 0° C. and then at RT for 18 h. The reaction completion was monitored by TLC. The reaction mixture was cooled to 0° C., diluted with sat. aq. $NH_4Cl$ (1 L) and extracted with EtOAc (2×600 mL). The combined organic layer was dried over anhydrous $Na_2SO_4$ and concentrated under reduced pressure to afford 60 g of, N N-dimethyl-8-phenyl-1,4-dioxaspiro-[4.5]-decan-8-amine as a liquid.

Step 3: 4-(dimethylamino)-4-phenylcyclohexanone

A solution of N,N-dimethyl-8-phenyl-1,4-dioxaspiro[4.5] decan-8-amine (32 g, 0.123 mol) in 6N aq. HCl (320 mL) was stirred at 0° C. for 2 h and then at RT for 18 h. The reaction completion was monitored by TLC. The reaction mixture was extracted with DCM (2×150 mL). The aqueous layer was basified to pH 10 with solid NaOH and extracted with ethyl acetate (2×200 mL). The combined organic layer was dried over anhydrous $Na_2SO_4$ and concentrated under reduced pressure. The solid residue was washed with hexane and dried in vacuo to afford 7 g of 4-dimethylamino-4-phenyl-cyclohexan-1-one (INT-965) (25% over 2 steps) as a brown solid. $[M+H]^+$ 218.1

Synthesis of INT-966: 3-[(4-Methoxyphenyl)-methyl]-1,3-diazaspiro[4.5]decane-2,8-dione

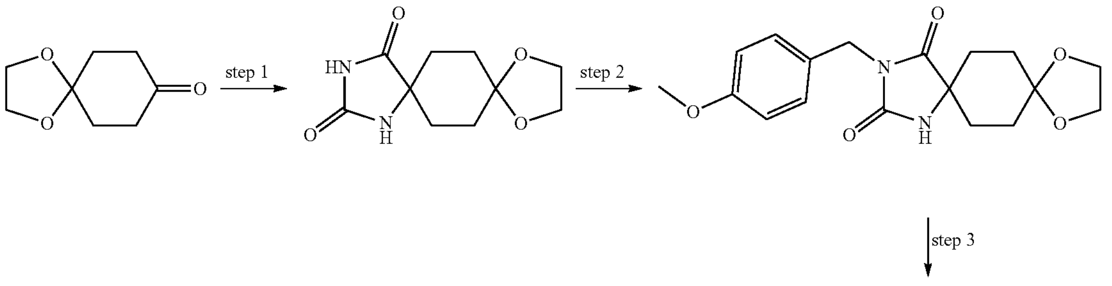

-continued

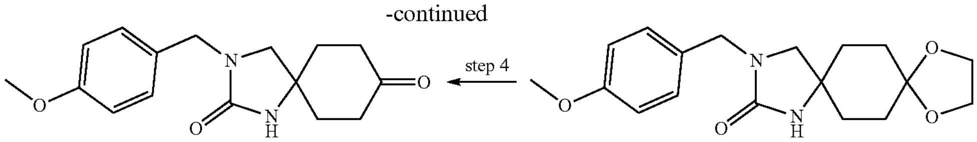

INT-966

Step 1: 9,12-Dioxa-2,4-diazadispiro[4.2.4^{8}.2^{5}]tetradecane-1,3-dione

KCN (93.8 g, 1441.6 mmol) and $(NH_4)_2CO_3$ (271.8 g, 1729.9 mmol) were added to the solution of 1,4-dioxaspiro[4.5]decan-8-one (150 g, 961 mmol) in MeOH:$H_2O$ (1:1 v/v) (1.92 L) at RT under argon atmosphere. The reaction mixture was stirred at 60° C. for 16 h. The reaction completion was monitored by TLC. The reaction mixture was cooled to 0° C., the precipitated solid was filtered off and dried in vacuo to afford 120 g (55%) of 9,12-dioxa-2,4-diazadispiro[4.2.4^{8}.2^{5}]tetradecane-1,3-dione. The filtrate was extracted with DCM (2×1.5 L). The combined organic layer was dried over anhydrous $Na_2SO_4$ and concentrated under reduced pressure to afford additional 30 g (14%) of 9,12-dioxa-2,4-diazadispiro[4.2.4^{8}.2^{5}]tetradecane-1,3-dione (TLC system: 10% Methanol in DCM; $R_f$: 0.4).

Step 2: 2-[(4-Methoxyphenyl)-methyl]-9,12-dioxa-2,4-diazadispiro[4.2.4^{8}.2^{5}]tetradecane-1,3-dione $Cs_2CO_3$ (258.7 g, 796.1 mmol) was added to the solution of 73a (150 g, 663.4 mmol) in MeCN (1.5 L) under argon atmosphere and the reaction mixture was stirred for 30 min. A solution of p-methoxybenzyl bromide (96 mL, 663.4 mmol) was added. The reaction mixture was stirred at RT for 48 h. The reaction completion was monitored by TLC. The reaction mixture was quenched with sat. aq. $NH_4Cl$ (1.0 L) and the organic product was extracted with EtOAc (2×1.5 L). The combined organic layer was dried over anhydrous $Na_2SO_4$ and concentrated under reduced pressure. The residue was washed with diethyl ether and pentane and dried under reduced pressure to afford 151 g (65%) of 2-[(4-Methoxyphenyl)-methyl]-9,12-dioxa-2,4-diazadispiro[4.2.4^{8}.2^{5}]tetradecane-1,3-dione as an off white solid (TLC system: 10% MeOH in DCM; $R_f$: 0.6).

Step 3: 2-[(4-Methoxyphenyl)-methyl]-9,12-dioxa-2,4-diazadispiro[4.2.4^{8}.2^{5}]tetradecan-3-one $AlCl_3$ (144.3 g, 1082.6 mmol) was added to a solution of $LiAlH_4$ (2M in THF) (433 mL, 866.10 mmol) in THF (4.5 L) at 0° C. under argon atmosphere and the resulting mixture was stirred at RT for 1 h. 2-[(4-Methoxyphenyl)-methyl]-9,12-dioxa-2,4-diazadispiro[4.2.4^{8}.2^{5}]tetradecane-1,3-dione (150 g, 433.05 mmol) was added at 0° C. The reaction mixture was stirred at RT for 16 h. The reaction completion was monitored by TLC. The reaction mixture was cooled to 0° C., quenched with sat. aq. $NaHCO_3$ (500 mL) and filtered through celite pad. The filtrate was extracted with EtOAc (2×2.0 L). The combined organic layer was dried over anhydrous $Na_2SO_4$ and concentrated in vacuo to afford 120 g (84%) of 2-[(4-methoxyphenyl)-methyl]-9,12-dioxa-2,4-diazadispiro[4.2.4^{8}.2^{5}]tetradecan-3-one as an off-white solid. (TLC system: 10% MeOH in DCM, $R_f$: 0.5).

Step 4: 3-[(4-Methoxyphenyl)-methyl]-1,3-diazaspiro[4.5]decane-2,8-dione

A solution of 2-[(4-methoxyphenyl)-methyl]-9,12-dioxa-2,4-diazadispiro[4.2.4^{8}.2^{5}]tetradecan-3-one (120 g, 361.03 mmol) in 6N aq. HCl (2.4 L) was stirred at 0° C. for 2 h and then at RT for 18 h. The reaction completion was monitored by TLC. The reaction mixture was extracted with DCM (2×2.0 L). The aqueous layer was basified to pH 10 with 50% aq. NaOH and then extracted with DCM (2×2.0 L). Combined organic extracts were dried over anhydrous $Na_2SO_4$ and concentrated under reduced pressure. The solid residue was washed with hexane and dried in vacuo to afford 90 g of 3-[(4-Methoxyphenyl)-methyl]-1,3-diazaspiro[4.5]decane-2,8-dione (INT-966) as an off-white solid (TLC system: 10% MeOH in DCM; $R_f$: 0.4) $[M+H]^+$ 289.11.

Synthesis of INT-975: CIS-8-Dimethylamino-3-[(4-methoxyphenyl)-methyl]-8-phenyl-1,3-diazaspiro[4.5]decan-2-one

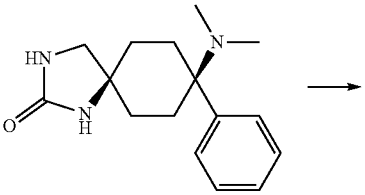

INT-976

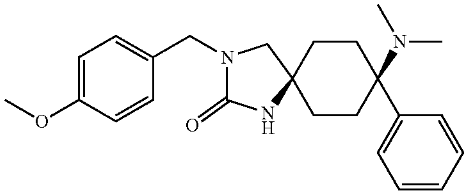

INT-975

KOtBu (1M in THF) (29.30 mL, 29.30 mmol) was added to the solution of CIS-8-Dimethylamino-8-phenyl-1,3-diazaspiro[4.5]decan-2-one INT-976 (8.0 g, 29.30 mmol) in THF (160 mL) under argon atmosphere and the reaction mixture was stirred for 30 min. 4-Methoxybenzyl bromide (4.23 mL, 29.30 mmol) was added and stirring was continued at RT for 4 h. The reaction completion was monitored by TLC. The reaction mixture was diluted with sat. aq. $NH_4Cl$ (150 mL) and the organic product was extracted with EtOAc (2×150 mL). The combined organic layer was dried over anhydrous $Na_2SO_4$ and concentrated in vacuo. The reaction was carried out in 2 batches (8 g×2) and the batches were combined for purification. Purification of the crude product by flash column chromatography on silica gel (0-10% methanol in DCM) and subsequently by washing with pentane yielded 11 g (47%) of CIS-8-Dimethylamino-3-[(4-methoxyphenyl)- methyl]-8-phenyl-1,3-diazaspiro[4.5]decan-2-one (INT-975) as a white solid. $[M+H]^+$ 394.2

Synthesis of INT-976: CIS-8-Dimethylamino-8-phenyl-1,3-diazaspiro[4.5]decan-2-one

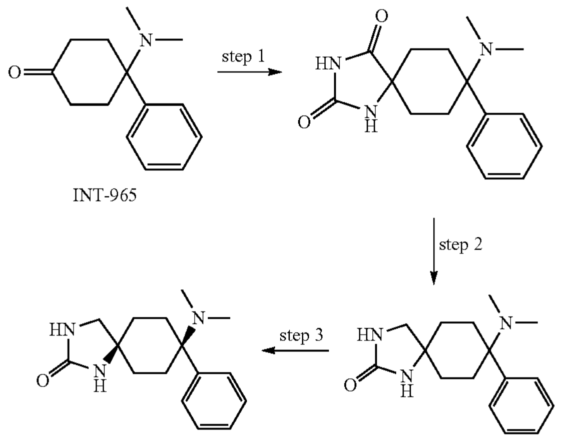

INT-965

INT-976

Step 1: 8-(dimethylamino)-8-phenyl-1,3-diazaspiro[4,5]decane-2,4-dione

In a sealed tube 4-dimethylamino-4-phenyl-cyclohexan-1-one (INT-965) (2 g, 9.22 mmol) was suspended in 40 mL $EtOH/H_2O$ (1:1 v/v) at RT under argon atmosphere. $(NH_4)_2CO_3$ (3.62 g, 23.04 mmol) and KCN (0.6 g, 9.22 mmol) were added. The reaction mixture was stirred at 60° C. for 18 h. The reaction mixture was cooled to 0° C. and diluted with ice-water and filtered through a glass filter. The solid residue was dried under reduced pressure to afford 8-(dimethylamino)-8-phenyl-1,3-diazaspiro[4,5]decane-2,4-dione (1.8 g, 86%) as an off white crystalline solid (TLC: 80% EtOAc in hexane; $R_f$: 0.25).

Step 2: 8-(dimethylamino)-8-phenyl-1,3-diazaspiro[4,5]decan-2-one $LiAlH_4$ (2M in THF) (70 mL, 139.4 mmol) was added to the solution of 8-(dimethylamino)-8-phenyl-1,3-diazaspiro[4,5]decane-2,4-dione (10 g, 34.8 mmol) in $THF/Et_2O$ (2:1 v/v) (400 mL) at 0° C. under argon atmosphere. The reaction mixture was stirred for 4 h at 60° C. The reaction completion was monitored by TLC. The reaction mixture was cooled to 0° C., quenched with saturated $Na_2SO_4$ solution (100 mL) and filtered through Celite pad. The filtrate was dried over anhydrous $Na_2SO_4$ and concentrated in vacuo to afford 5.7 g (59%) of 8-(dimethylamino)-8-phenyl-1,3-diazaspiro[4,5]decan-2-one as an off white solid. (TLC system: 10% MeOH in DCM, $R_f$: 0.3).

Step 3: CIS-8-Dimethylamino-8-phenyl-1,3-diazaspiro[4.5]decan-2-one

A mixture of CIS- and TRANS-8-(dimethylamino)-8-phenyl-1,3-diazaspiro[4,5]decan-2-one (8 g, 29.30 mmol) was purified by preparative chiral SFC (column: Chiralcel AS-H, 60% $CO_2$, 40% (0,5% DEA in MeOH)) to get 5 g of CIS-8-dimethylamino-8-phenyl-1,3-diazaspiro[4.5]decan-2-one (INT-976) as a white solid. $[M+H]^+$ 274.2.

Synthesis of INT-977: CIS-2-(8-Dimethylamino-2-oxo-8-phenyl-1,3-diazaspiro[4.5]decan-1-yl)-acetic Acid; 2,2,2-trifluoro-acetic Acid Salt

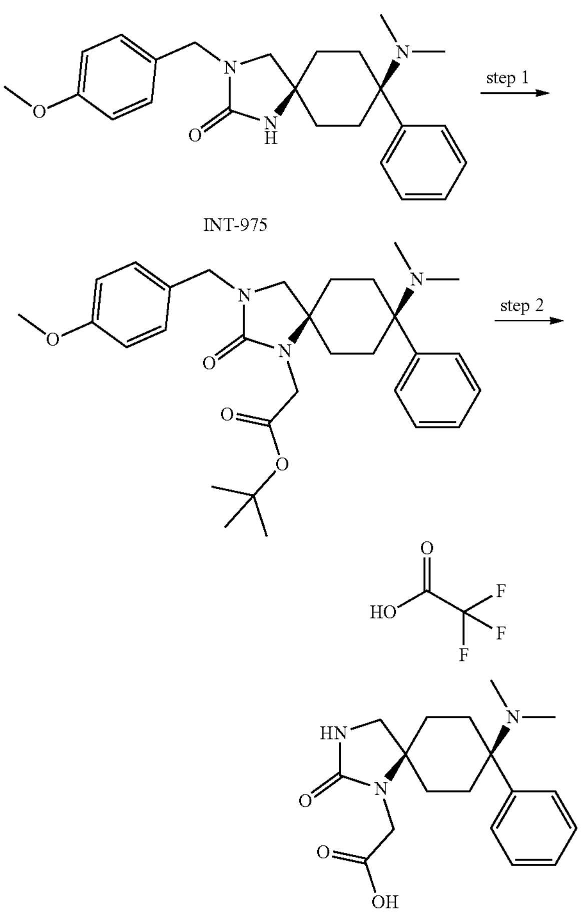

INT-975

INT-977

Step 1: CIS-2-[8-Dimethylamino-3-[(4-methoxyphenyl)-methyl]-2-oxo-8-phenyl-1,3-diazaspiro[4.5]decan-1-yl]-acetic Acid Tert-Butyl Ester A solution of CIS-8-Dimethylamino-3-[(4-methoxyphenyl)-methyl]-8-phenyl-1,3-diazaspiro[4.5]decan-2-one (INT-975) (5.0 g, 12.7 mmol) in THF (18 mL) was cooled to 0° C. and treated with LDA solution (2M in THF/heptane/ether, 25.4 mL, 50.8 mmol). The resulting mixture was allowed to warm up to RT over 30 min. The solution was then cooled to 0° C. again and tert-butyl-bromoacetate (5.63 mL, 38.1 mmol) was added. The reaction mixture was stirred at RT for 16 h, quenched with water and extracted with DCM (3x). The combined organic layers were dried over $Na_2SO_4$, filtered and concentrated under reduced pressure. Purification of the residue by column chromatography on silica gel provided CIS-2-[8-dimethylamino-3-[(4-methoxyphenyl)-methyl]-2-oxo-8-phenyl-1,3-diazaspiro[4.5]decan-1-yl]-acetic acid tert-butyl ester (4.4 g).

Step 2: cis-2-(8-Dimethylamino-2-oxo-8-phenyl-1,3-diazaspiro[4.5]decan-1-yl)-acetic Acid Trifluoroacetic Acid Salt CIS-2-[8-Dimethylamino-3-[(4-methoxyphenyl)-methyl]-2-oxo-8-phenyl-1,3-diazaspiro[4.5]decan-1-yl]-acetic acid tert-butyl ester (200 mg, 0.4 mmol) was dissolved in TFA (5 mL) and heated to reflux overnight. After cooling to RT all volatiles are removed in vacuo. The residue was taken up in THF (1 mL) and added dropwise to diethyl ether (20 mL). The resulting precipitate was filtered off and dried under reduced pressure to give CIS-2-(8-dimethylamino-2-oxo-8-phenyl-1,3-diazaspiro[4.5]decan-1-yl)-acetic acid; 2,2,2-trifluoro-acetic acid salt (INT-977) (119 mg) as a white solid. $[M+H]^+$ 332.2

Synthesis of INT-978: CIS-2-(8-Dimethylamino-2-oxo-8-phenyl-1,3-diazaspiro[4.5]decan-1-yl)-N,N-dimethyl-acetamide

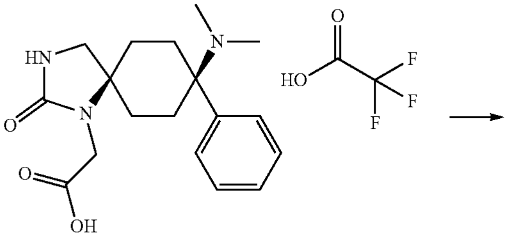

INT-977

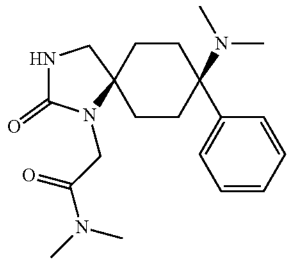

INT-978

CIS-2-(8-Dimethylamino-2-oxo-8-phenyl-1,3-diazaspiro[4.5]decan-1-yl)-acetic acid (INT-977)trifluoroacetic acid salt (119 mg, 0.35 mmol) was dissolved in DCM (5 mL). Triethylamine (0.21 mL, 1.6 mmol), dimethylamine (0.54 mL, 1.1 mmol) and T3P (0.63 mL, 1.1 mmol) were sequentially added. The reaction mixture was stirred at RT overnight, then diluted with 1 M aq. $Na_2CO_3$ (5 mL). The aqueous layer was extracted with DCM (3x5 mL), the combined organic layers were dried over $Na_2SO_4$ and concentrated under reduced pressure. The residue was purified by flash chromatography on silica gel to yield CIS-2-(8-dimethylamino-2-oxo-8-phenyl-1,3-diazaspiro[4.5]decan-1-yl)-N,N-dimethyl-acetamide (INT-978) (39 mg) as a white solid. $[M+H]^+$ 359.2

Synthesis of INT-982: CIS-8-Dimethylamino-1-[(1-methyl-cyclobutyl)-methyl]-8-phenyl-1,3-diazaspiro[4.5]decan-2-one

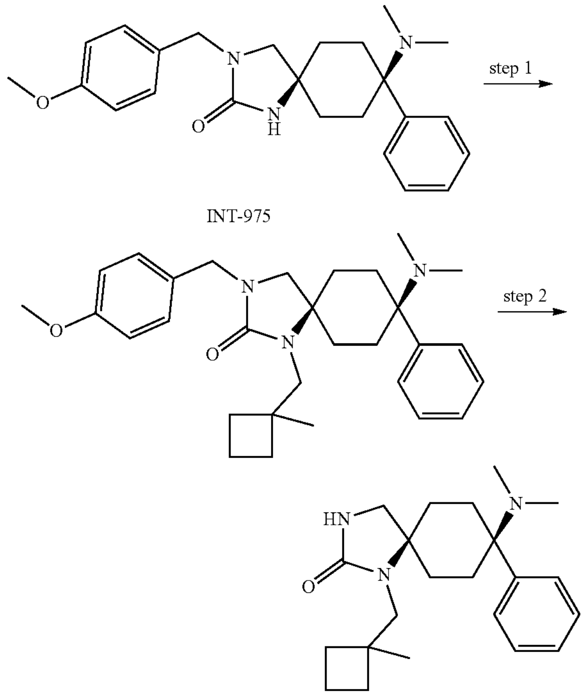

INT-982

Step 1: CIS-8-(dimethylamino)-3-(4-methoxybenzyl)-1-((1-methylcyclobutyl)methyl)-8-phenyl-1,3-diazaspiro[4.5]decan-2-one A solution of NaOH (2.85 g, 71.2 mmol) in DMSO (25 mL) was stirred at RT for 10 min. CIS-8-Dimethylamino-3-[(4-methoxyphenyl)-methyl]-8-phenyl-1,3-diazaspiro[4.5]decan-2-one (INT-975) (7.00 g, 17.8 mmol) was added and stirring was continued for 15 min. 1-(Bromo-methyl)-1-methyl-cyclobutane (8.7 g, 53.4 mmol) was added at 0° C. The reaction mixture was heated to 60° C. for 16 h. After cooling down to RT, water (100 mL) was added and the mixture was extracted with DCM (3x150 mL). The combined organic layers were washed with water (70 mL), brine (100 mL), dried over $Na_2SO_4$ and concentrated under reduced pressure. Purification of the residue by column chromatography on silica gel provided CIS-8-(dimethylamino)-3-(4-methoxybenzyl)-1-((1-methylcyclobutyl)methyl)-8-phenyl-1,3-diazaspiro[4.5]decan-2-one (6.5 g) as a light yellow solid.

Step 2: CIS-8-Dimethylamino-1-[(1-methyl-cyclobutyl)-methyl]-8-phenyl-1,3-diazaspiro[4.5]decan-2-one To the solution of CIS-8-Dimethylamino-1-[(1-methyl-cyclobutyl)-methyl]-8-phenyl-1,3-diazaspiro[4.5]decan-2-one (6.66 g, 14.0 mmol) in DCM (65 mL) was added TFA (65 mL) and the resulting mixture was stirred at RT for 16 h. The reaction mixture was concentrated under reduced pressure. The residue was taken up in DCM (100 mL) and water (60 mL) and basified with 2M aq. NaOH to pH 10. The organic layer was separated and washed with brine (40 mL), dried over $MgSO_4$, filtered and concentrated under reduced pressure. Crystallization of the residue from EtOAc provided CIS-8-Dimethylamino-1-[(1-methyl-cyclobutyl)-methyl]-8-phenyl-1,3-diazaspiro[4.5]decan-2-one (INT-982) (3.41 g) as an off-white solid. $[M+H]^+$ 356.3

Synthesis of INT-984: CIS-1-(Cyclobutyl-methyl)-8-(ethyl-methyl-amino)-8-phenyl-1,3-diazaspiro[4.5]decan-2-one

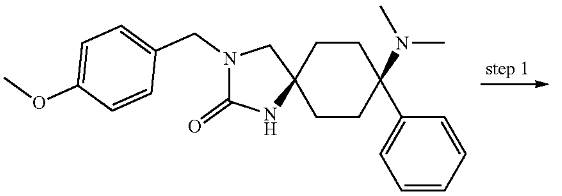

INT-975

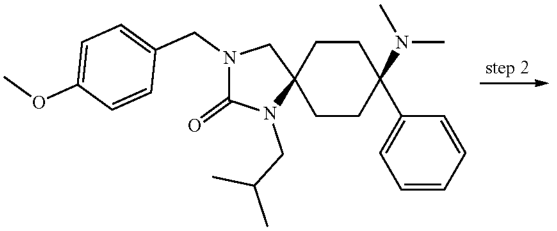

-continued

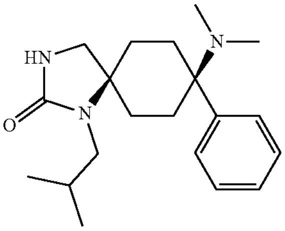

INT-984

Step 1: CIS-8-(dimethylamino)-1-isobutyl-3-(4-methoxybenzyl)-8-phenyl-1,3-diazaspiro[4.5]decan-2-one In analogy to the method described for INT-951 step 1 CIS-8-Dimethylamino-3-[(4-methoxyphenyl)-methyl]-8-phenyl-1,3-diazaspiro[4.5]decan-2-one (INT-975) was converted into CIS-8-(dimethylamino)-1-isobutyl-3-(4-methoxybenzyl)-8-phenyl-1,3-diazaspiro[4.5]decan-2-one.

Step 2: CIS-1-(Cyclobutyl-methyl)-8-(ethyl-methyl-amino)-8-phenyl-1,3-diazaspiro[4.5]decan-2-one In analogy to the method described for INT-982 step 2 CIS-8-(dimethylamino)-1-isobutyl-3-(4-methoxybenzyl)-8-phenyl-1,3-diazaspiro[4.5]decan-2-one was converted into CIS-1-(Cyclobutyl-methyl)-8-(ethyl-methyl-amino)-8-phenyl-1,3-diazaspiro[4.5]decan-2-one (INT-984).

Synthesis of INT-986: CIS-1-(Cyclobutyl-methyl)-8-(ethyl-methyl-amino)-8-phenyl-1,3-diazaspiro[4.5]decan-2-one

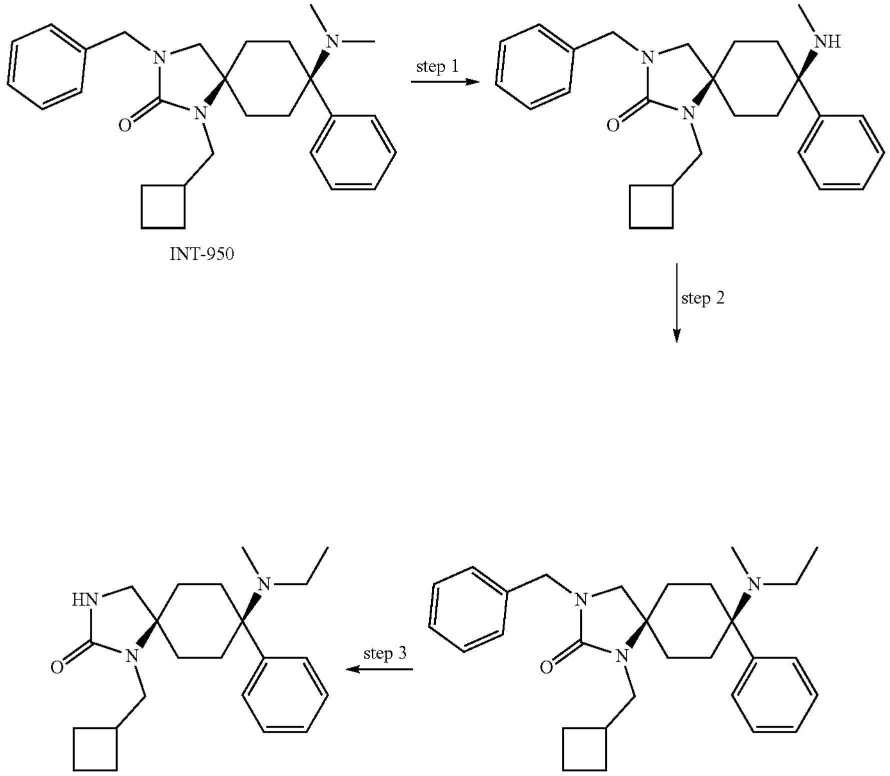

INT-950

INT-986

Step 1: CIS-3-benzyl-1-(cyclobutylmethyl)-8-(methylamino)-8-phenyl-1,3-diazaspiro[4.5]decan-2-one N-Iodosuccinimide (3.11 g, 13.92 mmol) was added to the solution of CIS-1-(Cyclobutyl-methyl)-8-dimethylamino-8-phenyl-3-[phenyl-methyl]-1,3-diazaspiro[4.5]decan-2-one (INT-950) (4 g, 9.28 mmol) in a mixture of acetonitrile and THF (1:1 v/v, 80 mL) and the resulting mixture was stirred at RT for 16 h. The reaction mixture was basified with 2N aq. NaOH to pH-10 and the organic product was extracted with DCM (3×10 mL). The combined organic extracts were dried over anhydrous $Na_2SO_4$ and concentrated in vacuo. The residue was stirred vigorously with a mixture of 10 wt % aq. citric acid (5 mL) and DCM (10 mL) at RT for 10 min. The reaction mixture was basified with 5N aq. NaOH to pH-10 and extracted with DCM (3×10 mL). The combined organic layer was dried over anhydrous $Na_2SO_4$ and concentrated in vacuo to give 3.5 g (crude) of CIS-3-benzyl-1-(cyclobutylmethyl)-8-(methylamino)-8-phenyl-1,3-diazaspiro[4.5]decan-2-one as semi solid (TLC system: 10% MeOH in DCM; $R_f$: 0.60.).

Step 2: CIS-3-benzyl-1-(cyclobutylmethyl)-8-(ethyl(methyl)amino)-8-phenyl-1,3-diazaspiro[4.5]decan-2-one Sodium cyanoborohydride (1.56 g, 25.17 mmol, 3 equiv.) was added to the solution of CIS-3-benzyl-1-(cyclobutylmethyl)-8-(methylamino)-8-phenyl-1,3-diazaspiro[4.5]decan-2-one (3.5 g, 8.39 mmol), acetaldehyde (738 mg, 16.78 mmol, 2 equiv.) and acetic acid (0.5 mL) in methanol (20 mL). The reaction mixture was stirred at RT for 3 h, then quenched with sat. aq. $NaHCO_3$ and the organic product was extracted with DCM (3×50 mL). The combined organic extracts were dried over anhydrous $Na_2SO_4$ and concentrated in vacuo. Purification of the residue by flash column chromatography on silica gel (230-400 mesh) (20-25% ethyl acetate in petroleum ether) yielded 2.3 g (62%) of CIS-3-benzyl-1-(cyclobutylmethyl)-8-(ethyl(methyl)amino)-8-phenyl-1,3-diazaspiro[4.5]decan-2-one as a solid. (TLC system: 50% EtOAc in Pet. Ether; $R_f$: 0.65).

Step 3: CIS-1-(Cyclobutyl-methyl)-8-(ethyl-methyl-amino)-8-phenyl-1,3-diazaspiro[4.5]decan-2-one (INT-986)

Sodium metal (1.18 g, 51.68 mmol, 10 equiv.) was added to liquid ammonia (~25 mL) at −78° C. The resulting mixture was stirred for 10 min at −78° C. A solution of CIS-3-benzyl-1-(cyclobutylmethyl)-8-(ethyl(methyl)amino)-8-phenyl-1,3-diazaspiro[4.5]decan-2-one (2.3 g, 5.16 mmol) in THF (25 mL) was added at −78° C. The reaction mixture was stirred for 15 min, then quenched with sat. aq. $NH_4Cl$, warmed to RT and stirred for 1 h. The organic product was extracted with DCM (3×50 mL). The combined organic layer was washed with water, brine and concentrated under reduced pressure to afford 1.30 g (72%) of CIS-1-(cyclobutylmethyl)-8-(ethyl(methyl)amino)-8-phenyl-1,3-diazaspiro[4.5]decan-2-one (INT-986) as an off-white solid. (TLC system: 10% MeOH in DCM $R_f$: 0.15.). $[M+H]^+$ 356.3

Synthesis of INT-987: CIS-1-(Cyclobutyl-methyl)-8-dimethylamino-8-phenyl-1,3-diazaspiro[4.5]decan-2-one

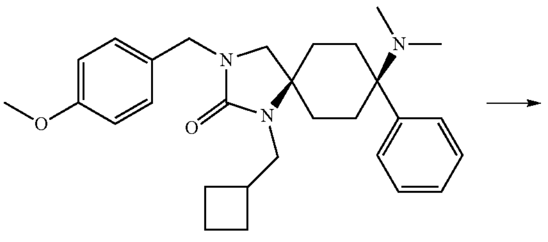

INT-952

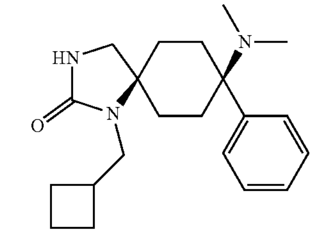

INT-987

In analogy to the method as described for INT-982 step 2 CIS-1-(Cyclobutyl-methyl)-8-dimethylamino-8-phenyl-3-[(4-methoxyphenyl)-methyl]-1,3-diazaspiro[4.5]decan-2-one (INT-952) was converted into CIS-1-(Cyclobutyl-methyl)-8-dimethylamino-8-phenyl-1,3-diazaspiro[4.5]decan-2-one (INT-987).

Synthesis of INT-988: CIS-8-(dimethylamino)-1-(2-(1-methoxycyclobutyl)ethyl)-8-phenyl-1,3-diazaspiro[4.5]decan-2-one

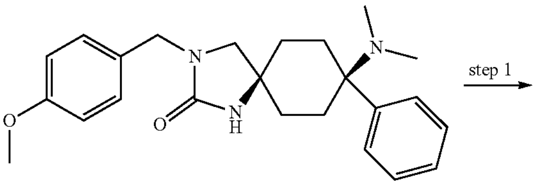

INT-975

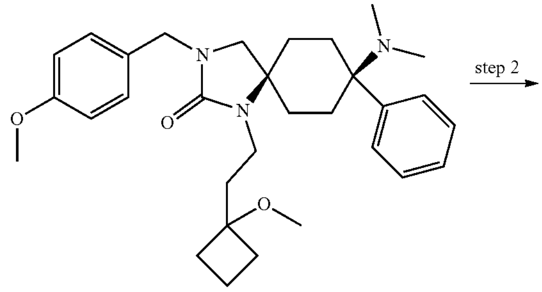

-continued

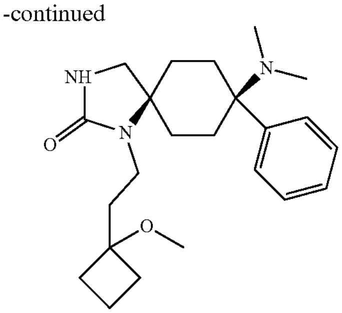

INT-988

Step 1: CIS-8-(dimethylamino)-1-[2-(1-methoxycyclobutyl)ethyl]-3-[(4-methoxyphenyl)methyl]-8-phenyl-1,3-diazaspiro[4.5]decan-2-one Sodium hydroxide (78.06 mg, 4.0 equiv.) was suspended in DMSO (3.5 mL), stirred for 10 minutes, 8-(dimethylamino)-3-[(4-methoxyphenyl)methyl]-8-phenyl-1,3-diazaspiro[4.5]decan-2-one (INT-975) (192.0 mg, 1.0 equiv.) was added, the reaction mixture was stirred for 5 min followed by addition of 2-(1-methoxycyclobutyl)ethyl 4-methylbenzenesulfonate (416.2 mg, 3.0 equiv.) in DMSO (1.5 mL). The resulting mixture was stirred overnight at 50° C. The reaction mixture was quenched with water and extracted with DCM (3×20 mL). The combined organic phases were washed with brine, dried over $Na_2SO_4$ and concentrated under reduced pressure. The residue (283 mg yellow oil) was purified by column chromatography on silica gel (eluent DCM/EtOH 98/2 to 96/4) to give 8-(dimethylamino)-1-[2-(1-methoxycyclobutyl)ethyl]-3-[(4-methoxyphenyl)methyl]-8-phenyl-1,3-diazaspiro[4.5]decan-2-one 163 mg (66%).

Step 2: CIS-8-(dimethylamino)-1-(2-(1-methoxycyclobutyl)ethyl)-8-phenyl-1,3-diazaspiro[4.5]decan-2-one (INT-988)

In analogy to the method described for INT-982 step 2 CIS-8-(dimethylamino)-1-[2-(1-methoxycyclobutyl)ethyl]-3-[(4-methoxyphenyl)methyl]-8-phenyl-1,3-diazaspiro[4.5]decan-2-one was converted into CIS-8-(dimethylamino)-1-(2-(1-methoxycyclobutyl)ethyl)-8-phenyl-1,3-diazaspiro[4.5]decan-2-one (INT-988). Mass: m/z 386.3 $(M+H)^+$.

Synthesis of INT-1008: CIS-8-ethylamino-8-phenyl-1,3-diaza-spiro[4.5]decan-2-one

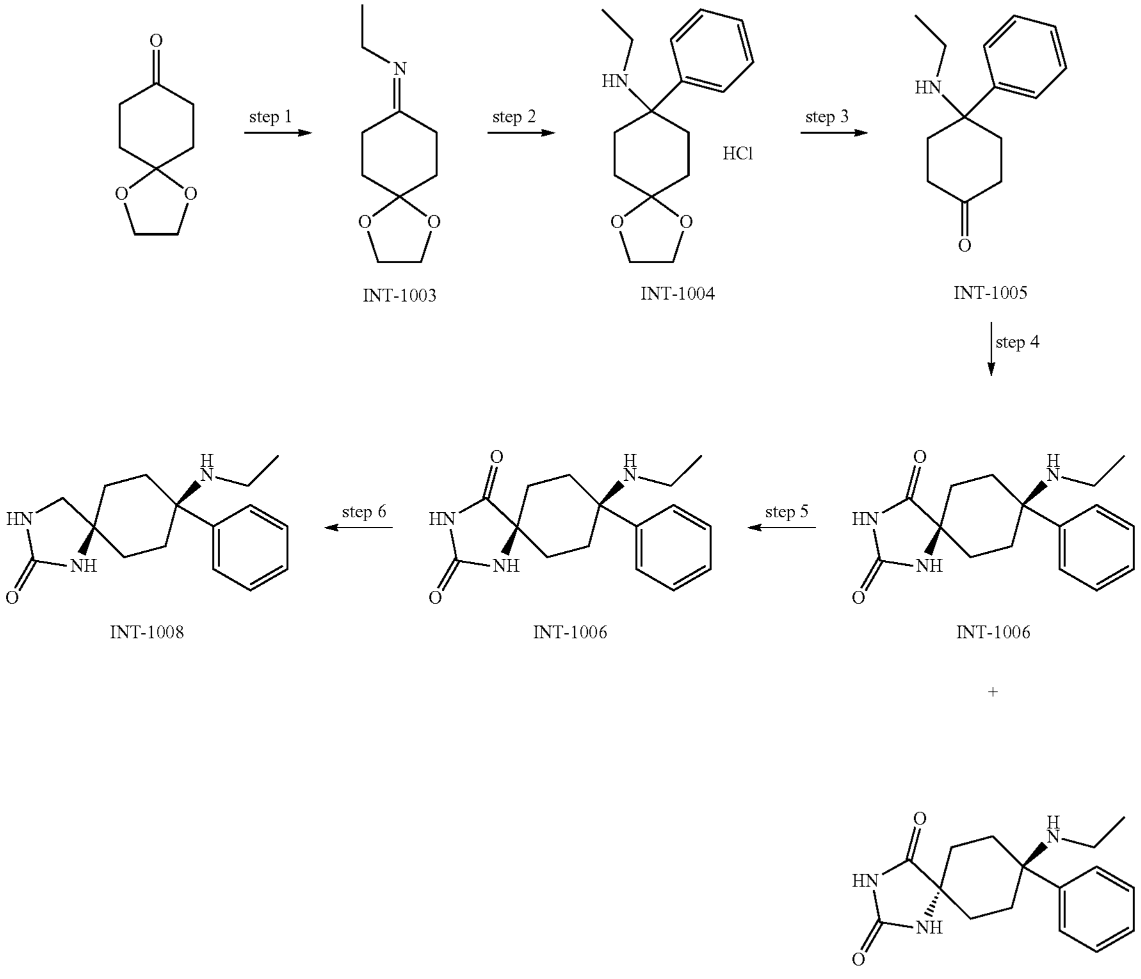

INT-1003 INT-1004 INT-1005

INT-1008 INT-1006 INT-1006

+

INT-1007

Step 1 and step 2: ethyl-(8-phenyl-1,4-dioxa-spiro[4.5]dec-8-yl)-amine hydrochloride (INT-1004)

A mixture of 1,4-dioxa-spiro[4.5]decan-8-one (25.0 g, 160.25 mmol, 1.0 eq.) and 2M solution of $EtNH_2$ in THF (200 ml, 2.5 eq. 400.64 mmol) in EtOH (30 ml) was stirred at RT for 48 h. The reaction mixture was concentrated under argon atmosphere and the residue was diluted with ether (60 ml), and a freshly prepared PhLi solution was added [prepared by addition of 2.5M n-BuLi in THF (70.5 ml, 1.1 eq. 176.27 mmol) to a solution of bromobenzene (27.675 g, 1.1 eq. 176.275 mmol) in ether (100 ml) at −30 OC and stirred at RT for 1 h). The reaction mixture was stirred at RT for 1.5 h, quenched with saturated $NH_4Cl$ solution (100 ml) at 0° C. and extracted with ethyl acetate (2×750 ml). The combined organic layer was washed with water (3×350 ml), brine (300 ml), dried over $Na_2SO_4$ and concentrated under reduced pressure. The resulting residue was dissolved in ethyl methyl ketone (100 ml) and trimethylsilyl chloride (37.5 ml) was added at 0° C. The resulting mixture was stirred at RT for 16 h. The precipitated solid was filtered off and washed with acetone followed by THF to get ethyl-(8-phenyl-1,4-dioxa-spiro[4.5]dec-8-yl)-amine hydrochloride as an off white solid. This reaction was done in 2 batches of 25 g scale and the yield is given for 2 combined batches. Yield: 18% (17.1 g, 57.575 mmol). LCMS: m/z 262.2 $(M+H)^+$.

Step 3: 4-ethylamino-4-phenyl-cyclohexanone (INT-1005)

To a solution of ethyl-(8-phenyl-1,4-dioxa-spiro[4.5]dec-8-yl)-amine hydrochloride (10.1 g, 34.0 mmol, 1 eq.) in water (37.5 ml) was added conc. aq. HCl (62.5 ml) at 0° C. and the resulting mixture was stirred at RT for 16 h. The reaction mixture was basified with aq. NaOH (pH ~14) at 0° C. and extracted with DCM (2×750 ml). Organic layer was washed with water (400 ml), brine (400 ml), dried over $Na_2SO_4$ and concentrated under reduced pressure to yield 4-ethylamino-4-phenyl-cyclohexanone which was used in the next step without further purification. This reaction was carried out in another batch of 15.1 g scale and the yield is given for 2 combined batches. Yield: 92% (17.0 g, 78.34 mmol).

Step 4: Cis and Trans Mixture of 8-ethylamino-8-phenyl-1,3-diaza-spiro[4.5]decane-2,4-dione (INT-1006 and INT-1007)

To a solution of 4-ethylamino-4-phenyl-cyclohexanone (17 g, 78.341 mmol, 1.0 eq.) in EtOH (250 ml) and water (200 ml) was added $(NH_4)_2CO_3$ (18.8 g, 195.85 mmol, 2.5 eq.) and the reaction mixture was stirred at RT for 15 min. KCN (5.09 g, 78.341 mmol, 1.0 eq.) was added and stirring was continued at 60° C. for 18 h. The reaction mixture was cooled down to RT. The precipitated solid was filtered off, washed with water (250 ml), EtOH (300 ml), hexane (200 ml) and dried under reduced pressure to yield cis and trans mixture of 8-ethylamino-8-phenyl-1,3-diaza-spiro[4.5]decane-2,4-dione (13.0 g, 45.29 mmol, 58%) as a white solid. Yield: 58% (13 g, 45.296 mmol). LC-MS: m/z $[M+1]^+$= 288.2.

Step 5: CIS-8-ethylamino-8-phenyl-1,3-diaza-spiro[4.5]decane-2,4-dione (INT-1006)

To a solution of cis and trans mixture of 8-ethylamino-8-phenyl-1,3-diaza-spiro[4.5]decane-2,4-dione (12 g) in MeOH-DCM (1:1, 960 ml) was added a solution of L-tartaric acid in MeOH (25 ml) and the resulting mixture stirred at RT for 2 h and then kept in refrigerator for 16 h. The precipitated solid was filtered off and washed with MeOH-DCM (1:5, 50 ml) to get tartrate salt of 8-ethylamino-8-phenyl-1,3-diaza-spiro[4.5]decane-2,4-dione (7.5 g) as a white solid. To this solid sat. aq. $NaHCO_3$ was added (pH-8) and the resulting mixture was extracted with 25% MeOH-DCM (2×800 ml). Combined organic layer was washed with water (300 ml), brine (300 ml), dried over anhydrous $Na_2SO_4$ and concentrated under reduced pressure. The residue was triturated with 20% DCM-hexane and the resulting solid was dried under reduced pressure to afford CIS-8-ethylamino-8-phenyl-1,3-diaza-spiro[4.5]decane-2,4-dione as white solid. This step was done in 2 batches (12 g & 2.4 g) and the yield is given for 2 combined batches. Yield: 31.2% (5.0 g, 17.421 mmol). LC-MS: m/z $[M+1]^+$=288.0.

Step 6: CIS-8-ethylamino-8-phenyl-1,3-diaza-spiro[4.5]decan-2-one (INT-1008)

To a slurry of $LiAlH_4$ (793 mg, 20.91 mmol, 3.0 eq.) in THF (15 ml) was added a suspension of CIS-8-ethylamino-8-phenyl-1,3-diaza-spiro[4.5]decane-2,4-dione (2.0 g, 6.97 mmol, 1.0 eq.) in THF (60 ml) at 0° C. and the reaction mixture was heated to 65° C. for 16 h. The reaction mixture was cooled to 0° C., quenched with sat. aq. $Na_2SO_4$ (20 ml), stirred at RT for 1 h and filtered through celite pad. The residue was washed with 15% MeOH-DCM (500 ml). The combined filtrate was dried over anhydrous $Na_2SO_4$ and concentrated under reduced pressure to give crude product which was triturated with 15% DCM-Hexane to afford CIS-8-ethylamino-8-phenyl-1,3-diaza-spiro[4.5]decan-2-one (INT-1008) (1.6 g, 5.86 mmol, 84%) as a white solid. Yield: 84% (1.6 g, 5.86 mmol). LC-MS: m/z $[M+1]^+$=274.2.

Synthesis of INT-1010: CIS-8-(dimethylamino)-8-phenyl-3-(prop-2-yn-1-yl)-1,3-diazaspiro[4.5]decan-2-one

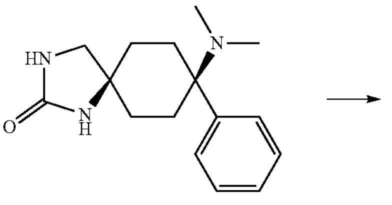

INT-976

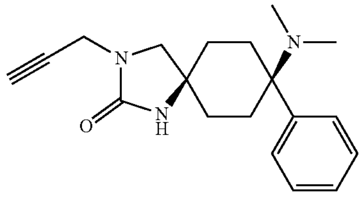

INT-1010

To a solution of CIS-8-(dimethylamino)-8-phenyl-1,3-diazaspiro[4.5]decan-2-one (INT-976) (5.0 g, 18.31 mmol, 1.0 eq.) in dry THF (500 ml) was added t-BuOK (3.07 g, 27.46 mmol, 1.5 eq.) and the reaction mixture was stirred at RT for 15 min. 3-Bromo-propyne (3.24 g, 13.18 mmol, 1.2 eq., 80% in toluene) was added and stirring was continued at RT for 18 h. The reaction mixture was poured into ice-water and extracted with DCM (800 ml). The organic layer was dried over $Na_2SO_4$ and concentrated under reduced pressure. The residue was purified by column chromatography (neutral alumina; 1% MeOH/Hexane) to yield CIS-8-(dimethylamino)-8-phenyl-3-(prop-2-yn-1-yl)-1,3-diazaspiro[4.5]decan-2-one (INT-1010) (3.0 g, 9.64 mmol, 52%) as an off white solid. Yield: 52% (3.0 g, 9.64 mmol). Mass: m/z 312.3 $(M+H)^+$.

Synthesis of INT-1011: ethyl CIS-2-(4-((8-(dimethylamino)-2-oxo-8-phenyl-1,3-diazaspiro[4.5]decan-3-yl)methyl)-1H-1,2,3-triazol-1-yl)acetate

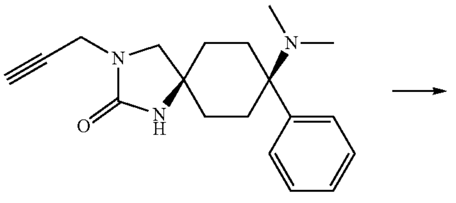

INT-1010

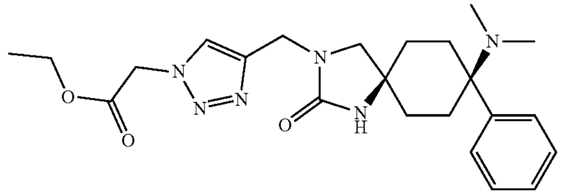

INT-1011

To a suspension of CIS-8-dimethylamino-8-phenyl-3-prop-2-ynyl-1,3-diaza-spiro[4.5]decan-2-one (INT-1010) (1.0 g, 3.21 mmol, 1.0 eq.) and azidoacetic acid ethyl ester (0.37 ml, 3.21 mmol, 1.0 eq.) in t-BuOH:$H_2O$ (1:1, 18 ml) and 1M aq. $CuSO_4$ (0.19 ml) was added sodium ascorbate (191 mg, 0.963 mmol, 0.3 eq.). The reaction mixture was stirred at RT for 18 h, then quenched with water and concentrated under reduced pressure. The residue was purified by column chromatography (silica gel neutralized with TEA; 10% MeOH/DCM) to yield ethyl CIS-2-(4-((8-(dimethylamino)-2-oxo-8-phenyl-1,3-diazaspiro[4.5]decan-3-yl)methyl)-1H-1,2,3-triazol-1-yl)acetate (INT-1011) (1.0 g, 2.27 mmol, 70%) as an off white solid. Yield: 70% (1.0 g, 2.27 mmol). Mass: m/z 441.4 $(M+H)^+$.

Synthesis of INT-1012: Methyl CIS-2-(4-((8-(dimethylamino)-1-((1-hydroxycyclobutyl)methyl)-2-oxo-8-phenyl-1,3-diazaspiro[4.5]decan-3-yl)methyl)-1H-1,2,3-triazol-1-yl)acetate

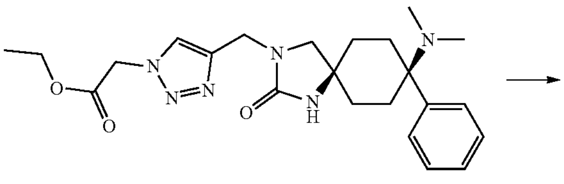

INT-1011

-continued

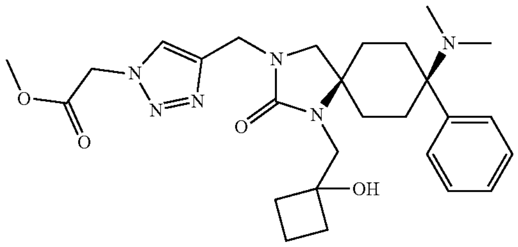

INT-1012

To a solution of CIS-2-(4-((8-(dimethylamino)-2-oxo-8-phenyl-1,3-diazaspiro[4.5]decan-3-yl)methyl)-1H-1,2,3-triazol-1-yl)acetate (INT-1011) (2.0 g, 4.54 mmol, 1.0 eq.) in DMSO (30 ml) was added NaOH (727 mg, 18.18 mmol, 4.0 eq.) at RT and the reaction mixture was heated to 70° C. for 30 min. The resulting mixture was cooled down to RT and a solution of 1-oxa-spiro[2.3]hexane (953 mg, 11.35 mmol, 2.5 eq.) in DMSO (5 ml) was added. The reaction mixture was stirred at 50° C. for 16 h, then cooled down to RT and diluted with MeOH (40 ml). Thionyl chloride (1.32 ml, 18.18 mmol, 4.0 eq.) was added at 0° C. and stirring was continued at RT for 16 h. The reaction mixture was concentrated under reduced pressure, then diluted with DCM (300 ml), sat. $NaHCO_3$ solution (200 ml) was added slowly at 0° C. and the resulting mixture was stirred at RT for 1 h. The organic layer was separated, dried over $Na_2SO_4$ and concentrated under reduced pressure. The residue was purified by column chromatography (silica gel; 4% MeOH/DCM) to yield methyl CIS-2-(4-((8-(dimethylamino)-1-((1-hydroxycyclobutyl)methyl)-2-oxo-8-phenyl-1,3-diazaspiro[4.5]decan-3-yl)methyl)-1H-1,2,3-triazol-1-yl)acetate (INT-1012) (950 mg, 1.86 mmol, 41%) as brown sticky solid. After purification, isolated compound was -60% pure and was used in the next steps without further purification. Yield: 41% (950 mg, 1.86 mmol). Mass: m/z 509.4 $(M+H)^+$.

Synthesis of INT-1021: CIS-1-(2-methoxybenzyl)-8-(methylamino)-8-phenyl-1,3-diazaspiro[4.5]decan-2-one

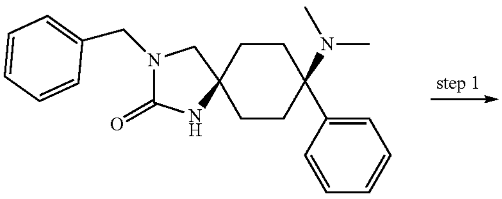

INT-963

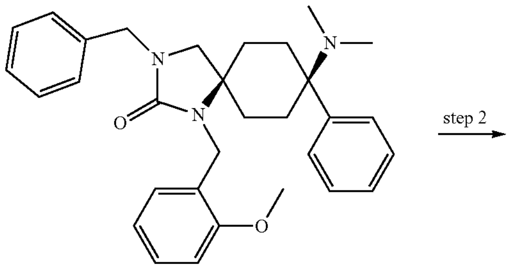

-continued

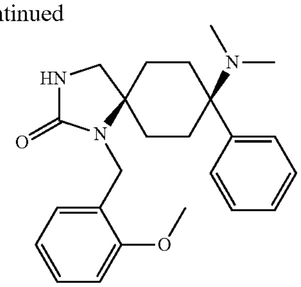

INT-1021

Step 1: CIS-3-benzyl-8-(dimethylamino)-1-(2-methoxybenzyl)-8-phenyl-1,3-diazaspiro[4.5]decan-2-one NaH (0.15 g, 3.30 mmol) was added to a solution of CIS-3-benzyl-8-(dimethylamino)-8-phenyl-1,3-diazaspiro[4.5]decan-2-one (INT-963) (0.4 g, 1.10 mmol) in DMF (8 mL) at 0° C. over 15 min. The reaction mixture was stirred for 5 min, 1-(bromomethyl)-2-methoxybenzene (0.33 g, 1.65 mmol) was added portionwise, ice bath was removed and stirring was continued at RT for 3 h. The resulting mixture was quenched with cold water (precipitation observed), the precipitate was filtered off and dried under reduced pressure to give 450 mg (84%) of CIS-3-benzyl-8-(dimethylamino)-1-(2-methoxybenzyl)-8-phenyl-1,3-diazaspiro[4.5]decan-2-one. The crude material was used in the next step without further purification. (TLC system: 10% MeOH in DCM; Rf: 0.7).

Step 2: CIS-8-(dimethylamino)-1-(2-methoxybenzyl)-8-phenyl-1,3-diazaspiro[4.5]decan-2-one (INT-1021)

CIS-3-benzyl-8-(dimethylamino)-1-(2-methoxybenzyl)-8-phenyl-1,3-diazaspiro[4.5]decan-2-one (0.45 g, 0.93 mmol) in THF (10 mL) was added to sodium metal (0.21 g, 9.316 mmol) in liquid ammonia (10 mL) at −78° C. The reaction mixture was stirred at −78° C. for 15 min, quenched with sat. aq. $NH_4Cl$ and the organic product was extracted with EtOAc (2×20 mL). The combined organic layer was dried over anhydrous $Na_2SO_4$ and concentrated in vacuo. Purification of the residue by preparative TLC using 2% methanol in DCM as eluent gave 170 mg of solid material, which was washed with pentane to give 150 mg (40%) of CIS-8-(dimethylamino)-1-(2-methoxybenzyl)-8-phenyl-1,3-diazaspiro[4.5]decan-2-one (INT-1021) as an off white solid. (TLC system: 10% MeOH in DCM; $R_f$: 0.3). $^1$H NMR (DMSO-d6): δ 7.34-7.18 (m, 7H), 6.96 (d, 1H), 6.90 (t, 1H), 6.33 (s, 1H), 4.19 (s, 2H), 3.83 (s, 3H), 3.20 (s, 2H), 2.59-2.55 (m, 2H), 1.98-1.90 (m, 8H), 1.37-1.30 (m, 4H). Mass: m/z 394.3 $[M+H]^+$ Synthesis of INT-1022: CIS-8-(dimethylamino)-1-(2-methoxybenzyl)-8-phenyl-1,3-diazaspiro[4.5]decan-2-one

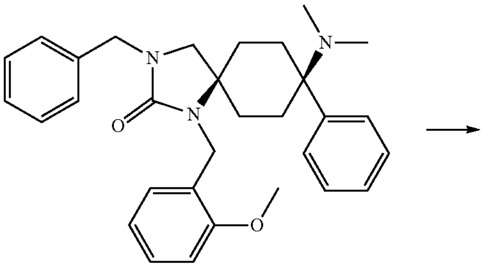

INT-1021

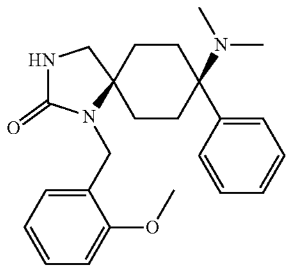

INT-1022

In analogy to the method described for INT-986 (step 1) CIS-8-(dimethylamino)-1-(2-methoxybenzyl)-8-phenyl-1,3-diazaspiro[4.5]decan-2-one was reacted with N-iodosuccinimide to be converted into CIS-1-(2-methoxybenzyl)-8-(methylamino)-8-phenyl-1,3-diazaspiro[4.5]decan-2-one (INT-1022). $^1$H NMR (DMSO-d6): δ 7.39 (d, 2H), 7.29 (t, 2H), 7.23-7.15 (m, 3H), 6.96 (d, 1H), 6.89 (t, 1H), 6.36 (s, 1H), 4.21 (s, 2H), 3.84 (s, 3H), 3.25 (s, 2H), 2.13 (m, 1H), 2.03-1.98 (m, 2H), 1.82-1.80 (m, 5H), 1.64-1.58 (m, 2H), 1.34-1.31 (m, 2H). Mass: m/z 380.2 $[M+H]^+$ Synthesis of INT_1023: CIS-8-(dimethylamino)-3-(4-methoxybenzyl)-8-phenyl-1-tosyl-1,3-diazaspiro[4.5]decan-2-one

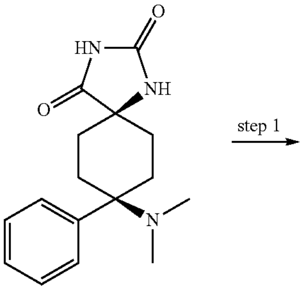

INT-795 (step 1)

-continued

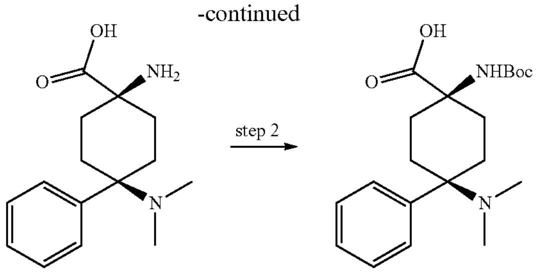

INT-1023

Step 1: synthesis of CIS-1-amino-4-(dimethylamino)-4-phenylcyclohexanecarboxylic Acid $Ba(OH)_2$x$8H_2O$ (36.87 g, 117.07 mmol) was added to the solution of CIS-8-(dimethylamino)-8-phenyl-1,3-diazaspiro[4.5]decane-2,4-dione (12 g, 41.81 mmol) in water (450 mL) at RT. The reaction mixture was stirred at 150° C. for 8 h. The resulting mixture was cooled down to RT and $(NH_4)_2CO_3$ (22.97 g, 146.34 mmol) was added. The reaction mixture was stirred at 65° C. for 8 h, then filtered through celite and the precipitate was washed with water. The combined filtrate was concentrated in vacuo to afford 6.5 g of crude CIS-1-amino-4-(dimethylamino)-4-phenylcyclohexanecarboxylic acid. The product was used in the next step without further purification. (TLC system: 10% MeOH in DCM; Rf: 0.1).

Step 2: synthesis of CIS-1-(tert-butoxycarbonylamino)-4-(dimethylamino)-4-phenylcyclohexanecarboxylic Acid (INT-1023)

$K_2CO_3$ (4.74 g, 34.34 mmol) was added to a solution of CIS-1-amino-4-(dimethylamino)-4-phenylcyclohexanecarboxylic acid (3.0 g, 11.4 mmol) in water-THF (40 mL, 1:1 v/v) at RT. After 15 min, $Boc_2O$ (3.24 g, 14.85 mmol) was added and the reaction mixture was stirred at RT for 16 h. The resulting mixture was diluted with water, acidified with glacial acetic acid (pH ~4) and extracted with 10% MeOH in DCM (2×150 mL). The organic layer was dried over anhydrous $Na_2SO_4$ and concentrated under reduced pressure. The residue was purified by flash column chromatography (neutral alumina, 10% methanol in DCM as eluent) and further purified by washing with pentane to give 1.0 g (24%) of CIS-1-(tert-butoxycarbonylamino)-4-(dimethylamino)-4-phenylcyclohexanecarboxylic acid (INT-1023) as a white solid. (TLC system: 10% MeOH in DCM; $R_f$: 0.10). Mass: m/z 361.2 $(M-H)^-$.

Synthesis of INT-1028: CIS-8-(dimethylamino)-8-phenyl-1-tosyl-1,3-diazaspiro[4.5]decan-2-one

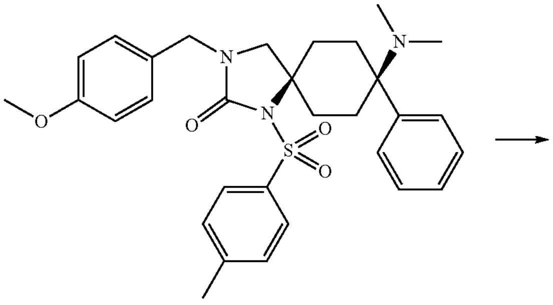

SC_2147

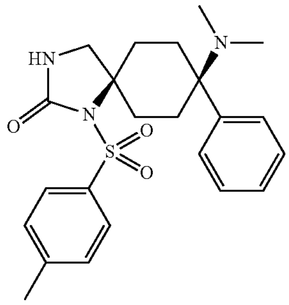

INT-1028

In analogy to the method described for INT-982 step 2 CIS-8-(dimethylamino)-3-(4-methoxybenzyl)-8-phenyl-1-tosyl-1,3-diazaspiro[4.5]decan-2-one (SC-2147) was treated with TFA to be converted into CIS-8-(dimethylamino)-8-phenyl-1-tosyl-1,3-diazaspiro[4.5]decan-2-one (INT-1028).

Synthesis of INT-1026: CIS-8-(methyl((tetrahydrofuran-3-yl)methyl)amino)-8-phenyl-1,3-diazaspiro[4.5]decan-2-one

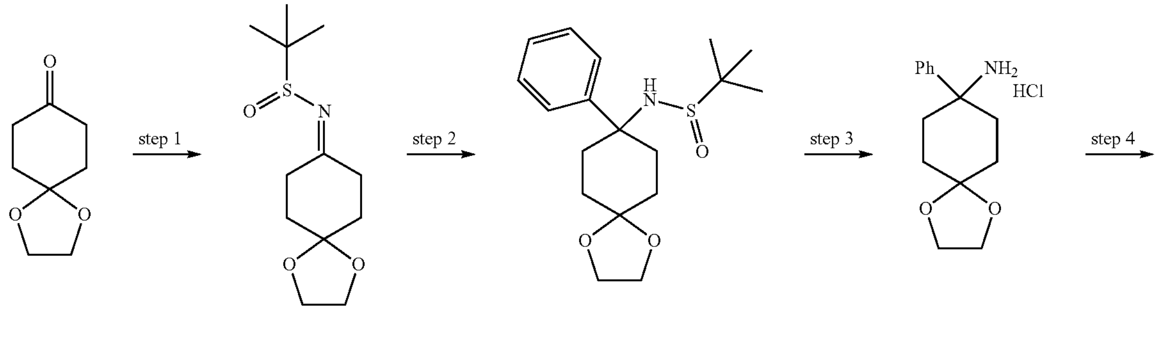

-continued

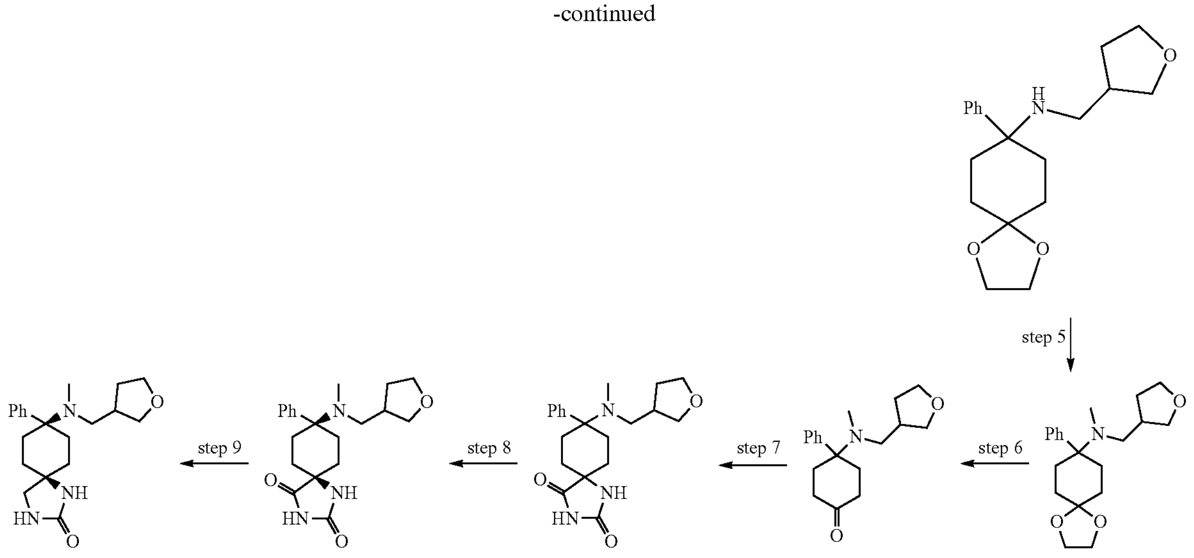

INT-1026

Step 1: 2-methyl-N-(1,4-dioxaspiro[4.5]decan-8-ylidene)propane-2-sulfinamide

Titanium ethoxide (58.45 g, 256.4 mmol) was added to a solution of 1,4-dioxaspiro[4.5]decan-8-one (20 g, 128.20 mmol) and 2-methylpropane-2-sulfinamide (15.51 g, 128.20 mmol) in THF (200 mL) at RT and the reaction mixture was stirred at RT for 18 h. The reaction mixture was cooled to 0° C. and quenched by dropwise addition of sat. aq. $NaHCO_3$ (500 mL) over a period of 30 min. The organic product was extracted with EtOAc (3×100 mL). The combined organic extracts were dried over anhydrous $Na_2SO_4$ and concentrated in vacuo to afford 10 g (crude) of 2-methyl-N-(1,4-dioxaspiro[4.5]decan-8-ylidene)propane-2-sulfinamide as a white solid (TLC system: 30% Ethyl acetate in hexane; $R_f$: 0.30).

Step 2: 2-methyl-N-(8-phenyl-1,4-dioxaspiro[4.5]decan-8-yl)propane-2-sulfinamide Phenylmagnesium bromide (1M in THF, 116 mL, 116 mmol) was added dropwise to a solution of 2-methyl-N-(1,4-dioxaspiro[4.5]decan-8-ylidene)propane-2-sulfinamide (10 g, 38.61 mmol) in THF (500 mL) at −10° C. under argon atmosphere. The reaction mixture was stirred for 2 h at −10° C. to 0° C. The reaction completion was monitored by TLC. The reaction mixture was quenched with sat. aq. $NH_4Cl$ (50 mL) at 0° C. and the organic product was extracted with EtOAc (3×100 mL). The combined organic extracts were dried over anhydrous $Na_2SO_4$ and concentrated in vacuo. The residue was purified by column chromatography (silica gel 230-400 mesh; 40-60% ethyl acetate in hexane) to yield 6.0 g (46%) of 2-methyl-N-(8-phenyl-1,4-dioxaspiro[4.5]decan-8-yl)propane-2-sulfinamide as a liquid (TLC system: 70% Ethyl acetate in hexane; Rf: 0.30).

Step 3: 8-phenyl-1,4-dioxaspiro[4.5]decan-8-amine hydrochloride 2N solution of HCl in diethyl ether (17.80 mL, 35.60 mmol) was added to a solution of 2-methyl-N-(8-phenyl-1,4-dioxaspiro[4.5]decan-8-yl)propane-2-sulfinamide (6.0 g, 17.80 mmol) in DCM (60 mL) at 0° C. The reaction mixture was stirred at RT for 2 h. The reaction mixture was concentrated in vacuo. The residue was washed with diethyl ether to yield 3 g (crude) of 8-phenyl-1,4-dioxaspiro[4.5]decan-8-amine hydrochloride as a brown solid (TLC system: 5% MeOH in DCM; Rf: 0.10).

Step 4: 8-phenyl-N—((tetrahydrofuran-3-yl)methyl)-1,4-dioxaspiro[4.5]decan-8-amine Sodium cyanoborohydride (2.17 g, 33.45 mmol) was added to a solution of 8-phenyl-1,4-dioxaspiro[4.5]decan-8-amine hydrochloride (3.0 g, 11.15 mmol) and tetrahydrofuran-3-carbaldehyde (4.46 mL, 22.30 mmol) and acetic acid (0.05 mL) in methanol (30 mL) at 0° C. The reaction mixture was stirred at RT for 16 h. The reaction mixture was concentrated in vacuo at 30° C. and to the residue sat. aq. $NaHCO_3$ was added. The organic product was extracted with DCM (3×30 mL). The combined organic extracts were dried over anhydrous $Na_2SO_4$ and solvent was concentrated under reduced pressure to get 3 g (crude) of 8-phenyl-N—((tetrahydrofuran-3-yl)methyl)-1,4-dioxaspiro[4.5]decan-8-amine as a semi-solid (TLC system: 10% MeOH in DCM; Rf: 0.22).

Step 5: N-methyl-8-phenyl-N—((tetrahydrofuran-3-yl)methyl)-1,4-dioxaspiro[4.5]decan-8-amine)

Sodium cyanoborohydride (1.76 g, 28.39 mmol) was added to a solution of 8-phenyl-N—((tetrahydrofuran-3-yl)methyl)-1,4-dioxaspiro[4.5]decan-8-amine (3.0 g, 9.46 mmol), 37% formaldehyde in water (7.70 mL, 94.60 mmol) and acetic acid (0.05 mL) in methanol (30 mL) at 0° C. The reaction mixture was stirred at RT for 16 h. The reaction mixture was concentrated in vacuo and to the residue sat. aq. $NaHCO_3$ was added. The organic product was extracted with DCM (3×30 mL). The combined organic extracts were dried over anhydrous $Na_2SO_4$ and solvent was concentrated under reduced pressure. The resulting residue was purified by column chromatography (silica gel 230-400 mesh; 5-6% MeOH in DCM) to yield 2.50 g (83%) of N-methyl-8- phenyl-N—((tetrahydrofuran-3-yl)methyl)-1,4-dioxaspiro[4.5]decan-8-amine as a semi solid (TLC system: 10% MeOH in DCM; Rf: 0.25).

Step 6: 4-(methyl((tetrahydrofuran-3-yl)methyl)amino)-4-phenylcyclohexanone

5% sulfuric acid in water (25 mL) was added to N-methyl-8-phenyl-N—((tetrahydrofuran-3-yl)methyl)-1,4-dioxaspiro[4.5]decan-8-amine (2.50 g, 7.55 mmol) at 0° C. and the resulting mixture was stirred at RT for 24 h. The reaction mixture was quenched with sat. aq. $NaHCO_3$ and the organic product was extracted with DCM (2×50 mL). The combined organic layers were dried over anhydrous $Na_2SO_4$ and concentrated in vacuo to afford 2.0 g (crude) of 4-(methyl((tetrahydrofuran-3-yl)methyl)amino)-4-phenylcyclohexanone as a thick liquid (TLC system: 10% MeOH in DCM, Rf: 0.20).

Step 7: 8-(methyl((tetrahydrofuran-3-yl)methyl)amino)-8-phenyl-1,3-diazaspiro[4.5]decane-2,4-dione 4-(methyl((tetrahydrofuran-3-yl)methyl)amino)-4-phenylcyclohexanone (1.50 g, 5.22 mmol) was suspended in 30 mL of $EtOH:H_2O$ (1:1 v/v) at RT under argon atmosphere. $(NH_4)_2CO_3$ (1.9 g, 13.05 mmol) and KCN (0.34 g, 5.22 mmol) were added. The reaction mixture was heated to 70° C. for 16 h. The reaction mixture was diluted with ice-water and the organic product was extracted with DCM (2×50 mL). The combined organic layer was dried over anhydrous $Na_2SO_4$ and concentrated in vacuo to give 1.0 g (crude) of 8-(methyl((tetrahydrofuran-3-yl)methyl)amino)-8-phenyl-1,3-diazaspiro[4.5]decane-2,4-dione as a solid (TLC system: 70% Ethyl acetate in hexane; Rf: 0.18).

Step 8: CIS-8-(methyl((tetrahydrofuran-3-yl)methyl)amino)-8-phenyl-1,3-diazaspiro[4.5]decane-2,4-dione Diastereomeric mixture of 8-(methyl((tetrahydrofuran-3-yl)methyl)amino)-8-phenyl-1,3-diazaspiro[4.5]decane-2,4-dione (1.0 g) was separated by reverse phase preparative HPLC to afford 400 mg of isomer 1 (CIS-8-(methyl((tetrahydrofuran-3-yl)methyl)amino)-8-phenyl-1,3-diazaspiro[4.5]decane-2,4-dione) and 60 mg of isomer 2 (TRANS-8-(methyl((tetrahydrofuran-3-yl)methyl)amino)-8-phenyl-1,3-diazaspiro[4.5]decane-2,4-dione) and 300 mg of mixture of both isomers. Reverse phase preparative HPLC conditions: mobile phase: 10 mM ammonium bicarbonate in $H_2O$/acetonitrile, column: X-BRIDGE-$C_{18}$ (150*30), 5 μm, gradient (T/B %): 0/35, 8/55, 8.1/98, 10/98, 10.1/35, 13/35, flow rate: 25 ml/min, diluent: mobile phase+ THF.

Step 9: CIS-8-(methyl((tetrahydrofuran-3-yl)methyl)amino)-8-phenyl-1,3-diazaspiro[4.5]decan-2-one (INT-1026)

$LiAlH_4$ (1M in THF) (4.48 mL, 4.48 mmol) was added to a solution of CIS-8-(methyl((tetrahydrofuran-3-yl)methyl)amino)-8-phenyl-1,3-diazaspiro[4.5]decane-2,4-dione (isomer-1) (0.4 g, 1.12 mmol) in $THF:Et_2O$ (2:1 v/v, 15 mL) at 0° C. under argon atmosphere. The reaction mixture was stirred at 65° C. for 16 h. The mixture was cooled to 0° C., quenched with sat. aq. $Na_2SO_4$ (1000 mL) and filtered through celite pad. The filtrate was dried over anhydrous $Na_2SO_4$ and concentrated in vacuo. The residue was purified by column chromatography (silica gel 230-400 mesh; 5-6% MeOH in DCM) to yield 0.3 g (78%) of CIS-8-(methyl((tetrahydrofuran-3-yl)methyl)amino)-8-phenyl-1,3-diazaspiro[4.5]decan-2-one (INT-1026) as an off white solid. (TLC system: 10% MeOH in DCM, Rf: 0.2). LC-MS: m/z $[M+1]^+$=344.2.

Synthesis of INT-1031: CIS-1-(Cyclobutyl-methyl)-8-dimethylamino-8-(3-fluorophenyl)-1,3-diazaspiro[4.5]decan-2-one

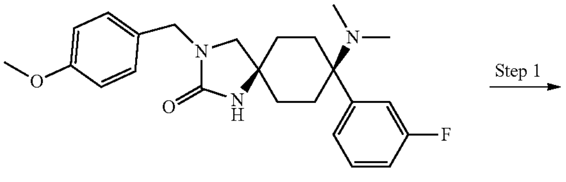

INT-974

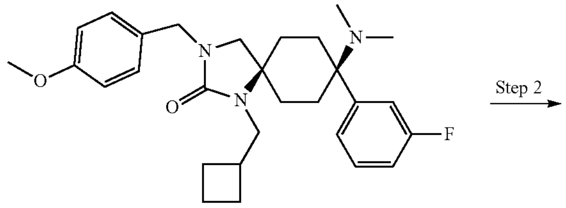

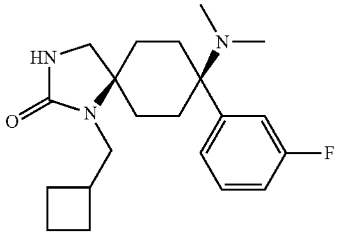

INT-1031

Step 1: CIS-1-(Cyclobutyl-methyl)-8-dimethylamino-8-(3-fluorophenyl)-3-[(4-methoxyphenyl)-methyl]-1,3-diazaspiro[4.5]decan-2-one In analogy to the method described for INT-952 CIS-8-dimethylamino-8-(3-fluorophenyl)-3-[(4-methoxyphenyl)-methyl]-1,3-diazaspiro[4.5]decan-2-one (INT-974) was converted into CIS-1-(cyclobutyl-methyl)-8-dimethylamino-8-(3-fluorophenyl)-3-[(4-methoxyphenyl)-methyl]-1,3-diazaspiro[4.5]decan-2-one.

Step 2: CIS-1-(Cyclobutyl-methyl)-8-dimethylamino-8-(3-fluorophenyl)-1,3-diazaspiro[4.5]decan-2-one In analogy to the method described for INT-982 step 2 1-(cyclobutyl-methyl)-8-dimethylamino-8-(3-fluorophenyl)-3-[(4-methoxyphenyl)-methyl]-1,3-diazaspiro[4.5]decan-2-one was converted into 1-(cyclobutyl-methyl)-8-dimethylamino-8-(3-fluorophenyl)-1,3-diazaspiro[4.5]decan-2-one (INT-1031).

Synthesis of INT-1037: 8-(dimethylamino)-2-oxo-1,3-diazaspiro[4.5]decane-8-carbonitrile

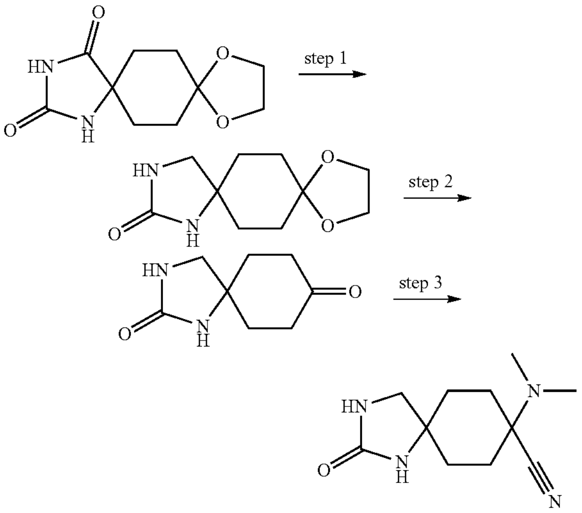

INT-1037

Step 1: 9,12-dioxa-2,4-diazadispiro[4.2.4^{8}.2^{5}]tetradecan-3-one

Lithiumaluminiumhydride (2.2 equiv., 292 mmol) was suspended in THF (400 mL) and the suspension was cooled to 0° C. 8-(Dimethylamino)-8-(m-tolyl)-1,3-diazaspiro[4.5]decan-2-one (B, 75 mg, 0,261 mmol) (step 1 of INT-965) was added portionwise at 0° C. The reaction mixture was stirred 1.5 h at 0° C., then overnight at RT and then 2 h at 40° C. The reaction mixture was cooled down to 0° C., quenched carefully with sat. aq. $Na_2SO_4$, EtOAc (400 mL) was added and the resulting mixture was stirred for 2 h and then left without stirring for 2 h at RT. The precipitate was filtered off and washed with EtOAc and MeOH. The resulting solid residue was suspended in methanol and stirred at RT overnight. The precipitate was filtered off and disposed. The filtrate was concentrated under reduced pressure, the residue was suspended thoroughly in water (50 mL) at 40° C., the precipitate was filtered off and dried under reduced pressure to yield 9,12-dioxa-2,4-diazadispiro[4.2.4^{8}.2^{5}]tetradecan-3-one (11.4 g, 41%). Mass: m/z 213.2 $(M+H)^+$.

Step 2: 1,3-diazaspiro[4.5]decane-2,8-dione

In analogy to the method described for INT-1003 step 3 9,12-dioxa-2,4-diazadispiro[4.2.4^{8}.2^{5}]tetradecan-3-one was treated with conc. aq. HCl to be converted into 1,3-diazaspiro[4.5]decane-2,8-dione. Mass: m/z 169.1 $(M+H)^+$.

Step 3: 8-(dimethylamino)-2-oxo-1,3-diazaspiro[4.5]decane-8-carbonitrile (INT-1037)

In analogy to the method described for INT-965 step 1 1,3-diazaspiro[4.5]decane-2,8-dione was treated with dimethyl amine and potassium cyanide to be converted into 8-(dimethylamino)-2-oxo-1,3-diazaspiro[4.5]decane-8-carbonitrile (INT-1037). Mass: m/z 223.2 $(M+H)^+$.

Synthesis of INT-1038: CIS-8-(dimethylamino)-8-(m-tolyl)-1,3-diazaspiro[4.5]decan-2-one

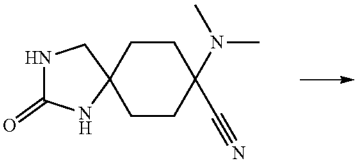

INT-1037

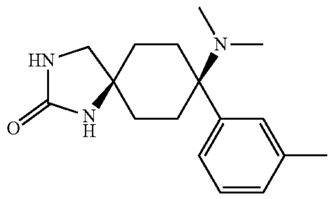

INT-1038

To the suspension of 8-(dimethylamino)-2-oxo-1,3-diazaspiro[4.5]decane-8-carbonitrile (200 mg, 0.90 mmol) in THF (4 mL) at RT was added dropwise 1M bromo(m-tolyl)magnesium in THF (4 equiv., 3.6 mmol, 3.6 mL) and the reaction mixture was stirred for 1 h at RT. Additional portion of 1M bromo(m-tolyl)magnesium in THF (1 equiv., 0.8 mL) was added. The reaction mixture was stirred at RT overnight, then quenched with methanol/water. Solid $NH_4Cl$ and DCM were added to the resulting mixture and the precipitate was filtered off. The organic phase of the filtrate was separated and the aqueous phase was extracted with DCM (3×). The combined organic phases were dried over anhydr. $Na_2SO_4$ and concentrated under reduced pressure. The residue was purified by flash chromatography on silica gel (DCM/MeOH, 100/0 to 65/35) to yield CIS-8-(dimethylamino)-8-(m-tolyl)-1,3-diazaspiro[4.5]decan-2-one (INT-1038) (81 mg, 31%). Mass: m/z 288.2 $(M+H)^+$.

Synthesis of INT-1064: CIS-1-acetyl-8-(dimethylamino)-8-phenyl-1,3-diazaspiro[4.5]decan-2-one

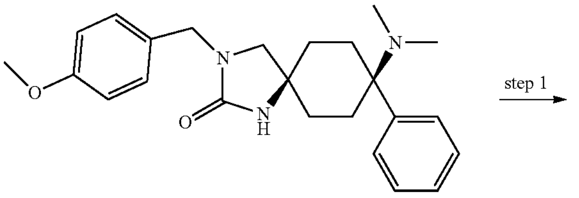

INT-975

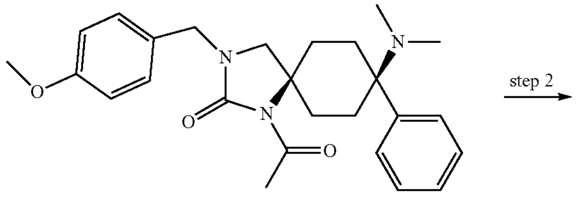

-continued

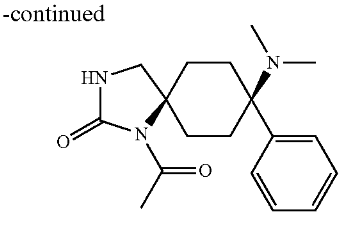

INT-1064

Step 1: CIS-1-acetyl-8-(dimethylamino)-3-(4-methoxybenzyl)-8-phenyl-1,3-diazaspiro[4.5]decan-2-one To a solution of CIS-8-dimethylamino-3-(4-methoxy-benzyl)-8-phenyl-1,3-diaza-spiro[4.5]decan-2-one (INT-975) (19.5 g, 49.6 mmol, 1.0 eq.) in THF (180 ml) was added 2.5M solution of n-BuLi in hexane (39.7 ml, 99.23 mmol, 2.0 eq.) at 0° C. and the resulting mixture was stirred for 1 h. A solution of acetyl chloride (7.7 g, 99.23 mmol, 2.0 eq.) in THF (20 ml) was added dropwise at 0° C. The cooling bath was removed, the reaction mixture was stirred at RT for 16 h, then cooled down to 0° C. again, quenched with water and extracted with ethyl acetate (2×200 ml). The combined organic extracts were washed with brine (250 ml), dried over $Na_2SO_4$ and concentrated under reduced pressure. The residue was purified by column chromatography (silica gel; 30% EtOAc/Hexane) to yield CIS-1-acetyl-8-dimethyl-amino-3-(4-methoxy-benzyl)-8-phenyl-1,3-diaza-spiro[4.5]decan-2-one (6.1 g, 14.02 mmol, 28%) as a light yellow sticky solid. Mass: m/z 436.3 $[M+H]^+$

Step 2: CIS-1-acetyl-8-(dimethylamino)-8-phenyl-1,3-diazaspiro[4.5]decan-2-one (INT-1064)

To a solution of CIS-1-acetyl-8-dimethylamino-3-(4-methoxy-benzyl)-8-phenyl-1,3-diaza-spiro[4.5]decan-2-one (5.0 g, 11.5 mmol, 1.0 eq.) in acetonitrile (60 ml) was added a solution cerium(IV) ammonium nitrate (18.98 g, 34.5 mmol, 3.0 eq.) in water (60 ml) at 0° C. and the reaction mixture was stirred at RT for 2 h. The reaction mixture was quenched with aq. $NaHCO_3$ solution (50 ml) and extracted with ethyl acetate (2×100 ml). The combined organic layer was washed with brine (2×100 ml), dried over $Na_2SO_4$ and concentrated under reduced pressure. The residue was purified by column chromatography (silica gel neutralized with TEA; 2/3 v/v EtOAc/Hexane) to yield CIS-1-acetyl-8-dimethylamino-8-phenyl-1,3-diaza-spiro[4.5]decan-2-one (INT-1064) as an off white solid. Yield: 61% (4.9 g, 15.55 mmol). $^1$HNMR (DMSO-d6, 400 MHz), δ (ppm)=7.57 (s, 1H), 7.33-7.23 (m, 5H), 3.21 (s, 2H), 3.03 (t, 2H, J=12.78 Hz), 2.60 (d, 2H, J=13.32 Hz), 2.32 (s, 3H), 1.89 (s, 6H), 1.37-1.32 (m, 4H). Mass: m/z 316.2 $[M+H]^+$

Synthesis of INT-1059: TRANS-8-(dimethylamino)-8-phenyl-1,3-diazaspiro[4.5]decan-2-one

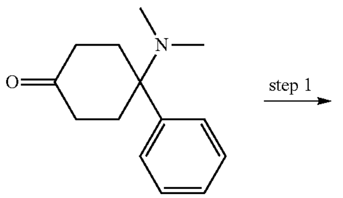

-continued

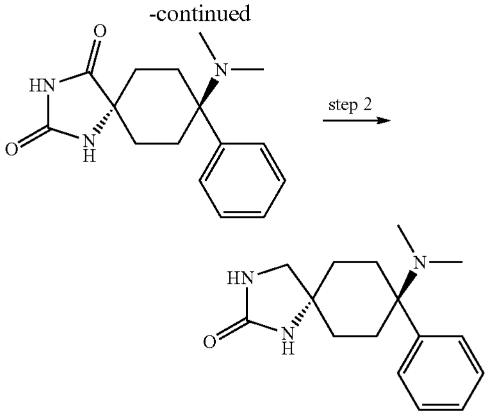

INT-1059

Step 1: TRANS-8-(dimethylamino)-8-phenyl-1,3-diazaspiro[4.5]decane-2,4-dione To a stirred solution of 4-dimethylamino-4-phenyl-cyclohexanone (250.0 g, 1.15 mol, 1.0 eq.) in EtOH (2.5 L) and water (2.1 L) was added $(NH_4)_2CO_3$ (276.2 g, 2.87 mol, 2.5 eq.) and the reaction mixture was stirred at RT for 15 min. KCN (74.92 g, 1.15 mol, 1.0 eq.) was added. The reaction mixture was stirred at 60° C. for 18 h and then filtered in hot condition to get white solid which was washed with water (2.5 L), ethanol (1 L) and hexane (2.5 L). The resulting solid was dried under reduced pressure to get CIS-8-dimethyl-amino-8-phenyl-1,3-diaza-spiro[4.5]decane-2,4-dione (223 g, 0.776 mol, 65%) as a white solid. The filtrate was collected from multiple batches (~450 g) which contained a mixture of cis and trans isomers. The filtrate was concentrated under reduced pressure and solid obtained was filtered and washed with water (1 L) and hexane (1 L). Solid material was dried under reduced pressure to get -100 g of a mixture of cis and trans (major) isomers. Crude material was partially dissolved in hot MeOH (600 mL) and cooled to RT, filtered through sintered funnel, washed with MeOH (200 mL) followed by ether (150 mL) and dried to get TRANS-8-dimethylamino-8-phenyl-1,3-diaza-spiro[4.5]decane-2,4-dione (50 g, 0.174 mmol, ~9-10%).

Step 2: TRANS-8-(dimethylamino)-8-phenyl-1,3-diazaspiro[4.5]decan-2-one (INT-1059)

In analogy to the method described for INT-976 step 2 TRANS-8-dimethylamino-8-phenyl-1,3-diaza-spiro[4.5]decane-2,4-dione was treated with $LiAlH_4$ to be converted into TRANS-8-(dimethylamino)-8-phenyl-1,3-diazaspiro[4.5]decan-2-one (INT-1059). Mass: m/z 274.2 $(M+H)^+$.

Synthesis of INT-1065: CIS-3-((2-chloropyridin-4-yl)methyl)-8-(dimethylamino)-8-phenyl-1,3-diazaspiro[4.5]decan-2-one

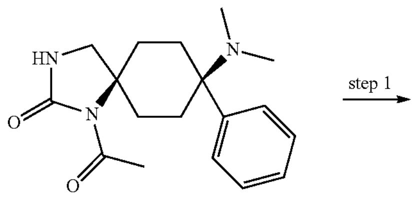

INT-1064

-continued

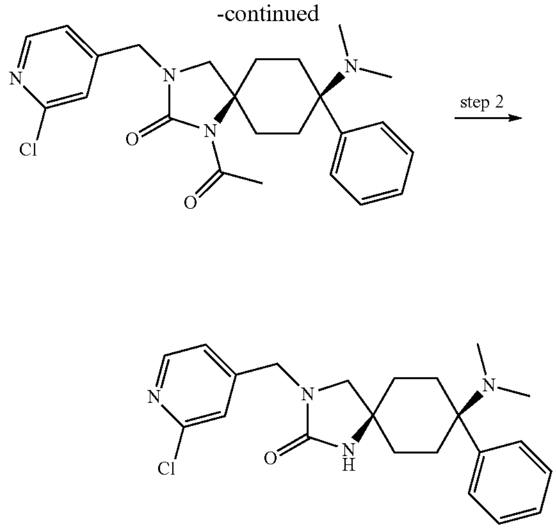

INT-1065

Step 1: CIS-1-acetyl-3-((2-chloropyridin-4-yl)methyl)-8-(dimethylamino)-8-phenyl-1,3-diazaspiro[4.5]decan-2-one To a solution of CIS-1-acetyl-8-(dimethylamino)-8-phenyl-1,3-diazaspiro[4.5]decan-2-one (INT-1064) (1 g, 3.17 mmol) in DMF (37 mL) was added sodium hydride (60 wt % in mineral oil, 1.25 equiv., 3.96 mmol, 159 mg) portion-wise at 0° C. The reaction mixture was stirred for 15 min at 0° C. and 2-chloro-4-(chloromethyl)pyridine (1.25 equiv., 3.96 mmol, 0.485 mL) was added. The reaction mixture was stirred at RT for 2 h, then cooled down to 0° C., quenched with sat. aq. $NaHCO_3$ (10 mL), water (10 mL) and extracted with EtOAc (2×50 mL). Combined organic phase was washed with brine, dried over anhydr. $Na_2SO_4$ and concentrated under reduced pressure. The resulting crude product was purified by flash chromatography on silica gel (eluent MeCN/DCM 98/2) to yield 1215 mg (87%) of CIS-1-acetyl-3-((2-chloropyridin-4-yl)methyl)-8-(dimethylamino)-8-phenyl-1,3-diazaspiro[4.5]decan-2-one. Mass: m/z 441.2 $(M+H)^+$.

Step 2: CIS-3-((2-chloropyridin-4-yl)methyl)-8-(dimethylamino)-8-phenyl-1,3-diazaspiro[4.5]decan-2-one (INT-1065)

To a solution of CIS-1-acetyl-3-((2-chloropyridin-4-yl)methyl)-8-(dimethylamino)-8-phenyl-1,3-diazaspiro[4.5]decan-2-one (1140 mg, 2.59 mmol) in THF/MeOH (2:1 v/v, 15 mL) was added 3M aq. NaOH (26 mL). The reaction mixture was stirred for 1.5 h at RT and then extracted with EtOAc (2×50 mL). The combined organic phase was dried over anhydr. $Na_2SO_4$ and concentrated under reduced pressure to yield 932 mg (90%) of CIS-3-((2-chloropyridin-4-yl)methyl)-8-(dimethylamino)-8-phenyl-1,3-diazaspiro[4.5]decan-2-one (INT-1065) which was used in the next steps without additional purification. Mass: m/z 399.2 $(M+H)^+$.

Synthesis of INT-1068 and INT-1069: CIS- and TRANS-8-(dimethylamino)-8-phenyl-1-(2,2,2-trifluoroethyl)-1,3-diazaspiro[4.5]decan-2-one

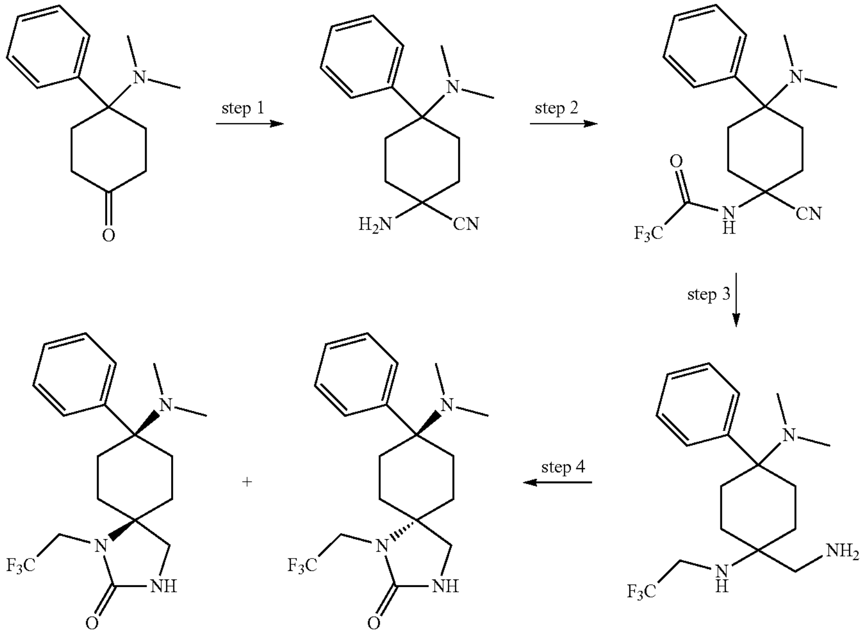

INT-1068 INT-1069

Step 1: 1-amino-4-dimethylamino-4-phenyl-cyclohexanecarbonitrile

To a stirred solution of 4-dimethylamino-4-phenyl-cyclohexanone (50 g, 230.096 mmol) in MeOH (400 mL) was added $NH_4Cl$ (24.6 g, 460.8 mmol) followed by $NH_4OH$ (400 mL) at RT and the reaction mixture was stirred for 15 min. NaCN (22.5 g, 460.83 mmol) was added and the resulting mixture was stirred for 16 h at RT. The reaction mixture was extracted with DCM (3×750 mL). Combined organic layer was washed with water (750 mL), brine (750 mL), dried over $Na_2SO_4$ and concentrated under reduced pressure. The residue was triturated with DCM/hexane to get crude 1-amino-4-dimethylamino-4-phenyl-cyclohexanecarbonitrile (50 g, 90%) as an off white solid which was used in next step without further purification. LC-MS: m/z $[M+H]^+$=244.2 (MW calc. 244.09).

Step 2: N-(1-cyano-4-dimethylamino-4-phenyl-cyclohexyl)-2,2,2-trifluoroacetamide To a solution of 1-amino-4-dimethylamino-4-phenyl-cyclohexanecarbonitrile (5.0 g, 20.57 mmol, 1.0 eq.) in THF (100 ml) were added DIPEA (10.72 ml, 61.71 mmol, 3.0 eq), trifluoroacetic acid (1.89 ml, 24.69 mmol, 1.2 eq) and T3P (18.2 ml, 30.85 mmol, 1.5 eq) at 0° C. The reaction mixture was stirred at RT for 16 h, then diluted with water (100 ml) and extracted with 10% MeOH in DCM (2×250 mL). Combined organic layer was washed with brine (100 mL), dried over $Na_2SO_4$ and concentrated under reduced pressure to get crude N-(1-cyano-4-dimethylamino-4-phenyl-cyclohexyl)-2,2,2-trifluoroacetamide as a light yellow sticky material which was used in the next step without further purification. LC-MS: m/z $[M+1]^+$=339.9 (MW calc. 339.36).

Step 3: 1-aminomethyl-N',N'-dimethyl-4-phenyl-N-(2,2,2-trifluoroethyl)cyclohexane-1,4-diamine To suspension of $LiAlH_4$ (4.03 g, 106.19 mmol, 6.0 eq.) in dry THF (40 mL) was added N-(1-cyano-4-dimethylamino-4-phenyl-cyclohexyl)-2,2,2-trifluoro-acetamide (6.0 g, 17.69 mmol, 1.0 eq.) in dry THF (100 mL) dropwise at 0° C. The reaction mixture was stirred at RT for 16 h, then quenched with sat. aq. $Na_2SO_4$ at 0° C., excess THF was added and the resulting mixture was stirred at RT for 2 h. The resulting suspension was filtered through celite and the filter cake was washed with 10% MeOH in DCM (150 mL). Combined filtrate was concentrated under reduced pressure to yield crude 1-aminomethyl-N',N'-dimethyl-4-phenyl-N-(2,2,2-trifluoro-ethyl)-cyclohexane-1,4-diamine (4.2 g, crude) as a light yellow sticky material which was directly used in the next step without further purification. LC-MS: m/z $[M+1]^+$=330.0 (MW calc. 329.40).

Step 4: CIS- and TRANS-8-dimethylamino-8-phenyl-1-(2,2,2-trifluoro-ethyl)-1,3-diaza-spiro[4.5]decan-2-one (INT-1068 and INT-1069)

To a solution of 1-aminomethyl-N',N'-dimethyl-4-phenyl-N-(2,2,2-trifluoro-ethyl)-cyclohexane-1,4-diamine (4.2 g, 12.76 mmol, 1.0 eq.) in toluene (60 ml) was added KOH (4.29 g, 76.56 mmol, 6.0 eq.) in water (120 ml) at 0° C. followed by addition of $COCl_2$ (15.6 ml, 44.66 mmol, 3.5 eq., 20% in toluene) at 0° C. and stirred at RT for 16 h. Reaction mixture was basified with sat $NaHCO_3$ solution and extracted with DCM (2×200 ml). Combined organic layer was dried over $Na_2SO_4$ and concentrated under reduced pressure to get crude product which was purified by prep HPLC to get CIS-8-dimethylamino-8-phenyl-1-(2,2,2-trifluoro-ethyl)-1,3-diaza-spiro[4.5]decan-2-one (INT-1068) (1.5 g) (major isomer, polar spot on TLC) and TRANS-8-dimethylamino-8-phenyl-1-(2,2,2-trifluoro-ethyl)-1,3-diaza-spiro[4.5]decan-2-one (INT-1069) as minor isomer (non-polar spot on TLC) (120 mg, 92.93% by HPLC) as off-white solids. CIS-isomer: LC-MS: m/z $[M+1]^+$=356.2 (MW calc.=355.40). HPLC: 98.53%, Column: Xbridge C-18 (100×4.6), 5 g, Diluent: MeOH, Mobile phase: A) 0.05% TFA in water; B) ACN flow rate: 1 ml/min, Rt=5.17 min. $^1$HNMR (DMSO-$d_6$, 400 MHz), δ (ppm)=7.43-7.27 (m, 5H), 6.84 (s, 1H), 3.30-3.25 (m, 4H), 2.66-2.63 (d, 2H, J=12.72 Hz), 1.89 (s, 6H), 1.58-1.51 (m, 2H), 1.46-1.43 (m, 2H), 1.33-1.23 (m, 2H).

For further intermediates the synthesis in analogy to previously described methods is given in the following table. The syntheses of the building blocks and intermediates have either been described previously within this application or can be performed in analogy to the herein described methods or by methods known to the person, skilled in the art. Such a person will also know which building blocks and intermediates need to be chosen for synthesis of each exemplary compound.

| Intermediate | Chemical Name | | in analogy to method | m/z [M + H]$^+$ |
|---|---|---|---|---|
| INT-794 | CIS-3-(3,4-dimethoxybenzyl)-8-(dimethylamino)-8-phenyl-1,3-diazaspiro[4.5]decan-2-one | 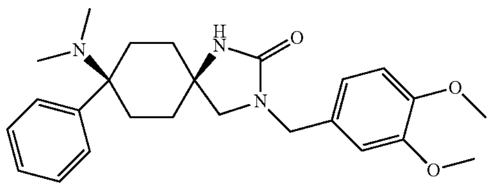 [SMILES: COc1ccc(CN2C[C@]3(CC[C@](c4ccccc4)(N(C)C)CC3)NC2=O)cc1OC] | SC_2097 | 424.3 |
| INT-796 | CIS-8-Dimethylamino-3-[(4-methoxyphenyl)-methyl]-8-(3-methoxy-propyl)-1,3-diazaspiro[4.5]decan-2-one | 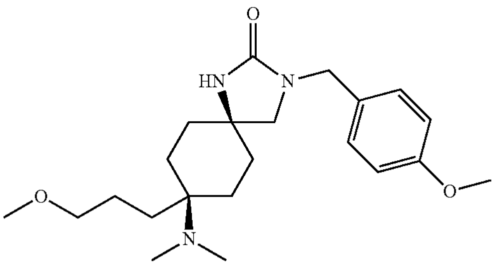 | SC_2017 | 390.3 |

-continued

| Intermediate | Chemical Name | | in analogy to method | m/z [M + H]+ |
|---|---|---|---|---|
| INT-797 | CIS-8-(Ethyl-methyl-amino)-8-phenyl-1,3-diazaspiro[4.5]decan-2-one | 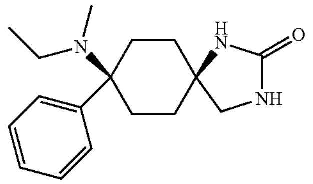 [SMILES: CCN(C)[C@]1(c2ccccc2)CC[C@]2(CC1)CNC(=O)N2] | INT-976 | 288.2 |
| INT-798 | CIS-3-[[8-(Ethyl-methyl-amino)-2-oxo-8-phenyl-1,3-diazaspiro[4.5]decan-3-yl]-methyl]-benzonitrile | 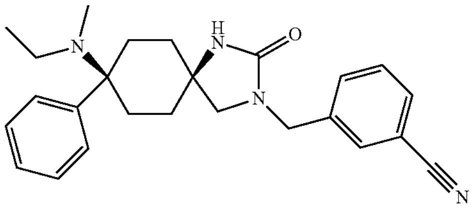 [SMILES: CCN(C)[C@]1(c2ccccc2)CC[C@]2(CC1)CN(Cc1cccc(C#N)c1)C(=O)N2] | SC_2097 | 403.3 |
| INT-949 | CIS-8-Dimethylamino-1-ethyl-8-phenyl-1,3-diazaspiro[4.5]decan-2-one | 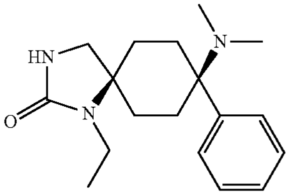 [SMILES: CCN1C(=O)NC[C@]12CC[C@](c1ccccc1)(N(C)C)CC2] | INT-984 | 302.2 |
| INT-950 | CIS-1-(Cyclobutyl-methyl)-8-dimethylamino-8-phenyl-3-[phenyl-methyl]-1,3-diazaspiro[4.5]decan-2-one | 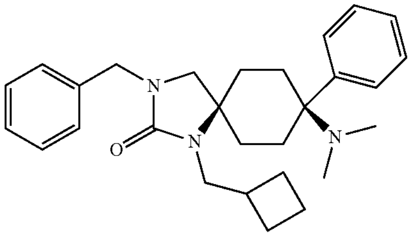 [SMILES: CN(C)[C@]1(c2ccccc2)CC[C@]2(CC1)CN(Cc1ccccc1)C(=O)N2CC1CCC1] | SC_2125 | 432.3 |
| INT-954 | 4-Dimethylamino-4-(5-methyl-thiophen-2-yl)-cyclohexan-1-one | 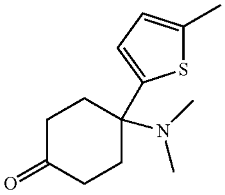 [SMILES: Cc1ccc(C2(N(C)C)CCC(=O)CC2)s1] | INT-965 | 238.1 |
| INT-955 | 4-Dimethylamino-4-thiophen-2-yl-cyclohexan-1-one | 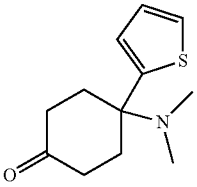 | INT-965 | 224.1 |
| INT-956 | 1-(1-Methyl-1H-pyrazol-3-yl)-4-oxo-cyclohexane-1-carbonitrile | 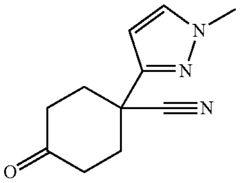 | INT-958 | 204.1 |

-continued

| Intermediate | Chemical Name | | in analogy to method | m/z [M + H]+ |
|---|---|---|---|---|
| INT-957 | 4-Oxo-1-pyrazin-2-yl-cyclohexane-1-carbonitrile | 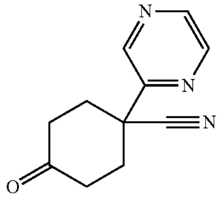 [SMILES: N#CC1(c2cnccn2)CCC(=O)CC1] | INT-958 | 202.1 |
| INT-959 | 4-Dimethylamino-4-(1-methyl-1H-pyrazol-3-yl)-cyclohexan-1-one | 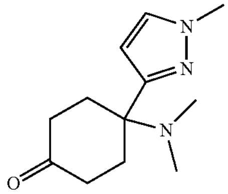 [SMILES: CN(C)C1(c2ccn(C)n2)CCC(=O)CC1] | INT-961 | 222.2 |
| INT-960 | 4-Dimethylamino-4-pyrazin-2-yl-cyclohexan-1-one | 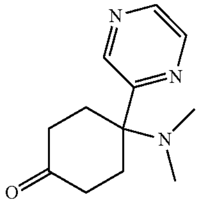 [SMILES: CN(C)C1(c2cnccn2)CCC(=O)CC1] | INT-961 | 220.1 |
| INT-962 | 4-Dimethylamino-4-(3-methoxyphenyl)-cyclohexan-1-one | 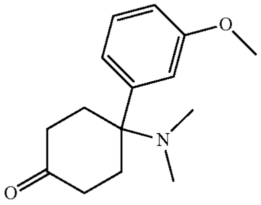 [SMILES: COc1cccc(C2(N(C)C)CCC(=O)CC2)c1] | INT-965 | 248.2 |
| INT-963 | CIS-3-Benzyl-8-dimethylamino-8-phenyl-1,3-diazaspiro[4.5]decan-2-one | 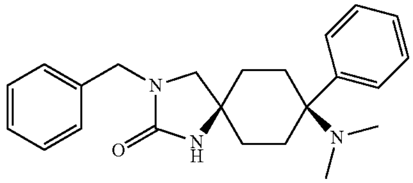 [SMILES: CN(C)[C@]1(c2ccccc2)CC[C@]2(CC1)CN(Cc1ccccc1)C(=O)N2] | INT-975 | 364.2 |
| INT-964 | 4-(Ethyl-methyl-amino)-4-phenyl-cyclohexan-1-one | 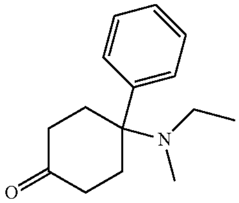 [SMILES: CCN(C)C1(c2ccccc2)CCC(=O)CC1] | INT-965 | 232.2 |
| INT-967 | CIS-8-Dimethylamino-8-[4-(methoxymethyloxy)-phenyl]-3-[(4-methoxyphenyl)-methyl]-1,3-diazaspiro[4.5]decan-2-one | 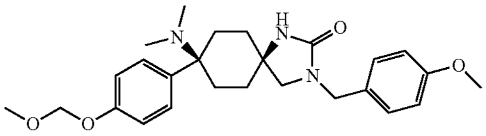 | SC_2017 | 454.3 |
| INT-968 | CIS-8-Dimethylamino-8-[3-(methoxymethyloxy)-phenyl]-3-[(4-methoxyphenyl)-methyl]-1,3-diazaspiro[4.5]decan-2-one | 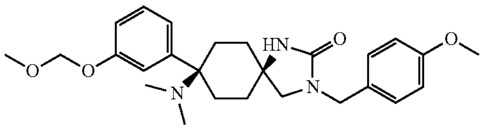 | SC_2017 | 454.3 |

-continued

| Intermediate | Chemical Name | | in analogy to method | m/z [M + H]+ |
|---|---|---|---|---|
| INT-969 | CIS-1-(Cyclobutyl-methyl)-8-dimethylamino-8-(4-hydroxyphenyl)-3-[(4-methoxyphenyl)-methyl]-1,3-diazaspiro[4.5]decan-2-one | 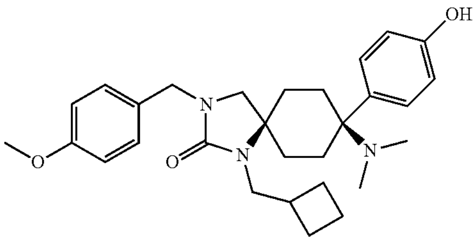 [SMILES: COc1ccc(CN2C[C@]3(CC[C@](c4ccc(O)cc4)(N(C)C)CC3)N(CC3CCC3)C2=O)cc1] | SC_2018 | 478.3 |
| INT-970 | CIS-8-Dimethylamino-8-(4-methoxyphenyl)-3-[(4-methoxyphenyl)-methyl]-1,3-diazaspiro[4.5]decan-2-one | 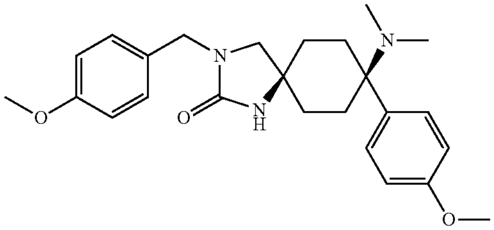 | SC_2017 | 424.3 |
| INT-972 | CIS-8-Dimethylamino-8-(3-methoxyphenyl)-3-[(4-methoxyphenyl)-methyl]-1,3-diazaspiro[4.5]decan-2-one | 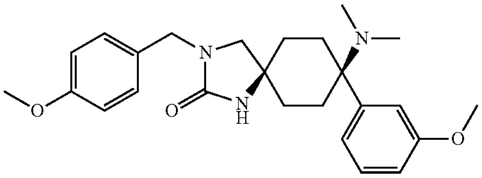 | SC_2017 | 424.3 |
| INT-979 | CIS-8-Dimethylamino-1-(3-methoxy-propyl)-8-phenyl-1,3-diazaspiro[4.5]decan-2-one | 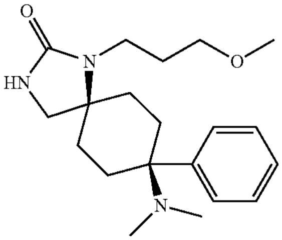 [SMILES: COCCCN1C(=O)NC[C@]12CC[C@](c1ccccc1)(N(C)C)CC2] | INT-984 | 346.2 |
| INT-980 | CIS-8-Dimethylamino-1-(2-methoxy-ethyl)-8-phenyl-1,3-diazaspiro[4.5]decan-2-one | 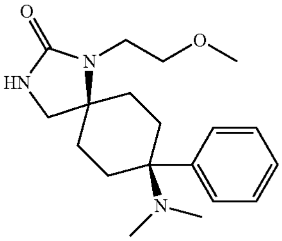 [SMILES: COCCN1C(=O)NC[C@]12CC[C@](c1ccccc1)(N(C)C)CC2] | INT-984 | 332.2 |
| INT-981 | CIS-8-Dimethylamino-8-phenyl-1-propyl-1,3-diazaspiro[4.5]decan-2-one | 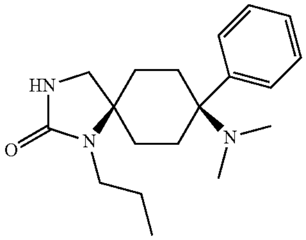 [SMILES: CCCN1C(=O)NC[C@]12CC[C@](c1ccccc1)(N(C)C)CC2] | INT-984 | 316.2 |

-continued

| Intermediate | Chemical Name | | in analogy to method | m/z [M + H]+ |
|---|---|---|---|---|
| INT-983 | CIS-1-(Cyclopropyl-methyl)-8-dimethylamino-8-phenyl-1,3-diazaspiro[4.5]decan-2-one | 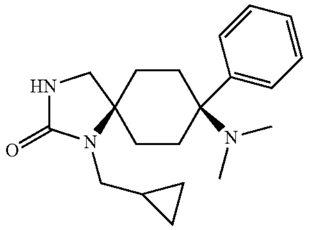 [SMILES: CN(C)[C@]1(c2ccccc2)CC[C@]2(CC1)CNC(=O)N2CC1CC1] | INT-984 | 328.2 |
| INT-985 | CIS-1-(Cyclobutyl-methyl)-8-(methyl-propyl-amino)-8-phenyl-1,3-diazaspiro[4.5]decan-2-one | 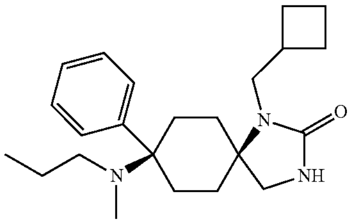 [SMILES: CCCN(C)[C@]1(c2ccccc2)CC[C@]2(CC1)CNC(=O)N2CC1CCC1] | INT-986 | 370.3 |
| INT-993 | 4-benzyl-4-(dimethylamino)cyclohexanone | 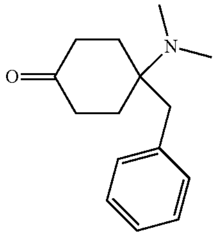 [SMILES: CN(C)C1(Cc2ccccc2)CCC(=O)CC1] | INT-965 | 232.3 |
| INT-994 | CIS-8-benzyl-8-(dimethylamino)-1,3-diazaspiro[4.5]decan-2-one | 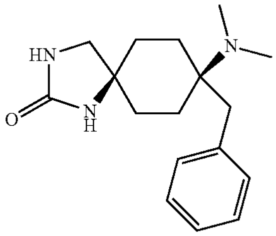 [SMILES: CN(C)[C@]1(Cc2ccccc2)CC[C@]2(CC1)CNC(=O)N2] | INT-976 | 288.2 |
| INT-995 | TRANS-8-benzyl-8-(dimethylamino)-1,3-diazaspiro[4.5]decan-2-one | 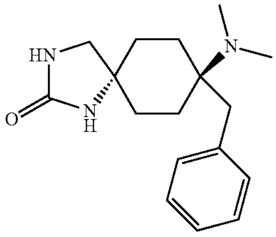 [SMILES: CN(C)[C@]1(Cc2ccccc2)CC[C@@]2(CC1)CNC(=O)N2] | INT-976 | 288.2 |
| INT-997 | CIS-8-(dimethylamino)-8-(thiophen-2-yl)-1,3-diazaspiro[4.5]decan-2-one | 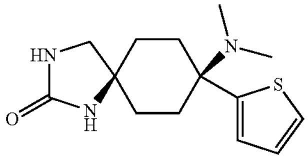 [SMILES: CN(C)[C@]1(c2cccs2)CC[C@]2(CC1)CNC(=O)N2] | INT-976 | 280.1 |
| INT-998 | TRANS-8-(dimethylamino)-8-(thiophen-2-yl)-1,3-diazaspiro[4.5]decan-2-one | 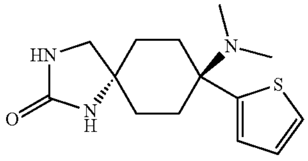 [SMILES: CN(C)[C@]1(c2cccs2)CC[C@@]2(CC1)CNC(=O)N2] | INT-976 | 280.1 |

-continued

| Intermediate | Chemical Name | | in analogy to method | m/z [M + H]+ |
|---|---|---|---|---|
| INT-999 | 4-(dimethylamino)-4-(1-methyl-1H-benzo[d]imidazol-2-yl)cyclohexanone | 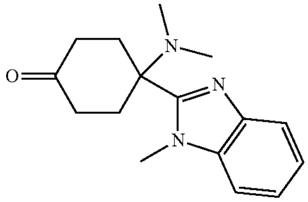 [SMILES: CN(C)C1(c2nc3ccccc3n2C)CCC(=O)CC1] | INT-965 | 272.2 |
| INT-1000 | CIS-8-(dimethylamino)-8-(1-methyl-1H-benzo[d]imidazol-2-yl)-1,3-diazaspiro[4.5]decan-2-one | 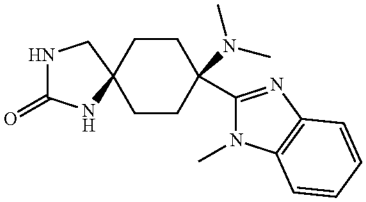 [SMILES: Cn1c2ccccc2nc1[C@]1(N(C)C)CC[C@@]2(CC1)CNC(=O)N2] | INT-976 | 328.2 |
| INT-1001 | TRANS-8-(dimethylamino)-8-(1-methyl-1H-benzo[d]imidazol-2-yl)-1,3-diazaspiro[4.5]decan-2-one | 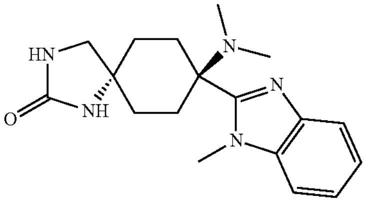 [SMILES: Cn1c2ccccc2nc1[C@]1(N(C)C)CC[C@]2(CC1)CNC(=O)N2] | INT-976 | 328.2 |
| INT-1009 | TRANS-8-ethylamino-8-phenyl-1,3-diaza-spiro[4.5]decan-2-one | 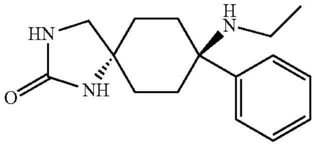 [SMILES: CCN[C@]1(c2ccccc2)CC[C@@]2(CC1)CNC(=O)N2] | INT-1008 | 274.2 |
| INT-1024 | CIS-8-(dimethylamino)-8-(3-fluorophenyl)-1,3-diazaspiro[4.5]decan-2-one | 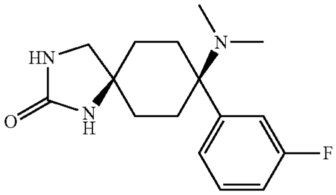 [SMILES: CN(C)[C@]1(c2cccc(F)c2)CC[C@]2(CC1)CNC(=O)N2] | INT-977 (step 2) | 292.2 |
| INT-1025 | CIS-8-(dimethylamino)-8-(4-fluorophenyl)-1,3-diazaspiro[4.5]decan-2-one | 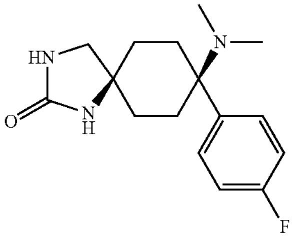 [SMILES: CN(C)[C@]1(c2ccc(F)cc2)CC[C@]2(CC1)CNC(=O)N2] | INT-974, INT-977 (step 2) | 292.2 |
| INT-1029 | CIS-1-(cyclobutylmethyl)-8-(dimethylamino)-8-phenyl-3-(prop-2-yn-1-yl)-1,3-diazaspiro[4.5]decan-2-one | 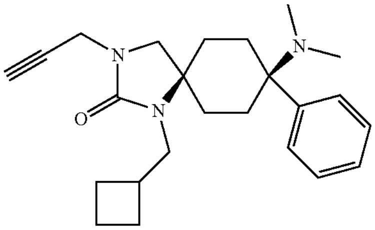 [SMILES: C#CCN1C[C@]2(CC[C@](c3ccccc3)(N(C)C)CC2)N(CC2CCC2)C1=O] | INT-1010 | 380.3 |

-continued

| Intermediate | Chemical Name | | in analogy to method | m/z [M + H]+ |
|---|---|---|---|---|
| INT-1030 | ethyl CIS-2-(4-((1-(cyclobutylmethyl)-8-(dimethylamino)-2-oxo-8-phenyl-1,3-diazaspiro[4.5]decan-3-yl)methyl)-1H-1,2,3-triazol-1-yl)acetate | 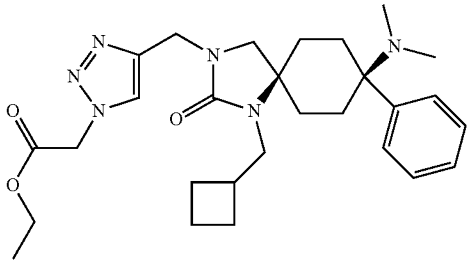 [SMILES: CCOC(=O)Cn1cc(CN2C[C@]3(CC[C@](c4ccccc4)(N(C)C)CC3)N(CC3CCC3)C2=O)nn1] | INT-1011 | 509.3 |
| INT-1039 | CIS-8-(dimethylamino)-8-(3-(trifluoromethoxy)phenyl)-1,3-diazaspiro[4.5]decan-2-one | 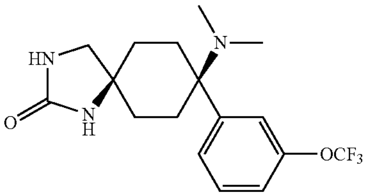 [SMILES: CN(C)[C@]1(c2cccc(OC(F)(F)F)c2)CC[C@]2(CC1)CNC(=O)N2] | INT-1038 | 358.2 |
| INT-1040 | (CIS)-8-(dimethylamino)-8-(3-(trifluoromethyl)phenyl)-1,3-diazaspiro[4.5]decan-2-one | 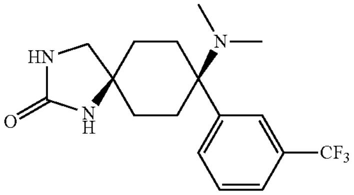 [SMILES: CN(C)[C@]1(c2cccc(C(F)(F)F)c2)CC[C@]2(CC1)CNC(=O)N2] | INT-1038 | 342.2 |
| INT-1041 | (CIS)-8-(dimethylamino)-8-(3-methoxyphenyl)-1,3-diazaspiro[4.5]decan-2-one | 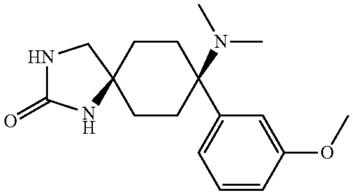 [SMILES: COc1cccc([C@]2(N(C)C)CC[C@@]3(CC2)CNC(=O)N3)c1] | INT-1038 | 304.2 |
| INT-1042 | (CIS)-8-(5-chlorothiophen-2-yl)-8-(dimethylamino)-1,3-diazaspiro[4.5]decan-2-one | 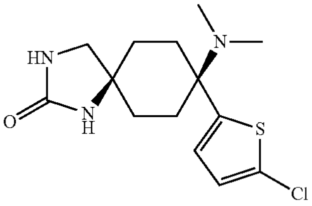 [SMILES: CN(C)[C@]1(c2ccc(Cl)s2)CC[C@]2(CC1)CNC(=O)N2] | INT-1038 | 314.1 |
| INT-1043 | (CIS)-8-(dimethylamino)-8-(3-fluoro-5-methylphenyl)-1,3-diazaspiro[4.5]decan-2-one | 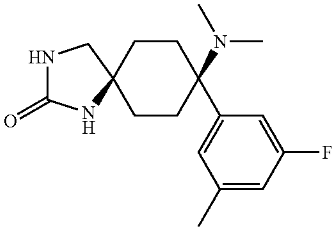 [SMILES: Cc1cc(F)cc([C@]2(N(C)C)CC[C@@]3(CC2)CNC(=O)N3)c1] | INT-1038 | 306.2 |
| INT-1044 | (CIS)-8-(3-chlorophenyl)-8-(dimethylamino)-1,3-diazaspiro[4.5]decan-2-one | 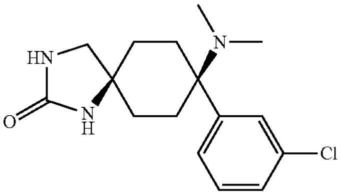 [SMILES: CN(C)[C@]1(c2cccc(Cl)c2)CC[C@]2(CC1)CNC(=O)N2] | INT-1038 | 308.2 |

-continued

| Intermediate | Chemical Name | | in analogy to method | m/z [M + H]+ |
|---|---|---|---|---|
| INT-1047 | (CIS)-8-(methyl(oxetan-3-ylmethyl)amino)-8-phenyl-1,3-diazaspiro[4.5]decan-2-one | 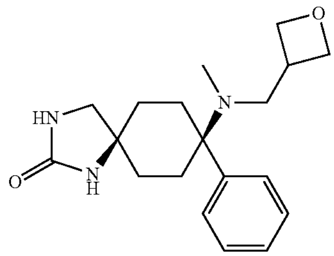 [SMILES: CN(CC1COC1)[C@]1(c2ccccc2)CC[C@]2(CC1)CNC(=O)N2] | INT-1026 | 330.5 |
| INT-1061 | TRANS-1-(cyclopropyl-methyl)-8-dimethylamino-8-phenyl-1,3-diazaspiro[4.5]decan-2-one | 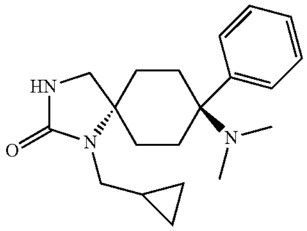 [SMILES: CN(C)[C@]1(c2ccccc2)CC[C@@]2(CC1)CNC(=O)N2CC1CC1] | INT-984 | 328.2 |
| INT-1063 | CIS-1-(cyclopropylmethyl)-8-(dimethylamino)-8-(3-fluorophenyl)-1,3-diazaspiro[4.5]decan-2-one | 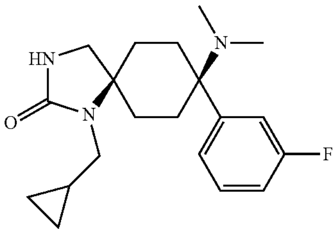 [SMILES: CN(C)[C@]1(c2cccc(F)c2)CC[C@]2(CC1)CNC(=O)N2CC1CC1] | INT-1031 | 346.2 |
| INT-1066 | TRANS-1-(cyclobutylmethyl)-8-(dimethylamino)-8-phenyl-1,3-diazaspiro[4.5]decan-2-one | 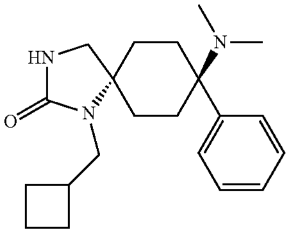 [SMILES: CN(C)[C@]1(c2ccccc2)CC[C@@]2(CC1)CNC(=O)N2CC1CCC1] | INT-987 | 342.3 |
| INT-1070 | CIS-8-(dimethylamino)-8-phenyl-1-(3,3,3-trifluoropropyl)-1,3-diazaspiro[4.5]decan-2-one | 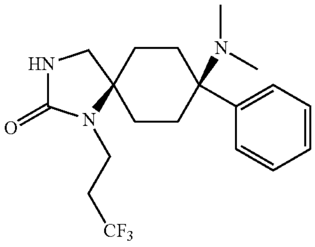 [SMILES: CN(C)[C@]1(c2ccccc2)CC[C@]2(CC1)CNC(=O)N2CCC(F)(F)F] | INT-1068 | 360.2 |
| INT-1074 | CIS-8-(dimethylamino)-8-(3-fluorophenyl)-1-((1-hydroxycyclobutyl)methyl)-1,3-diazaspiro[4.5]decan-2-one | 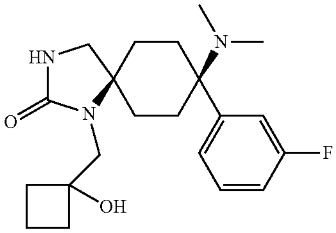 [SMILES: CN(C)[C@]1(c2cccc(F)c2)CC[C@]2(CC1)CNC(=O)N2CC1(O)CCC1] | INT-1031 | 376.2 |

Synthesis of Exemplary Compounds

Synthesis of SC_2002: CIS-1-(Cyclobutyl-methyl)-8-dimethylamino-3-[(3-methoxyphenyl)-methyl]-8-phenyl-1,3-diazaspiro[4.5]decan-2-one

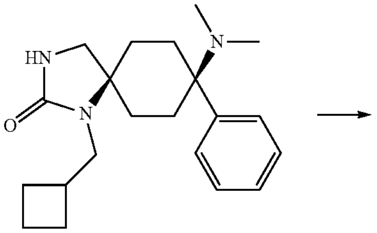

INT-987

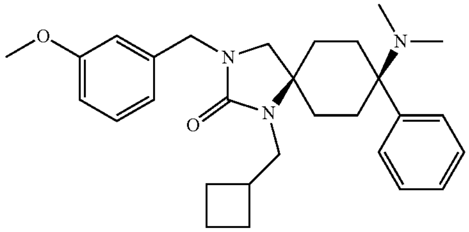

SC_2002

NaH (60% in mineral oil) (70 mg, 2.93 mmol) and 1-(bromomethyl)-3-methoxybenzene (58 mg, 0.29 mmol) were sequentially added to a suspension of CIS-1-(cyclobutyl-methyl)-8-dimethylamino-8-phenyl-1,3-diazaspiro[4.5]decan-2-one INT-987 (100 mg, 0.29 mmol) in DMF (3 mL) at 0° C. and the reaction mixture was stirred at RT for 30 min. The reaction completion was monitored by TLC. The reaction mixture was quenched with sat. aq. $NH_4Cl$ solution and the organic product was extracted with EtOAc (2×12 mL). The combined organic layer was dried over anhydrous $MgSO_4$ and concentrated in vacuo. Purification of the residue by flash column chromatography over silica gel (230-400 mesh) using 30-35% ethyl acetate in petroleum ether as eluent yielded 42 mg of CIS-1-(cyclobutyl-methyl)-8-dimethylamino-3-[(3-methoxyphenyl)-methyl]-8-phenyl-1,3-diazaspiro[4.5]decan-2-one SC_2002 as solid. $[M+H]^+$ 462.3

Synthesis of SC_2008: CIS-8-(Allyl-methyl-amino)-1-(cyclobutyl-methyl)-3-[(4-methoxyphenyl)-methyl]-8-phenyl-1,3-diazaspiro[4.5]decan-2-one

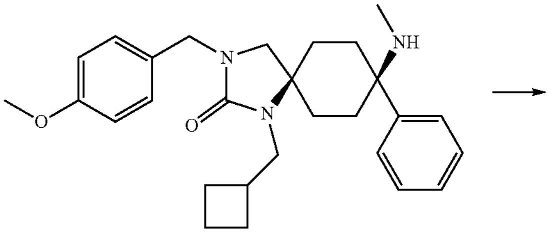

SC_2044

-continued

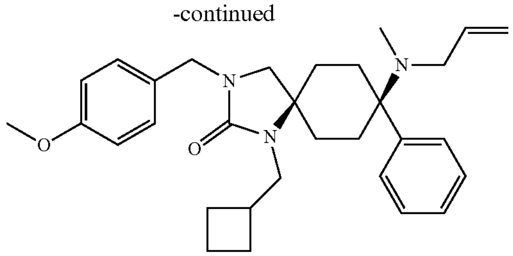

SC_2008

To the solution of CIS-1-(cyclobutyl-methyl)-3-[(4-methoxyphenyl)-methyl]-8-methylamino-8-phenyl-1,3-diazaspiro[4.5]decan-2-one SC_2044 (70 mg, 0.16 mmol) in MeCN (1 mL) was added potassium carbonate (216 mg, 1.56 mmol). The reaction mixture was stirred for 15 min, 3-bromo-prop-1-ene (41 µL, 0.47 mmol) was added and stirring was continued at RT for 3 days. The mixture was then diluted with DCM, filter through celite and the filtrate was concentrated in vacuo. Purification of the residue by flash column chromatography provided 44 mg of CIS-8-(allyl-methyl-amino)-1-(cyclobutyl-methyl)-3-[(4-methoxyphenyl)-methyl]-8-phenyl-1,3-diazaspiro[4.5]decan-2-one SC_2008 as a solid. $[M+H]^+$ 488.3.

Synthesis of SC_2010: CIS-1-(Cyclobutyl-methyl)-8-dimethylamino-8-(3-fluorophenyl)-3-[(4-methoxyphenyl)-methyl]-1,3-diazaspiro[4.5]decan-2-one

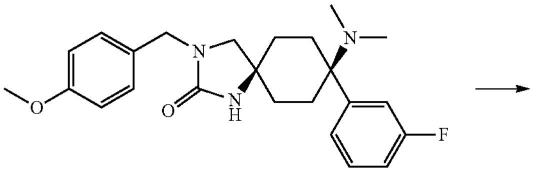

SC_2017

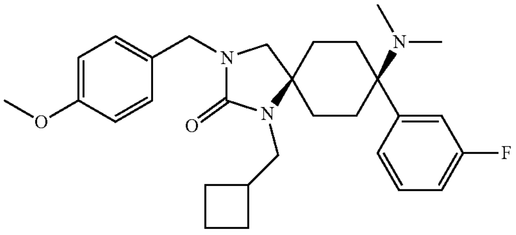

SC_2010

CIS-8-Dimethylamino-8-(3-fluorophenyl)-3-[(4-methoxyphenyl)-methyl]-1,3-diazaspiro[4.5]decan-2-one (SC_2017) (0.2 g, 0.48 mmol) was added to the solution of NaH (60% in mineral oil) (0.08 g, 1.94 mmol) in DMF (5 mL) and the reaction mixture was stirred at RT for 1 h. The reaction mixture was cooled to 0° C., (bromomethyl)cyclobutane (0.21 mL, 1.94 mmol) was added dropwise and stirring was continued for 30 min at 0° C. and then for 2 days at RT. The reaction completion was monitored by TLC. The reaction mixture was quenched with sat. aq. $NH_4Cl$ and the organic product was extracted with EtOAc (2×10 mL). The combined organic extracts were dried over anhydrous $Na_2SO_4$ and concentrated under reduced pressure. Purification of the residue by column chromatography on silica gel (100-200 mesh) using 0-50% EtOAc in petroleum ether as eluent gave 0.1 g of product which was further purified by preparative TLC using 30% EtOAc in petroleum ether as mobile phase to give 65 mg (28%) of CIS-1-(cyclobutyl-methyl)-8-dimethylamino-8-(3-fluorophenyl)-3-[(4-methoxyphenyl)-methyl]-1,3-diazaspiro[4.5]decan-2-one (SC_2010) as an off white solid. (TLC system: 30% EtOAc in petroleum ether; $R_f$: 0.6). $[M+H]^+$ 480.3

Synthesis of SC_2014: CIS-8-Dimethylamino-3-[(4-methoxyphenyl)-methyl]-1-(2-methyl-propyl)-8-phenyl-1,3-diazaspiro[4.5]decan-2-one

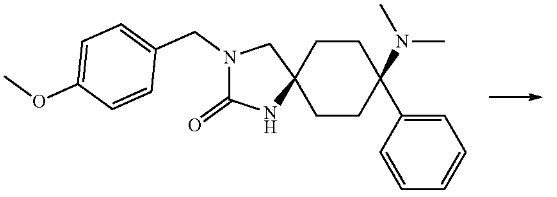

SC_2097

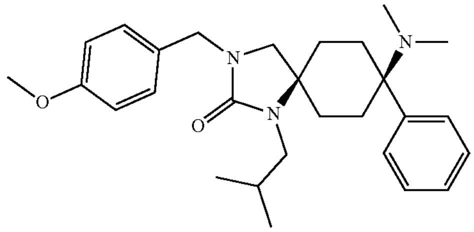

SC_2014

A solution of NaOH (81 mg, 2.0 mmol) in DMSO (1 mL) was stirred at RT for 10 min. CIS-8-Dimethylamino-3-[(4-methoxyphenyl)-methyl]-8-phenyl-1,3-diazaspiro[4.5]decan-2-one (SC_2097) (200 mg, 1.52 mmmol) was added and stirring was continued for 15 min. Isobutyl-bromide (20 mg, 1.52 mmol) was added and the reaction mixture was heated to 60° C. for 16 h. After cooling to RT, water (100 mL) was added and the resulting mixture was extracted with DCM (3x150 mL). The combined organic layers were washed with water (70 mL) and brine (100 mL), dried over $Na_2SO_4$, filtered and concentrated in vacuo. Purification of the residue by column chromatography provided CIS-8-dimethyl-amino-3-[(4-methoxyphenyl)-methyl]-1-(2-methyl-propyl)-8-phenyl-1,3-diazaspiro[4.5]decan-2-one SC_2014 (72 mg) as a solid. $[M+H]^+$ 450.3

Synthesis of SC_2017: CIS-8-Dimethylamino-8-(3-fluorophenyl)-3-[(4-methoxyphenyl)-methyl]-1,3-diazaspiro[4.5]decan-2-one

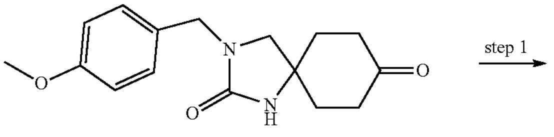

INT-966

-continued

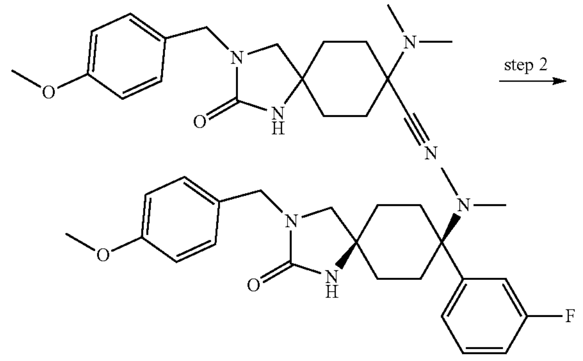

SC_2017

Step 1: 8-(dimethylamino)-3-(4-methoxybenzyl)-2-oxo-1,3-diazaspiro[4.5]decane-8-carbonitrile Dimethylamine hydrochloride (76.36 g, 936.39 mmol) was added to a solution of 3-[(4-methoxyphenyl)-methyl]-1,3-diazaspiro[4.5]decane-2,8-dione INT-966 (90 g, 312.13 mmol) in MeOH (180 mL) at RT under argon atmosphere. The solution was stirred for 15 min and 40% aq. dimethyl-amine (780 mL) and KCN (48.76 g, 749.11 mmol) were sequentially added. The reaction mixture was stirred for 48 h while being monitored by NMR. The reaction mixture was diluted with water (1.0 L) and the organic product was extracted with EtOAc (2x2.0 L). The combined organic layer was dried over anhydrous $Na_2SO_4$ and concentrated under reduced pressure to afford 90 g (85%) of 8-(dimeth-ylamino)-3-(4-methoxybenzyl)-2-oxo-1,3-diazaspiro[4.5]decane-8-carbonitrile as an off white solid (TLC system: TLC system: 10% MeOH in DCM; Rf: 0.35, 0.30).

Step 2: CIS-8-Dimethylamino-8-(3-fluorophenyl)-3-[(4-methoxyphenyl)-methyl]-1,3-diazaspiro[4.5]decan-2-one 3-Fluorophenylmagnesium bromide (1M in THF) (220 mL, 219.17 mmol) was added dropwise to a solution of 8-(dimethylamino)-3-(4-methoxybenzyl)-2-oxo-1,3-diaz-aspiro[4.5]decane-8-carbonitrile (15 g, 43.83 mmol) in THF (300 mL) at 0° C. under argon atmosphere. The reaction mixture was stirred for 16 h at RT. The reaction completion was monitored by TLC. The reaction mixture was cooled to 0° C., quenched with sat. aq. $NH_4Cl$ (200 mL) and the organic product was extracted with EtOAc (2x200 mL). The combined organic layer was dried over anhydrous $Na_2SO_4$ and concentrated under reduced pressure. The reaction was carried out in 4 batches (15 gx2 and 5 gx2) and the batches were purified together. Purification of the residue by flash column chromatography over silica gel (230-400 mesh) (2 times) by using 0-20% methanol in DCM as eluent and further purified by washing with pentane yielded 5.6 g (11%) of CIS-8-Dimethylamino-8-(3-fluorophenyl)-3-[(4-methoxyphenyl)-methyl]-1,3-diazaspiro[4.5]decan-2-one SC_2017 as off-white solid. (TLC system: 5% MeOH in DCM in presence of ammonia; Rf: 0.1). $[M+H]^+$ 412.2

Synthesis of SC_2018: CIS-1-(Cyclobutyl-methyl)-8-dimethylamino-8-(3-hydroxyphenyl)-3-[(4-methoxyphenyl)-methyl]-1,3-diazaspiro[4.5]decan-2-one

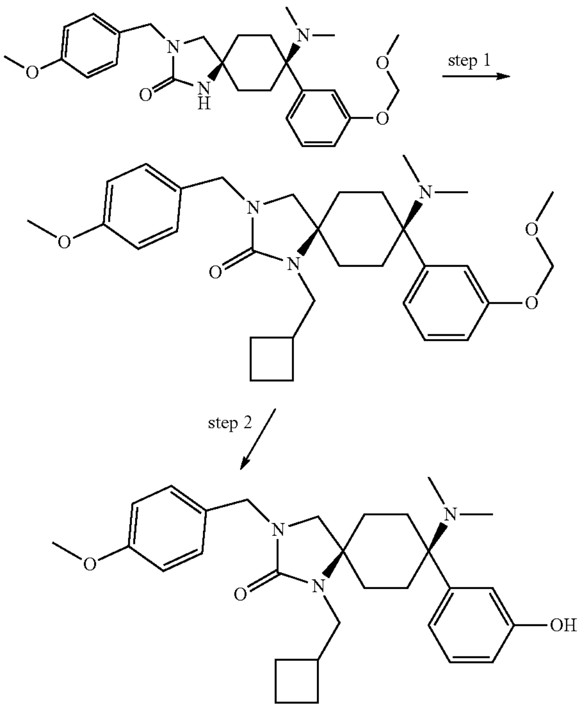

SC_2018

Step 1: CIS-8-(dimethylamino)-1-isobutyl-3-(4-methoxybenzyl)-8-phenyl-1,3-diazaspiro[4.5]decan-2-one In analogy to the method described for INT-951 step 1 CIS-8-dimethylamino-8-[3-(methoxymethyloxy)-phenyl]-3-[(4-methoxyphenyl)-methyl]-1,3-diazaspiro[4.5]decan-2-one (INT-968) was converted into CIS-1-(cyclobutylmethyl)-8-(dimethylamino)-3-(4-methoxybenzyl)-8-(3-(methoxymethoxy)phenyl)-1,3-diazaspiro[4.5]decan-2-one.

Step 2: CIS-1-(Cyclobutyl-methyl)-8-dimethylamino-8-(3-hydroxyphenyl)-3-[(4-methoxyphenyl)-methyl]-1,3-diazaspiro[4.5]decan-2-one TFA (0.2 mL) was added to a solution of CIS-1-(cyclobutylmethyl)-8-(dimethylamino)-3-(4-methoxybenzyl)-8-(3-methoxyphenyl)-1,3-diazaspiro[4.5]decan-2-one (300 mg, 0.57 mmol) in DCM (1.5 mL) at 0° C. The reaction mixture was stirred at 0° C. for 3 h. The reaction completion was monitored by TLC. The reaction mixture was quenched with sat. aq. $NaHCO_3$ and the organic product was extracted with DCM (3×10 mL). The combined organic extracts were dried over anhydrous $Na_2SO_4$ and concentrated under reduced pressure. Purification of the residue by preparative TLC using 3% MeOH in DCM as a mobile phase yielded 50 mg (18%) of CIS-1-(cyclobutyl-methyl)-8-dimethylamino-8-(3-hydroxyphenyl)-3-[(4-methoxyphenyl)-methyl]-1,3-diazaspiro[4.5]decan-2-one (SC_2018) as an off white solid. (TLC system: 10% MeOH in DCM; Rf: 0.20) $[M+H]^+$ 478.3

Synthesis of SC_2019: CIS-1-(Cyclobutyl-methyl)-8-dimethylamino-8-phenyl-3-(pyridin-3-yl-methyl)-1,3-diazaspiro[4.5]decan-2-one

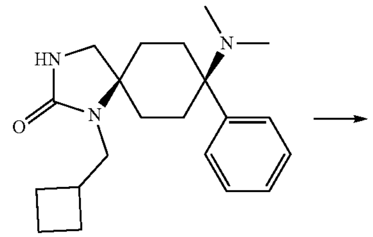

INT-987

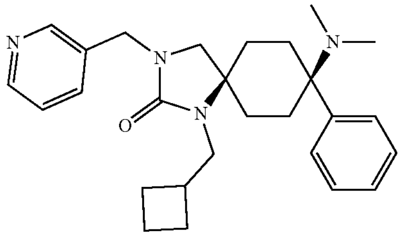

SC_2019

KOtBu (411 mg, 3.66 mmol) was added to a solution of CIS-1-(Cyclobutyl-methyl)-8-dimethylamino-8-phenyl-1,3-diazaspiro[4.5]decan-2-one (INT-987) (250 mg, 0.73 mmol) in THF (6 mL) under nitrogen atmosphere and the reaction mixture was stirred at RT for 30 min. After cooling to 0° C. 3-(chloromethyl)pyridine hydrochloride (180 mg, 1.10 mmol) was added and the reaction mixture was stirred at 0° C. for 30 min and then at RT for 3 days. The resulting mixture was diluted with water, extracted with DCM (3×), the combined organic layers were dried over $MgSO_4$, filtered and concentrated in vacuo. Purification of the residue by flash column chromatography provided 208 mg of CIS-1-(cyclobutyl-methyl)-8-dimethylamino-8-phenyl-3-(pyridin-3-yl-methyl)-1,3-di-azaspiro[4.5]decan-2-one (SC_2019). $[M+H]^+$ 433.3

Synthesis of SC_2025: CIS-8-Dimethylamino-1-(2-methoxy-2-methyl-propyl)-3-[(4-methoxyphenyl)-methyl]-8-phenyl-1,3-diazaspiro[4.5]decan-2-one

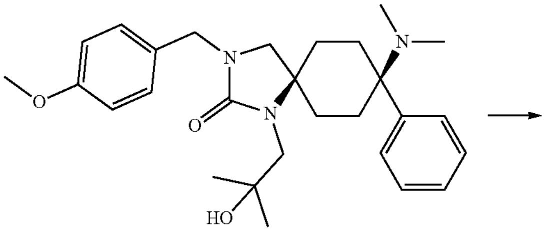

SC_2024

-continued

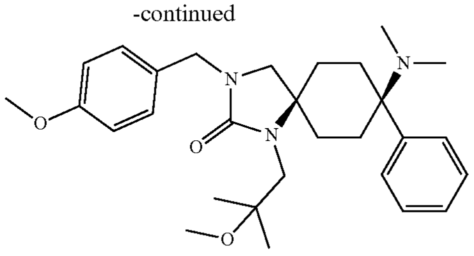

SC_2025

CIS-8-Dimethylamino-1-(2-hydroxy-2-methyl-propyl)-3-[(4-methoxyphenyl)-methyl]-8-phenyl-1,3-diazaspiro[4.5]decan-2-one SC_2024 (0.2 g, 0.42 mmol) was added to a solution of NaH (60% in mineral oil) (0.01 g, 0.42 mmol) in DMF (5 mL) at RT. The reaction mixture was stirred at RT for 30 min, then cooled to 0° C. and methyl iodide (0.08 g, 1.28 mmol) was added dropwise. the resulting mixture was stirred for 30 min at 0° C. and then for 16 h at RT. The reaction completion was monitored by TLC. The reaction mixture was quenched with sat. aq. $NH_4Cl$ and the organic product was extracted with EtOAc (2x0 mL). The combined organic extracts were dried over anhydrous $Na_2SO_4$ and concentrated under reduced pressure. The residue was purified by preparative TLC using 30% EtOAc in petroleum ether as a mobile phase to give 40 mg (20%) of CIS-8-dimethylamino-1-(2-methoxy-2-methyl-propyl)-3-[(4-methoxyphenyl)-methyl]-8-phenyl-1,3-diazaspiro[4.5]decan-2-one (SC_2025) as an off white solid. (TLC system: 30% EtOAc in Pet. Ether; $R_f$: 0.6). $[M+H]^+$ 480.3.

Synthesis of SC_2026: CIS-1-(Cyclobutyl-methyl)-3-[(3-methoxyphenyl)-methyl]-8-methylamino-8-phenyl-1,3-diazaspiro[4.5]decan-2-one

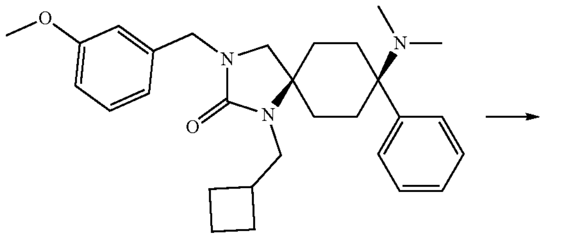

SC_2024

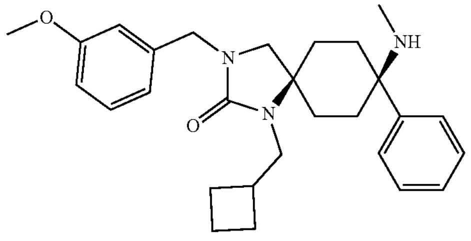

SC_2026

N-Iodosuccinimide (437 mg, 1.95 mmol) was added to a suspension of CIS-1-(cyclobutyl-methyl)-8-dimethylamino-3-[(3-methoxyphenyl)-methyl]-8-phenyl-1,3-diazaspiro[4.5]decan-2-one (SC_2002) (600 mg, 1.30 mmol) in a mixture of acetonitrile and THF (1:1 v/v, 20 mL) at RT and the resulting mixture was stirred at RT for 16 h. The reaction mixture was basified with 2N aq. NaOH to pH~10 and the organic product was extracted with DCM (3x10 mL). The combined organic extracts were dried over anhydrous sodium sulfate and concentrated under reduced pressure. The residue was stirred vigorously with a mixture of 10% aqueous citric acid solution (5 mL) and DCM (10 mL) at RT for 10 min. The resulting mixture was basified with 5N aq. NaOH to pH-10 and extracted with DCM (3x10 mL). The combined organic layer was dried over anhydrous sodium sulfate and was concentrated in vacuo. The residue was purified by preparative reverse phase HPLC [Column: KINETEX C-18 (150*21.2) 5μ and mobile phase: 10 mM ammonium bicarbonate-acetonitrile] to give 120 mg (20%) of CIS-1-(Cyclobutyl-methyl)-3-[(3-methoxyphenyl)-methyl]-8-methylamino-8-phenyl-1,3-diazaspiro[4.5]decan-2-one (SC_2026) as semi solid (TLC system: 10% MeOH in DCM; $R_f$: 0.20.). $[M+H]^+$ 448.3

Synthesis of SC_2028: CIS-1-(Cyclobutyl-methyl)-3-[(3-methoxyphenyl)-methyl]-8-(methyl-propyl-amino)-8-phenyl-1,3-diazaspiro[4.5]decan-2-one

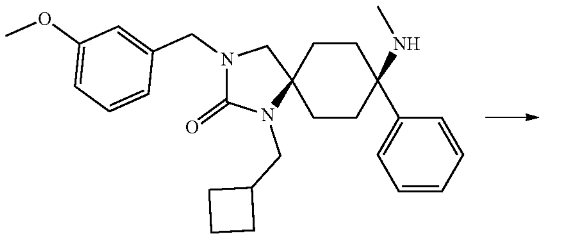

SC_2026

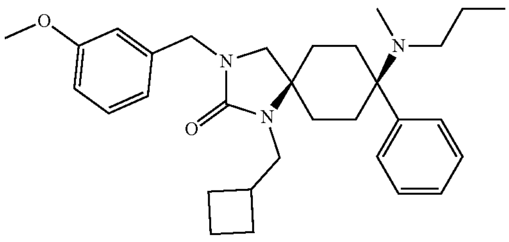

SC_2028

Sodium cyanoborohydride (20 mg, 0.33 mmol) was added to a solution of CIS-1-(cyclobutyl-methyl)-3-[(3-methoxyphenyl)-methyl]-8-methylamino-8-phenyl-1,3-diazaspiro[4.5]decan-2-one (SC_2026) (60 mg, 0.13 mmol), propionaldehyde (19 mg, 0.33 mmol) and acetic acid (0.05 mL) in methanol (5 mL) at RT. The reaction mixture was stirred at RT for 3 h. The reaction mixture was quenched with sat. aq. $NaHCO_3$ and the organic product was extracted with DCM (10 mL 3). The combined organic extracts were dried over anhydr. $Na_2SO_4$ and concentrated under reduced pressure. A second batch of this reaction was carried out starting from 100 mg of CIS-1-(Cyclobutyl-methyl)-3-[(3-methoxyphenyl)-methyl]-8-methylamino-8-phenyl-1,3-diazaspiro[4.5]decan-2-one SC_2026 in a similar manner. Both batches were combined and purified by preparative TLC to give 45 mg (25%) of CIS-1-(cyclobutyl-methyl)-3-[(3-methoxyphenyl)-methyl]-8-(methyl-propyl-amino)-8-phenyl-1,3-diazaspiro[4.5]decan-2-one (SC_2028) as semi solid (TLC system: 10% MeOH in DCM; $R_f$: 0.25). $[M+H]^+$ 490.3

Synthesis of SC_2034: CIS-8-Dimethylamino-1-(2-hydroxy-ethyl)-3-[(4-methoxyphenyl)-methyl]-8-phenyl-1,3-diazaspiro[4.5]decan-2-one

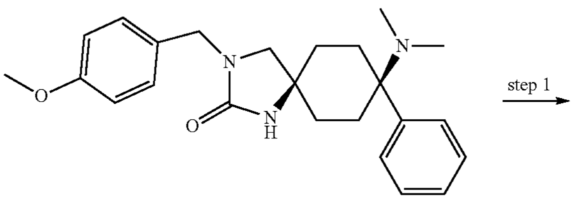

SC_2097

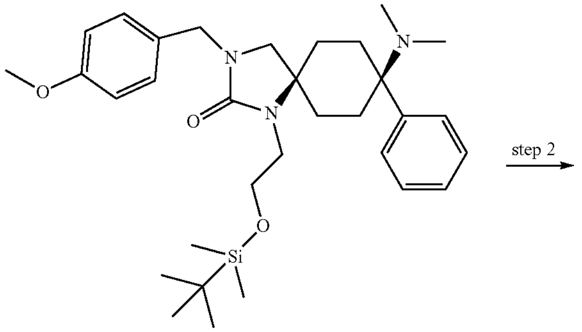

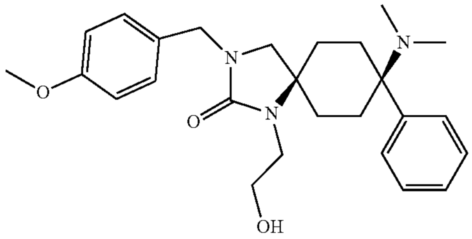

SC_2034

NaH (55% in mineral oil) (0.26 g, 6.10 mmol) was added to a solution of CIS-8-dimethylamino-3-[(4-methoxyphenyl)-methyl]-8-phenyl-1,3-diazaspiro[4.5]decan-2-one (SC_2097) (0.4 g, 1.02 mmol) in DMF (10 mL) at 0° C. The reaction mixture was stirred at 0° C. for 15 min. To the reaction mixture (2-bromoethoxy)(tert-butyl)dimethylsilane (1.45 g, 6.10 mmol) was added dropwise over 5 min at 0° C. The reaction mixture was allowed to stir at RT for 16 h and then diluted with water (15 mL). The organic product was extracted with ethyl acetate (3x25 mL). The combined organic extracts were dried over anhydrous $Na_2SO_4$ and concentrated under reduced pressure. The residue was dissolved in THF (8 mL) and cooled to 0° C. Then a 1M TBAF solution in THF (1.8 mL, 1.81 mmol) was added at 0° C. The reaction mixture was allowed to stir at RT for 2 h. The reaction mixture was diluted with water (10 mL), the organic product was extracted with DCM (3x25 mL). The combined organic extracts were washed with sat. aq. $NaHCO_3$, water and brine, dried over anhydrous $Na_2SO_4$ and concentrated under reduced pressure. Purification by prep HPLC using 10 Mm ammonium bicarbonate-acetonitrile as mobile phase yielded 93 mg of compound which was further washed with n-pentane (5 mL) to give 85 mg (19% after two steps) of CIS-8-dimethyl-amino-1-(2-hydroxy-ethyl)-3-[(4-methoxyphenyl)-methyl]-8-phenyl-1,3-diazaspiro[4.5]decan-2-one (SC_2034) as off white solid. (TLC system: 5% MeOH in DCM $R_f$: 0.30). $[M+H]^+$ 438.3

Synthesis of SC_2040: CIS-2-[[1-(Cyclobutyl-methyl)-3-[(4-methoxyphenyl)-methyl]-2-oxo-8-phenyl-1,3-diazaspiro[4.5]decan-8-yl]-methyl-amino]-acetonitrile

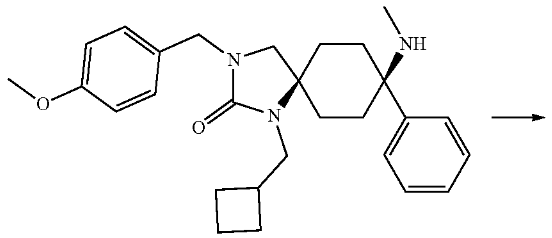

SC_2040

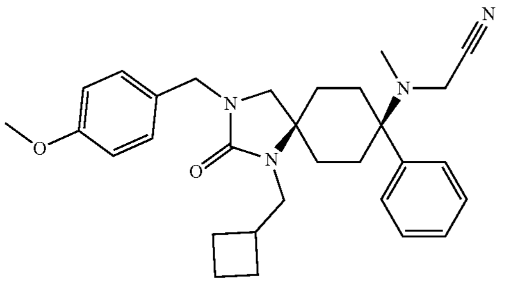

SC_2044

NaH (50% in mineral oil) (24 mg, 0.6 mmol) was added to a stirred solution of CIS-1-(cyclobutyl-methyl)-3-[(4-methoxyphenyl)-methyl]-8-methylamino-8-phenyl-1,3-diazaspiro decan-2-one (SC_2044) (134 mg, 0.3 mmol) in DMF (1 mL) at 0° C. Then iodoacetonitrile (0.11 mL, 1.5 mmol) was added dropwise at 0° C. over a period of 10 min. The reaction mixture was allowed to stir at RT for 16 h. The reaction mixture was quenched with water and the organic product was extracted with EtOAc (3x). The combined organic extracts were washed with brine, dried over anhydrous $MgSO_4$, filtered and concentrated under reduced pressure. Purification of the residue by flash column chromatography provided 13 mg of CIS-2-[[1-(cyclobutyl-methyl)-3-[(4-methoxyphenyl)-methyl]-2-oxo-8-phenyl-1,3-diazaspiro[4.5]decan-8-yl]-methyl-amino]-acetonitrile (SC_2040). $[M+H]^+$ 487.3

Synthesis of SC_2042: CIS-2-[8-Dimethylamino-3-[(4-methoxyphenyl)-methyl]-2-oxo-8-phenyl-1,3-diazaspiro[4.5]decan-1-yl]-acetic Acid tert-butyl Ester

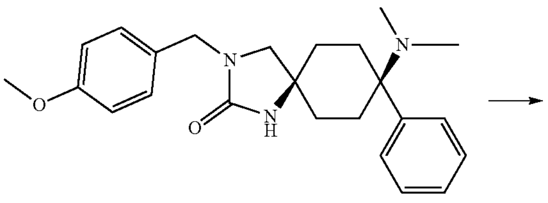

SC_2097

-continued

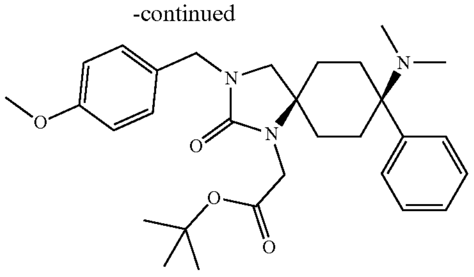

SC_2042

CIS-8-Dimethylamino-3-[(4-methoxyphenyl)-methyl]-8-phenyl-1,3-diazaspiro[4.5]decan-2-one SC_2097 (500 mg, 1.3 mmol) was dissolved in 1.7 mL THF and LDA (2M solution in THF, 2.5 mL) was added at 0° C. The reaction mixture was stirred at RT for 30 min, then cooled to 0° C. and tert-butylbromoacetate (0.5 mL, 3.8 mmol) was added. The reaction was stirred for 18 h, then diluted with water and extracted with DCM (3×10 ml). The combined organic layers were dried over $Na_2SO_4$, concentrated in vacuo and the residue was purified by flash chromatography to yield CIS-2-[8-dimethylamino-3-[(4-methoxyphenyl)-methyl]-2-oxo-8-phenyl-1,3-diazaspiro[4.5]decan-1-yl]-acetic acid tert-butyl ester (SC_2042) (470 mg) as a white solid. $[M+H]^+$ 508.3

Synthesis of SC_2043: CIS-2-[8-Dimethylamino-3-[(4-methoxyphenyl)-methyl]-2-oxo-8-phenyl-1,3-diazaspiro[4.5]decan-1-yl]-acetic acid 2,2,2-trifluoroacetic Acid Salt

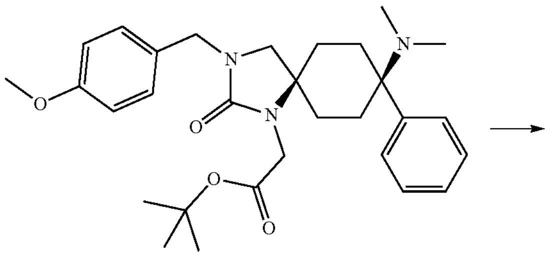

SC_2042

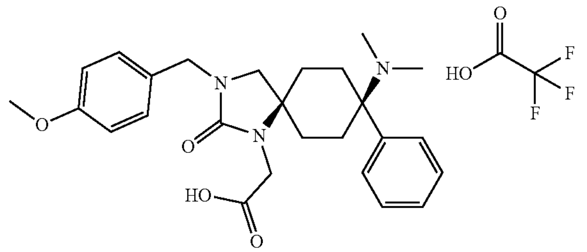

SC_2043

CIS-2-[8-Dimethylamino-3-[(4-methoxyphenyl)-methyl]-2-oxo-8-phenyl-1,3-diazaspiro[4.5]decan-1-yl]-acetic acid tert-butyl ester SC_2042 (200 mg, 0.4 mmol) was dissolved in trifluoroacetic acid (5 mL) and stirred at RT for 30 min. All volatiles are removed in vacuo to yield CIS-2-[8-dimethylamino-3-[(4-methoxyphenyl)-methyl]-2-oxo-8-phenyl-1,3-diazaspiro[4.5]decan-1-yl]-acetic acid 2,2,2-trifluoro-acetic acid salt SC_2043 (190 mg) as a solid. $[M+H]^+$ 452.3

Synthesis of SC_2049: CIS-2-[8-Dimethylamino-3-[(4-methoxyphenyl)-methyl]-2-oxo-8-phenyl-1,3-diazaspiro[4.5]decan-1-yl]-N-propyl-acetamide

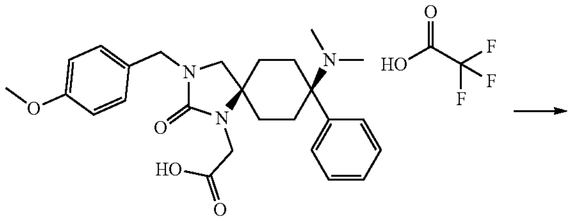

SC_2043

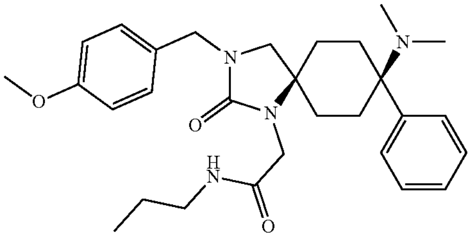

SC_2049

To a mixture of CIS-2-[8-dimethylamino-3-[(4-methoxyphenyl)-methyl]-2-oxo-8-phenyl-1,3-diazaspiro[4.5]decan-1-yl]-acetic acid 2,2,2-trifluoro-acetic acid salt (SC_2043) (60 mg, 0.11 mmol), n-propylamine (35 μL, 0.43 mmol) and DIPEA (109 μL, 0.64 mmol) in DMF (1 ml) was added HATU (60 mg, 0.16 mmol) and the reaction mixture was stirred at RT for 16 h. The reaction mixture was quenched with a 1M aq. $NaHCO_3$, diluted with water and extracted with DCM (3×). The combined organic layers were washed with water (3 mL), brine (3 ml), dried over $Na_2SO_4$, filtered and concentrated in vacuo. Flash column chromatography of the residue provided CIS-2-[8-dimethylamino-3-[(4-methoxyphenyl)-methyl]-2-oxo-8-phenyl-1,3-diazaspiro[4.5]decan-1-yl]-N-propyl-acetamide (SC_2049) (20 mg). $[M+H]^+$ 493.3

Synthesis of SC_2053: CIS-2-[8-Dimethylamino-3-[(4-methoxyphenyl)-methyl]-2-oxo-8-phenyl-1,3-diazaspiro[4.5]decan-1-yl]-acetonitrile

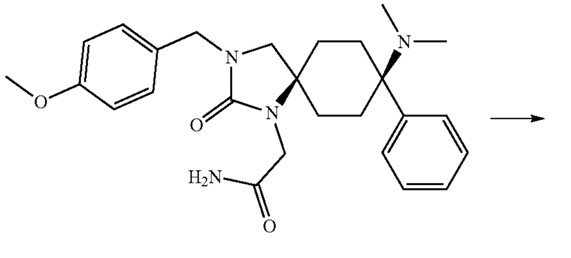

SC_2046

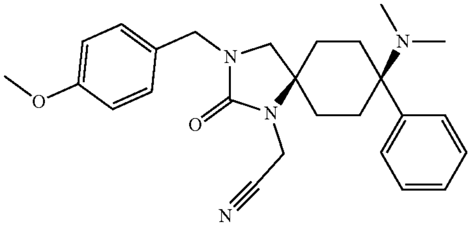

SC_2053

CIS-2-[8-Dimethylamino-3-[(4-methoxyphenyl)-methyl]-2-oxo-8-phenyl-1,3-diazaspiro[4.5]decan-1-yl]-acetamide (SC_2046) (37 mg, 0.083 mmol) was dissolved in EtOAc (1 mL) and triethylamine (23 μL, 0.166 mmol) and T3P (59 μL, 0.099 mmol) were sequentially added. The reaction mixture was stirred at RT for 16 h and then heated at reflux for another 3 h. After cooling to RT the reaction mixture was partitioned between water and DCM. The organic layer was separated and the aqueous layers was extracted twice with DCM. The combined organic layers were dried over $MgSO_4$, concentrated in vacuo and the residue was purified by flash chromatography to yield CIS-2-[8-dimethylamino-3-[(4-methoxyphenyl)-methyl]-2-oxo-8-phenyl-1,3-diazaspiro[4.5]decan-1-yl]-acetonitrile (SC_2053) (31 mg) as a solid. $[M+H]^+$ 433.3

Synthesis of SC_2073: CIS-1-(Cyclobutyl-methyl)-8-[(2-hydroxy-ethyl)-methyl-amino]-3-[(4-methoxy-phenyl)-methyl]-8-phenyl-1,3-diazaspiro[4.5]decan-2-one

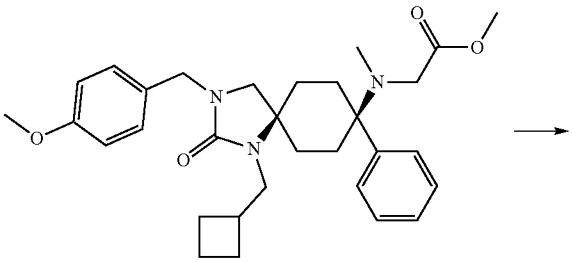

SC_2134

-continued

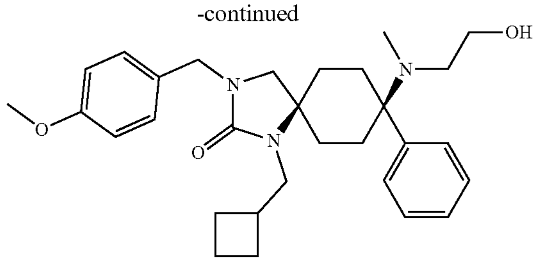

SC_2073

To a solution of CIS-2-[[1-(cyclobutyl-methyl)-3-[(4-methoxyphenyl)-methyl]-2-oxo-8-phenyl-1,3-diazaspiro[4.5]decan-8-yl]-methyl-amino]-acetic acid methyl ester (SC_2134) (125 mg, 0.24 mmol) in THF (1 mL) was added lithium borohydride (2M in THF, 0.36 mL, 0.72 mmol) at RT. The reaction mixture was stirred at RT for 16 h followed by addition of another portion of lithium borohydride (2M in THF, 0.36 mL, 0.72 mmol). After stirring at RT for 16 h, the reaction mixture was quenched with water. The organic layer was separated, washed with a 1M aq. NaOH and water, dried over $MgSO_4$, filtered and concentrated in vacuo. Purification of the residue by flash chromatography provided 37 mg of CIS-1-(cyclobutyl-methyl)-8-[(2-hydroxy-ethyl)-methyl-amino]-3-[(4-methoxyphenyl)-methyl]-8-phenyl-1,3-diazaspiro[4.5]decan-2-one (SC_2073). $[M+H]^+$ 492.3

Synthesis of SC_2087: CIS-1-(Cyclobutyl-methyl)-8-dimethylamino-3-[[4-[2-[2-[2-[2-[2-[2-[2-(2-methoxy-ethoxy)-ethoxy]-ethoxy]-ethoxy]-ethoxy]-ethoxy]-ethoxy]-ethoxy]-phenyl]-methyl]-8-phenyl-1,3-diazaspiro[4.5]decan-2-one

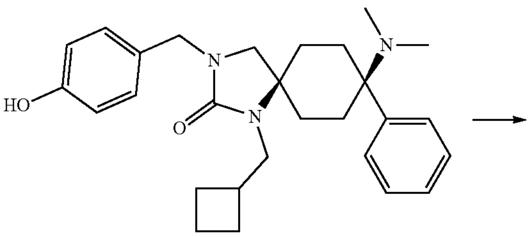

SC_2049

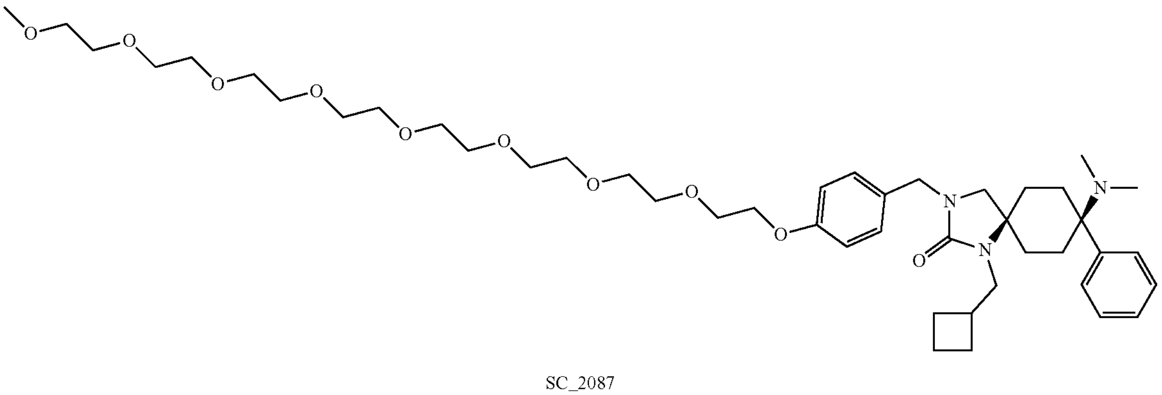

SC_2087

Powdered sodium hydroxide (21 mg, 0.5 mmol) was dissolved in 0.2 mL of dry DMSO. After stirring at RT for 30 min CIS-1-(cyclobutyl-methyl)-8-dimethylamino-3-[(4-hydroxyphenyl)-methyl]-8-phenyl-1,3-diazaspiro[4.5]decan-2-one (SC_2089) (60 mg, 0.13 mmol) was added and the resulting mixture was stirred for another 30 min. Then 2,5,8,11,14,17,20,23-octaoxapentacosan-25-yl 4-methylbenzenesulfonate (prepared via tosylation of 2,5,8,11,14,17,20,23-octaoxapentacosan-25-ol following standard procedures) (216 mg, 0.4 mmol) was added. The reaction mixture was stirred at 60° C. for 16 h. The reaction mixture was quenched with water and the organic product was extracted with DCM (2×20 mL). The combined organic extracts were dried over anhydrous $Na_2SO_4$, concentrated in vacuo and the residue was purified by flash chromatography to yield CIS-1-(cyclobutyl-methyl)-8-dimethylamino-3-[[4-[2-[2-[2-[2-[2-[2-[2-(2-methoxy-ethoxy)-ethoxy]-ethoxy]-ethoxy]-ethoxy]-ethoxy]-ethoxy]-ethoxy]-phenyl]-methyl]-8-phenyl-1,3-diazaspiro[4.5]decan-2-one (SC_2087) (25 mg) as a white solid. $[M+H]^+$ 814.5

Synthesis of SC_2089: CIS-1-(Cyclobutyl-methyl)-8-dimethylamino-3-[(4-hydroxyphenyl)-methyl]-8-phenyl-1,3-diazaspiro[4.5]decan-2-one

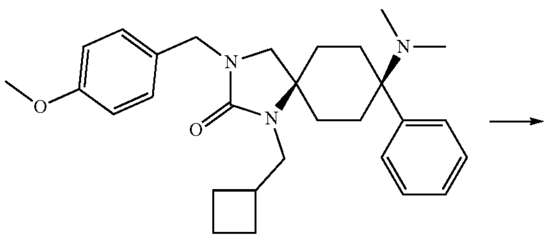

SC_2125

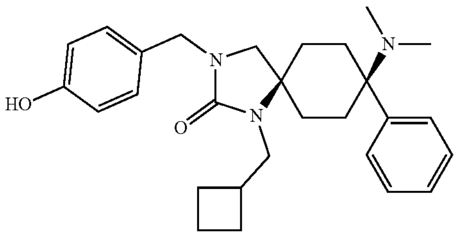

SC_2089

CIS-1-(Cyclobutyl-methyl)-8-dimethylamino-3-[(4-methoxyphenyl)-methyl]-8-phenyl-1,3-diazaspiro[4.5]decan-2-one (SC_2125) (153 mg, 0.33 mmol) was dissolved in DCM (7 mL) and boron tribromide (1M solution in DCM, 1.3 mL) was added at 0° C. The reaction was stirred for 18 h, then water and methanol (1:1 mixture, 6 mL) was added. The reaction mixture was extracted with DCM (3×10 ml). The combined organic layers were dried over $Na_2SO_4$, concentrated in vacuo and the residue was purified by flash chromatography to yield CIS-1-(cyclobutyl-methyl)-8-dimethylamino-3-[(4-hydroxyphenyl)-methyl]-8-phenyl-1,3-diazaspiro[4.5]decan-2-one (SC_2089) (21 mg) as a white solid. $[M+H]^+$ 448.3

Synthesis of SC_2093: CIS-1-(Cyclobutyl-methyl)-8-dimethylamino-3-[(3-methylsulfonyl-phenyl)-methyl]-8-phenyl-1,3-diazaspiro[4.5]decan-2-one

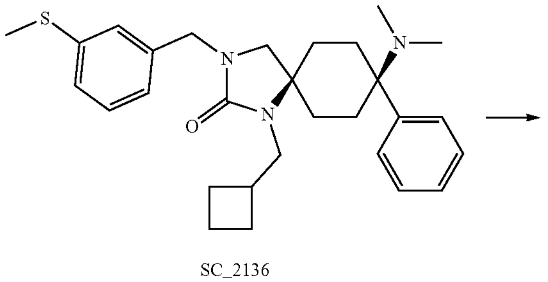

SC_2136

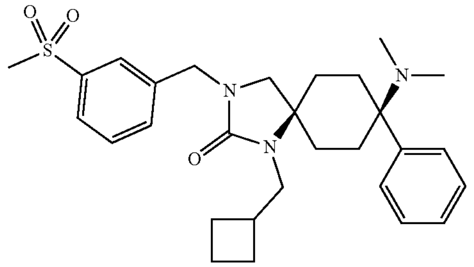

SC_2093

CIS-1-(Cyclobutyl-methyl)-8-dimethylamino-3-[(3-methylsulfanyl-phenyl)-methyl]-8-phenyl-1,3-diazaspiro[4.5]decan-2-one (SC_2136) (109 mg) was dissolved in methanol (3 mL) and water (2 mL) and oxone (105 mg) was added at RT. The reaction mixture was stirred for 24 h, another portion of oxone (105 mg) was added, the reaction mixture was stirred for 12 h at RT, then diluted with water and extracted with DCM (3×10 mL). The combined organic layers were dried over $Na_2SO_4$ and concentrated in vacuo. The residue was purified by flash chromatography to yield CIS-1-(cyclobutyl-methyl)-8-dimethylamino-3-[(3-methylsulfonyl-phenyl)-methyl]-8-phenyl-1,3-diazaspiro[4.5]decan-2-one (SC_2093) as a white solid. $[M+H]^+$ 510.3

Synthesis of SC_2097: CIS-8-Dimethylamino-3-[(4-methoxyphenyl)-methyl]-8-phenyl-1,3-diazaspiro[4.5]decan-2-one

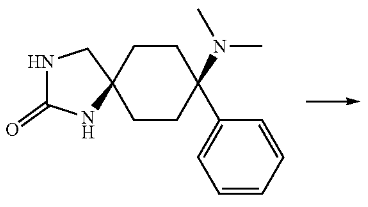

INT-976

-continued

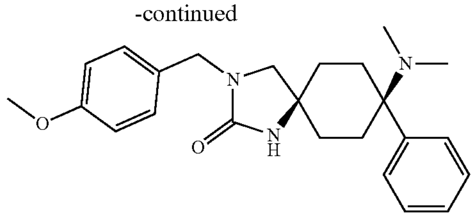

SC_2097

KOtBu (1M in THF) (29.30 mL, 29.30 mmol) was added to the solution of CIS-8-Dimethylamino-8-phenyl-1,3-diazaspiro[4.5]decan-2-one INT-976 (8.0 g, 29.30 mmol) in THF (160 mL) under argon atmosphere and the reaction mixture was stirred for 30 min. 4-Methoxybenzyl bromide (4.23 mL, 29.30 mmol) was added and stirring was continued at RT for 4 h. The reaction completion was monitored by TLC. The reaction mixture was diluted with sat. aq. $NH_4Cl$ (150 mL) and the organic product was extracted with EtOAc (2×150 mL). The combined organic layer was dried over anhydrous $Na_2SO_4$ and concentrated in vacuo. The reaction was carried out in 2 batches (8 g×2) and the batches were combined for purification. Purification of the crude product by flash column chromatography on silica gel (0-10% methanol in DCM) and subsequently by washing with pentane yielded 11 g (47%) of CIS-8-Dimethylamino-3-[(4-methoxyphenyl)-methyl]-8-phenyl-1,3-diazaspiro[4.5]decan-2-one (SC_2097) as a white solid. $[M+H]^+$ 394.2

Synthesis of SC_2107: CIS-8-Dimethylamino-1-(3-hydroxy-3-methyl-butyl)-3-[(4-methoxyphenyl)-methyl]-8-phenyl-1,3-diazaspiro[4.5]decan-2-one

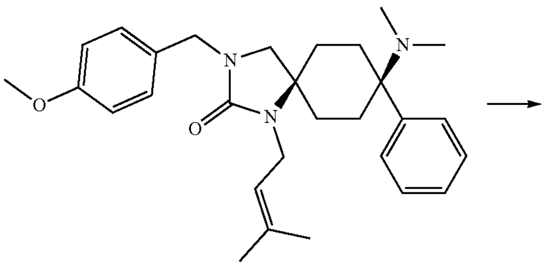

SC_2135

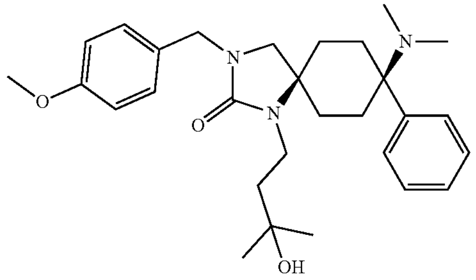

SC_2107

50 wt % aq. sulphuric acid (0.57 mL) was added to the solution of CIS-8-dimethylamino-3-[(4-methoxyphenyl)-methyl]-1-(3-methyl-but-2-enyl)-8-phenyl-1,3-diazaspiro[4.5]decan-2-one (SC_2135) (0.25 g, 0.54 mmol) in 1,4-dioxane (5.75 mL) at RT and the reaction mixture was stirred for 3 h at RT. The reaction mixture was quenched with sat. aq. $NaHCO_3$ and the organic product was extracted with ethyl acetate (2×10 mL). The combined organic extracts were dried over anhydr. $Na_2SO_4$ and concentrated under reduced pressure. The residue was purified by reverse phase preparative HPLC to give 0.04 g (15%) of CIS-8-dimethylamino-1-(3-hydroxy-3-methyl-butyl)-3-[(4-methoxyphenyl)-methyl]-8-phenyl-1,3-diazaspiro[4.5]decan-2-on (SC_2107) as an off white solid. (TLC system: 10% MeOH in DCM; Rf: 0.4). $[M+H]^+$ 480.3

Synthesis of SC_2109: CIS-2-[[8-dimethylamino-1-[(1-hydroxy-cyclobutyl)-methyl]-2-oxo-8-phenyl-1,3-diazaspiro[4.5]decan-3-yl]-methyl]-benzamide

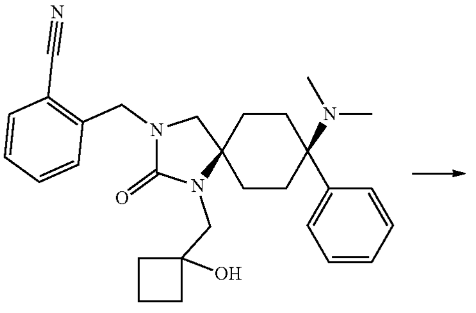

SC_2138

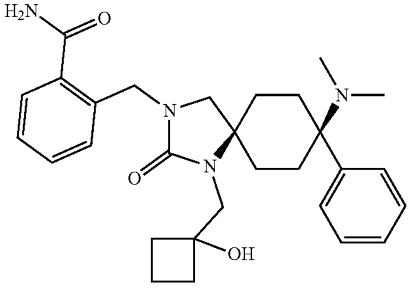

SC_2109

30% aq. $H_2O_2$ (0.3 mL, 2.54 mmol) was added to a solution of CIS-2-((8-(dimethylamino)-1-((1-hydroxycyclobutyl)methyl)-2-oxo-8-phenyl-1,3-diazaspiro[4.5]decan-3-yl)methyl)benzonitrile (SC_2138) (0.4 g, 0.85 mmol) in DMSO (8 mL) at 0° C. A solution of potassium hydroxide (0.23 g, 4.23 mmol) in water (0.5 mL) was added dropwise. The reaction mixture was allowed to warm up to RT and stirred for 30 min and then quenched with cold water (20 mL). The precipitated product was filtered off and washed with water. Purification by preparative TLC using 5% methanol in DCM as mobile phase yielded 78 mg of target compound which was further washed with n-pentane (5 mL) to give 70 mg (17%) of CIS-2-[[8-dimethylamino-1-[(1-hydroxy-cyclobutyl)-methyl]-2-oxo-8-phenyl-1,3-diazaspiro[4.5]decan-3-yl]-methyl]-benzamide (SC_2109) as an off-white solid. (TLC system: 10% MeOH in DCM $R_f$: 0.4). $[M+H]^+$ 491.3

Synthesis of SC_2123: CIS-8-amino-1-[(1-hydroxy-cyclobutyl)-methyl]-3-[(4-methoxyphenyl)-methyl]-8-phenyl-1,3-diazaspiro[4.5]decan-2-one

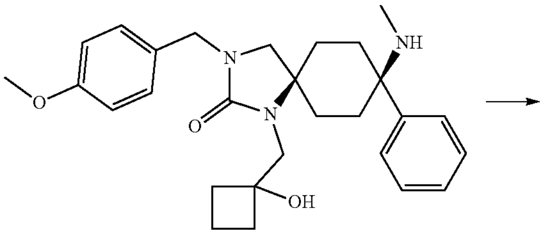

SC_2026

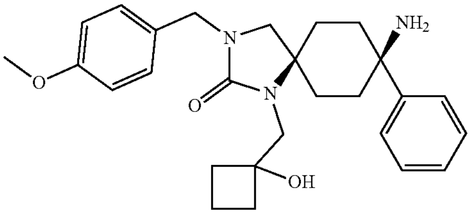

SC_2123

N-Iodosuccinimide (233 mg, 1.035 mmol) was added to a solution of CIS-1-[(1-hydroxy-cyclobutyl)-methyl]-3-[(4-methoxyphenyl)-methyl]-8-methylamino-8-phenyl-1,3-diazaspiro[4.5]decan-2-one (SC_2026) (320 mg, 0.690 mmol) in a mixture of acetonitrile and THF (1:1 v/v, 30 mL) at 0° C. and the resulting mixture was stirred for 5 h at RT. The reaction mixture was cooled to 0° C. and another portion of N-Iodosuccinimide (233 mg, 1.035 mmol) was added. The reaction mixture was allowed to warm up to RT and was stirred for further 11 h. The reaction mixture was basified with 2N aq. NaOH to pH~10 and the organic product was extracted with ethyl acetate (3×30 mL). The combined organic extracts were dried over anhydrous sodium sulfate and concentrated under reduced pressure. The residue was purified by preparative TLC by using 3% methanol in DCM as a mobile phase to give 100 mg of target compound which was further purified by preparative reverse phase HPLC to give 65 mg (21%) of CIS-8-amino-1-((1-hydroxycyclobutyl)methyl)-3-(4-methoxybenzyl)-8-phenyl-1,3-diaza-spiro[4.5]decan-2-one (SC_2123) as an off-white solid (TLC system: 5% MeOH in DCM; $R_f$: 0.40.). $[M+H]^+$ 450.3

Synthesis of SC_2124: CIS-8-dimethylamino-1-[(1-hydroxy-cyclobutyl)-methyl]-8-phenyl-3-(2-phenyl-ethyl)-1,3-diazaspiro[4.5]decan-2-one

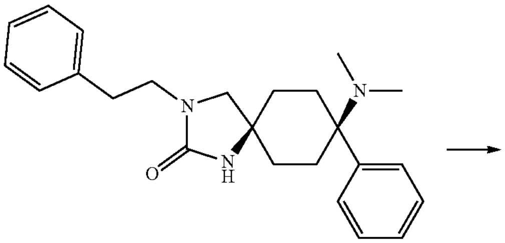

INT-795

-continued

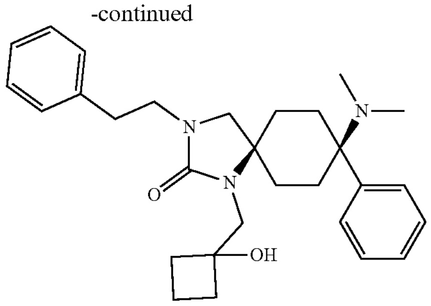

SC_2124

NaOH (0.53 g, 13.26 mmol) was added to a solution of CIS-8-dimethylamino-8-phenyl-3-(2-phenyl-ethyl)-1,3-diazaspiro[4.5]decan-2-one INT-795 (1 g, 2.65 mmol) in DMSO (50 mL) under argon atmosphere at RT and the reaction mixture was stirred at 70° C. for 30 min. (1-(Tert-butyldimethylsilyloxy)cyclobutyl)methyl-4-methylbenzenesulfonate (2.94 g, 7.95 mmol) was added and stirring was continued for 2 days at 70° C. The reaction completion was monitored by TLC. The reaction mixture was diluted with sat. aq. $NaHCO_3$ (20 mL) and the organic product was extracted with EtOAc (4×50 mL). The combined organic layer was dried over anhydr. $Na_2SO_4$ and concentrated in vacuo. The crude product was purified by column chromatography (using 230-400 mesh silica gel and 2-5% MeOH in DCM as eluent) to afford 250 mg of product which was further purified by prep. TLC (4% MeOH: DCM as an eluent) followed by washing with pentane to yield 133 mg (11%) of CIS-8-dimethylamino-1-[(1-hydroxy-cyclobutyl)-methyl]-8-phenyl-3-(2-phenyl-ethyl)-1,3-diazaspiro[4.5]decan-2-one (SC_2124) as an off-white solid. (TLC system: 10% MeOH in DCM; Rf: 0.8). $[M+H]^+$ 462.3

Synthesis of SC_2125: CIS-1-(Cyclobutyl-methyl)-8-dimethylamino-8-phenyl-3-[(4-methoxyphenyl)-methyl]-1,3-diazaspiro[4.5]decan-2-one

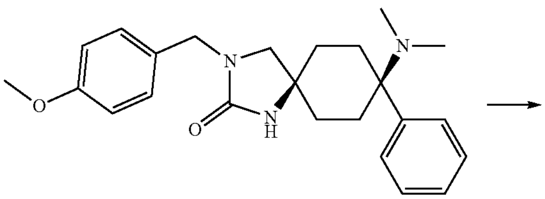

SC_2097

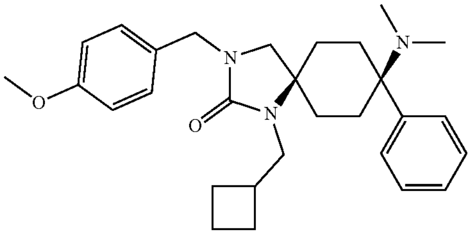

SC_2125

To a solution of CIS-8-dimethylamino-3-[(4-methoxyphenyl)-methyl]-8-phenyl-1,3-diazaspiro[4.5]decan-2-one (SC_2097) (10 g, 25 mmol) in 500 mL THF was added KOtBu (7.1 g, 63 mmol) at 50° C. The reaction mixture was heated up to reflux and cyclobutylmethylbromide (11.3 g, 76 mmol) was added quickly in one portion. After 12 h new portions of KOtBu (7.1 g) and cyclobutylmethylbromide (11.3 g) were added and the reaction mixture was allowed to stir for 2 h at reflux and was then cooled to RT. Water (150 mL) was added and the organic layer separated. The aqueous layer was extracted with ethyl acetate (3x300 mL). The combined organic layers were dried over $Na_2SO_4$ and then concentrated in vacuo. The residue was filtered through a pad of silica gel using DCM/MeOH (19/1 v/v). The filtrate was concentrated in vacuo and the resulting solid was recrystallized from hot ethanol to yield 7.8 g of CIS-1-(cyclobutyl-methyl)-8-dimethylamino-8-phenyl-3-[(4-methoxyphenyl)-methyl]-1,3-diazaspiro[4.5]decan-2-one (SC_2125). $[M+H]^+$ 461.3

Synthesis of SC_2136: CIS-1-(Cyclobutyl-methyl)-8-dimethylamino-3-[(3-methylsulfanyl-phenyl)-methyl]-8-phenyl-1,3-diazaspiro[4.5]decan-2-one

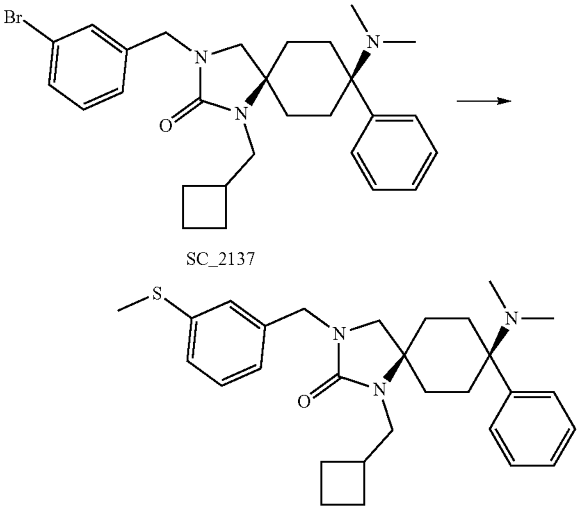

SC_2137

SC_2136

CIS-3-[(3-Bromophenyl)-methyl]-1-(cyclobutyl-methyl)-8-dimethylamino-8-phenyl-1,3-diaza-spiro[4.5]decan-2-one (SC_2137) (100 mg, 0.2 mmol), sodium thiomethoxide (20 mg, 0.3 mmol), $Pd_2(dba)_3$ (8 mg, 0.02 mmol) and 9,9-dimethyl-4,5-bis(diphenyl-phosphino)xanthene (10 mg, 0.02 mmol) were placed in an oven dried flask. After three vacuum/nitrogen purge cycles, toluene (2 mL) and DIPEA (66 μL, 0.4 mmol) were added and the resulting suspension was heated to 100° C. for 24 h. The reaction mixture was cooled to RT, water was added and the mixture was extracted with DCM (3x5 mL). The combined organic layers were dried over $Na_2SO_4$, concentrated in vacuo and the residue was purified by flash chromatography to yield CIS-1-(cyclobutyl-methyl)-8-dimethylamino-3-[(3-methylsulfanyl-phenyl)-methyl]-8-phenyl-1,3-diazaspiro[4.5]decan-2-one (SC_2136) as a white solid. $[M+H]^+$ 478.3

Synthesis of SC_2143: CIS-3-((1H-1,2,3-triazol-4-yl)methyl)-8-(dimethylamino)-8-phenyl-1,3-diazaspiro[4.5]decan-2-one

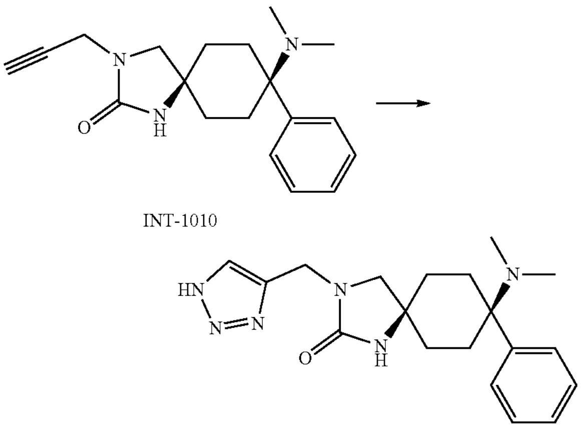

INT-1010

SC_2143

To a solution of CIS-8-dimethylamino-8-phenyl-3-prop-2-ynyl-1,3-diaza-spiro[4.5]decan-2-one (INT-1010) (1.0 g, 3.21 mmol, 1.0 eq.) in dioxane/MeOH (50 ml, 9:1) were added sodium azide (418 mg, 6.42 mmol, 2.0 eq.) and cuprous chloride (32 mg, 0.32 mmol, 0.1 eq.) at RT. The reaction mixture was stirred at 80° C. for 18 h, then quenched with water and concentrated under reduced pressure. The resulting residue was purified by column chromatography (silica gel neutralized with aq. $NH_3$; 0.5% aq $NH_3$ in 10% MeOH/DCM) to yield CIS-3-((1H-1,2,3-triazol-4-yl)methyl)-8-(dimethylamino)-8-phenyl-1,3-diazaspiro[4.5]decan-2-one (SC_2143) (600 mg, 1.69 mmol, 52%) as an off white solid. Yield: 52% (600 mg, 1.69 mmol). $^1$HNMR (DMSO-$d_6$, 400 MHz), δ (ppm)=14.84 (bs, 1H), 7.65 (s, 1H), 7.32-7.24 (m, 5H), 6.93 (bs, 1H), 4.27 (s, 2H), 2.98 (s, 2H), 2.28 (bs, 2H), 1.92 (s, 6H), 1.76 (bs, 4H), 1.31 (bs, 2H). Mass: m/z 355.0 $(M+H)^+$.

Synthesis of SC_2144: CIS-8-(dimethylamino)-3-((1-(2-hydroxyethyl)-1H-1,2,3-triazol-4-yl)methyl)-8-phenyl-1,3-diazaspiro[4.5]decan-2-one

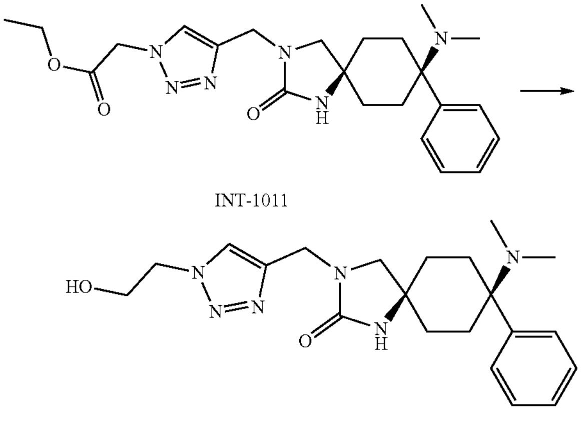

INT-1011

SC_2144

To a suspension of $LiAlH_4$ (207 mg, 5.45 mmol, 3.0 eq.) in dry THF (20 ml) was added ethyl CIS-2-(4-((8-(dimethylamino)-2-oxo-8-phenyl-1,3-diazaspiro[4.5]decan-3-yl) methyl)-1H-1,2,3-triazol-1-yl)acetate (INT-1011) (800 mg, 1.82 mmol, 1.0 eq.) in dry THF (20 ml) dropwise at 0° C. and the resulting mixture was stirred at RT for 1 h. The reaction mixture was quenched with sat. aq. $Na_2SO_4$, excess THF was added and the resulting mixture was stirred at RT for 1 h. The reaction mixture was filtered through celite and washed with THF. The filtrate was concentrated under reduced pressure to get crude product which was purified by column chromatography (silica gel, neutralized with aq. $NH_3$; 1% aq $NH_3$ in 20% MeOH/DCM) to yield CIS-8-(dimethylamino)-3-((1-(2-hydroxyethyl)-1H-1,2,3-triazol-4-yl)methyl)-8-phenyl-1,3-diazaspiro[4.5]decan-2-one (SC_2144) (450 mg, 1.13 mmol, 62%) as a white solid. Yield: 62% (450 mg, 1.13 mmol). $^1$HNMR (DMSO-$d_6$, 400 MHz), δ (ppm)=7.86 (s, 1H), 7.36-7.22 (m, 5H), 6.89 (bs, 1H), 4.97 (t, 1H, J=5.3 Hz), 4.34 (t, 2H, J=5.42 Hz), 4.24 (s, 2H), 3.72 (q, 2H, J=5.32 Hz), 3.01 (s, 2H), 2.30 (bs, 2H), 1.91 (s, 6H), 1.77-1.75 (m, 4H), 1.33-1.31 (m, 2H). Mass: m/z 399.1 $(M+H)^+$.

Synthesis of SC_2145: CIS-2-(4-((8-(dimethylamino)-2-oxo-8-phenyl-1,3-diazaspiro[4.5]decan-3-yl)methyl)-1H-1,2,3-triazol-1-yl)acetamide

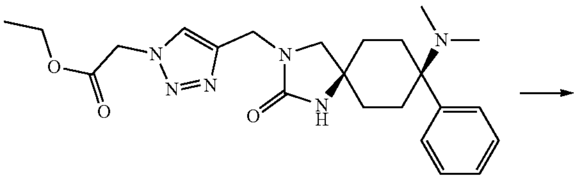

INT-1011

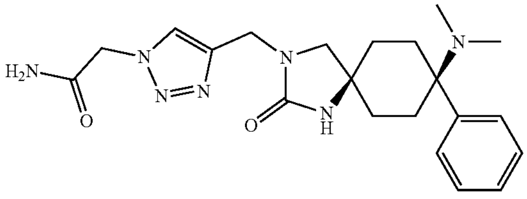

SC_2145

To a solution of CIS-2-(4-((8-(dimethylamino)-2-oxo-8-phenyl-1,3-diazaspiro[4.5]decan-3-yl)methyl)-1H-1,2,3-triazol-1-yl)acetate (INT-1011) (300 mg, 0.68 mmol, 1.0 eq.) in MeOH (6 ml) was added 7 M $NH_3$ solution in MeOH (2 ml) at RT and the reaction mixture was stirred at 80° C. in a sealed tube for 18 h. The reaction mixture was cooled down to RT and concentrated under reduced pressure. The crude product was purified by column chromatography (silica gel, neutralized with TEA; 2% aq. $NH_3$ in 20% MeOH/DCM) to yield CIS-2-(4-((8-(dimethylamino)-2-oxo-8-phenyl-1,3-diazaspiro[4.5]decan-3-yl)methyl)-1H-1,2,3-triazol-1-yl)acetamide (SC_2145) (220 mg, 0.54 mmol, 78%) as an off white solid. Yield: 78% (220 mg, 0.54 mmol).

$^1$HNMR (DMSO-$d_6$, 400 MHz), δ (ppm)=7.85 (s, 1H), 7.67 (s, 1H), 7.34-7.22 (m, 6H), 6.93 (bs, 1H), 5.00 (s, 2H), 4.25 (s, 2H), 3.01 (s, 2H), 2.30 (bs, 2H), 1.92 (s, 6H), 1.76 (bs, 4H), 1.31 (bs, 2H). Mass: m/z 412.3 $(M+H)^+$.

Synthesis of SC_2147: CIS-8-(dimethylamino)-3-(4-methoxybenzyl)-8-phenyl-1-tosyl-1,3-diazaspiro[4.5]decan-2-one

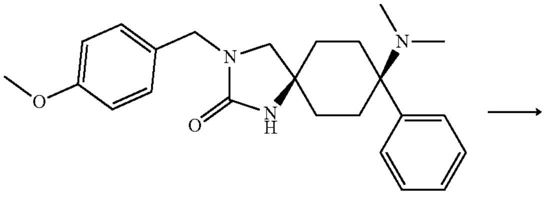

SC_2097

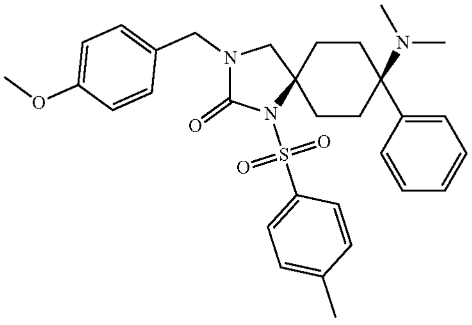

SC_2147

CIS-8-(dimethylamino)-3-[(4-methoxyphenyl)methyl]-8-phenyl-1,3-diazaspiro[4.5]decan-2-one (SC_2097) (500 mg, 1.271 mmol) was dissolved in THF (8 mL) under nitrogen atmosphere and the solution was cooled down to -78° C. [Bis(trimethylsilyl)amino]lithium (1M in THF, 1.5 equiv., 1.906 mmol, 1.9 mL) was added dropwise and the reaction mixture was stirred at −78° C. for 30 min, then at 0° C. for 30 min. The reaction mixture was cooled down to −78° C. again and the solution of p-toluenesulfonyl chloride (1.5 equiv., 1.906 mmol) in THF (5 mL) was added. The reaction mixture was stirred further 2.5 h at −78° C. and then the temperature was allowed to increase to RT overnight. The reaction mixture was quenched by the addition of sat. aq. $NaHCO_3$ (20 mL). The aqueous phase was extracted with EtOAc (3×40 mL). The combined organic extracts were washed with brine (30 mL), dried over $MgSO_4$ and concentrated under reduced pressure. Purification by flash chromatography on silica gel (elution with gradient DCM/EtOH 100/0 to 97/3) yielded 281 mg (40%) of CIS-8-(dimethylamino)-3-(4-methoxybenzyl)-8-phenyl-1-tosyl-1,3-diazaspiro[4.5]decan-2-one (SC_2147). $^1$H NMR (600 MHz, DMSO) δ 7.90-7.84 (m, 2H), 7.47-7.40 (m, 2H), 7.42-7.27 (m, 4H), 7.27-7.22 (m, 1H), 7.15-7.06 (m, 2H), 6.92-6.83 (m, 2H), 4.16 (s, 2H), 3.72 (s, 3H), 3.24 (s, 2H), 2.99 (ddd, 2H), 2.70-2.62 (m, 2H), 2.42 (s, 3H), 2.01 (s, 6H), 1.56-1.49 (m, 2H), 1.31 (td, 2H). Mass: m/z 548.3 $(M+H)^+$.

Synthesis of SC_2170: CIS-8-(dimethylamino)-8-phenyl-3-(2-phenylpropan-2-yl)-1,3-diazaspiro[4.5]decan-2-one

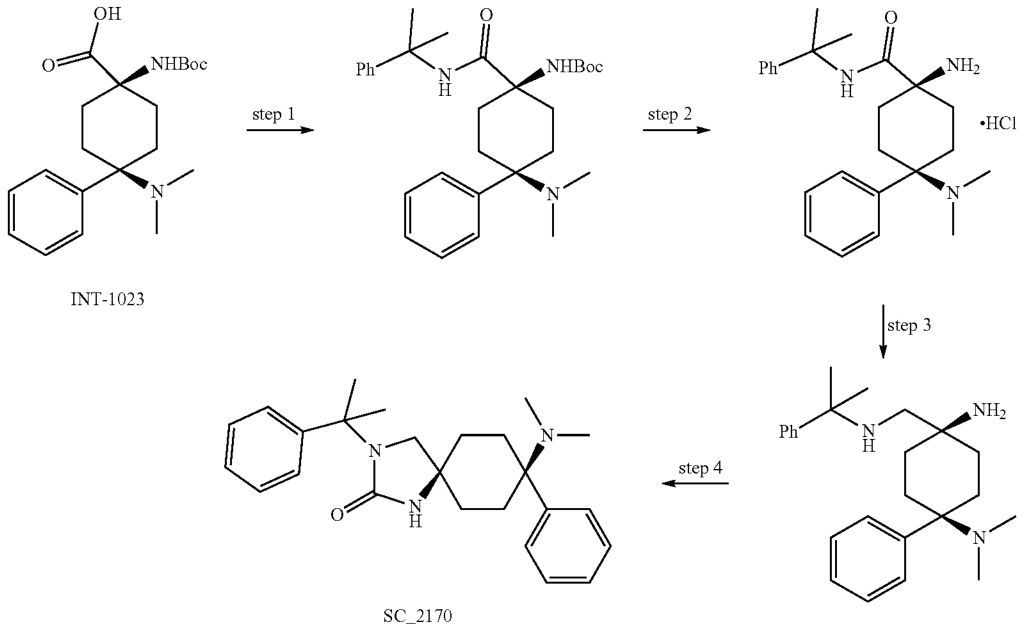

Step 1: synthesis of tert-butyl CIS-4-(dimethylamino)-4-phenyl-1-(2-phenylpropan-2-ylcarbamoyl)cyclohexylcarbamate To a stirred solution of CIS-1-(tert-butoxycarbonylamino)-4-(dimethylamino)-4-phenylcyclohexanecarboxylic acid (INT-1023) (1 g, 2.76 mmol) in DMF (15 mL) were added diisopropylethyl amine (1.78 g, 13.81 mmol) and HATU (2.09 g, 5.52 mmol) at 0° C. The reaction mixture was stirred at 0° C. for 45 min and then 2-phenylpropan-2-amine (0.74 g, 5.52 mmol) was added. The reaction mixture was warmed to RT and stirred for 16 h. The reaction mixture was quenched with sat. aq. $NaHCO_3$ and the organic product was extracted with EtOAc (3x25 mL). The combined organic extracts were dried over anhydr. $Na_2SO_4$ and concentrated under reduced pressure. Purification of the residue by flash column chromatography (silica gel 230-400 mesh) using 5-8% methanol in DCM as eluent gave 0.7 g (52%) of tert-butyl CIS-4-(dimethylamino)-4-phenyl-1-(2-phenylpropan-2-ylcarbamoyl)cyclohexylcarbamate as a liquid. (TLC system: 10% MeOH in DCM a Rf: 0.30).

Step 2: synthesis of CIS-1-amino-4-(dimethylamino)-4-phenyl-N-(2-phenylpropan-2-yl)cyclohexanecarboxamide Hydrochloride 4N HCl in dioxane (15 mL) was added to a stirred solution of tert-butyl CIS-4-(dimethylamino)-4-phenyl-1-(2-phenylpropan-2-ylcarbamoyl)cyclohexylcarbamate (0.7 g, 1.46 mmol) in DCM (15 mL) at 0° C. The reaction mixture was stirred at RT for 2 h and then concentrated under reduced pressure to afford 0.7 g of CIS-1-amino-4-(dimethylamino)-4-phenyl-N-(2-phenylpropan-2-yl)cyclohexanecarboxamide hydrochloride as an off-white solid. The product was used in the next step without additional purification. (TLC system: 10% MeOH in DCM a Rf: 0.20).

Step 3: synthesis of CIS-N,N-dimethyl-1-phenyl-4-((2-phenylpropan-2-ylamino)methyl)cyclohexane-1,4-diamine A solution of CIS-1-amino-4-(dimethylamino)-4-phenyl-N-(2-phenylpropan-2-yl)cyclohexanecarboxamide (0.7 g, 1.84 mmol) in THF (10 mL) was added to $BH_3$xTHF solution (1M in THF, 18 mL, 18.46 mmol) at RT. The resulting mixture was refluxed for 2 h. The reaction mixture was cooled to 0° C. and slowly quenched with 6N HCl (20 mL). The aqueous layer was extracted with EtOAc and then basified (pH~10) with 20% aq. NaOH. The organic product was extracted with 10% MeOH/DCM (20 mL×4). The combined organic layer was washed with brine, dried over anhydr. $Na_2SO_4$ and concentrated in vacuo to give 0.3 g of CIS-N,N-dimethyl-1-phenyl-4-((2-phenylpropan-2-ylamino)methyl)cyclohexane-1,4-diamine as a liquid. The product was used in the next step without additional purification. (TLC system: 10 vol % methanol in DCM, Rf: 0.10).

Step 3: synthesis of CIS-8-(dimethylamino)-8-phenyl-3-(2-phenylpropan-2-yl)-1,3-diazaspiro[4.5]decan-2-one SC_2170

1,1'-Carbonyldiimidazole (0.90 g, 5.58 mmol) was added to a solution of CIS-N,N-dimethyl-1-phenyl-4-((2-phenylpropan-2-ylamino)methyl)cyclohexane-1,4-diamine (1.7 g, 4.65 mmol) in DMF (20 mL) at RT. The reaction mixture was stirred at RT for 16 h. The reaction mixture was quenched with cold water, the precipitated solid was filtered off and dried under reduced pressure to give the product which was further purified by preparative HPLC (column: Column: Kinetex-C18 (150*21.2 mm) 5 µm, mobile phase: 0.1% formic acid in water (A): Acetonitrile(B), gradient: T/% B: 0/20, 7/50, 7.1/98, 9/98, 9.1/20, 12/20, flow rate: 18 ml/min, diluent: mobile phase+THF) to yield 0.83 g (55%) of CIS-8-(dimethylamino)-8-phenyl-3-(2-phenylpropan-2-yl)-1,3-diazaspiro[4.5]decan-2-one (SC_2170) as a white solid. (TLC system: 10% MeOH in DCM Rf: 0.30). 1H NMR (DMSO-d6): δ 7.36-7.22 (m, 9H), 7.16-7.13 (m, 1H), 6.64 (s, 1H), 3.10 (s, 2H), 2.28 (m, 2H), 1.93-1.79 (m, 10H), 1.52 (s, 6H), 1.37 (m, 2H). Mass: m/z 392.2 $[M+H]^+$.

Synthesis of SC_2180: CIS-8-(dimethylamino)-8-phenyl-3-(pyridin-4-ylmethyl)-1,3-diazaspiro[4.5]decan-2-one

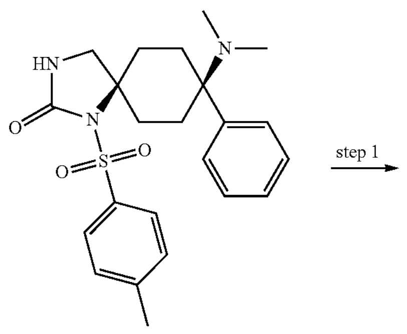

INT-1028

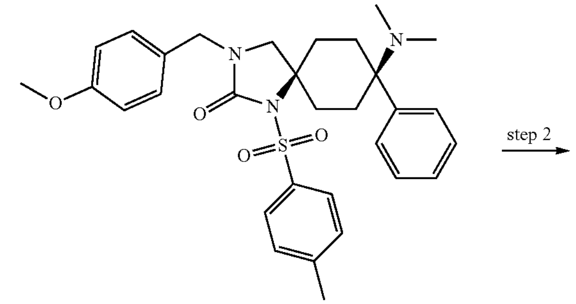

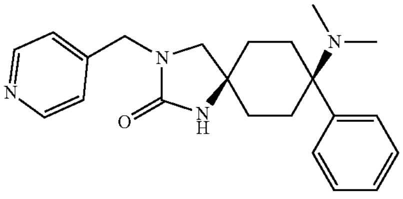

SC_2180

Step 1: synthesis of CIS-8-(dimethylamino)-3-(4-methoxybenzyl)-8-phenyl-1-tosyl-1,3-diazaspiro[4.5]decan-2-one CIS-8-(dimethylamino)-8-phenyl-1-(p-tolylsulfonyl)-1,3-diazaspiro[4.5]decan-2-one (INT-1028) (200 mg, 0.47 mmol, 1 equiv.) was dissolved in DMF (3.6 mL) under argon atmosphere and the solution was cooled down to 0° C. Sodium hydride (60 wt % in mineral oil, 2.1 equiv., 0.98 mmol, 39 mg) was added and the reaction mixture was stirred at RT for 15 min. 4-(Bromomethyl)pyridine hydrobromide (1.05 equiv., 0.49 mmol, 124 mg) was added at 0° C. The reaction mixture was stirred overnight at RT, then quenched with sat. aq. $NaHCO_3$ (2 mL) and water (2 mL) and extracted with EtOAc (2×15 mL). The combined organic extract was washed with brine, dried over $Na_2SO_4$ and concentrated under reduced pressure. The residue was purified by flash chromatography on silica gel (100% acetonitrile) to yield CIS-8-(dimethylamino)-3-(4-methoxybenzyl)-8-phenyl-1-tosyl-1,3-diazaspiro[4.5]decan-2-one (112 mg, 46%). Mass: m/z 519.2 $[M+H]^+$.

Step 2: synthesis of CIS-8-(dimethylamino)-8-phenyl-3-(pyridin-4-ylmethyl)-1,3-diazaspiro[4.5]decan-2-one (SC_2180)

CIS-8-(dimethylamino)-3-(4-methoxybenzyl)-8-phenyl-1-tosyl-1,3-diazaspiro[4.5]decan-2-one (110 mg, 0.212 mmol, 1 equiv.) was dissolved in THF (2 mL) and MeOH (4.4 mL) under argon atmosphere. Magnesium turnings (103 mg, 4.24 mmol, 20 equiv.) were added and the resulting mixture was stirred at RT for 18 h. The reaction mixture was diluted with DCM (30 mL) and water (10 mL), stirred at RT for 1.5 h, filtered through celite and the solid residue was washed with DCM (3×). The organic phase of the filtrate was separated and concentrated under reduced pressure. The residue was purified by flash chromatography on silica gel (EtOH 100% to EtOH/MeOH 70/30) to yield 33 mg (43%) of CIS-8-(dimethylamino)-8-phenyl-3-(pyridin-4-ylmethyl)-1,3-diazaspiro[4.5]decan-2-one (SC_2180). $^1$H NMR (600 MHz, DMSO-d6) δ 8.52-8.47 (m, 2H), 7.36-7.28 (m, 4H), 7.25-7.21 (m, 1H), 7.21-7.17 (m, 2H), 7.01 (s, 1H), 4.23 (s, 2H), 2.98 (s, 2H), 2.37-2.22 (m, 2H), 1.93 (s, 6H), 1.87-1.61 (m, 4H), 1.42-1.29 (m, 2H). Mass: m/z 365.2 $[M+H]^+$.

Synthesis of SC_2183: CIS-8-(dimethylamino)-3-((2-(4-methylpiperazin-1-yl)pyridin-4-yl)methyl)-8-phenyl-1,3-diazaspiro[4.5]decan-2-one

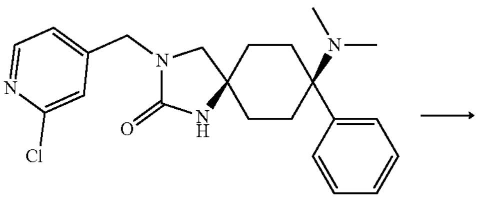

INT-1065

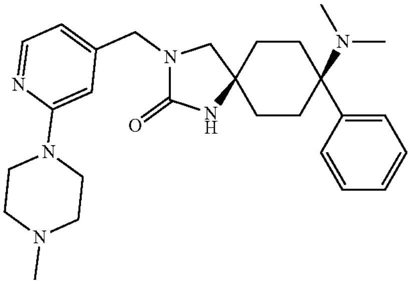

SC_2183

A mixture of 3-[(2-chloro-4-pyridyl)methyl]-8-(dimethylamino)-8-phenyl-1,3-diazaspiro[4.5]decan-2-one (INT-1065) (100 mg, 0.251 mmol), 1-methylpiperazine (50 equiv., 12.54 mmol, 1.39 mL) and DIPEA (5 equiv., 1.25 mmol, 0.22 mL) was stirred at 140° C. under microwave irradiation until complete conversion of INT-1065 (LCMS control). The reaction mixture was diluted with 2 N aq. NaOH and EtOAc, the organic phase was separated, washed with brine, dried over anhydr. $Na_2SO_4$ and concentrated under reduced pressure. The resulting crude product was purified by flash chromatography on silica gel (eluent gradient 0.2 N $NH_3$ in MeOH/EtOH/DCM 10/40/50 to 25/25/50 v/v/v) to yield CIS-8-(dimethylamino)-3-((2-(4-methylpiperazin-1-yl)pyridin-4-yl)methyl)-8-phenyl-1,3-diazaspiro [4.5]decan-2-one (SC_2183) (87 mg, 75%). $^1H$ NMR (600 MHz, DMSO) δ 8.02 (d, 1H), 7.36-7.30 (m, 2H), 7.31-7.26 (m, 2H), 7.23 (td, 1H), 6.94 (s, 1H), 6.58 (s, 1H), 6.45 (dd, 1H), 4.12 (s, 2H), 3.45-3.39 (m, 4H), 2.94 (s, 2H), 2.36 (t, 4H), 2.33-2.22 (m, 2H), 2.19 (s, 3H), 1.92 (s, 6H), 1.86-1.62 (m, 4H), 1.34 (t, 2H). Mass: m/z 463.3 $(M+H)^+$.

Synthesis of SC_2186: CIS-8-(dimethylamino)-8-phenyl-3-((2-(piperazin-1-yl)pyridin-4-yl)methyl)-1,3-diazaspiro[4.5]decan-2-one

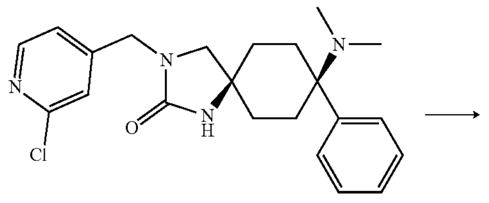

INT-1065

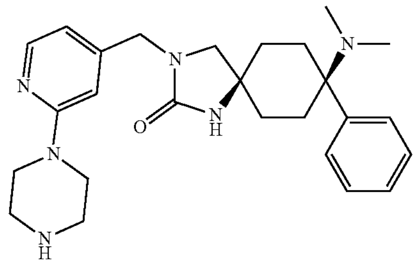

SC_2186

A mixture of 3-[(2-chloro-4-pyridyl)methyl]-8-(dimethylamino)-8-phenyl-1,3-diazaspiro[4.5]decan-2-one (INT-1065) (100 mg, 0.251 mmol), piperazine (1.5 equiv., 0.38 mmol, 32 mg), DIPEA (5 equiv., 1.25 mmol, 0.22 mL) and n-butanol (1 mL) was stirred 4 h at 140° C. under microwave irradiation. A new portion of piperazine (4.5 equiv, 1.13 mmol, 97 mg) was added and the reaction mixture was stirred further 16 h at 140° C. under microwave irradiation. The resulting mixture was concentrated under reduced pressure, taken in water/EtOAc, organic phase separated, aqueous phase extracted with EtOAc. The combined organic phase was washed with brine, dried over anhydr. $Na_2SO_4$ and concentrated under reduced pressure. The resulting crude product was purified by flash chromatography on silica gel (eluent gradient 0.2 N $NH_3$ in MeOH/EtOH/DCM 0/20/80 to 30/0/70 v/v/v) to yield CIS-8-(dimethylamino)-8-phenyl-3-((2-(piperazin-1-yl)pyridin-4-yl)methyl)-1,3-diazaspiro[4.5]decan-2-one (SC_2186) (48 mg, 43%). $^1H$ NMR (600 MHz, CDCl3) δ 8.13-8.09 (m, 1H), 7.37 (t, 2H), 7.31-7.24 (m, 3H), 6.49 (d, 2H), 5.20-5.16 (m, 1H), 4.25 (s, 2H), 3.51-3.46 (m, 4H), 3.01-2.95 (m, 6H), 2.18-2.09 (m, 2H), 2.05 (s, 6H), 2.03-1.92 (m, 2H), 1.92-1.84 (m, 2H), 1.50-1.42 (m, 2H). Mass: m/z 449.3 $(M+H)^+$.

For further exemplary compounds the last synthesis step in analogy to previously described methods is given in the following table. The syntheses of the building blocks and intermediates have either been described previously within this application or can be performed in analogy to the herein described methods or by methods known to the person, skilled in the art. Such a person will also know which building blocks and intermediates need to be chosen for synthesis of each exemplary compound.

| Example | Chemical Name | Reactant I | Reactant II | in analogy to method | m/z $[M + H]^+$ |
|---|---|---|---|---|---|
| SC_2001 | CIS-1-(Cyclobutyl-methyl)-8-dimethylamino-3-[(4-methylsulfonyl-phenyl)-methyl]-8-phenyl-1,3-diazaspiro[4.5]decan-2-one | SC_2136 | — | SC_2093 | 510.3 |
| SC_2003 | CIS-8-Dimethylamino-1-isopropyl-3-[(4-methoxyphenyl)-methyl]-8-phenyl-1,3-diazaspiro[4.5]decan-2-one | SC_2097 | 2-bromo-propane | SC_2014 | 436.3 |
| SC_2004 | CIS-1-(Cyclopropyl-methyl)-8-dimethylamino-3-[(4-methoxyphenyl)-methyl]-8-phenyl-1,3-diazaspiro[4.5]decan-2-one | SC_2097 | cyclopropyl-methylbromide | SC_2125 | 448.3 |
| SC_2005 | CIS-1-(Cyclobutyl-methyl)-3-[(4-methoxyphenyl)-methyl]-8-[methyl-(2-methyl-propyl)-amino]-8-phenyl-1,3-diazaspiro[4.5]decan-2-one | SC_2026 | Isobutyraldehyde | SC_2028 | 504.4 |
| SC_2006 | CIS-2-[[1-(Cyclobutyl-methyl)-8-dimethylamino-2-oxo-8-phenyl-1,3-diazaspiro[4.5]decan-3-yl]-methyl]-benzamide | SC_2092 | — | SC_2109 | 475.3 |
| SC_2007 | CIS-1-(Cyclobutyl-methyl)-8-dimethylamino-8-phenyl-3-(pyrazin-2-yl-methyl)-1,3-diazaspiro[4.5]decan-2-one | INT-987 | 2-(bromomethyl)pyrazine | SC_2002 | 434.3 |
| SC_2009 | CIS-4-[[1-(Cyclobutyl-methyl)-8-dimethylamino-2-oxo-8-phenyl-1,3-diazaspiro[4.5]decan-3-yl]-methyl]-benzamide | SC_2085 | — | SC_2109 | 475.3 |
| SC_2011 | CIS-1-(Cyclobutyl-methyl)-8-dimethylamino-8-(4-fluorophenyl)-3-[(4-methoxyphenyl)-methyl]-1,3-diazaspiro[4.5]decan-2-one | SC_2016 | (bromomethyl)cyclobutan | SC_2010 | 480.3 |
| SC_2012 | CIS-1-(Cyclobutyl-methyl)-8-dimethylamino-8-(3-methoxyphenyl)-3-[(4-methoxyphenyl)-methyl]-1,3-diazaspiro[4.5]decan-2-one | SC_2139 | (bromomethyl)cyclobutan | SC_2010 | 492.3 |

-continued

| Example | Chemical Name | Reactant I | Reactant II | in analogy to method | m/z [M + H]$^+$ |
|---|---|---|---|---|---|
| SC_2013 | CIS-1-(Cyclobutyl-methyl)-8-dimethylamino-8-(4-methoxyphenyl)-3-[(4-methoxyphenyl)-methyl]-1,3-diazaspiro[4.5]decan-2-one | SC_2140 | (bromomethyl)cyclobutan | SC_2010 | 492.3 |
| SC_2015 | CIS-1-Butyl-8-dimethylamino-3-[(4-methoxyphenyl)-methyl]-8-phenyl-1,3-diazaspiro[4.5]decan-2-one | SC_2097 | 1-bromobutane | SC_2010 | 450.3 |
| SC_2016 | CIS-8-Dimethylamino-8-(4-fluorophenyl)-3-[(4-methoxyphenyl)-methyl]-1,3-diazaspiro[4.5]decan-2-one | INT-966 | dimethylamine/KCN 4-fluorophenylmagnesium bromide | SC_2017 | 412.2 |
| SC_2020 | CIS-1-(Cyclobutyl-methyl)-8-dimethylamino-3-[[3-[2-[2-[2-[2-[2-(2-methoxy-ethoxy)-ethoxy]-ethoxy]-ethoxy]-ethoxy]-ethoxy]-phenyl]-methyl]-8-phenyl-1,3-diazaspiro[4.5]decan-2-one | SC_2089 | 2,5,8,11,14,17-hexaoxanon-adecan-19-ol | SC_2089 | 726.5 |
| SC_2021 | CIS-1-(Cyclobutyl-methyl)-8-dimethylamino-8-(4-hydroxyphenyl)-3-[(4-methoxyphenyl)-methyl]-1,3-diazaspiro[4.5]decan-2-one hydrochloride | INT-967 | — | SC_2018 | 478.3 |
| SC_2022 | CIS-8-Dimethylamino-1-[(1-hydroxy-cyclobutyl)-methyl]-3-[(3-methoxyphenyl)-methyl]-8-phenyl-1,3-diazaspiro[4.5]decan-2-one | INT-799 | 1-(bromomethyl)-3-methoxybenzene | SC_2019 | 478.3 |
| SC_2023 | CIS-1-(Cyclopentyl-methyl)-8-dimethylamino-3-[(4-methoxyphenyl)-methyl]-8-phenyl-1,3-diazaspiro[4.5]decan-2-one | SC_2097 | (bromomethyl)cyclopentane | SC_2010 | 476.3 |
| SC_2024 | CIS-8-Dimethylamino-1-(2-hydroxy-2-methyl-propyl)-3-[(4-methoxyphenyl)-methyl]-8-phenyl-1,3-diazaspiro[4.5]decan-2-one | SC_2097 | 2,2-dimethyl-oxirane | SC_2010 | 466.3 |
| SC_2027 | CIS-3-[[1-(Cyclobutyl-methyl)-8-(ethyl-methyl-amino)-2-oxo-8-phenyl-1,3-diazaspiro[4.5]decan-3-yl]-methyl]-benzonitrile | INT-798 | (bromomethyl)cyclobutan | SC_2010 | 471.3 |
| SC_2029 | CIS-1-(Cyclobutyl-methyl)-8-(ethyl-methyl-amino)-3-[(3-methoxyphenyl)-methyl]-8-phenyl-1,3-diazaspiro[4.5]decan-2-one | SC_2026 | acetaldehyde | SC_2028 | 476.3 |
| SC_2030 | CIS-3-[8-Dimethylamino-3-[(4-methoxyphenyl)-methyl]-2-oxo-8-phenyl-1,3-diazaspiro[4.5]decan-1-yl]-propionitrile | SC_2097 | 3-bromopropanenitrile | SC_2010 | 447.3 |
| SC_2031 | CIS-1-(Cyclobutyl-methyl)-8-methylamino-8-phenyl-3-(pyridin-3-yl-methyl)-1,3-diazaspiro[4.5]decan-2-one | SC_2019 | — | SC_2026 | 419.3 |
| SC_2032 | CIS-8-Dimethylamino-3-[(4-methoxyphenyl)-methyl]-1-(oxetan-3-yl-methyl)-8-phenyl-1,3-diazaspiro[4.5]decan-2-one | SC_2097 | 3-(bromomethyl)oxetane | SC_2014 | 464.3 |
| SC_2033 | CIS-1-(Cyclobutyl-methyl)-8-(ethyl-methyl-amino)-8-phenyl-3-(pyridin-3-yl-methyl)-1,3-diazaspiro[4.5]decan-2-one | INT-986 | bromomethylpyridine hydrobromide | SC_2002 | 447.3 |
| SC_2035 | CIS-8-Dimethylamino-1-(2,2-dimethyl-propyl)-3-[(4-methoxyphenyl)-methyl]-8-phenyl-1,3-diazaspiro[4.5]decan-2-one | SC_2097 | 1-bromo-2,2-dimethylpropane | SC_014 | 464.3 |
| SC_2036 | CIS-8-Dimethylamino-3-[(4-methoxyphenyl)-methyl]-1-(3-methyl-butyl)-8-phenyl-1,3-diazaspiro[4.5]decan-2-one | SC_2097 | 1-bromo-3-methylbutane | SC_2010 | 464.3 |
| SC_2037 | CIS-8-Dimethylamino-3-[(4-methoxyphenyl)-methyl]-8-phenyl-1-[3-(trifluoromethyloxy)-propyl]-1,3-diazaspiro[4.5]decan-2-one | SC_2097 | 1-bromo-3-(trifluoro-methoxy)propane | SC_2010 | 520.3 |
| SC_2038 | CIS-1-(2-Cyclobutyl-ethyl)-8-dimethylamino-3-[(4-methoxyphenyl)-methyl]-8-phenyl-1,3-diazaspiro[4.5]decan-2-one | SC_2097 | 2-cyclobutylethyl 4-methylbenzenesulfonate | SC_2010 | 476.3 |
| SC_2039 | CIS-1-[(3,3-Difluoro-cyclobutyl)-methyl]-8-dimethylamino-3-[(4-methoxyphenyl)-methyl]-8-phenyl-1,3-diazaspiro[4.5]decan-2-one | SC_2097 | 3-(bromomethyl)-1,1-difluorocyclobutane | SC_2010 | 498.3 |
| SC_2041 | CIS-1-(Cyclobutyl-methyl)-8-[(2-methoxy-ethyl)-methyl-amino]-3-[(4-methoxyphenyl)-methyl]-8-phenyl-1,3-diazaspiro[4.5]decan-2-one | SC_2044 | 1-bromo-2-methoxyethane | SC_2008 | 506.3 |
| SC_2044 | CIS-1-(Cyclobutyl-methyl)-3-[(4-methoxyphenyl)-methyl]-8-methylamino-8-phenyl-1,3-diazaspiro[4.5]decan-2-one | SC_2125 | — | SC_2026 | 448.3 |
| SC_2045 | CIS-2-[8-Dimethylamino-3-[(4-methoxyphenyl)-methyl]-2-oxo-8-phenyl-1,3-diazaspiro[4.5]decan-1-yl]-acetic acid methyl ester | SC_2097 | methyl 2-bromoacetate | SC_2010 | 466.3 |
| SC_2046 | CIS-2-[8-Dimethylamino-3-[(4-methoxyphenyl)-methyl]-2-oxo-8-phenyl-1,3-diazaspiro[4.5]decan-1-yl]-acetamide | SC_2043 | $NH_4Cl$ | SC_2049 | 451.3 |
| SC_2047 | CIS-1-Benzyl-8-dimethylamino-3-[(4-methoxyphenyl)-methyl]-8-phenyl-1,3-diazaspiro[4.5]decan-2-one | SC_2097 | (bromomethyl)benzene | SC_2010 | 484.3 |
| SC_2048 | CIS-2-[8-Dimethylamino-3-[(4-methoxyphenyl)-methyl]-2-oxo-8-phenyl-1,3-diazaspiro[4.5]decan-1-yl]-N-methyl-acetamide | SC_2043 | methylamine | SC_2049 | 465.3 |
| SC_2050 | CIS-8-Dimethylamino-3-[(4-methoxyphenyl)-methyl]-1-(3-methoxy-propyl)-8-phenyl-1,3-diazaspiro[4.5]decan-2-one | SC_2097 | 1-bromo-3-methoxypropane | SC_2010 | 466.3 |
| SC_2051 | CIS-8-Dimethylamino-1-[(1-hydroxy-cyclobutyl)-methyl]-3-[(4-methoxyphenyl)-methyl]-8-phenyl-1,3-diazaspiro[4.5]decan-2-one | SC_799 | 1-(bromomethyl)-4-methoxybenzene | SC_2019 | 478.3 |

-continued

| Example | Chemical Name | Reactant I | Reactant II | in analogy to method | m/z [M + H]$^+$ |
|---|---|---|---|---|---|
| SC_2052 | CIS-8-Dimethylamino-1-(2-methoxy-ethyl)-3-[(4-methoxyphenyl)-methyl]-8-phenyl-1,3-diazaspiro[4.5]decan-2-one | SC_2097 | 1-bromo-2-methoxyethane | SC_2014 | 452.3 |
| SC_2054 | CIS-8-Dimethylamino-1-hexyl-3-[(4-methoxyphenyl)-methyl]-8-phenyl-1,3-diazaspiro[4.5]decan-2-one | SC_2097 | 1-bromohexane | SC_2014 | 478.3 |
| SC_2055 | CIS-8-Dimethylamino-3-[(4-methoxyphenyl)-methyl]-8-phenyl-1-(tetrahydro-pyran-4-yl-methyl)-1,3-diazaspiro[4.5]decan-2-one | SC_2097 | 4-(bromomethyl)tetrahydro-2H-pyran | SC_2014 | 492.3 |
| SC_2056 | CIS-1-(Cyclohexyl-methyl)-8-dimethylamino-3-[(4-methoxyphenyl)-methyl]-8-phenyl-1,3-diazaspiro[4.5]decan-2-one | SC_097 | (bromomethyl)cyclohexane | SC_2014 | 490.3 |
| SC_2057 | CIS-N-(Cyano-methyl)-2-[8-dimethylamino-3-[(4-methoxyphenyl)-methyl]-2-oxo-8-phenyl-1,3-diazaspiro[4.5]decan-1-yl]-acetamide | SC_2043 | 2-aminoacetonitrile | SC_2049 | 490.3 |
| SC_2058 | CIS-8-Dimethylamino-3-[(4-methoxyphenyl)-methyl]-8-phenyl-1-(pyridin-3-yl-methyl)-1,3-diazaspiro[4.5]decan-2-one | SC_2097 | 3-(bromomethyl)pyridine | SC_2014 | 485.3 |
| SC_2059 | CIS-8-Dimethylamino-3-[(4-methoxyphenyl)-methyl]-8-(3-methoxy-propyl)-1,3-diazaspiro[4.5]decan-2-one | INT-966 | dimethylamine/KCN 3-methoxypropyl magnesium bromide | SC_2017 | 390.3 |
| SC_2060 | CIS-2-[8-Dimethylamino-3-[(4-methoxyphenyl)-methyl]-2-oxo-8-phenyl-1,3-diazaspiro[4.5]decan-1-yl]-N-(2-methoxy-ethyl)-acetamide | SC_2043 | 2-methoxyethanamine | SC_2049 | 509.3 |
| SC_2062 | CIS-8-Dimethylamino-3-[(4-methoxyphenyl)-methyl]-1-(2-oxo-2-pyrrolidin-1-yl-ethyl)-8-phenyl-1,3-diazaspiro[4.5]decan-2-one | SC_2043 | pyrrolidine | SC_2049 | 505.3 |
| SC_2063 | CIS-2-[8-Dimethylamino-3-[(4-methoxyphenyl)-methyl]-2-oxo-8-phenyl-1,3-diazaspiro[4.5]decan-1-yl]-N,N-dimethyl-acetamide | SC_2043 | dimethylamine | SC_2049 | 479.3 |
| SC_2064 | CIS-N-(1-Cyano-cyclopropyl)-2-[8-dimethylamino-3-[(4-methoxyphenyl)-methyl]-2-oxo-8-phenyl-1,3-diazaspiro[4.5]decan-1-yl]-acetamide | SC_2043 | 1-aminocyclopropane-carbonitrile | SC_2049 | 516.3 |
| SC_2065 | CIS-2-[8-Dimethylamino-3-[(4-methoxyphenyl)-methyl]-2-oxo-8-phenyl-1,3-diazaspiro[4.5]decan-1-yl]-N-methyl-N-propyl-acetamide | SC_2043 | N-methylpropan-1-amine | SC_2049 | 507.3 |
| SC_2066 | CIS-1-(Cyclobutyl-methyl)-8-dimethylamino-3-[(4-methoxyphenyl)-methyl]-8-(3-methoxy-propyl)-1,3-diazaspiro[4.5]decan-2-one | SC_2059 | (bromomethyl)cyclobutane | SC_2125 | 458.3 |
| SC_2067 | CIS-8-Dimethylamino-1-(3-hydroxy-propyl)-3-[(4-methoxyphenyl)-methyl]-8-phenyl-1,3-diazaspiro[4.5]decan-2-one | SC_2097 | (3-bromopropoxy)(tert-butyl)dimethylsilane | SC_2034 | 452.3 |
| SC_2068 | CIS-8-Dimethylamino-1-(4-methoxy-butyl)-3-[(4-methoxyphenyl)-methyl]-8-phenyl-1,3-diazaspiro[4.5]decan-2-one | SC_2097 | 1-bromo-4-methoxybutane | SC_2014 | 480.3 |
| SC_2069 | CIS-8-Dimethylamino-3-[(4-methoxyphenyl)-methyl]-1-[(1-methyl-cyclobutyl)-methyl]-8-phenyl-1,3-diazaspiro[4.5]decan-2-one | SC_2097 | 1-(bromo-methyl)-1-methyl-cyclobutane | INT-982 step 1 | 476.3 |
| SC_2070 | CIS-8-Dimethylamino-1-[(1-hydroxy-cyclohexyl)-methyl]-3-[(4-methoxyphenyl)-methyl]-8-phenyl-1,3-diazaspiro[4.5]decan-2-one | SC_2097 | O-tert-butyldimethylsilyl-1-(4-methylbenzenesulfon-oxymethyl)cyclohexanol | SC_2124 | 506.3 |
| SC_2071 | CIS-5-[8-Dimethylamino-3-[(4-methoxyphenyl)-methyl]-2-oxo-8-phenyl-1,3-diazaspiro[4.5]decan-1-yl]-pentanenitrile | SC_2097 | 5-aminopentanenitrile | SC_2014 | 475.3 |
| SC_2072 | CIS-3-[8-Dimethylamino-3-[(4-methoxyphenyl)-methyl]-2-oxo-8-phenyl-1,3-diazaspiro[4.5]decan-1-yl]-propionamide | SC_2132 | $NH_4Cl$ | SC_2049 | 465.3 |
| SC_2074 | CIS-1-[[8-Dimethylamino-3-[(4-methoxyphenyl)-methyl]-2-oxo-8-phenyl-1,3-diazaspiro[4.5]decan-1-yl]-methyl]-cyclobutane-1-carbonitrile | SC_2097 | 1-(aminomethyl)cyclobutane-carbonitrile | SC_2014 | 487.3 |
| SC_2075 | CIS-8-Dimethylamino-1-[(1-hydroxy-cyclopentyl)-methyl]-3-[(4-methoxyphenyl)-methyl]-8-phenyl-1,3-diazaspiro[4.5]decan-2-one | SC_2097 | O-tert-butyldimethylsilyl-1-(4-methylbenzenesulfon-oxymethyl)cyclopentanol | SC_2124 | 492.3 |
| SC_2076 | CIS-3-[(2-Bromophenyl)-methyl]-1-(cyclobutyl-methyl)-8-dimethylamino-8-phenyl-1,3-diazaspiro[4.5]decan-2-one | INT-987 | 1-bromo-2-(bromo-methyl)benzene | SC_2002 | 510.2 |
| SC_2077 | CIS-3-[8-Dimethylamino-3-[(4-methoxyphenyl)-methyl]-2-oxo-8-phenyl-1,3-diazaspiro[4.5]decan-1-yl]-N-methyl-propionamide | SC_2132 | methylamine | SC_2049 | 479.3 |
| SC_2078 | CIS-3-[8-Dimethylamino-3-[(4-methoxyphenyl)-methyl]-2-oxo-8-phenyl-1,3-diazaspiro[4.5]decan-1-yl]-N-propyl-propionamide | SC_2132 | propan-l-amine | SC_2049 | 507.3 |
| SC_2079 | CIS-8-Dimethylamino-1-[(1-fluoro-cyclobutyl)-methyl]-3-[(4-methoxyphenyl)-methyl]-8-phenyl-1,3-diazaspiro[4.5]decan-2-one | SC_2097 | 1-(bromomethyl)-1-fluorocyclobutane | SC_2014 | 480.3 |
| SC_2080 | CIS-1-(2-Cyclohexyl-ethyl)-8-dimethylamino-3-[(4-methoxyphenyl)-methyl]-8-phenyl-1,3-diazaspiro[4.5]decan-2-one | SC_2097 | 2-cyclohexylethanamine | SC_2014 | 504.4 |

-continued

| Example | Chemical Name | Reactant I | Reactant II | in analogy to method | m/z [M + H]$^+$ |
|---|---|---|---|---|---|
| SC_2081 | CIS-3-[[1-(Cyclobutyl-methyl)-8-dimethylamino-2-oxo-8-phenyl-1,3-diazaspiro[4.5]decan-3-yl]-methyl]-benzonitrile | | 3-(aminomethyl)benzonitrile | SC_2002 | 457.3 |
| SC_2082 | CIS-8-Dimethylamino-3-[(4-methoxyphenyl)-methyl]-1-methyl-8-phenyl-1,3-diazaspiro[4.5]decan-2-one | SC_2097 | Iodo-methane | SC_2010 | 408.3 |
| SC_2083 | CIS-8-Dimethylamino-1-[2-[2-[2-[2-[2-[2-(2-methoxy-ethoxy)-ethoxy]-ethoxy]-ethoxy]-ethoxy]-ethoxy]-ethoxy]-ethyl]-3-[(4-methoxyphenyl)-methyl]-8-phenyl-1,3-diazaspiro[4.5]decan-2-one | SC_2097 | 25-bromo-2,5,8,11,14,17,20,23-octaoxapentacosane | SC_2014 | 760.5 |
| SC_2084 | CIS-8-Dimethylamino-3-[(4-methoxyphenyl)-methyl]-8-phenyl-1-(2-tetrahydro-pyran-4-yl-ethyl)-1,3-diazaspiro[4.5]decan-2-one | SC_2097 | 4-(2-bromoethyl)tetrahydro-2H-pyran | SC_2014 | 506.3 |
| SC_2085 | CIS-4-[[1-(Cyclobutyl-methyl)-8-dimethylamino-2-oxo-8-phenyl-1,3-diazaspiro[4.5]decan-3-yl]-methyl]-benzonitrile | INT-987 | 4-(bromomethyl)benzonitrile | SC_2002 | 457.3 |
| SC_2086 | CIS-1-(Cyclobutyl-methyl)-8-dimethylamino-8-phenyl-3-[[6-(trifluoromethyl)-pyridin-3-yl]-methyl]-1,3-diazaspiro[4.5]decan-2-one | INT-987 | 5-(bromomethyl)-2-(trifluoromethyl)pyridine | SC_2002 | 501.3 |
| SC_2088 | CIS-34[[1-(Cyclobutyl-methyl)-8-dimethylamino-2-oxo-8-phenyl-1,3-diazaspiro[4.5]decan-3-yl]-methyl]-benzamide | SC_2081 | — | SC_2109 | 475.3 |
| SC_2090 | CIS-1-(Cyclobutyl-methyl)-8-(ethyl-methyl-amino)-3-[(4-methoxyphenyl)-methyl]-8-phenyl-1,3-diazaspiro[4.5]decan-2-one | SC_2044 | acetaldehyde | SC_2028 | 476.3 |
| SC_2091 | CIS-8-Dimethylamino-1-[(1-methoxy-cyclobutyl)-methyl]-3-[(4-methoxyphenyl)-methyl]-8-phenyl-1,3-diazaspiro[4.5]decan-2-one | SC_2075 | methyliodide | SC_2025 | 492.3 |
| SC_2092 | CIS-2-[[1-(Cyclobutyl-methyl)-8-dimethylamino-2-oxo-8-phenyl-1,3-diazaspiro[4.5]decan-3-yl]-methyl]-benzonitrile | INT-987 | 2-(aminomethyl)benzonitrile | SC_2002 | 457.3 |
| SC_2094 | CIS-8-Dimethylamino-1-ethyl-3-[(4-methoxyphenyl)-methyl]-8-phenyl-1,3-diazaspiro[4.5]decan-2-one | SC_2097 | 1-iodo-ethane | SC_2010 | 422.3 |
| SC_2095 | CIS-8-Dimethylamino-3-[(4-methoxyphenyl)-methyl]-8-phenyl-1-propyl-1,3-diazaspiro[4.5]decan-2-one | SC_2097 | 1-iodopropane | SC_2010 | 436.3 |
| SC_2096 | CIS-3-Benzyl-1-(cyclobutyl-methyl)-8-dimethylamino-8-phenyl-1,3-diazaspiro[4.5]decan-2-one | INT-963 | cyclobutyl-methylbromide | SC_2014 | 432.3 |
| SC_2099 | CIS-8-Dimethylamino-3-[(4-methoxyphenyl)-methyl]-8-phenyl-1-(pyrimidin-4-yl-methyl)-1,3-diazaspiro[4.5]decan-2-one | SC_2097 | 4-(bromomethyl)pyrimidine | SC_2010 | 486.3 |
| SC_2100 | CIS-3-[8-Dimethylamino-3-[(4-methoxyphenyl)-methyl]-2-oxo-8-phenyl-1,3-diazaspiro[4.5]decan-1-yl]-2,2-dimethyl-propionitrile | SC_2097 | 3-amino-2,2-dimethyl-propanenitrile | SC_2014 | 475.3 |
| SC_2101 | CIS-2-[[8-Dimethylamino-3-[(4-methoxyphenyl)-methyl]-2-oxo-8-phenyl-1,3-diazaspiro[4.5]decan-1-yl]-methyl]-benzoic acid methyl ester | SC_2097 | methyl 2-(bromo-methyl)benzoate | SC_2125 | 542.3 |
| SC_2102 | CIS-1-(Cyclobutyl-methyl)-8-dimethylamino-8-phenyl-3-(pyridin-2-yl-methyl)-1,3-diazaspiro[4.5]decan-2-one | INT-987 | 2-(bromomethyl)pyridine | SC_2002 | 433.3 |
| SC_2103 | CIS-1-(Cyclobutyl-methyl)-8-dimethylamino-8-phenyl-3-(pyridin-4-yl-methyl)-1,3-diazaspiro[4.5]decan-2-one | INT-987 | 4-(bromomethyl)pyridine | SC_2002 | 433.3 |
| SC_2104 | CIS-8-Dimethylamino-3-[(4-methoxyphenyl)-methyl]-8-phenyl-1-(tetrahydro-furan-3-yl-methyl)-1,3-diazaspiro[4.5]decan-2-one | SC_2097 | 3-(bromomethyl)tetra-hydrofuran | SC_2014 | 478.3 |
| SC_2105 | CIS-1-(Cyclobutyl-methyl)-8-dimethylamino-8-phenyl-3-(pyrimidin-2-yl-methyl)-1,3-diazaspiro[4.5]decan-2-one | INT-987 | 2-(bromomethyl)pyrimidine | SC_2002 | 434.3 |
| SC_2106 | CIS-3[[1-[(5-Cyano-2-methoxy-phenyl)-methyl]-8-dimethylamino-2-oxo-8-phenyl-1,3-diazaspiro[4.5]decan-3-yl]-methyl]-4-methoxy-benzonitrile | SC_2142 | 3-(bromomethyl)-4-methoxybenzonitrile | SC_2125 | 564.3 |
| SC_2108 | CIS-8-Dimethylamino-1-(3-methoxy-3-methyl-butyl)-3-[(4-methoxyphenyl)-methyl]-8-phenyl-1,3-diazaspiro[4.5]decan-2-one | SC_2107 | Methyliodide | SC_2025 | 494.3 |
| SC_2110 | CIS-3-[[8-Dimethylamino-1-[(1-hydroxy-cyclobutyl)-methyl]-2-oxo-8-phenyl-1,3-diazaspiro[4.5]decan-3-yl]-methyl]-benzamide | SC_2141 | — | SC_2109 | 491.3 |
| SC_2111 | CIS-8-Dimethylamino-3-[(4-methoxyphenyl)-methyl]-1-(2-methylsulfonyl-ethyl)-8-phenyl-1,3-diazaspiro[4.5]decan-2-one | SC_2097 | 1-bromo-2-(methyl-sulfonyl)ethane | SC_2010 | 500.3 |
| SC_2112 | CIS-1-[(1-Hydroxy-cyclobutyl)-methyl]-3-[4-methoxyphenyl)-methyl]-8-methylamino-8-phenyl-1,3-diazaspiro[4.5]decan-2-one | SC_2051 | — | SC_2026 | 464.3 |
| SC_2113 | CIS-8-Dimethylamino-3-[(4-methoxyphenyl)-methyl]-8-phenyl-1-(tetrahydro-furan-2-yl-methyl)-1,3-diazaspiro[4.5]decan-2-one | SC_2097 | (tetrahydrofuran-2-yl)methanamine | SC_2014 | 478.3 |
| SC_2114 | CIS-3-Benzyl-8-dimethylamino-8-phenyl-1,3-diazaspiro[4.5]decan-2-one | INT-976 | (bromomethyl)benzene | SC_2097 | 364.2 |
| SC_2115 | CIS-3-Benzyl-8-dimethylamino-1-ethyl-8-phenyl-1,3-diazaspiro[4.5]decan-2-one | SC_2114 | 1-bromoethane | SC_2010 | 392.3 |

-continued

| Example | Chemical Name | Reactant I | Reactant II | in analogy to method | m/z [M + H]+ |
|---|---|---|---|---|---|
| SC_2117 | CIS-8-Dimethylamino-3-[(4-methoxyphenyl)-methyl]-1-[2-(methylsulfinyl)-ethyl]-8-phenyl-1,3-diazaspiro[4.5]decan-2-one | SC_2097 | 1-chloro-2-(methyl-sulfinyl)ethane | SC_2010 | 484.3 |
| SC_2118 | CIS-8-Dimethylamino-1-[(2R)-2-hydroxy-propyl]-3-[(4-methoxyphenyl)-methyl]-8-phenyl-1,3-diazaspiro[4.5]decan-2-one | SC_2087 | (R)-propylene oxide | SC_2010 | 452.3 |
| SC_2119 | CIS-8-Dimethylamino-1-[(2S)-2-hydroxy-propyl]-3-[(4-methoxyphenyl)-methyl]-8-phenyl-1,3-diazaspiro[4.5]decan-2-one | | (S)-propylene oxide | SC_2010 | 452.3 |
| SC_2120 | CIS-8-Dimethylamino-3-[(4-methoxyphenyl)-methyl]-8-phenyl-1-(tetrahydro-furan-3-yl-methyl)-1,3-diazaspiro[4.5]decan-2-one | SC_2097 | 3-(bromomethyl)tetra-hydrofuran | SC_2010 | 478.3 |
| SC_2122 | CIS-8-Dimethylamino-1-ethyl-3-[(4-methoxyphenyl)-methyl]-8-phenyl-1,3-diazaspiro[4.5]decan-2-one | SC_2097 | 1-bromoethane | SC_2010 | 422.3 |
| SC_2126 | CIS-3-[[8-Dimethylamino-1-[(1-hydroxy-cyclobutyl)-methyl]-2-oxo-8-phenyl-1,3-diazaspiro[4.5]decan-3-yl]-methyl]-4-methoxy-benzonitrile | SC_2142 | (1-(tert-butyldimethylsilyloxy)-cyclobutyl)methyl-4-methylbenzenesulfonate | SC_2124 | 503.3 |
| SC_2127 | CIS-8-Dimethylamino-1-ethyl-8-phenyl-3-(pyridin-3-yl-methyl)-1,3-diazaspiro[4.5]decan-2-one | INT-949 | 3-(bromomethyl)pyridine | SC_2019 | 393.3 |
| SC_2129 | CIS-8-Dimethylamino-1-[2-(1-methoxy-cyclobutyl)-ethyl]-3-[(4-methoxyphenyl)-methyl]-8-phenyl-1,3-diazaspiro[4.5]decan-2-one | SC_2097 | 3-(bromomethyl)pyridine | SC_2014 | 506.3 |
| SC_2130 | CIS-8-Dimethylamino-8-[3-(methoxymethyloxy)-phenyl]-3-[(4-methoxyphenyl)-methyl]-1,3-diazaspiro[4.5]decan-2-one | INT-966 | dimethylamine/KCN 3-methoxymethoxy-phenyl-magnesium bromide | SC_2017 | 454.3 |
| SC_2131 | CIS-8-Dimethylamino-8-[4-(methoxymethyloxy)-phenyl]-3-[(4-methoxyphenyl)-methyl]-1,3-diazaspiro[4.5]decan-2-one | INT-966 | dimethylamine/KCN 4-methoxymethoxy-phenyl-magnesium bromide | SC_2017 | 454.3 |
| SC_2132 | CIS-3-[8-Dimethylamino-3-[(4-methoxyphenyl)-methyl]-2-oxo-8-phenyl-1,3-diazaspiro[4.5]decan-1-yl]-propionic acid | SC_2133 | — | SC_2043 | 466.3 |
| SC_2133 | CIS-3-[8-Dimethylamino-3-[(4-methoxyphenyl)-methyl]-2-oxo-8-phenyl-1,3-diazaspiro[4.5]decan-1-yl]-propionic acid tert-butyl ester | SC_2097 | tert-butyl acrylate | SC_2042 | 522.3 |
| SC_2134 | CIS-2-[[1-(Cyclobutyl-methyl)-3-[(4-methoxyphenyl)-methyl]-2-oxo-8-phenyl-1,3-diazaspiro[4.5]decan-8-yl]-methyl-amino]-acetic acid methyl ester | SC_2044 | methyl 2-bromoacetate | SC_2040 | 520.3 |
| SC_2135 | CIS-8-Dimethylamino-3-[(4-methoxyphenyl)-methyl]-1-(3-methyl-but-2-enyl)-8-phenyl-1,3-diazaspiro[4.5]decan-2-one | SC_2097 | 1 -bromo-3-methylbut-2-ene | SC_2010 | 462.3 |
| SC_2137 | CIS-3-[(3-Bromophenyl)-methyl]-1-(cyclobutyl-methyl)-8-dimethylamino-8-phenyl-1,3-diazaspiro[4.5]decan-2-one | INT-987 | 1-bromo-3-(bromo-methyl)benzene | SC_2002 | 510.2 |
| SC_2138 | CIS-2-((8-(dimethyl amino)-1-((1-hydroxycyclobutyl)methyl)-2-oxo-8-phenyl-1,3-diazaspiro[4.5]decan-3-yl)methyl)benzonitrile | INT-987 | 2-(bromomethyl)benzonitrile | SC_2019 | 473.3 |
| SC_2139 | CIS-8-Dimethyl amino-8-(3-methoxyphenyl)-3-[(4-methoxyphenyl)-methyl]-1,3-diazaspiro[4.5]decan-2-one | INT-966 | dimethylamine/KCN 3-methoxy-phenylmagnesium bromide | SC_2017 | 424.3 |
| SC_2140 | CIS-8-Dimethylamino-8-(4-methoxyphenyl)-3-[(4-methoxyphenyl)-methyl]-1,3-diazaspiro[4.5]decan-2-one | INT-966 | dimethylamine/KCN 4-methoxy-phenylmagnesium bromide | SC_2017 | 424.3 |
| SC_2141 | CIS-3-((8-(dimethylamino)-1-((1-hydroxycyclobutyl)methyl)-2-oxo-8-phenyl-1,3-diazaspiro[4.5]decan-3-yl)methyl)benzonitrile | INT-987 | 3-(bromomethyl)benzonitrile | SC_2019 | 473.3 |
| SC_2142 | CIS-3-((8-(dimethyl amino)-2-oxo-8-phenyl-1,3-diazaspiro[4.5]decan-3-yl)methyl)-4-methoxybenzonitrile | INT-976 | 3-(bromomethyl)-4-methoxybenzonitrile | SC_2097 | 419.2 |

| Example | Chemical name | Reactant I | Reactant II | in analogy to method | $^1$H NMR data | m/z (M + H)+ |
|---|---|---|---|---|---|---|
| SC_2146 | CIS-8-Methylamino-8-phenyl-3-(1H-[1,2,3]triazol-4-yl-methyl)-1,3-diazaspiro[4.5]decan-2-one | SC_2143 | | SC_2026 | 1HNMR (DMSO-d6, 400 MHz), δ (ppm) = 14.33 (bs, 1H), 7.67 (s, 1H), 7.38 (d, 2H, J = 7.4 Hz), 7.29 (t, 2H, J = 7.56 Hz), 7.17 (t, 1H, J = 7.12 Hz), 6.65 (s, 1H), 4.30 (s, 2H), 3.10 (s, 2H), 1.92 (t, 2H, J = 11.86 Hz), 1.83-1.78 (m, 5H), 1.63 (t, 2H, J = 11.76 Hz), 1.36 (d, 2H, J = 12.12 Hz). | 341.4 |

-continued

| Example | Chemical name | Reactant I | Reactant II | in analogy to method | $^1$H NMR data | m/z (M + H)$^+$ |
|---|---|---|---|---|---|---|
| SC_2148 | CIS-2-[4-[(8-Methylamino-2-oxo-8-phenyl-1,3-diazaspiro [4.5]decan-3-yl)-methyl]-1H-[1,2,3]triazol-1-yl]-acetamide | SC_2145 | | SC_2026 | 1HNMR (DMSO-d6, 400 MHz), δ (ppm) = 7.87 (s, 1H), 7.67 (bs, 1H), 7.41-7.27 (m, 5H),7.17 (t, 1H, J = 7.16 Hz), 6.64 (bs, 1H), 5.02 (s, 2H), 4.28 (s, 2H), 3.13 (s, 2H), 1.95-1.79 (m, 8H, J = 11.32 Hz), 1.66-1.60 (m, 2H), 1.37 (d, 2H, J = 12.16 Hz). | 398.2 |
| SC_2149 | CIS-8-Dimethylamino-3-[(4-methoxyphenyl)-methyl]-2-oxo-8-phenyl-1,3-diazaspiro[4.5]decane-1-carboxylic acid benzyl ester | SC_2097 | benzyl carbonochloridate | SC_2147 | 1H NMR (600 MHz, DMSO) δ 7.52-7.45 (m, 2H), 7.44-7.37 (m, 2H), 7.38-7.29 (m, 3H), 7.30-7.24 (m, 2H), 7.26-7.19 (m, 1H), 7.21-7.15 (m, 2H), 6.93-6.86 (m, 2H), 5.23 (s, 2H), 4.28 (s, 2H), 3.73 (s, 3H), 3.19 (s, 2H), 2.84 (ddd, 2H), 2.63-2.56 (m, 2H), 1.88 (s, 6H), 1.37-1.23 (m, 4H). | 528.3 |
| SC_2150 | CIS-3-[[1-(2-Hydroxy-ethyl)-1H-[1,2,3]triazol-4-yl]-methyl]-8-methylamino-8-phenyl-1,3-diazaspiro[4.5]decan-2-one | SC_2144 | | SC_2026 | 1HNMR (DMSO-d6, 400 MHz), δ (ppm) = 7.88 (s, 1H), 7.39 (d, 2H, J = 7.0 Hz), 7.29 (t, 2H, J = 7.38 Hz), 7.19-7.17 (m, 1H), 6.64 (bs, 1H), 4.99 (t, 1H, J = 5.24 Hz), 4.35 (t, 2H, 5.32 Hz), 4.27 (s, 2H), 3.75-3.73 (m, 2H), 3.12 (s, 2H), 1.94-1.79 (m, 7H), 1.64 (m, 2H), 1.36 (d, 2H, J = 12.2 Hz). | 385.2 |
| SC_2151* | CIS-8-Dimethylamino-8-phenyl-3-(2-pyridin-2-yl-ethyl)-1,3-diazaspiro[4.5]decane-2,4-dione | INT-795 step1 | 2-(2-bromoethyl)pyridine | step 2 of INT-795 | 1H NMR (DMSO-d6): δ 8.64 (br s, 1H), 8.42-8.41 (m, 1H), 7.67-7.63 (m, 1H),7.40-7.37 (m, 2H), 7.32-7.26 (m, 3H) 7.19-7.16 (m, 2H), 3.68-3.61 (t, 2H), 2.92-2.90 (t, 2H), 2.46-2.45 (m, 2H),1.91 (m, 8H), 1.51 (m, 2H), 1.45-1.42 (m, 2H). | 393.3 |
| SC_2152 | CIS-8-Dimethylamino-8-phenyl-3-(2-pyridin-2-yl-ethyl)-1,3-diazaspiro[4.5]decane-2-one | SC_2151 | | step 3 of INT-795 | 1H NMR (DMSO-d6: δ 8.45-8.44 (d, 1H), 7.69-7.65 (m, 1H), 7.37-7.30 (m, 4H), 7.26-7.16 (m, 3H), 6.65 (br s, 1H), 3.37-3.32 (m, 2H), 2.99 (s, 2H), 2.86-2.82 (t, 2H), 2.28 (m, 2H), 1.91 (m, 6H), 1.72-1.71 (m, 4H), 1.28-1.26 (m, 2H). | 379.3 |
| SC_2153 | CIS-8-Dimethylamino-1-[(1-hydroxy-cyclobutyl)-methyl]-3-[[1-(2-hydroxy-ethyl)-1H-[1,2,3]triazol-4-yl]-methyl]-8-pheyl-1,3-diazaspiro[4.5]decan-2-one | INT-1012 | | SC_2144 | 1HNMR (DMSO-d6, 400 MHz), δ (ppm) = 7.92 (s, 1H), 7.36-7.24 (m, 5H), 6.00 (s, 1H), 4.97 (t, 1H, J = 5.32 Hz) 4.36-4.34 (m, 4H), 3.73 (q, 2H, J = 5.36 Hz), 3.24 (s, 2H), 3.11 (s, 2H), 2.62 (d, 2H, J = 14.0 Hz), 2.08-1.84 (m, 12H), 1.64-1.61 (m, 1H), 1.38-1.28 (m, 5H). | 483.2 |
| SC_2154* | CIS-8-Dimethylamino-3-[2-(1H-imidazol-1-yl)-ethyl]-8-phenyl-1,3-diazaspiro[4.5]decan-2,4-dione | INT-795 step1 | 1-(2-bromoethyl)-1H-imidazole hydrobromide | step 2 of INT-795 | 1H NMR (DMSO-d6: δ 8.71 (br s, 1H), 7.42-7.37 (m, 3H), 7.32-7.26 (m, 3H), 7.00 (s, 1H), 6.79 (s, 1H) 4.15-4.12 (t, 2H), 3.65-3.62 (t, 2H), 2.46 (m, 2H), 1.91 (s, 8H), 1.47-1.37 (m, 4H). | 382.3 |
| SC_2155 | CIS-2-[4-[[8-Dimethylamino-1-[(1-hydroxy-cyclobutyl)-methyl]-2-oxo-8-pheyl-1,3-diazaspiro[4.5]decan-3-yl]-methyl]-1H-[1,2,3]trazol-1-yl]-acetamide | INT-1012 | | SC_2145 | 1HNMR (DMSO-d6, 400 MHz), δ (ppm) = 7.91 (s, 1H), 7.67 (s, 1H), 7.34-7.24 (m, 6H), 5.99 (s, 1H), 5.01 (s, 2H), 4.36 (s, 2H), 3.25 (s, 2H), 3.11 (s, 2H), 2.62-2.65 (m, 2H), 2.08-1.86 (m, 12H), 164-.161 (m, 1H), 1.38-1.18 (m, 5H). | 496.3 |
| SC_2156 | CIS-1-[(1-Hydroxy-cyclobutyl)-methyl]-3-[[1-(2-hydroxy-ethyl)-1H-[1,2,3]triazol-4-yl]-methyl]-8-methylamino-8-phenyl-1,3-diazaspiro[4.5]decan-2-one | SC_2153 | | SC_2026 | 1HNMR (DMSO-d6, 400 MHz), δ (ppm) = 7.93 (s, 1H), 7.44-7.17 (m, 5H), 6.03 (s, 1H), 4.98 (t, 1H) 4.36 (s, 4H), 3.73-3.75 (q, 2H, J = 5.48 Hz), 3.27 (s, 2H), 3.20 (s, 2H), 2.11-2.03 (m, 4H), 1.86 (bs, 7H), 1.62-1.33 (m, 7H). | 469.3 |
| SC_2157* | CIS-8-Dimethylamino-8-phenyl-3-(2-pyridin-3-yl-ethyl)-1,3-diazaspiro[4.5]decane-2,4-dione | INT-795 step1 | 3-(2-bromoethyl)pyridine | step 2 of INT-795 | 1H NMR (DMSO-d6: δ 8.65 (br s, 1H), 8.38-8.37 (m, 1H), 8.28 (d, 1H), 7.54 (d, 1H), 7.40-7.36 (m, 2H), 7.31-7.24 (m, 4H) 3.56 (t, 2H), 2.83 (t, 2H), | 393.3 |

-continued

| Example | Chemical name | Reactant I | Reactant II | in analogy to method | $^1$H NMR data | m/z (M + H)$^+$ |
|---|---|---|---|---|---|---|
| | | | | | 2.44-2.41 (m, 2H), 1.95-1.90 (m, 8H), 1.42-1.35 (m, 4H). | |
| SC_2158* | CIS-8-Dimethylamino-8-phenyl-3-(2-pyridin-4-yl-ethyl)-1,3-diazaspiro[4.5]decan-2,4-dione | INT-795 step1 | 4-(2-bromoethyl)pyridine | step 2 of INT-795 | 1H NMR (DMSO-d6): δ 8.67 (br s, 1H), 8.42-8.40 (d, 2H), 7.40-7.36 (m, 2H), 7.31-7.25 (m, 3H), 7.14-7.12 (d, 2H), 3.60-3.56 (t, 2H), 2.85-2.82 (t, 2H), 2.45-2.41 (m, 2H), 1.95-1.85 (m, 8H), 1.44-1.35 (m, 4H). | 393.3 |
| SC_2159 | CIS-2-[4-[[1(Cyclobutyl-methyl-8-dimethylamino-2-oxo-8-phenyl-1,3-diazaspiro[4.5]decan-3-yl]-methyl]-1H-[1,2,3]triazol-1-yl]-acetamide | INT-1030 | ammonia | SC_2145 | 1HNMR (DMSO-d6, 400 MHz), δ (ppm) = 7.86 (s, 1H), 7.66 (s, 1H), 7.23-7.33 (m, 6H), 5.00 (s, 2H), 4.30 (s, 2H), 3.09(s, 2H), 3.04 (s, 2H) 2.61-2.64 (m, 2H), 1.95-2.02 (m, 11H), 1.69-1.78 (m, 4H), 1.28-1.33 (m, 4H). | 480.1 |
| SC_2160 | CIS-1-(Cyclobutyl-methyl)-8-dimethylamino-3-[[1-(2-hydroxy-ethyl)-1H-[1,2,3]triazol-4-yl]-methyl]-8-phenyl-1,3-diazaspiro[4.5]decan-2-one | INT-1030 | | SC_2144 | 1HNMR (DMSO-d6, 400 MHz), δ (ppm) = 7.87 (s, 1H), 7.23-7.35 (m, 5H), 4.97 (t, 1H, J = 5.28 Hz), 4.34 (t, 2H, J = 5.34 Hz), 4.29 (s, 2H), 3.71-3.75 (q, 2H), 3.09 (s, 2H), 3.04-3.05 (d, 2H, J = 7.2 Hz), 1.95-2.05 (m, 11H), 1.67-1.85 (m, 4H), 1.25-.133 (bs, 4H). | 467.0 |
| SC_2161 | CIS-2-[4-[[1-[(1-Hydroxy-cyclobutyl)-methyl]-8-methylamino-2-oxo-8-phenyl-1,3-diazaspiro[4.5]decan-3-yl]-methyl]-1H-[1,2,3]triazol-1-yl]-acetamide | SC_2155 | | SC_2026 | 1HNMR (DMSO-d6, 400 MHz), δ (ppm) = 7.91 (s, 1H), 7.68 (s, 1H), 7.44-7.42 (m, 2H), 7.35-7.28 (m, 3H), 7.19-7.16 (m, 1H), 6.03 (s, 1H), 5.02 (s, 2H), 4.37 (s, 2H), 3.28 (s, 2H), 3.20 (s, 2H), 2.14-2.01 (m, 4H), 1.90-1.84 (m, 7H), 1.62-1.56 (m, 3H), 1.46.133 (m, 3H). | 482.3 |
| SC_2162 | CIS-1-(Cyclobutyl-methyl)-3-[[1-(2-hydroxy-ethyl)-1H-[1,2,3]triazol-4-yl]-methyl]-8-methylamino-8-phenyl-1,3-diazaspiro[4.5]decan-2-one | SC_2160 | | SC_2026 | 1HNMR (DMSO-d6, 400 MHz), δ (ppm) = 7.87 (s, 1H), 7.40-7.42 (d, 2H, J = 7.64 Hz), 7.29 (t, 2H, J = 7.48 Hz), 7.17 (t, 1H, J = 7.18 Hz), 4.98 (t, 1H, J = 5.32 Hz), 4.35 (t, 2H, J = 5.44 Hz), 4.31 (s, 2H), 3.71-3.75 (q, 2H), 3.13 (s, 2H), 3.07-3.09 (d, 2H, J = 7.36 Hz), 2.53-2.57 (m, 1H), 2.05-2.32 (m, 3H), 1.93-197 (m, 2H), 1.67-1.86 (m, 8H), 1.53-1.60 (m, 2H), 1.22-1.25 (m, 2H). | 453.1 |
| SC_2163 | CIS-2-[4-[[1-(Cyclobutyl-methyl)-8-methylamino-2-oxo-8-phenyl-1,3-diazaspiro[4.5]decan-3-yl]-methyl]-1H-[1,2,3]triazol-1-yl]-acetamide | SC_2159 | | SC_2026 | 1HNMR (DMSO-d6, 400 MHz), δ (ppm) = 7.86 (s, 1H), 7.27-7.37 (m, 5H), 7.17 (t, 1H, J = 7.10 Hz), 5.02 (s, 2H), 4.32 (s, 2H), 3.07-3.13 (m, 4H), 2.26 (sb, 2H), 1.67-1.86 (m, 8H), 1.57-1.60 (m, 2H), 1.22-1.25 (m, 2H). | 466.3 |
| SC_2164 | CIS-8-Dimethylamino-8-phenyl-3-(2-pyridin-3-yl-ethyl)-1,3-diazaspiro[4.5]decan-2-one | SC_2157 | | step 3 of INT-795 | 1H NMR (DMSO-d6) δ 8.39-8.37 (m, 2H), 7.61-7.60 (m, 1H), 7.38-7.23 (m, 6H), 6.67 (br s, 1H), 3.26 (t, 2H), 3.01 (s, 2H), 2.72 (t, 2H), 2.27 (m, 2H), 1.91 (s, 6H), 1.73-1.71 (m, 4H),1.28-1.24 (m, 2H). | 379.3 |
| SC_2165 | CIS-8-Dimethylamino-3-[2-(1H-imidozol-1-yl)-ethyl]-8-phenyl-1,3-diazaspiro[4.5]decan-2-one | SC_2154 | | step 3 of INT-795 | 1H NMR (CDC13): δ 7.45 (s, 1H), 7.38-7.34 (m, 2H), 7.31-7.21 (m, 3H), 7.04 (s, 1H), 6.92(s, 1H) 4.95 (br s, 1H), 4.12-4.09 (t, 2H), 3.45-3.43 (t, 2H), 2.67 (s, 2H), 2.03-1.96 (s, 8H), 1.84-1.68 (m, 4H),1.38-1.29 (m, 2H). | 368.2 |
| SC_2166 | CIS-8-Dimethylamino-8-phenyl-3-(2-pyridin-4-yl-ethyl)-1,3-diazaspiro[4.5]decan-2-one | SC_2158 | | step 3 of INT-795 | 1H NMR (DMSO-d6) δ 8.50-8.48 (m, 2H), 7.39-7.35 (m, 2H), 7.30-7.27 (m, 3H), 7.14-7.12 (d, 2H), 4.62 (br s, 1H), 3.46-3.43 (t, 2H), 2.95 (s, 2H), 2.82-2.78 (t, 2H), 2.17-2.02 (m, 10H), 1.85-1.75 (m, 2H), 1.41-1.29 (m, 2H). | 379.2 |
| SC_2167 | CIS-8-Dimethylamino-8-phenyl-3-(2-pyrimidin-2-yl-ethyl)-1,3- | INT-976 | 2-(2-bromoethyl)pyrimidine | SC_2097 | 1H NMR (DMSO-d6) δ 8.70 (d, 2H), 7.38-7.23 (m, 6H), 6.65 (br s, 1H), 3.45 | 380.3 |

-continued

| Example | Chemical name | Reactant I | Reactant II | in analogy to method | $^1$H NMR data | m/z (M + H)$^+$ |
|---|---|---|---|---|---|---|
| | diazaspiro[4.5]decan-2-one | | | | (t, 2H), 3.00-2.49 (m, 4H), 2.28 (br m, 2H), 1.91 (s, 6H), 1.73-1.71 (m, 4H), 1.29-1.27 (m, 2H). | |
| SC_2168 | CIS-8-Dimethylamino-8-phenyl-3-(2-pyrimidin-5-yl-ethyl)-1,3-diazaspiro[4.5]decan-2-one | INT-976 | 5-(2-chloroethyl)pyrimidine | SC_2097 | 1H NMR (DMSO-d6) δ 9.00 (s, 1H), 8.64 (s, 2H), 7.38-7.31 (m, 4H), 7.26-7.23 (m, 1H), 6.69 (br s, 1H), 3.26 (m, 2H), 3.05 (s, 2H), 2.74 (t, 2H), 2.27 (br m, 2H), 1.92-1.69 (m, 10H), 1.28-1.24 (m, 2H). | 380.2 |
| SC_2169 | CIS-8-Dimethylamino-1-ethyl-3-[(4-methylsulfonyl-phenyl)-methyl]-8-phenyl-1,3-diazaspiro[4.5]decan-2-one | INT-976 | 1-(chloromethyl)-4-methylsulfonyl-benzene (step 1), bromoethane (step 2) | SC_2097 (for step 1), SC_2010 (for step 2) | 1H NMR (600 MHz, DMSO) δ 7.92-7.86 (m, 2H), 7.50-7.46 (m, 2H), 7.38-7.28 (m, 4H), 7.27-7.19 (m, 1H), 4.37 (s, 2H), 3.19 (s, 3H), 3.15-3.03 (m, 4H), 2.69-2.60 (m, 2H), 2.15-2.06 (m, 2H), 1.97 (s, 6H), 1.38-1.27 (m, 4H), 1.14 (t, 3H). | 470.3 |
| SC_2171 | CIS-8-Dimethylamino-8-phenyl-3-(1-phenyl-cyclopropyl)-1,3-diazaspiro[4.5]decan-2-one | INT-1023 | 1-phenylcyclopropanamine (step 1) | SC_2170 | 1H NMR (DMSO-d6) δ 7.36-7.14 (m, 8H), 7.08 (d, 2H), 6.77 (br s, 1H), 3.08 (s, 2H), 2.29 (m, 2H), 1.92 (s, 6H), 1.79-1.77 (m, 4H), 1.35-1.33 (m, 2H), 1.23-1.21(m, 2H), 1.09-1.06 (m, 2H). | 390.2 |
| SC_2172 | CIS-8-Dimethylamino-1,3-bis[(2-methoxyphenyl)-methyl]-8-phenyl-1,3-diazaspiro[4.5]decan-2-one | INT-976 | 1-(bromomethyl)-2-methoxybenzene | SC_2097 | 1H NMR (DMSO-d6) δ 7.32-7.14 (m, 9H), 6.99-6.90 (m, 4H), 4.32-4.27 (m, 4H), 3.84-3.77 (m, 6H), 3.14 (s, 2H), 2.58-2.54 (m, 2H), 2.03-1.97 (m, 2H), 1.89 (s, 6H), 1.29-1.22 (m, 4H). | 514.2 |
| SC_2173 | CIS-8-Dimethylamino-3-[(3-methylsulfonyl-phenyl)-methyl]-8-phenyl-1,3-diazaspiro[4.5]decan-2-one | INT-976 | 1-(bromomethyl)-3-methylsulfonyl-benzene | SC_2097 | 1H NMR (600 MHz, DMSO) δ 7.84-7.79 (m, 1H), 7.74 (d, 1H), 7.62 (t, 1H), 7.55 (d, 1H), 7.36-7.27 (m, 4H), 7.23 (t, 1H), 6.99 (br s, 1H), 4.33 (s, 2H), 3.19 (s, 2H), 2.97 (s, 2H), 2.35-2.24 (m, 2H), 1.93 (d, 6H), 1.85-1.66 (m, 4H), 1.38-1.31 (m, 2H). | 442.2 |
| SC_2174 | CIS-8-Dimethylamino-1-[(1-hydroxy-cyclobutyl)-methyl]-3-(1-methyl-1-phenyl-ethyl)-8-phenyl-1,3-diazaspiro[4.5]decan-2-one | SC_2170 | (1-(tert-butyldimethyl-silyloxy)cyclobutyl)methyl-4-methylbenzenesulfonate | INT-799 (step 1) | 1H NMR (DMSO-d6) δ 7.36-7.14 (m, 10H), 5.88 (m, 1H), 3.33 (s, 2H), 3.03 (s, 2H), 2.68-2.64 (m, 2H), 2.09-1.95 (m, 10H), 1.89-1.81 (m, 2H), 1.61-1.56 (m, 7H), 1.48-1.28 (m, 5H). | 476.3 |
| SC_2175 | CIS-3-[(3-Cyclopropyl-phenyl)-methyl]-8-dimethylamino-8-phenyl-1,3-diazaspiro[4.5]decan-2-one | INT-976 | 1-(bromoethyl)-3-cycloprpyl-benzene | SC_2097 | 1H NMR (600 MHz, DMSO) δ 8.17 (s, 1H), 7.41-7.29 (m, 4H), 7.30-7.20 (m, 1H), 7.18 (t, 1H), 6.98-6.89 (m, 3H), 6.87 (t, 1H), 4.15 (s, 2H), 2.89 (s, 2H), 2.28 (s, 2H), 1.97 (s, 6H), 1.91-1.83 (m, 1H), 1.80-1.75 (m, 3H), 1.34-1.27 (m, 2H), 0.96-0.88 (m, 2H), 0.65-0.57 (m, 2H). | 403.3 |
| SC_2176 | CIS-3-(1,3-Benzodioxol-4-yl-methyl)-8-dimethylamino-8-phenyl-1,3-diazaspiro[4.5]decan-2-one | INT_976 | | SC_2097 | 1H NMR (600 MHz, DMSO) δ 7.37-7.27 (m,4H), 7.27-7.20 (m, 1H), 6.88 (s, 1H), 6.83-6.76 (m, 2H), 6.67 (dd, 1H), 5.96 (s, 2H), 4.18 (s, 2H), 2.95 (s, 2H), 2.30-2.26 (m, 2H), 1.93 (s, 6H), 1.84-1.63 (m, 4H), 1.33 (t, 2H). | 408.2 |
| SC_2177 | CIS-8-Dimethylamino-1-[(1-hydroxy-cyclobutyl)-methyl]-8-phenyl-3-(1-phenyl-cyclopropyl)-1,3-diazaspiro[4.5]decan-2-one | SC_2171 | (1-(tert-butyldimethyl-silyloxy)cyclobutyl)methyl-4-methylbenzenesulfonate | INT-799 (step 1) | 1H NMR (DMSO-d6): δ 7.34-7.17 (m, 8H), 7.15-7.13 (m, 2H), 5.89 (s, 1H), 3.29 (s, 2H), 3.09 (s, 2H), 2.64-2.61 (m, 2H), 2.08-2.03 (m, 4H), 1.96 (s, 6H), 1.91-1.84 (m, 2H), 1.64-1.61 (m, 1H), 1.42-1.29 (m, 5H), 1.29-1.26 (m, 2H),1.13-1.01 (m, 2H) | 474.2 |
| SC_2178 | CIS-4-[[8-Dimethylamino-3-[(2-methoxyphenyl)-methyl]-2-oxo-8-phenyl-1,3-diazaspiro[4.5]decan-1-yl]-methyl]-benzonitrile | SC_2179 | 4-(bromoethyl)benzonitrile | SC_2097 | 1H NMR (DMSO-d6) δ 7.81 (d, 2H). 7.53 (d, 2H), 7.32-7.21 (m, 6H), 7.15-7.13 (m, 1H), 6.99-6.92 (m, 2H), 4.38-4.31 (m, 4H), 3.77 (s, 3H), 3.16 (s, 2H), 2.58-2.55 (m, 2H), 2.00-1.89 (m, 8H), 1.28-1.23 (m, 4H). | 509.2 |

-continued

| Example | Chemical name | Reactant I | Reactant II | in analogy to method | $^1$H NMR data | m/z $(M+H)^+$ |
|---|---|---|---|---|---|---|
| SC_2179 | CIS-8-Dimethylamino-3-[(2-methoxyphenyl)-methyl]-8-phenyl-1,3-diazaspiro[4.5]decan-2-one | INT-976 | 1-(bromomethyl)-2-methoxybenzene | SC_2097 | 1H NMR (600 MHz, DMSO) δ 7.37-7.27 (m, 4H), 7.27-7.19 (m, 2H), 7.08 (dd, 1H), 6.96 (dd, 1H), 6.91 (td, 1H), 6.85 (s, 1H), 4.19 (s, 2H), 3.75 (s, 3H), 2.96 (s, 2H), 2.30 (d, 2H), 1.93 (s, 6H), 1.86-1.69 (m, 4H), 1.38-1.32 (m, 2H). | 394.3 |
| SC_2181 | CIS-8-Dimethylamino-8-phenyl-3-(pyridin-2-yl-methyl)-1,3-diazaspiro[4.5]decan-2-one | INT-1028 | 2-bromoethyl)pyridine hydrobromide (step 1) | SC_2180 | 1H NMR (600 MHz, DMSO) δ 8.48 (ddd, 1H), 7.76 (td, 1H), 7.37-7.27 (m, 4H), 7.29-7.17 (m, 3H), 6.93 (s, 1H), 4.30 (s, 2H), 3.05 (s, 2H), 2.36-2.21 (m, 2H), 1.93 (s, 6H), 1.88-1.58 (m, 4H), 1.41-1.31 (m, 2H). | 365.2 |
| SC_2182 | CIS-8-Dimethylamino-8-phenyl-3-(pyridin-3-yl-methyl)-1,3-diazaspiro[4.5]decan-2-one | INT-1028 | 3-bromomethyl)pyridine hydrobromide (step 1) | SC_2180 | 1H NMR (600 MHz, DMSO) δ 8.46 (dd, 1H), 8.42 (dd, 1H), 7.60 (dt, 1H), 7.38-1.30 (m, 3H), 7.31-7.26 (m, 2H), 7.26-7.20 (m, 1H), 6.97-6.93 (m, 1H), 4.24 (s, 2H), 2.95 (s, 2H), 2.33-2.20 (m, 2H), 1.92 (s, 6H), 1.84-1.60 (m, 4H), 1.35-1.29 (m, 2H). | 365.2 |
| SC_2184 | CIS-8-Dimethylamino-8-phenyl-3-[(2-piperidin-1-yl-pyridin-4-yl)-methyl]-1,3-diazaspiro[4.5]decan-2-one | INT-1065 | piperidine | SC_2183 | 1H NMR (600 MHz, CDC13) δ 8.09 (d, 1H), 7.38 (dd, 2H), 7.30 (d, 3H), 6.48 (s, 1H), 6.42 (dd, 1H), 5.47 (s, 1H), 4.23 (s, 2H), 3.54-3.46 (m, 4H), 2.96 (s, 2H), 2.20-2.15 (m, 4H), 2.07 (s, 6H), 1.92-1.84 (m, 2H), 1.66-1.60 (m, 6H), 1.47-1.39 (m, 2H). | 448.3 |
| SC_2185 | CIS-8-Dimethylamino-3-[(2-morpholin-4-yl-pyridin-4-yl)-methyl]-8-phenyl-1,3-diazaspiro[4.5]decan-2-one | INT-1065 | morpholine | SC_2183 | 1H NMR (600 MHz, DMSO) δ 8.05 (d, 1H), 7.37-7.27 (m, 4H), 7.26-7.20 (m, 1H), 6.94 (s, 1H), 6.59 (s, 1H), 6.50 (dd, 1H), 4.13 (s, 2H), 3.68 (t, 4H), 3.41-3.36 (m, 4H), 2.96 (s, 2H), 2.37-2.22 (m, 2H), 1.93 (s, 6H), 1.86-1.62 (m, 4H), 1.42-1.29 (m, 2H). | 450.3 |

(*Comparative Example)

Chemical Structure of all Examples

SC_2001

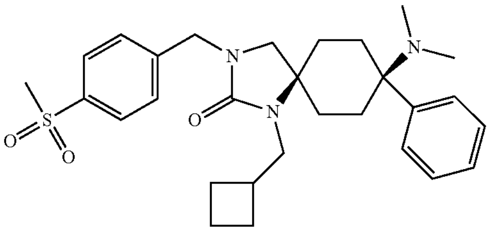

SC_2002

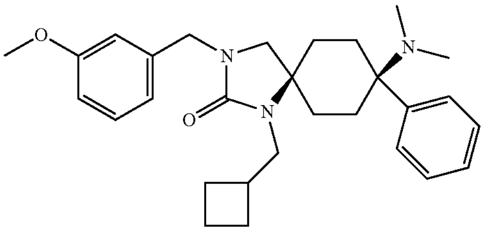

SC_2003

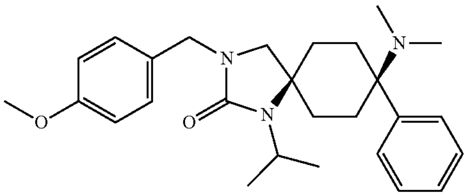

SC_2004

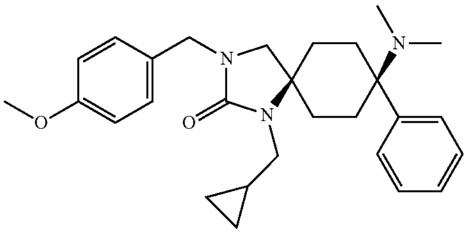

-continued
SC_2005
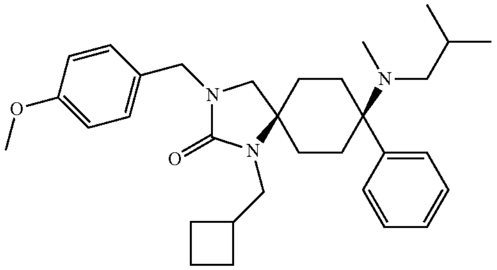
SC_2006
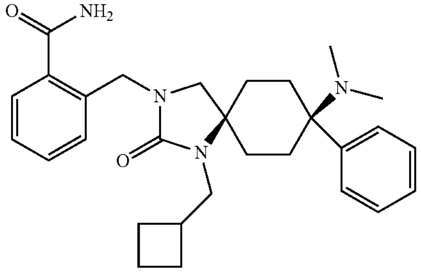
SC_2007
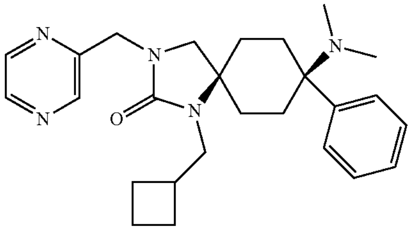
SC_2008
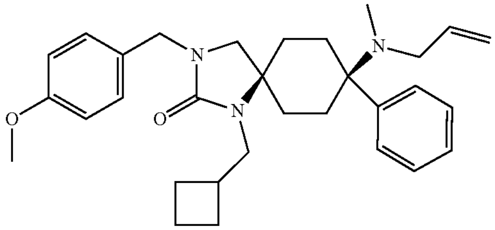
SC_2009
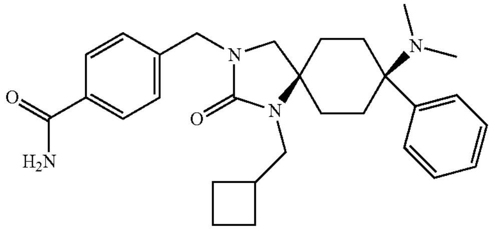
SC_2010
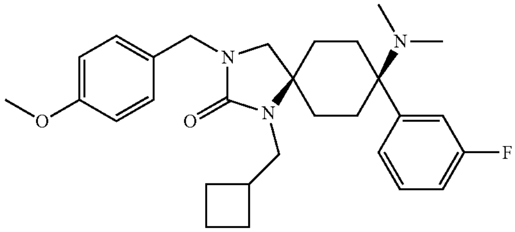
SC_2011
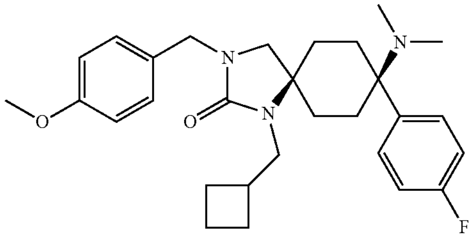
SC_2012
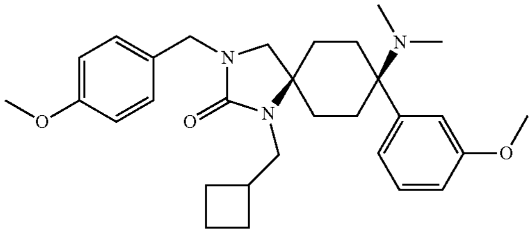
SC_2013
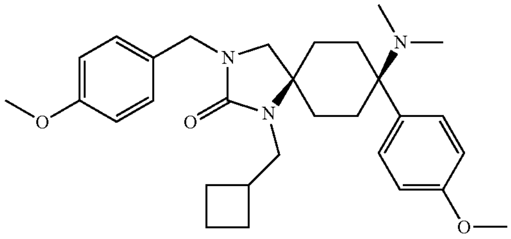
SC_2014
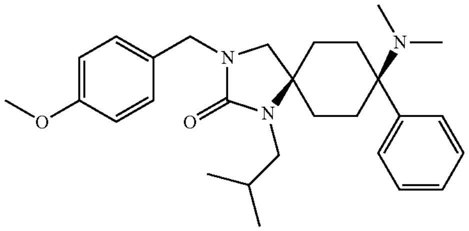
SC_2015
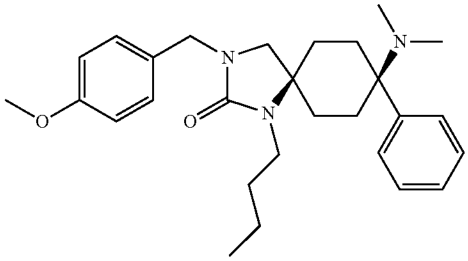
SC_2016
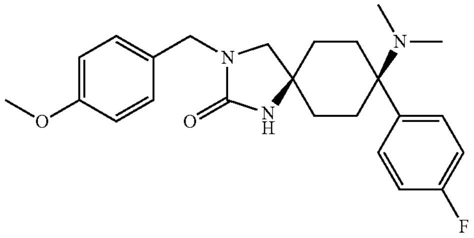

-continued
SC_2017
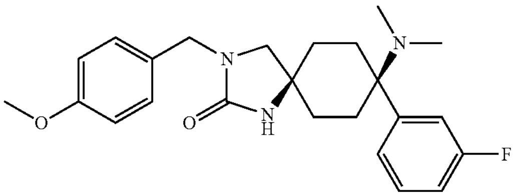
SC_2018
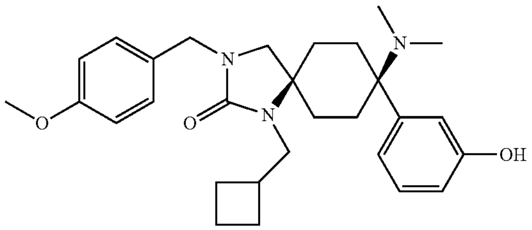
SC_2019
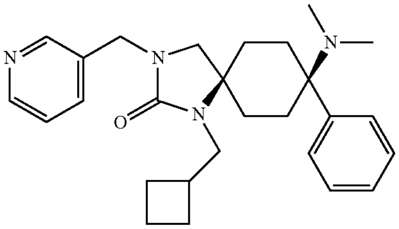
SC_2020
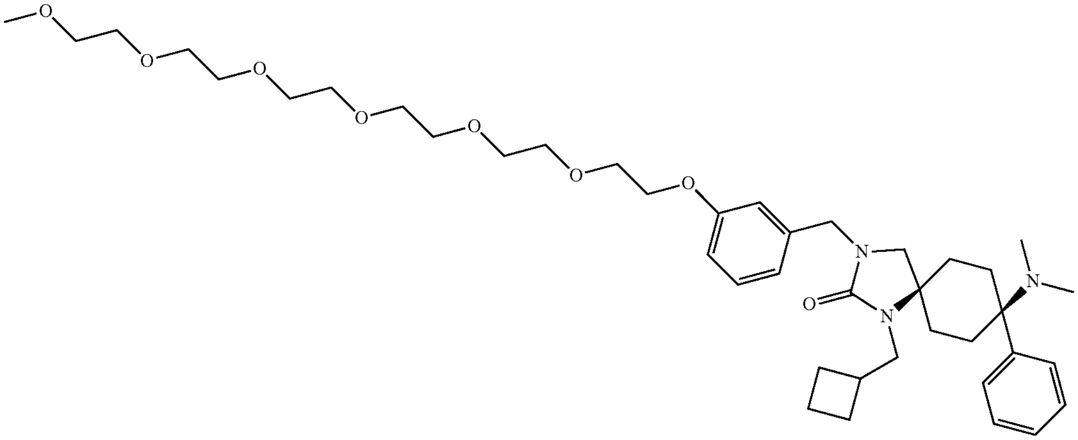
SC_2021
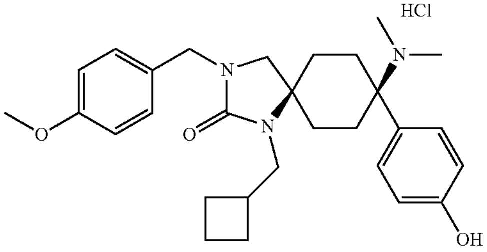
SC_2022
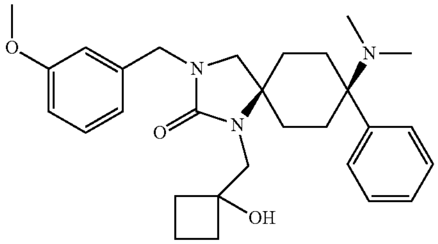
SC_2023
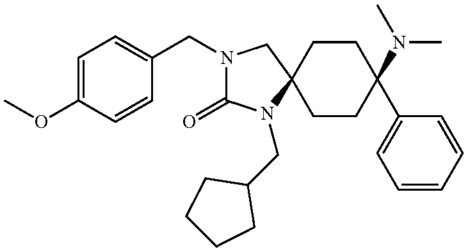
SC_2024
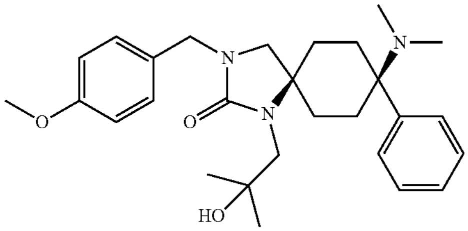

-continued
SC_2025
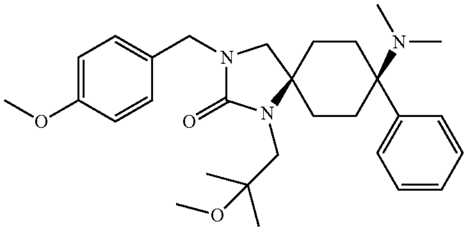
SC_2026
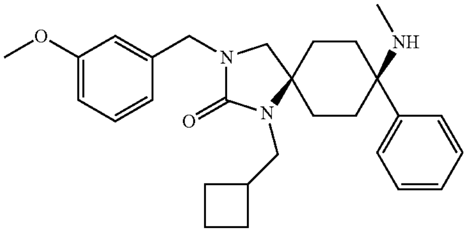
SC_2027
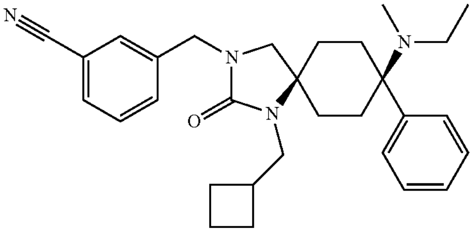
SC_2028
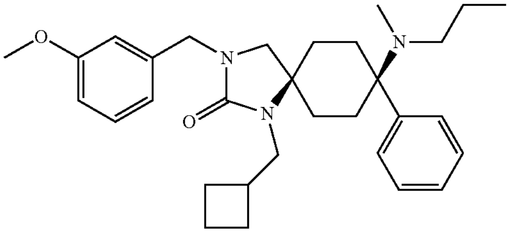
SC_2029
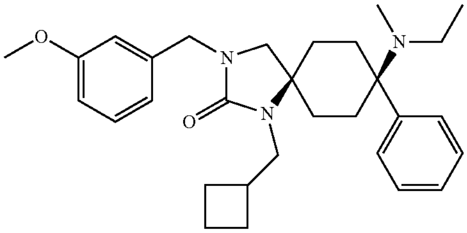
SC_2030
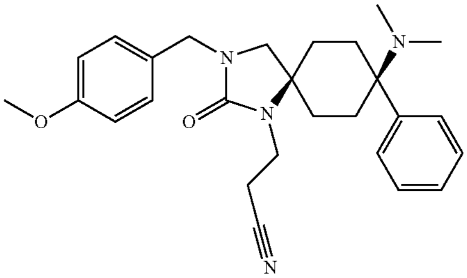
SC_2031
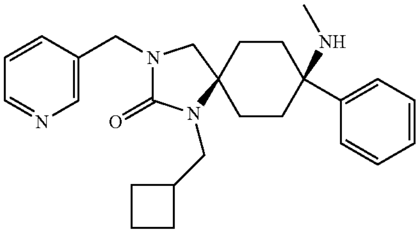
SC_2032
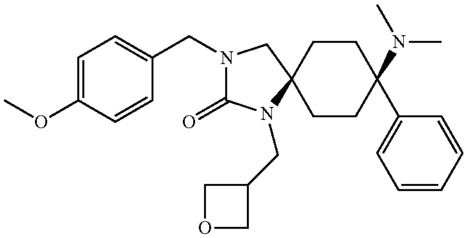
SC_2033
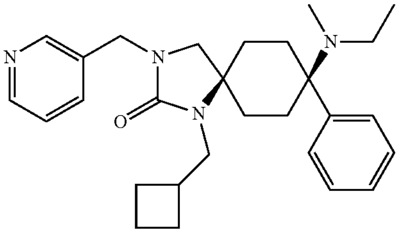
SC_2034
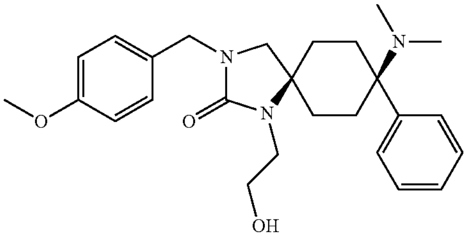
SC_2035
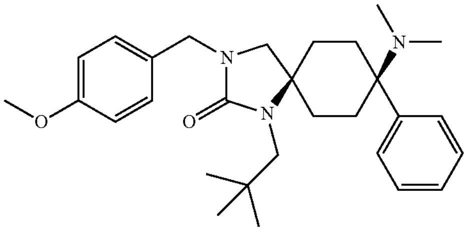
SC_2036
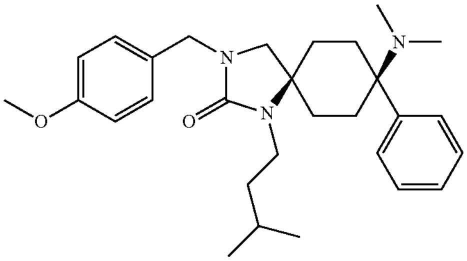

-continued
SC_2037
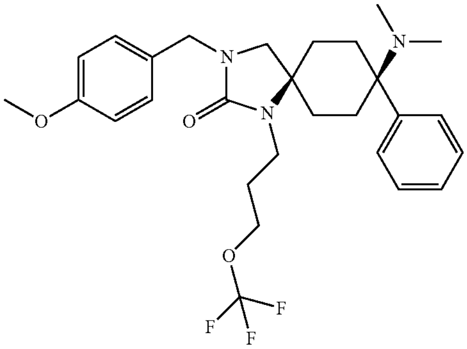
SC_2038
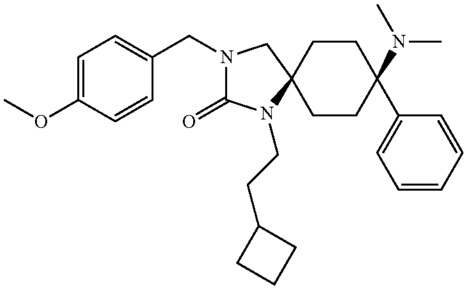
SC_2039
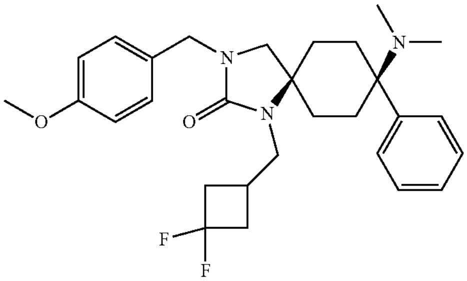
SC_2040
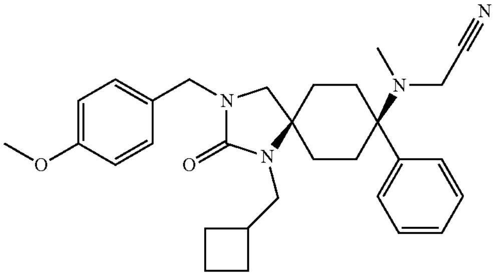
SC_2041
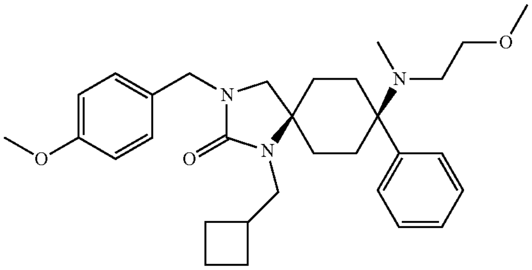
SC_2042
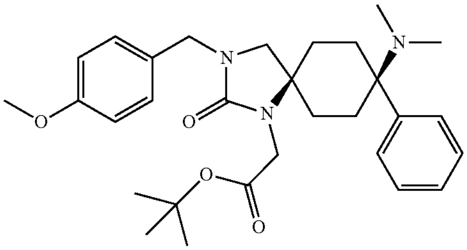
SC_2043
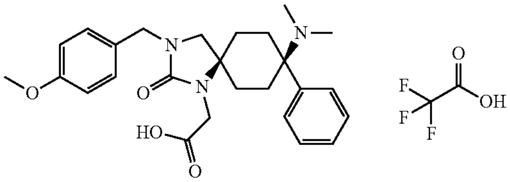
SC_2044
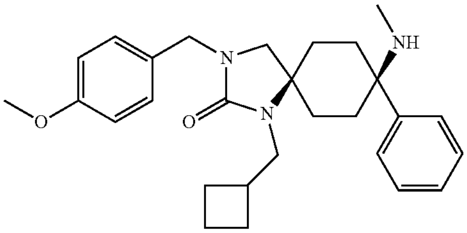
SC_2045
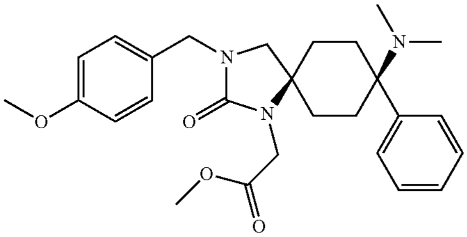
SC_2046
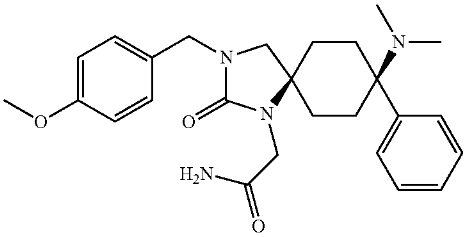

-continued
SC_2047
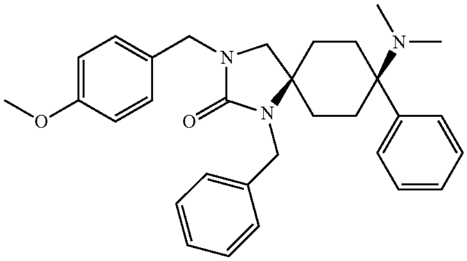
SC_2048
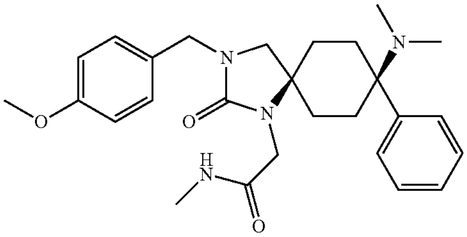
SC_2049
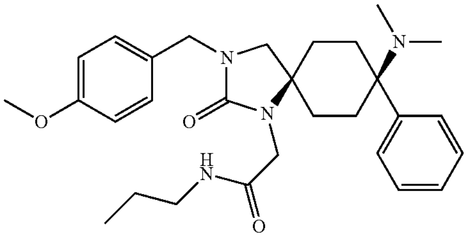
SC_2050
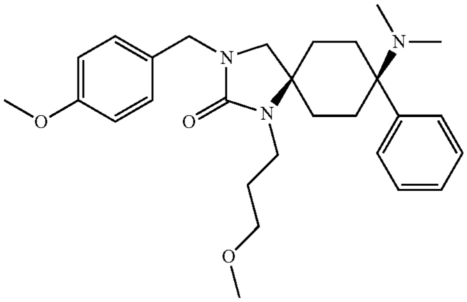
SC_2051
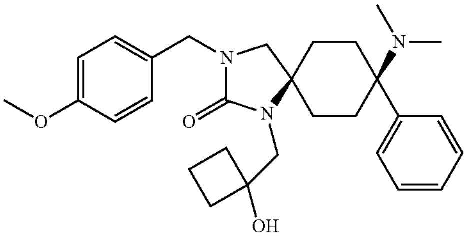
SC_2052
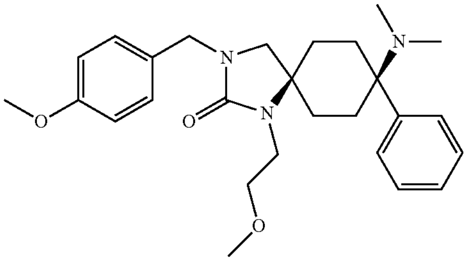
SC_2053
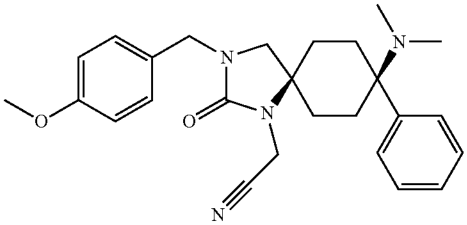
SC_2054
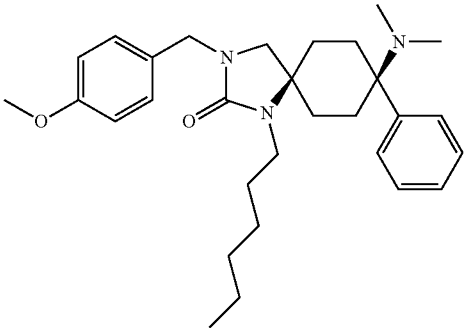
SC_2055
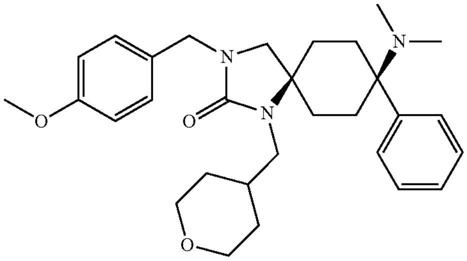
SC_2056
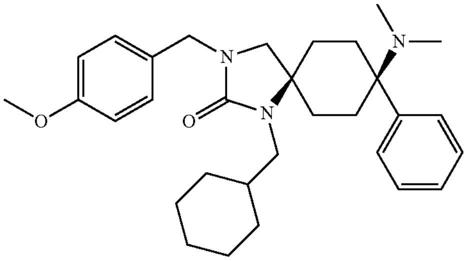

-continued
SC_2057
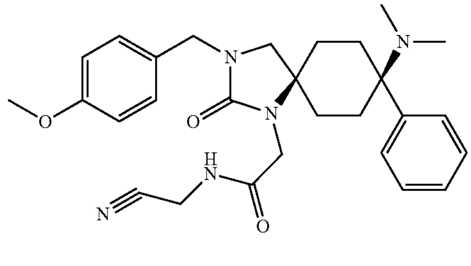
SC_2058
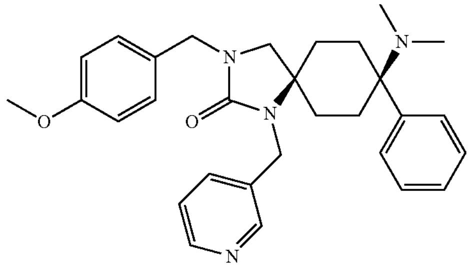
SC_2059
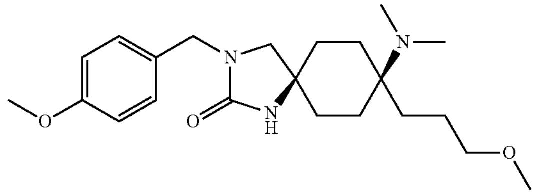
SC_2060
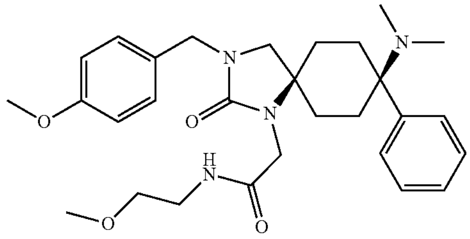
SC_2061
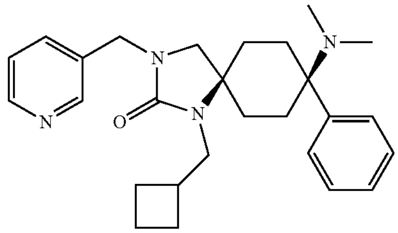
SC_2062
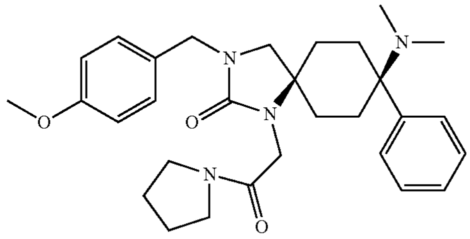
SC_2063
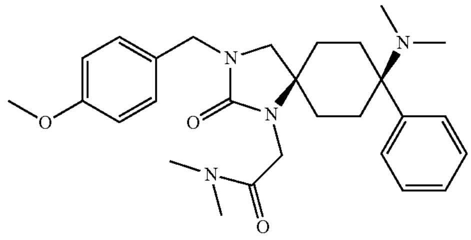
SC_2064
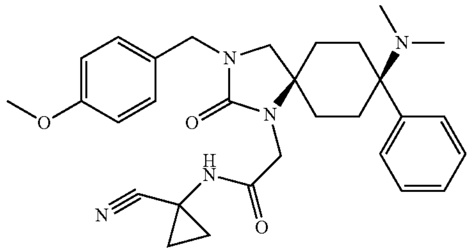
SC_2065
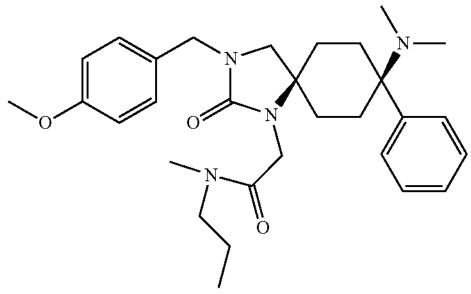
SC_2066
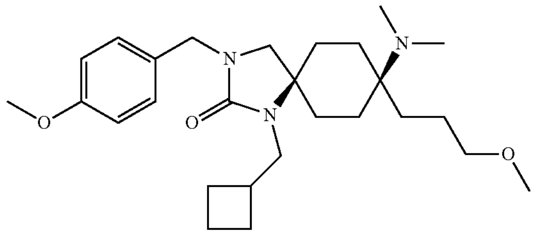

-continued
SC_2067
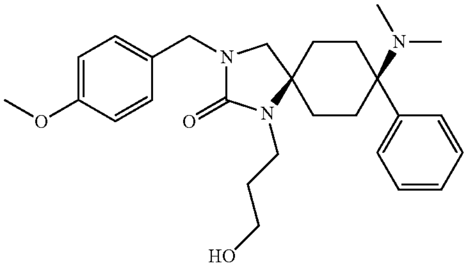
SC_2068
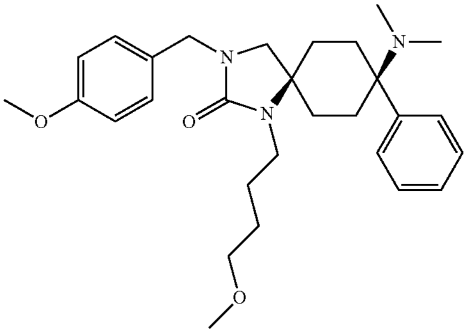
SC_2069
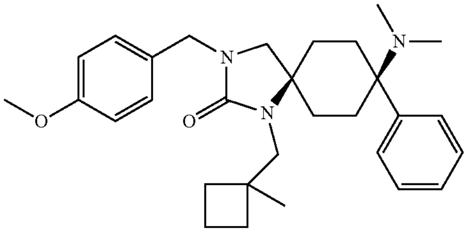
SC_2070
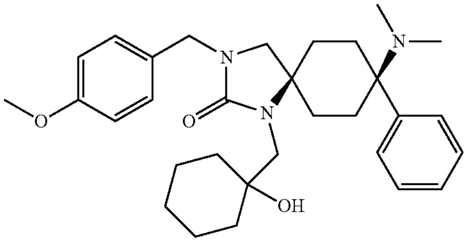
SC_2071
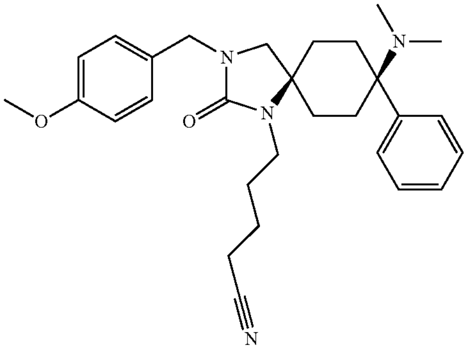
SC_2072
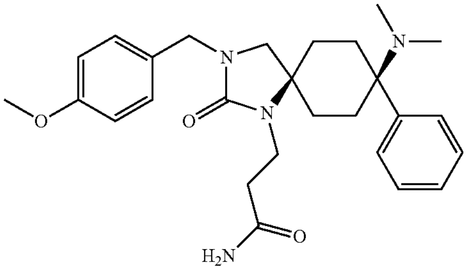
SC_2073
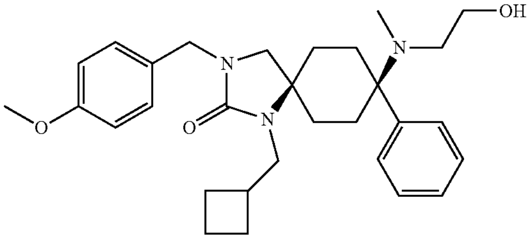
SC_2074
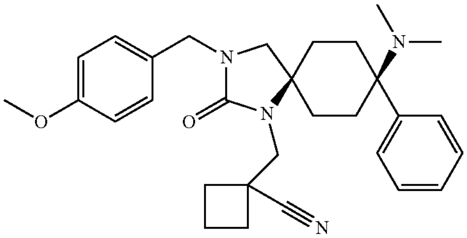
SC_2075
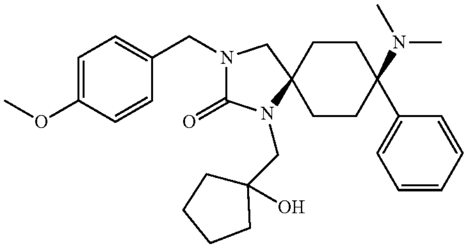
SC_2076
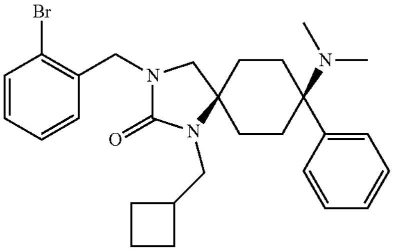

-continued
SC_2077
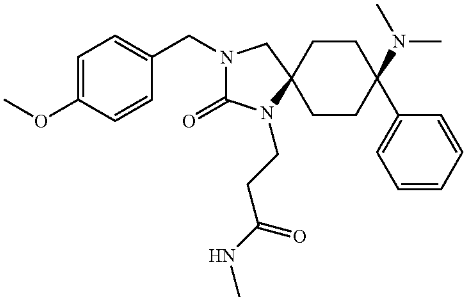
SC_2078
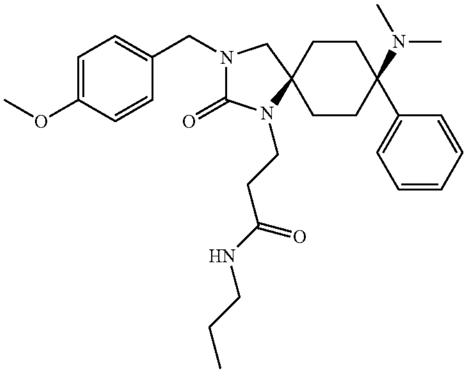
SC_2079
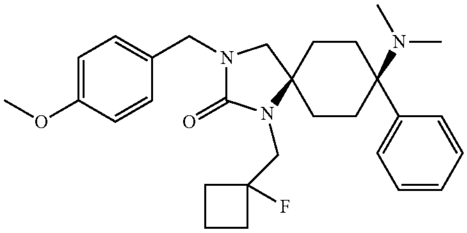
SC_2080
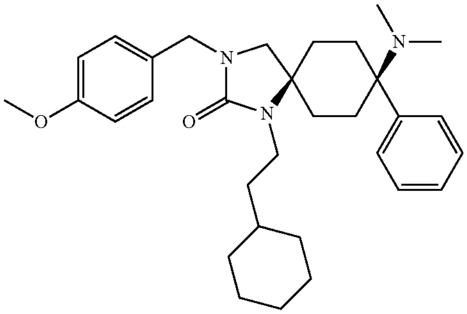
SC_2081
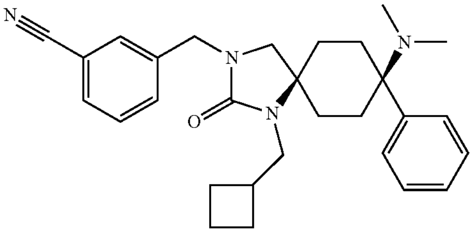
SC_2082
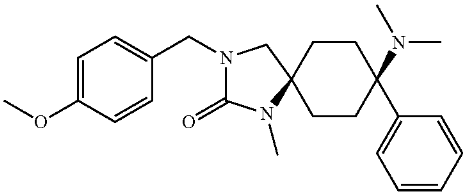
SC_2083
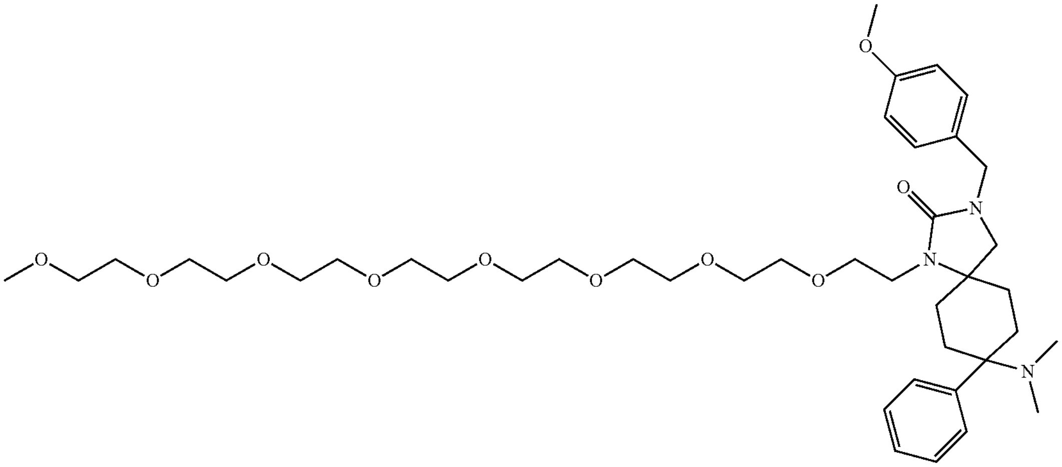

-continued
SC_2084
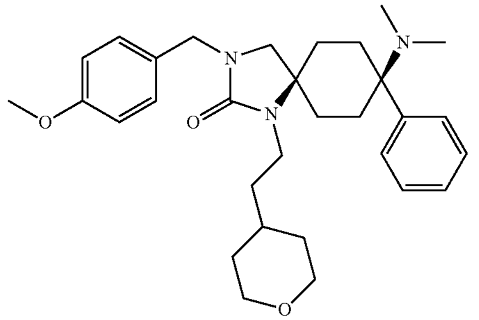
SC_2085
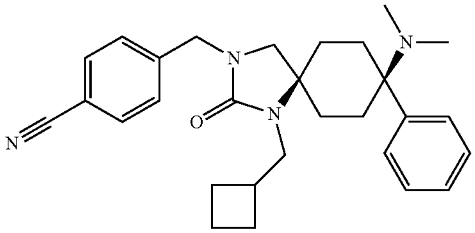
SC_2086
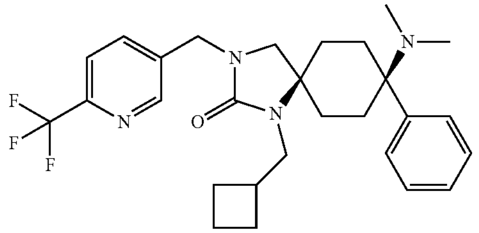
SC_2087
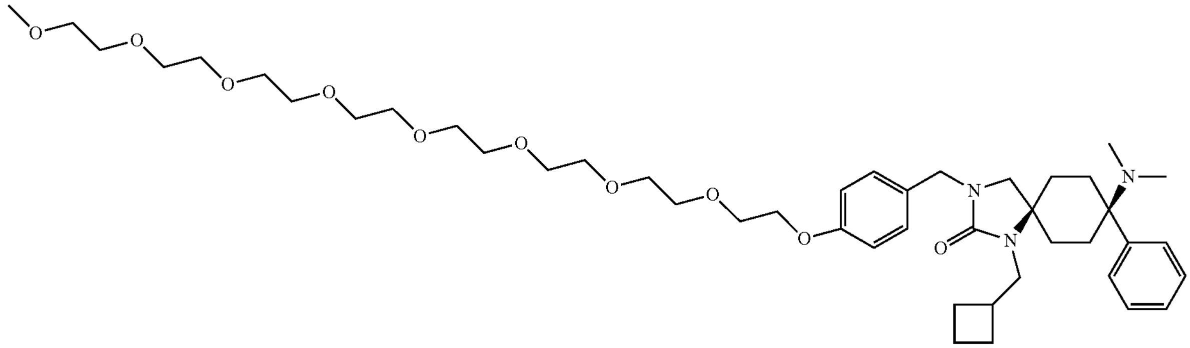
SC_2088
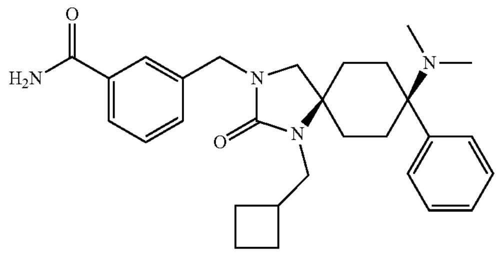
SC_2089
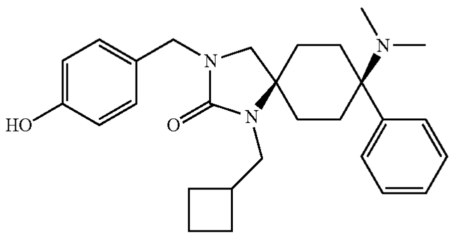
SC_2090
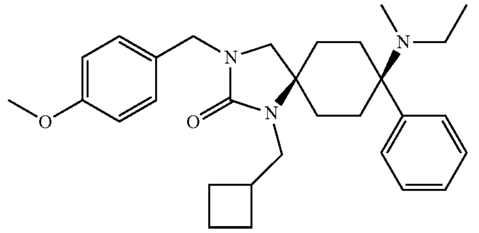
SC_2091
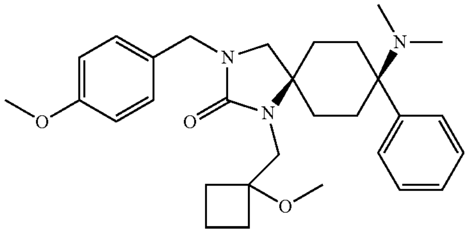

-continued
SC_2092
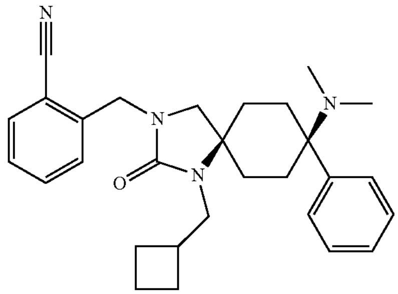
SC_2093
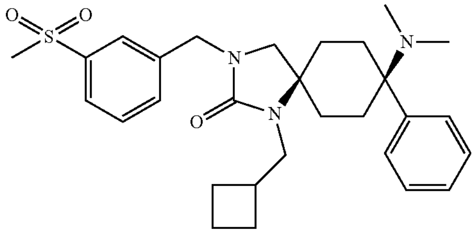
SC_2094
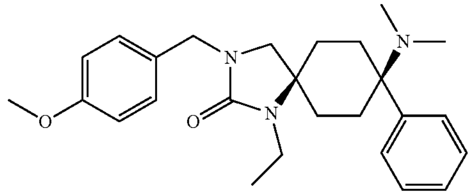
SC_2095
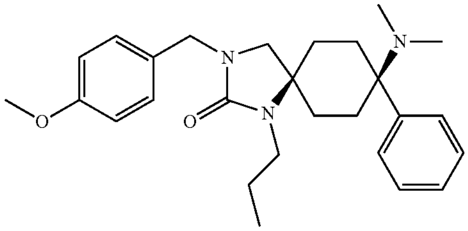
SC_2096
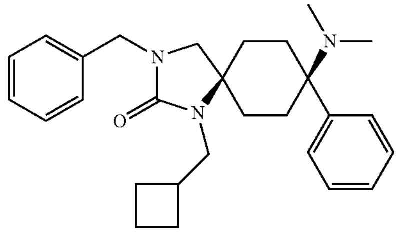
SC_2097
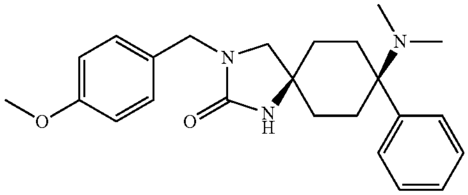
SC_2099
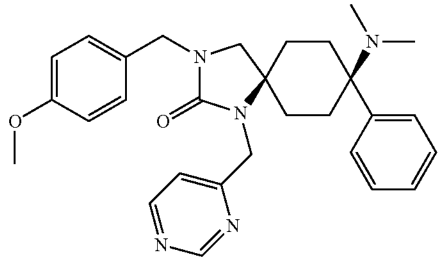
SC_2100
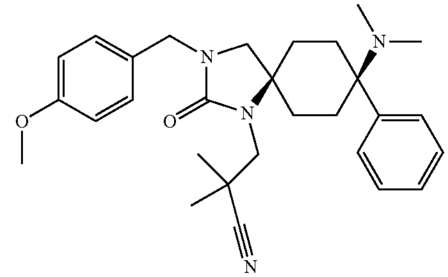
2101
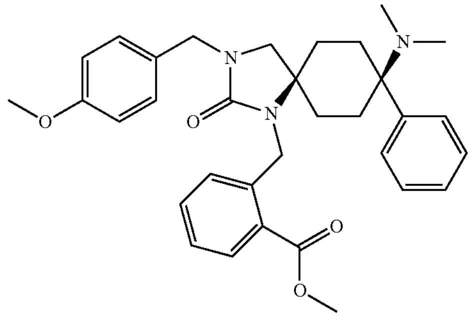
2102
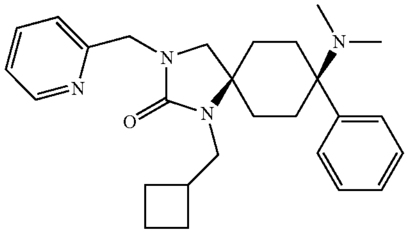

-continued
SC_2103
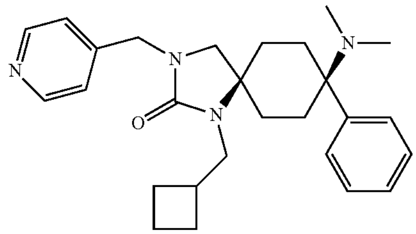
SC_2104
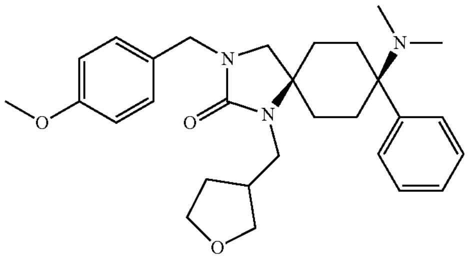
SC_2105
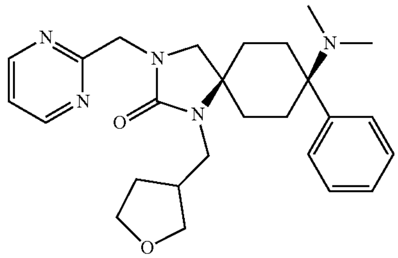
SC_2106
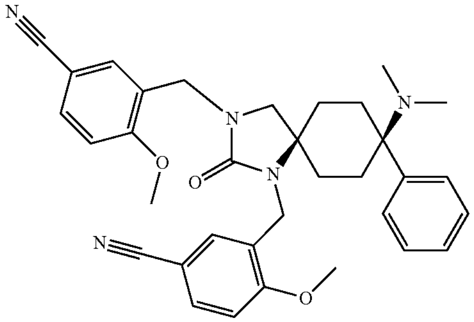
SC_2107
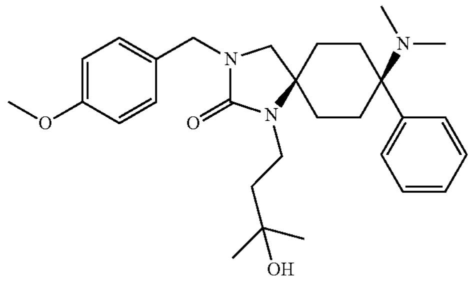
SC_2108
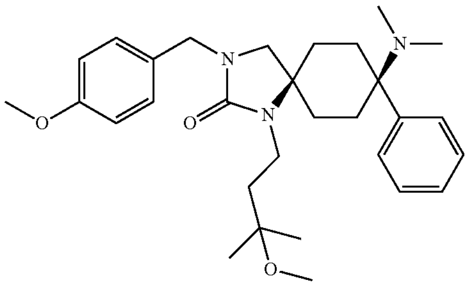
SC_2109
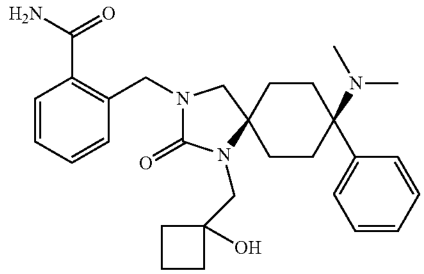
SC_2110
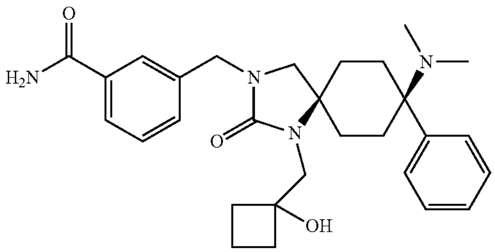
SC_2111
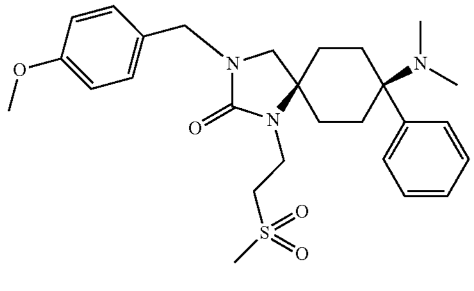
SC_2112
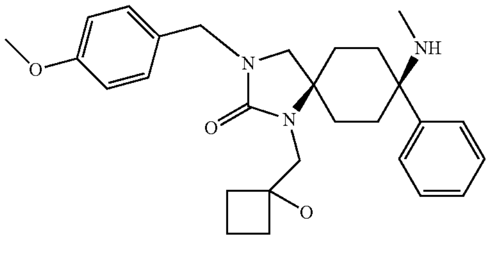

-continued
SC_2113
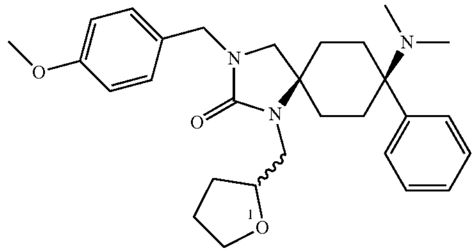
1 = R/S Mixture
SC_2114
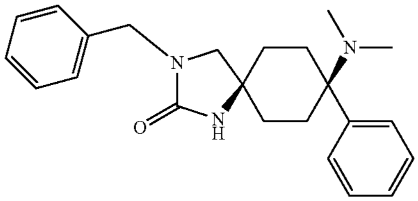
SC_2115
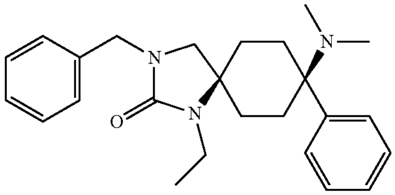
SC_2117
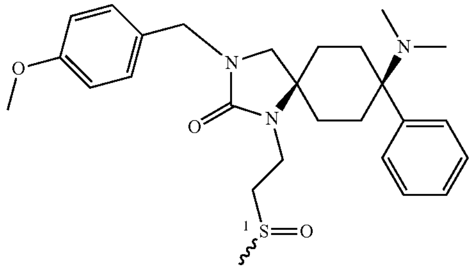
SC_2118
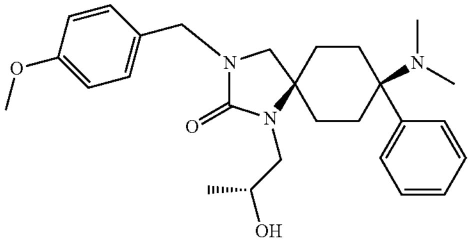
SC_2119
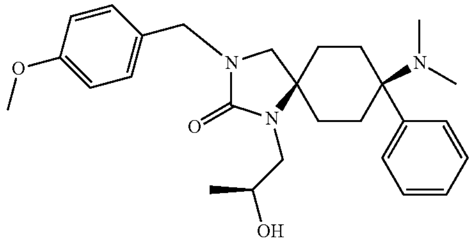
SC_2120
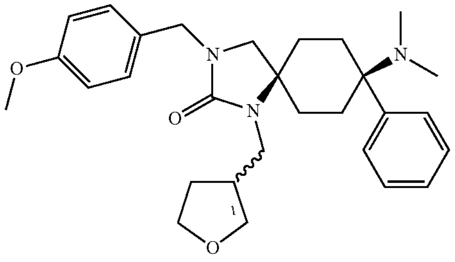
1 = R/S Mixture
SC_2122
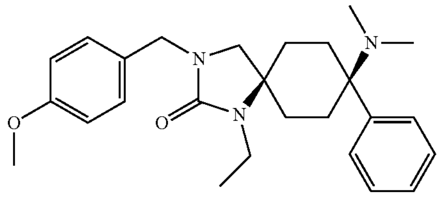
SC_2123
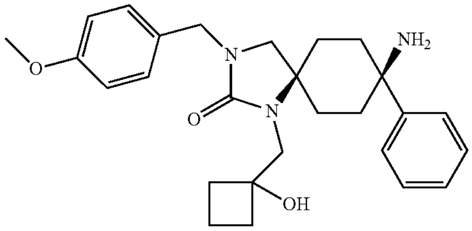
SC_2124
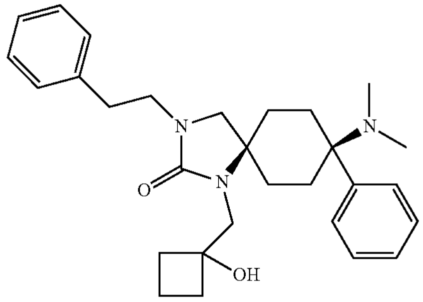

-continued
SC_2125
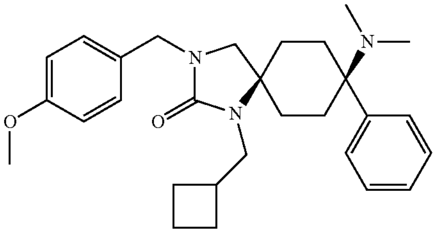
SC_2126
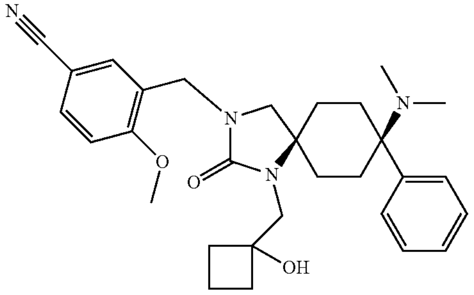
SC_2127
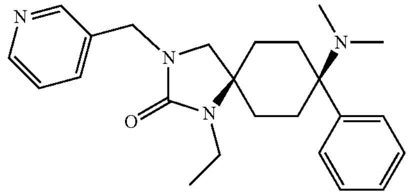
SC_2129
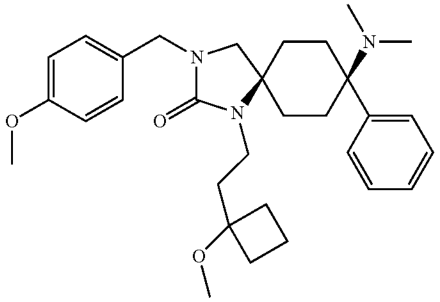
SC_2130
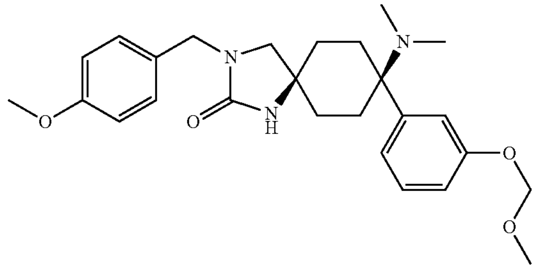
SC_2131
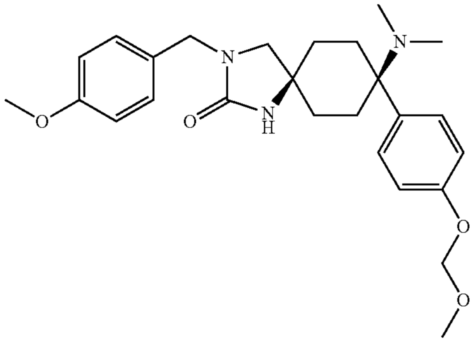
SC_2132
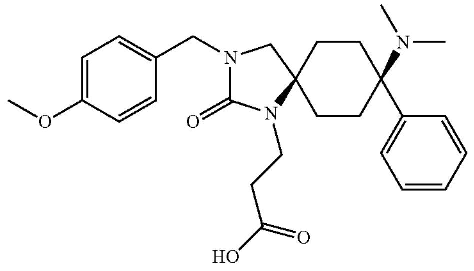
SC_2133
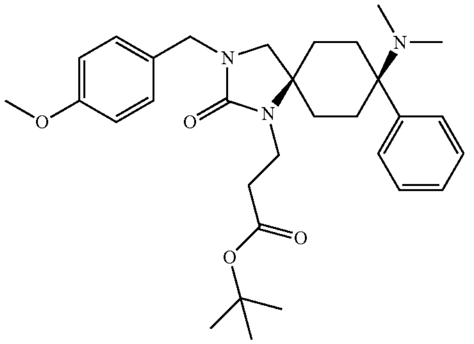
SC_2134
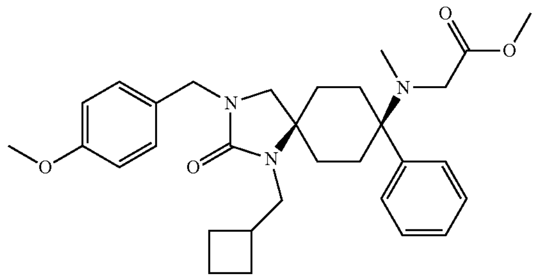
SC_2135
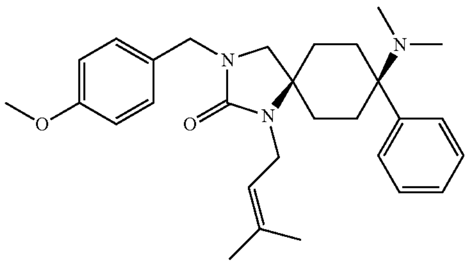

-continued
SC_2136
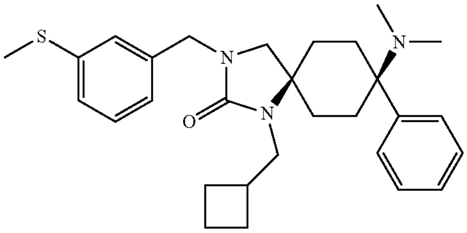
SC_2137
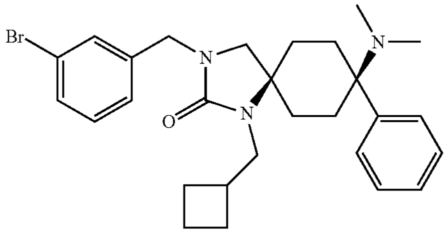
SC_2138
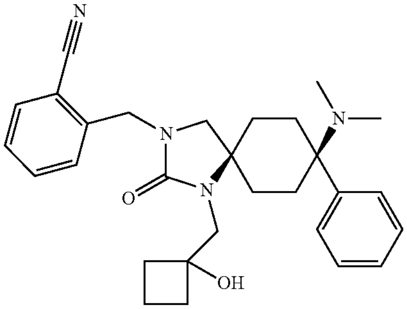
SC_2139
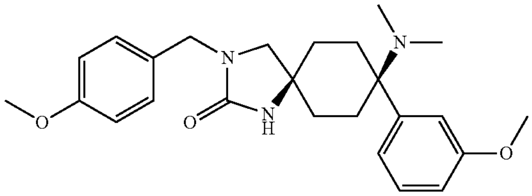
SC_2140
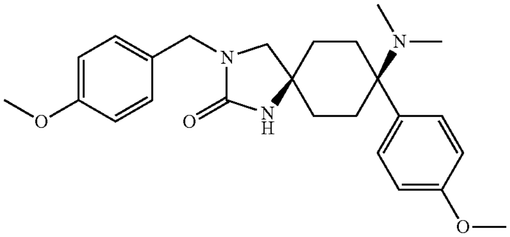
SC_2141
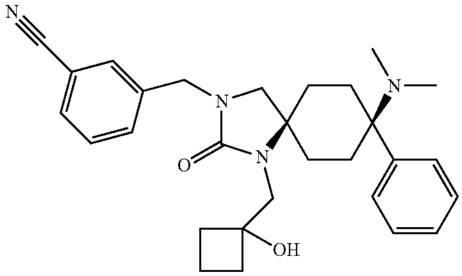
SC_2142
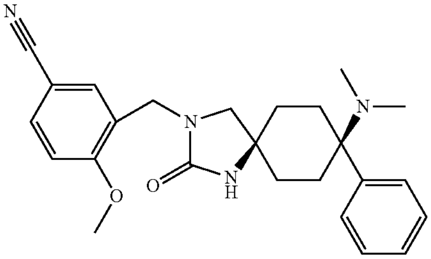
SC_2143
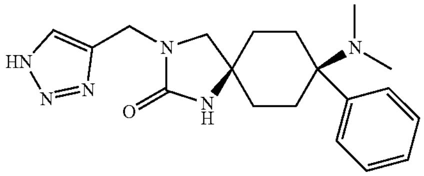
SC_2144
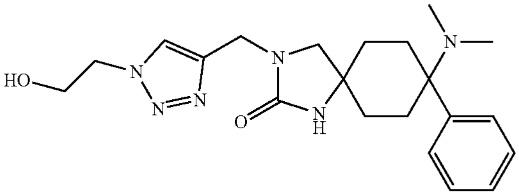
SC_2145
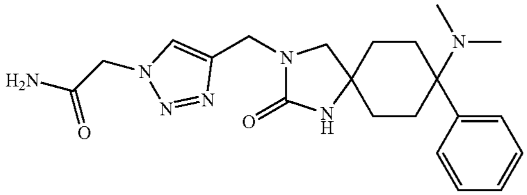

-continued
SC_2146
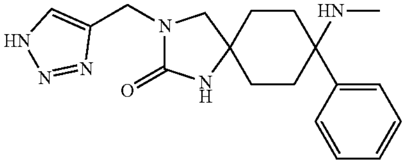
SC_2147
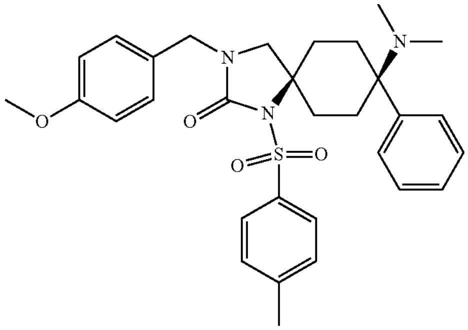
SC_2148
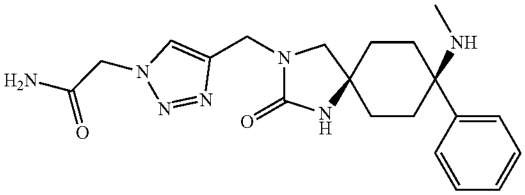
SC_2149
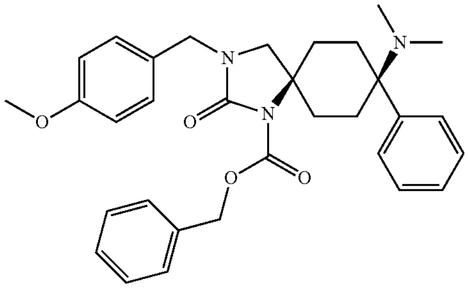
SC_2150
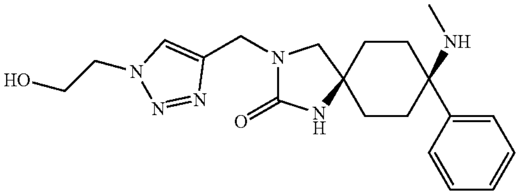
SC_2151*
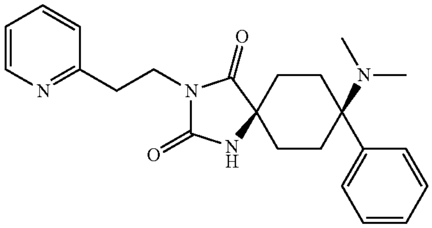
SC_2152
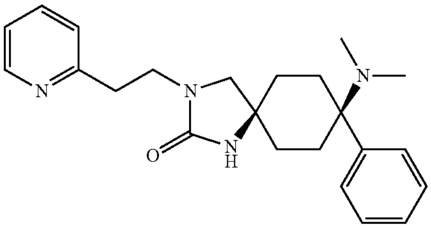
SC_2153
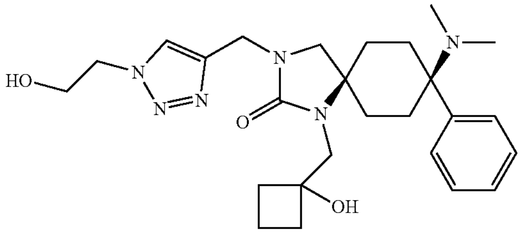
SC_2154*
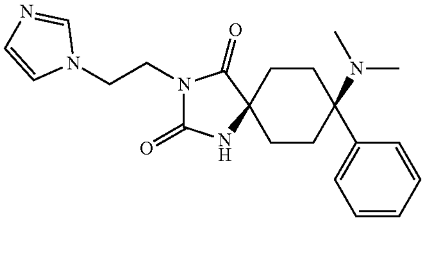
SC_2155
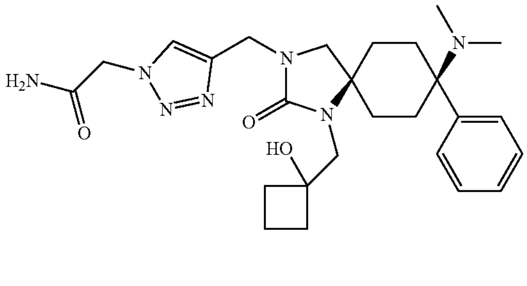

-continued
SC_2156
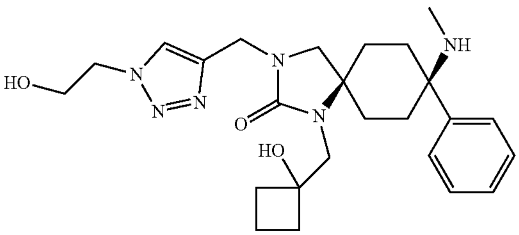
SC_2157*
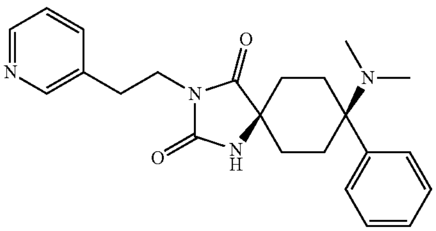
SC_2158*
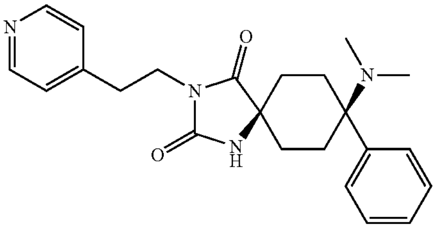
SC_2159
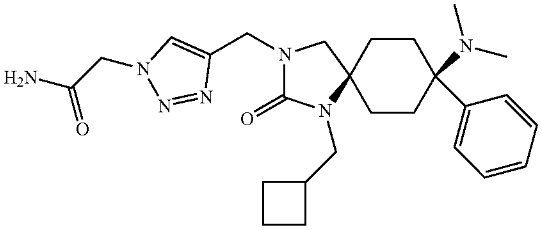
SC_2160
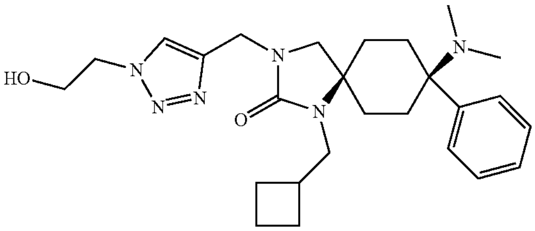
SC_2161
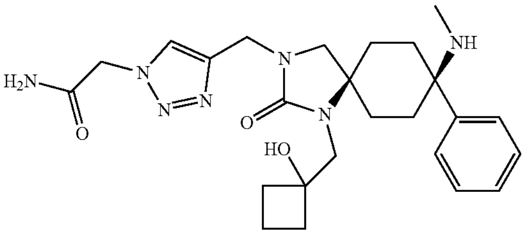
SC_2162
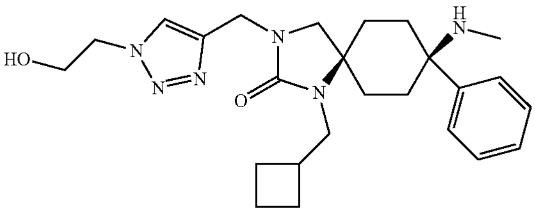
SC_2163
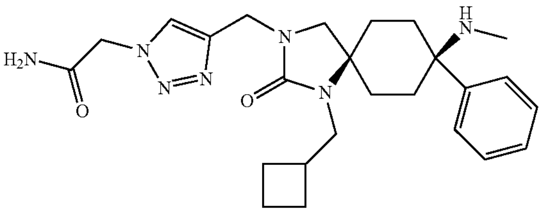
SC_2164
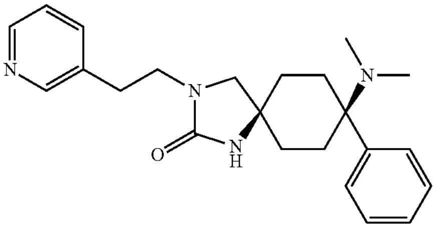
SC_2165
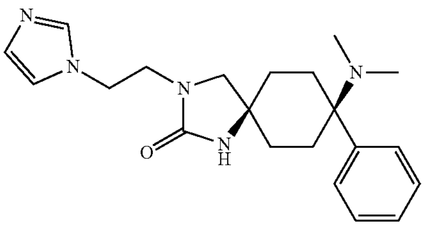
SC_2166
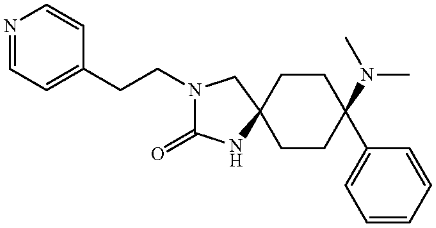
SC_2167
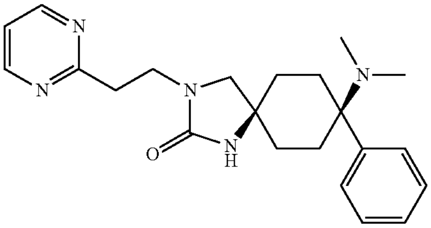

-continued
SC_2168
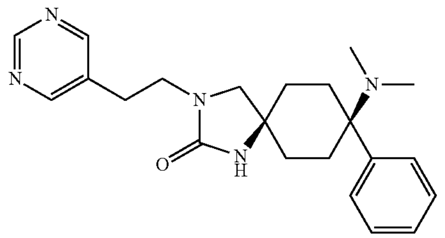
SC_2169
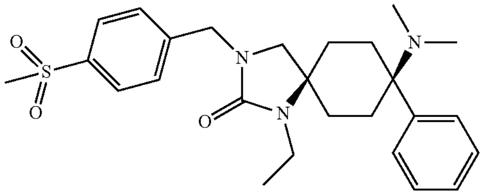
SC_2170
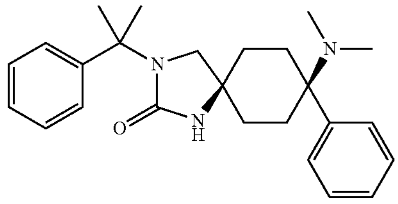
SC_2171
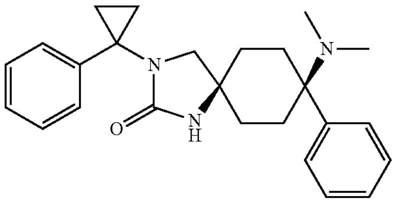
SC_2172
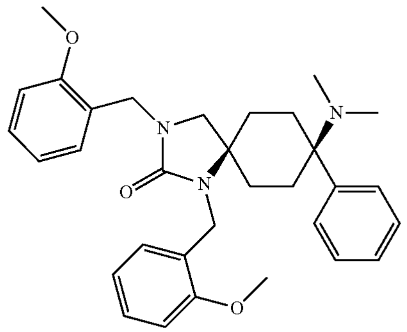
SC_2173
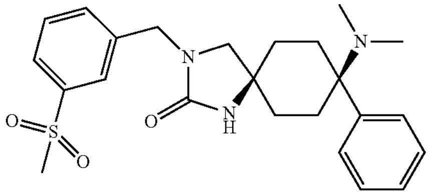
SC_2174
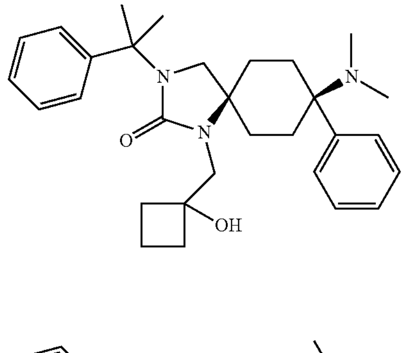
SC_2175
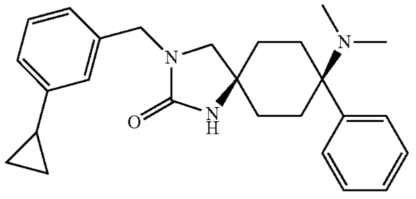
SC_2176
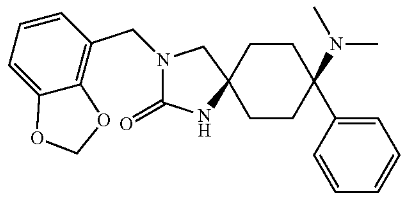
SC_2177
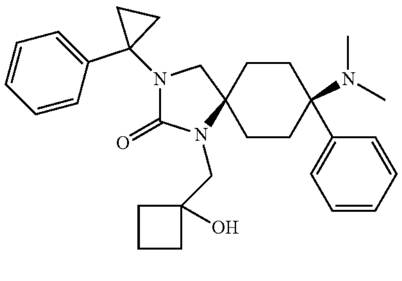

-continued

SC_2178

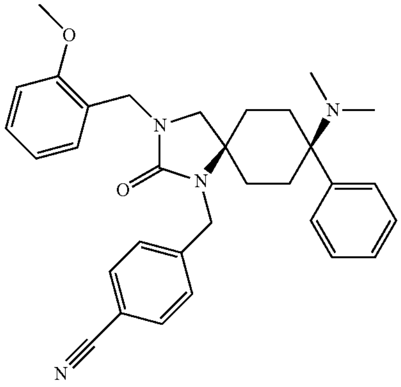

SC_2179

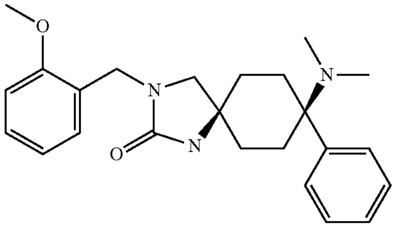

SC_2180

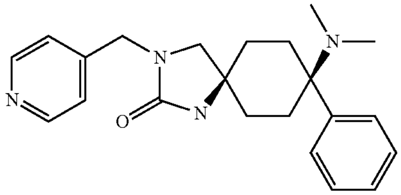

SC_2181

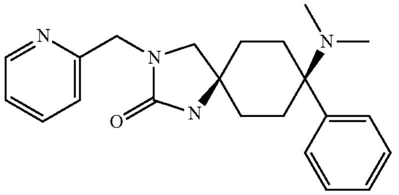

SC_2182

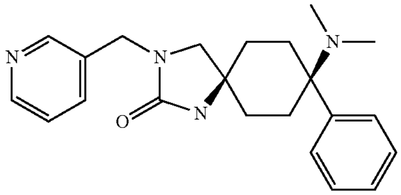

SC_2183

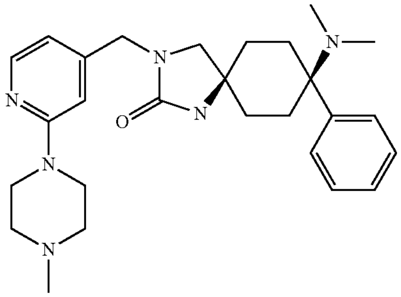

SC_2184

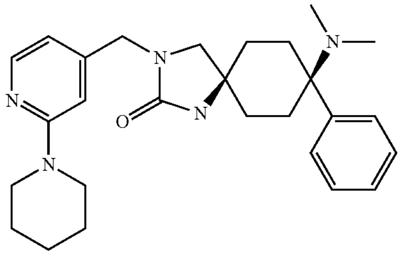

SC_2185

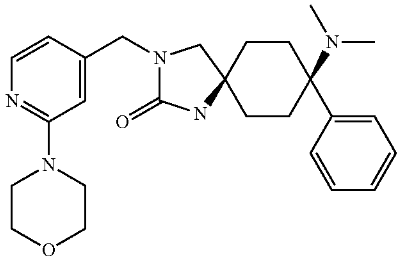

SC_2186

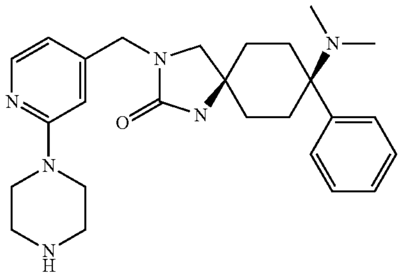

*Comparative Example

Pharmacological Investigations

Functional investigation on the human mu-opioid receptor (hMOP), human kappa-opioid receptor (hKOP), human delta-opioid receptor (hDOP), and human nociceptin/orphanin FQ peptide receptor (hNOP)

Human Mu-Opioid Peptide (hMOP) Receptor Binding Assay

The hMOP receptor binding assay was performed as homogeneous SPA-assay (scintillation proximity assay) using the assay buffer 50 mM TRIS-HCl (pH 7.4) supplemented with 0.052 mg/ml bovine serum albumin (Sigma-Aldrich Co. St. Louis. Mo.). The final assay volume (250 µl/well) included 1 nM of [N-allyl-2.3-$^3$H]naloxone as ligand (PerkinElmer Life Sciences. Inc. Boston. Mass. USA). and either test compound in dilution series or 25 µM unlabelled naloxone for determination of unspecific binding. The test compound was diluted with 25% DMSO in $H_2O$ to yield a final 0.5% DMSO concentration. which also served as a respective vehicle control. The assay was started by adding wheat germ agglutinin coated SPA beads (GE Healthcare UK Ltd. Buckinghamshire. UK) which had been preloaded with hMOP receptor membranes (PerkinElmer Life Sciences. Inc. Boston. Mass. USA). After incubation for 90 minutes at RT and centrifugation for 20 minutes at 500 rpm the signal rate was measured by means of a 1450 Microbeta Trilux β-counter (PerkinElmer Life Sciences/Wallac. Turku. Finland). Half-maximal inhibitory concentration (IC50) values reflecting 50% displacement of [$^3$H] naloxone-specific receptor binding were calculated by nonlinear regression analysis and Ki values were calculated by using the Cheng-Prusoff equation. (Cheng and Prusoff 1973).

Human Kappa-Opioid Peptide (hKOP) Receptor Binding Assay

The hKOP receptor binding assay is run as homogeneous SPA-assay (scintillation proximity assay) using the assay buffer 50 mM TRIS-HCl (pH 7.4) supplemented with 0.076 mg BSA/ml. The final assay volume of 250 µl per well includes 2 nM of [$^3$H]U69,593 as ligand, and either test compound in dilution series or 100 µM unlabelled naloxone for determination of unspecific binding. The test compound is diluted with 25% DMSO in $H_2O$ to yield a final 0.5% DMSO concentration which serves as respective vehicle control, as well. The assays are started by the addition of wheat germ agglutinin coated SPA beads (1 mg SPA beads/250 µl final assay volume per well) which has been preloaded for 15 minutes at room temperature with hKOP receptor membranes (14.8 µg/250 µl final assay volume per well). After short mixing on a mini-shaker, the microtiter plates are covered with a lid and the assay plates are incubated for 90 minutes at room temperature. After this incubation, the microtiter plates are sealed with a topseal and centrifuged for 20 minutes at 500 rpm. The signal rate is measured after a short delay of 5 minutes by means of a 1450 Microbeta Trilux β-counter (PerkinElmer Life Sciences/Wallac, Turku, Finland). Half-maximal inhibitory concentration (IC50) values reflecting 50% displacement of [$^3$H] U69.593-specific receptor binding are calculated by nonlinear regression analysis and $K_i$ values are calculated by using the Cheng-Prusoff equation, (Cheng and Prusoff, 1973).

Human Delta-Opioid Peptide (hDOP) Receptor Binding Assay

The hDOP receptor binding assay is performed as homogeneous SPA-assay using the assay buffer 50 mM TRIS-HCl, 5 mM $MgCl_2$ (pH 7.4). The final assay volume (250 µl/well) includes 1 nM of [Tyrosyl-3,5-$^3$H]2-D-Ala-deltorphin II as ligand, and either test compound in dilution series or 10 µM unlabelled naloxone for determination of unspecific binding. The test compound is diluted with 25% DMSO in $H_2O$ to yield a final 0.5% DMSO concentration which serves as respective vehicle control, as well. The assays are started by the addition of wheat germ agglutinin coated SPA beads (1 mg SPA beads/250 µl final assay volume per well) which has been preloaded for 15 minutes at room temperature with hDOP receptor membranes (15.2 µg/250 µl final assay volume per well). After short mixing on a mini-shaker, the microtiter plates are covered with a lid and the assay plates are incubated for 120 minutes at room temperature and centrifuged for 20 minutes at 500 rpm. The signal rate is measured by means of a 1450 Microbeta Trilux β-counter (PerkinElmer Life Sciences/Wallac, Turku, Finland). Half-maximal inhibitory concentration (IC50) values reflecting 50% displacement of [Tyrosyl-3,5-$^3$H]2-D-Ala-deltorphin II-specific receptor binding are calculated by nonlinear regression analysis and $K_i$ values are calculated by using the Cheng-Prusoff equation, (Cheng and Prusoff, 1973).

Human Nociceptin/Orphanin FQ Peptide (hNOP) Receptor Binding Assay

The hNOP receptor binding assay was performed as homogeneous SPA-assay (scintillation proximity assay) using the assay buffer 50 mM TRIS-HCl. 10 mM $MgCl_2$. 1 mM EDTA (pH 7.4). The final assay volume (250 µl/well) included 0.5 nM of [leucyl-$^3$H]nociceptin as ligand (PerkinElmer Life Sciences. Inc. Boston. Mass. USA). and either test compound in dilution series or 1 µM unlabelled nociceptin for determination of unspecific binding. The test compound was diluted with 25% DMSO in $H_2O$ to yield a final 0.5% DMSO concentration. which also served as a respective vehicle control. The assay was started by adding wheat germ agglutinin coated SPA beads (GE Healthcare UK Ltd. Buckinghamshire. UK) which had been preloaded with hMOP receptor membranes (PerkinElmer Life Sciences. Inc. Boston. Mass. USA). After incubation for 60 minutes at RT and centrifugation for 20 minutes at 500 rpm the signal rate was measured by means of a 1450 Microbeta Trilux β-counter (PerkinElmer Life Sciences/Wallac. Turku. Finland). Half-maximal inhibitory concentration (IC50) values reflecting 50% displacement of [$^3$H]nociceptin-specific receptor binding were calculated by nonlinear regression analysis and $K_i$ values were calculated by using the Cheng-Prusoff equation. (Cheng and Prusoff. 1973).

| Example | hNOP Ki [nM] or % inhibition @ 1 µM | hMOP Ki [nM] or % inhibition @ @ 1 µM | Example | hNOP Ki [nM] or % inhibition @ 1 µM | hMOP Ki [nM] or % inhibition @ @ 1 µM |
|---|---|---|---|---|---|
| SC_2001 | 2.7 | 245 | SC_2003 | 585 | 5875 |
| SC_2002 | 4.3 | 965 | SC_2004 | 21.5 | 1310 |
| SC_2005 | 12% @ 1 µM | — | SC_2037 | 19.5 | 160 |
| SC_2006 | 0.8 | 43 | SC_2038 | 13.5 | 380 |
| SC_2007 | 1.1 | 43.5 | SC_2039 | 2.8 | 54.5 |
| SC_2008 | 690 | not determined | SC_2040 | 34 | 705 |
| SC_2009 | 17.6 | 385 | SC_2041 | 195 | 1925 |
| SC_2010 | 88.5 | not determined | SC_2042 | 16.5 | 1275 |
| SC_2011 | 50.5 | 880 | SC_2043 | 530 | 20% @ 1 µM |
| SC_2012 | 50 | 1350 | SC_2044 | 10.8 | 275 |
| SC_2013 | 125 | 18.4 | SC_2045 | 21 | 1035 |

-continued

| Example | hNOP Ki [nM] or % inhibition @ 1 μM | hMOP Ki [nM] or % inhibition @ @ 1 μM |
|---|---|---|
| SC_2014 | 23.5 | 470 |
| SC_2015 | 6.4 | 162.5 |
| SC_2017 | 80 | 5460 |
| SC_2018 | 70.8 | 66.8 |
| SC_2019 | 0.8 | 50.8 |
| SC_2020 | 15.5 | 305 |
| SC_2021 | 1200 | 4615 |
| SC_2022 | 5.4 | 420 |
| SC_2023 | 3.8 | 180 |
| SC_2024 | 48 | 1450 |
| SC_2025 | 49.5 | 920 |
| SC_2026 | 11 | 255 |
| SC_2027 | 12 | 1415 |
| SC_2028 | 135 | 3260 |
| SC_2029 | 50 | 2150 |
| SC_2030 | 96.5 | 1260 |
| SC_2031 | 4.6 | 139.5 |
| SC_2032 | 36 | 1035 |
| SC_2033 | 27 | 855 |
| SC_2034 | 490 | 4025 |
| SC_2035 | 39 | 1240 |
| SC_2036 | 3.1 | 215 |
| SC_2068 | 34.5 | 230 |
| SC_2069 | 14 | 675 |
| SC_2070 | 18.5 | 5875 |
| SC_2071 | 40 | 860 |
| SC_2072 | 620 | 19% @ 1 μM |
| SC_2073 | 200 | 3440 |
| SC_2074 | 3.4 | 310 |
| SC_2075 | 9.1 | 480 |
| SC_2076 | 51.5 | 925 |
| SC_2077 | 325 | 3460 |
| SC_2078 | 170 | 563.3 |
| SC_2079 | 19.3 | 710 |
| SC_2080 | 87.5 | 625 |
| SC_2081 | 1.2 | 147 |
| SC_2082 | 180 | 2390 |
| SC_2083 | 405 | 5250 |
| SC_2084 | 34 | 880 |
| SC_2085 | 3.8 | 230 |
| SC_2086 | 3.5 | 150 |
| SC_2087 | 47 | 1365 |
| SC_2088 | 1.9 | 110 |
| SC_2089 | 1.8 | 73 |
| SC_2090 | 106 | 3185 |
| SC_2091 | 26 | 1620 |
| SC_2092 | 5.6 | 380 |
| SC_2093 | 0.8 | 53.7 |
| SC_2094 | 19 | 50.5 |
| SC_2095 | 11.2 | 575 |
| SC_2096 | 1.3 | 81 |
| SC_2097 | 91 | 2645 |
| SC_2099 | 215 | 5135 |
| SC_2149 | 160 | 250 |
| SC_2150 | 6% | 4% |
| SC_2152 | 175 | 2475 |
| SC_2153 | 22 | 130 |
| SC_2155 | 12.5 | 98 |
| SC_2156 | 130 | 330 |
| SC_2159 | 2.35 | 40.5 |
| SC_2160 | 4 | 39 |
| SC_2161 | 100.5 | 295 |
| SC_2162 | 31 | 82.5 |
| SC_2163 | 13 | 93.5 |
| SC_2164 | 130 | 2765 |
| SC_2165 | 255 | 2000 |
| SC_2166 | 106.5 | 3690 |
| SC_2168 | 240 | 13% |
| SC_2169 | 785 | 790 |
| SC_2170 | 325 | not determined |
| SC_2171 | 49.25 | 362.5 |
| SC_2172 | 50 | 630 |
| SC_2173 | 145 | 5245 |
| SC_2174 | 8.15 | 235 |
| SC_2046 | 38% @ 1 μM | 23% @ 1 μM |
| SC_2047 | 85.5 | 600 |
| SC_2048 | 390 | 3430 |
| SC_2049 | 24 | 1570 |
| SC_2050 | 11.5 | 310 |
| SC_2051 | 9 | 515 |
| SC_2052 | 26.2 | 996.7 |
| SC_2053 | 220 | 1385 |
| SC_2054 | 43.5 | 340 |
| SC_2055 | 96.5 | 2780 |
| SC_2056 | 31 | 545 |
| SC_2057 | 330 | 5475 |
| SC_2058 | 49.5 | 195 |
| SC_2059 | 4% @ 1 μM | 26% @ 1 μM |
| SC_2060 | 45 | 1035 |
| SC_2061 | 0.5 | 86.5 |
| SC_2062 | 20.5 | 1750 |
| SC_2063 | 18 | 3430 |
| SC_2064 | 41 | 2000 |
| SC_2065 | 27 | 650 |
| SC_2066 | 455 | 90 |
| SC_2067 | 217.5 | 4700 |
| SC_2100 | 11.8 | 1320 |
| SC_2101 | 135 | 1170 |
| SC_2102 | 3.3 | 84.5 |
| SC_2103 | 1.5 | 54 |
| SC_2104 | 22.5 | 1000 |
| SC_2105 | 2.4 | 45 |
| SC_2106 | 16.5 | 1540 |
| SC_2107 | 57 | 1700 |
| SC_2108 | 10.1 | 195 |
| SC_2109 | 17 | 260 |
| SC_2110 | 16.5 | 134 |
| SC_2111 | 159 | 1675 |
| SC_2112 | 135 | 925 |
| SC_2113 | 4 | 310 |
| SC_2114 | 300 | 3045 |
| SC_2115 | 720 | 2480 |
| SC_2117 | 630 | not determined |
| SC_2118 | 195 | 995 |
| SC_2119 | 85 | 90 |
| SC_2120 | 19 | 1000 |
| SC_2122 | 310 | 830 |
| SC_2123 | not determined | 3840 |
| SC_2124 | 4 | 43 |
| SC_2125 | 3.4 | 120 |
| SC_2143 | 405 | 5290 |
| SC_2144 | 715 | 5180 |
| SC_2145 | 340 | 4940 |
| SC_2146 | 2% | 9% |
| SC_2147 | 14% | 10% |
| SC_2148 | 8% | 0% |
| SC_2185 | 115 | 6980 |
| SC_2186 | 40 | 2775 |

-continued

| Example | hNOP Ki [nM] or % inhibition @ 1 μM | hMOP Ki [nM] or % inhibition @ @ 1 μM | Example | hNOP Ki [nM] or % inhibition @ 1 μM | hMOP Ki [nM] or % inhibition @ @ 1 μM |
|---|---|---|---|---|---|
| SC_2175 | 90.5 | 1830 | | | |
| SC_2176 | 110 | 3090 | | | |
| SC_2177 | 18 | 99.5 | | | |
| SC_2178 | 390 | 1050 | | | |
| SC_2179 | 108.5 | 2660 | | | |
| SC_2180 | 240 | 4085 | | | |
| SC_2181 | 190 | 19% | | | |
| SC_2182 | 250 | 13% | | | |
| SC_2183 | 63 | 3580 | | | |
| SC_2184 | 25 | 845 | | | |

Protocol for [$^{35}$S]GTPγS Functional NOP/MOP/KOP/DOP Assays

Cell membrane preparations of CHO-K1 cells transfected with the human MOP receptor (Art.-No. RBHOMM) or the human DOP receptor (Art.-No. RBHODM), and HEK293 cells transfected with the human NOP receptor (Art.-No. RBHORLM) or the human KOP receptor (Art.-No. 6110558) are available from PerkinElmer (Waltham, Mass.). Membranes from CHO-K1 cells transfected with the human nociceptin/orphanin FQ peptide (hNOP) receptor (Art.-No. 93-0264C2, DiscoveRx Corporation, Freemont, Calif.) are also used. [$^{35}$S]GTPγS(Art.-No. NEG030H; Lot-No. #0112, #0913, #1113 calibrated to 46.25 TBq/mmol) is available from PerkinElmer (Waltham, Mass.).

The [$^{35}$S]GTPγS assays are carried out essentially as described by Gillen et al (2000). They are run as homogeneous scintillation proximity (SPA) assays in microtiter luminescence plates, where each well contains 1.5 mg of WGA-coated SPA-beads. To test the agonistic activity of test compounds on recombinant hNOP, hMOP, hDOP, and hKOP receptor expressing cell membranes from CHO-K1 or HEK293 cells, 10 or 5 μg membrane protein per assay are incubated with 0.4 nM [$^{35}$S]GTPγS and serial concentrations of receptor-specific agonists in buffer containing 20 mM HEPES pH 7.4, 100 mM NaCl, 10 mM MgCl2, 1 mM EDTA, 1 mM dithiothreitol, 1.28 mM $NaN_3$, and 10 μM GDP for 45 min at room temperature. The microtiter plates are then centrifuged for 10 min at 830 to sediment the SPA beads. The microtiter plates are sealed and the bound radioactivity [cpm] is determined after a delay of 15 min by means of a 1450 Microbeta Trilux (PerkinElmer, Waltham, Mass.).

The unstimulated basal binding activity ($UBS_{obs}$ [cpm]) is determined from 12 unstimulated incubates and is set as 100% basal binding. For determination of the potency and the efficacy, the arithmetic mean of the observed total [$^{35}$S]GTPγS binding ($TB_{obs}$ [cpm]) of all incubates (duplicates) stimulated by the receptor-specific agonists (i.e. N/OFQ, SNC80, DAMGO, or U69,593) are transformed in percent total binding ($TB_{obs}$ [%]) relative to the basal binding activity (i.e. 100% binding). The potency ($EC_{50}$) of the respective agonist and its maximal achievable total [$^{35}$S]GTPγS binding ($TB_{calc}$ [%]) above its calculated basal binding ($UBS_{calc}$ [%]) are determined from its transformed data ($TB_{obs}$ [%]) by means of nonlinear regression analysis with XLfit for each individual concentration series. Then the difference between the calculated unstimulated [$^{35}$S]GTPγS binding ($UBS_{calc}$ [%]) and the maximal achievable total [$^{35}$S]GTPγS binding ($TB_{calc}$ [%]) by each tested agonist is determined (i.e. $B1_{calc}$ [%]). This difference ($B1_{calc}$ [%]) as a measure of the maximal achievable enhancement of [$^{35}$S]GTPγS binding by a given agonist is used to calculate the relative efficacy of test compounds versus the maximal achievable enhancement by a receptor-specific full agonist, e.g. N/OFQ ($B1_{calc\text{-}N/OFQ}$ [%]) which is set as 100% relative efficacy for the hNOP receptor. Likewise, the percentage efficacies of test compounds at the hDOP, hMOP, or hKOP receptor are determined versus the calculated maximal enhancement of [$^{35}$S]GTPγS binding by the full agonists SNC80 ($B1_{calc\text{-}SNC80}$ [%]), DAMGO ($B1_{calc\text{-}DAMGO}$ [%]) and U69,593 ($B1_{calc\text{-}U69,593}$ [%]) which are set as 100% relative efficacy at each receptor, respectively.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A compound according to general formula (I)

(I)

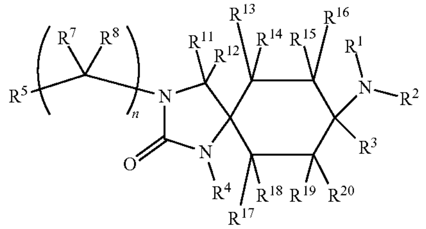

wherein n means 1, 2 or 3;

$R^1$ and $R^2$ independently of one another mean

—H;

—$C_1$-$C_6$-alkyl, linear or branched, saturated or unsaturated, unsubstituted or substituted with one, two, three or four substituents independently of one another selected from the group consisting of —F, —Cl, —Br, —I, —OH, —$OCH_3$, —CN and —$CO_2CH_3$;

a 3-12-membered cycloalkyl moiety, saturated or unsaturated, unsubstituted or substituted with one, two, three or four substituents independently of one another selected from the group consisting of —F, —Cl, —Br, —I, —OH, —$OCH_3$, —CN and —$CO_2CH_3$; wherein said 3-12-membered cycloalkyl moiety is optionally connected through —$C_1$-$C_6$-alkylene-, linear or branched, saturated or unsaturated, unsubstituted; or a 3-12-membered heterocycloalkyl moiety, saturated or unsaturated, unsubstituted or substituted with one, two, three or four substituents independently of one another selected from the group consisting of —F, —Cl, —Br, —I, —OH, —$OCH_3$, —CN and —$CO_2CH_3$; wherein said 3-12-membered heterocycloalkyl moiety is optionally connected through —$C_1$-$C_6$-alkylene-, linear or branched, saturated or unsaturated, unsubstituted;

or $R^1$ and $R^2$ together with the nitrogen atom to which they are attached form a ring and mean —$(CH_2)_{3-6}$; —$(CH_2)_2$—O—$(CH_2)_2$—; or —$(CH_2)_2$—$NR^A$—$(CH_2)_2$—, wherein $R^A$ means —H or —$C_1$-$C_6$-alkyl, linear or branched, saturated or unsaturated, unsubstituted or substituted with one, two, three or four substituents independently of one another selected from the group consisting of —F, —Cl, —Br and —I;

$R^3$ means

—$C_1$-$C_6$-alkyl, linear or branched, saturated or unsaturated, unsubstituted, mono- or polysubstituted;

a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted;

a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted;

$R^4$ means

—H;

—$C_1$-$C_6$-alkyl, linear or branched, saturated or unsaturated, unsubstituted, mono- or polysubstituted; wherein said —$C_1$-$C_6$-alkyl is optionally connected through —C(═O)—, —C(═O)O—, or —S(═O)$_2$—;

a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted; or wherein said 3-12-membered cycloalkyl moiety is optionally connected through —C(═O)—, —C(═O)O—, —C(═O)O—$CH_2$—, or —S(═O)$_2$—;

a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted; or wherein said 3-12-membered heterocycloalkyl moiety is optionally connected through —C(═O)—, —C(═O)O—, —C(═O)O—$CH_2$—, or —S(═O)$_2$—;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or wherein said 6-14-membered aryl moiety is optionally connected through —C(═O)—, —C(═O)O—, —C(═O)O—$CH_2$—, or —S(═O)$_2$—; or a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted; or wherein said 5-14-membered heteroaryl moiety is optionally connected through —C(═O)—, —C(═O)O—, —C(═O)O—$CH_2$—, or —S(═O)$_2$—;

$R^5$ means a 6-14-membered aryl moiety, unsubstituted, mono- or polysubstituted; or a 5-14-membered heteroaryl moiety, unsubstituted, mono- or polysubstituted;

$R^7$, $R^8$, $R^{11}$, $R^{12}$, $R^{13}$, $R^{14}$, $R^{15}$, $R^{16}$, $R^{17}$, $R^{18}$, $R^{19}$, and $R^{20}$ independently of one another mean —H, —F, —Cl, —Br, —I, —OH, or —$C_1$-$C_6$-alkyl, linear or branched, saturated or unsaturated, unsubstituted, mono- or polysubstituted;

or wherein $R^7$ and $R^8$ together with the carbon atom to which they are attached form a ring and mean —$(CH_2)_2$— or —$(CH_2)_3$—;

wherein "mono- or polysubstituted" means that one or more hydrogen atoms are replaced by a substituent independently of one another selected from the group consisting of —F, —Cl, —Br, —I, —CN, —$R^{21}$, —C(═O)$R^{21}$, —C(═O)O$R^{21}$, —C(═O)N$R^{21}R^{22}$, —O—$(CH_2CH_2$—O$)_{1-30}$—H, —O—$(CH_2CH_2$—O$)_{1-30}$—$CH_3$, ═O, —O$R^{21}$, —OC(═O)$R^{21}$, —OC(═O)O$R^{21}$, —OC(═O)N$R^{21}R^{22}$, —$NO_2$, —N$R^{21}R^{22}$, —N$R^{21}$—$(CH_2)_{1-6}$—C(═O)$R^{22}$, —N$R^{21}$—$(CH_2)_{1-6}$—C(═O)O$R^{22}$, —N$R^{23}$—$(CH_2)_{1-6}$—C(═O)N$R^{21}R^{22}$, —N$R^{21}$C(═O)$R^{22}$, —N$R^{21}$C(═O)—O$R^{22}$, —N$R^{23}$C(═O)N$R^{21}R^{22}$, —N$R^{21}$S(═O)$_2R^{22}$, —S$R^{21}$, —S(═O)$R^{21}$, —S(═O)$_2R^{21}$, —S(═O)$_2$O$R^{21}$, and —S(═O)$_2$N$R^{21}R^{22}$;

wherein $R^{21}$, $R^{22}$ and $R^{23}$ independently of one another mean

—H;

—$C_1$-$C_6$-alkyl, linear or branched, saturated or unsaturated, unsubstituted or substituted with one, two, three or four substituents independently of one another selected from the group consisting of —F, —Cl, —Br, —I, —CN, —OH, —$NH_2$, and —O—$C_1$-$C_6$-alkyl;

a 3-12-membered cycloalkyl moiety, saturated or unsaturated, unsubstituted; wherein said 3-12-membered cycloalkyl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl;

a 3-12-membered heterocycloalkyl moiety, saturated or unsaturated, unsubstituted; wherein said 3-12-membered heterocycloalkyl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl;

a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl;

or $R^{21}$ and $R^{22}$ within —C(═O)$NR^{21}R^{22}$, —OC(═O)$NR^{21}R^{22}$, —$NR^{21}R^{22}$, —$NR^{23}$—$(CH_2)_{1-6}$—C(═O)$NR^{21}R^{22}$, —$NR^{23}$C(═O)$NR^{21}R^{22}$, or —S(═O)$_2$ $NR^{21}R^{22}$ together with the nitrogen atom to which they are attached form a ring and mean —$(CH_2)_{3-6}$—; —$(CH_2)_2$—O—$(CH_2)_2$—; or —$(CH_2)_2$—$NR^B$—$(CH_2)_2$—, wherein $R^B$ means —H or —$C_1$-$C_6$-alkyl, linear or branched, saturated or unsaturated, unsubstituted or substituted with one, two, three or four substituents independently of one another selected from the group consisting of —F, —Cl, —Br and —I;

or a physiologically acceptable salt thereof.

2. The compound according to claim 1, wherein $R^7$, $R^8$, $R^{11}$, $R^{12}$, $R^{13}$, $R^{14}$, $R^{15}$, $R^{16}$, $R^{17}$, $R^{18}$, $R^{19}$, and $R^{20}$ independently of one another mean —H, —F, —OH, or —$C_1$-$C_6$-alkyl; or $R^7$ and $R^8$ together with the carbon atom to which they are attached form a ring and mean —$(CH_2)_2$—.

3. The compound according to claim 1, wherein $R^1$ means —H; and $R^2$ means —$C_1$-$C_6$-alkyl, linear or branched, saturated or unsaturated, unsubstituted, mono- or polysubstituted.

4. The compound according to claim 1, wherein $R^1$ means —$CH_3$; and $R^2$ means —$C_1$-$C_6$-alkyl, linear or branched, saturated or unsaturated, unsubstituted, mono- or polysubstituted.

5. The compound according to claim 1, wherein $R^1$ means —H or —$CH_3$; and wherein $R^2$ means —$CH_2$-cycloalkyl, —$CH_2$-cyclobutyl, —$CH_2$-cyclopentyl, —$CH_2$-oxetanyl or —$CH_2$-tetrahydrofuranyl.

6. The compound according to claim 1, wherein $R^1$ and $R^2$ together with the nitrogen atom to which they are attached form a ring and mean —$(CH_2)_{3-6}$—.

7. The compound according to claim 1, wherein $R^3$ means —$C_1$-$C_6$-alkyl, linear or branched, saturated or unsaturated, unsubstituted, mono- or polysubstituted.

8. The compound according to claim 1, wherein $R^3$ means a 6-14-membered aryl moiety, unsubstituted, mono- or polysubstituted.

9. The compound according to claim 1, wherein $R^3$ means a 5-14-membered heteroaryl moiety, unsubstituted, mono- or polysubstituted.

10. The compound according to claim 1, wherein $R^4$ means —H.

11. The compound according to claim 1, wherein $R^4$ means —$C_1$-$C_6$-alkyl, linear or branched, saturated or unsaturated, unsubstituted, mono- or polysubstituted.

12. The compound according to claim 1, wherein $R^4$ means a 3-12-membered cycloalkyl moiety, saturated or unsaturated, unsubstituted, mono- or polysubstituted; wherein the 3-12-membered cycloalkyl moiety is connected through —$C_1$-$C_6$-alkylene-, linear or branched, saturated or unsaturated, unsubstituted, mono- or polysubstituted.

13. The compound according to claim 1, wherein $R^4$ means a 3-12-membered heterocycloalkyl moiety, saturated or unsaturated, unsubstituted, mono- or polysubstituted; wherein said 3-12-membered heterocycloalkyl moiety is connected through —$C_1$-$C_6$-alkylene-, linear or branched, saturated or unsaturated, unsubstituted, mono- or polysubstituted.

14. The compound according to claim 1, wherein $R^4$ means a 6-14-membered aryl moiety, unsubstituted, mono- or polysubstituted; wherein said 6-14-membered aryl moiety is connected through —$C_1$-$C_6$-alkylene-, linear or branched, saturated or unsaturated, unsubstituted, mono- or polysubstituted.

15. The compound according to claim 1, wherein $R^4$ means a 5-14-membered heteroaryl moiety, unsubstituted, mono- or polysubstituted; wherein said 5-14-membered heteroaryl moiety is connected through —$C_1$-$C_6$-alkylene-, linear or branched, saturated or unsaturated, unsubstituted, mono- or polysubstituted.

16. The compound according to claim 1, wherein n means 1 or 2.

17. The compound according to claim 1, wherein $R^5$ means -phenyl, unsubstituted, mono- or polysubstituted.

18. The compound according to claim 1, wherein $R^5$ means -pyrazinyl, -pyridazinyl, -pyridinyl, -pyrimidinyl, -thienyl, -imidazolyl, triazolyl, or -1,3-benzodioxolyl in each case unsubstituted, mono- or polysubstituted.

19. The compound according to claim 1, which has a structure according to any of general formulas (II-A) to (VIII-C):

(II-A)

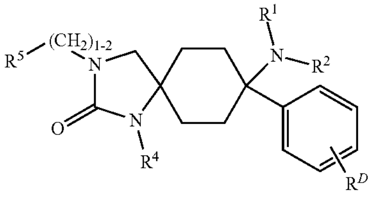

(II-B)

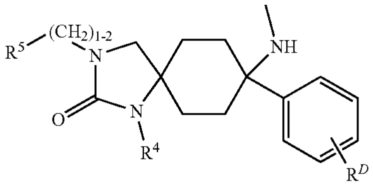

(II-C)

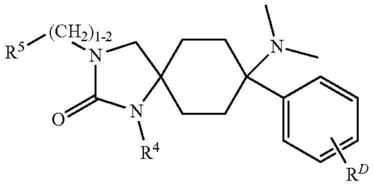

-continued
(III-A)
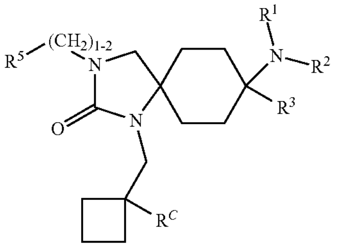
(III-B)
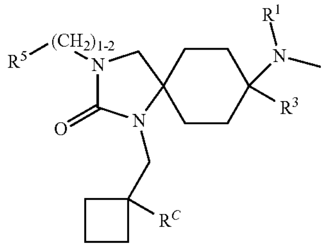
(III-C)
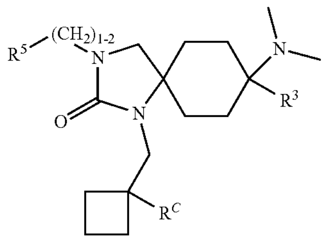
(IV-A)
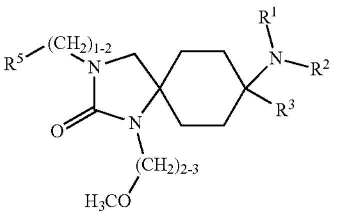
(IV-B)
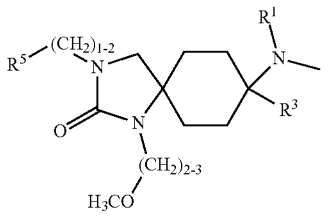
(IV-C)
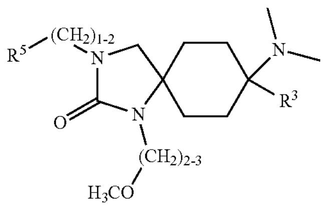
-continued
(V-A)
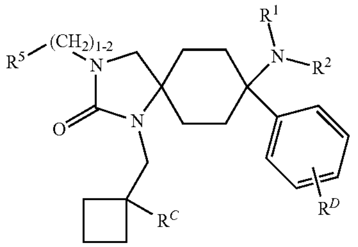
(V-B)
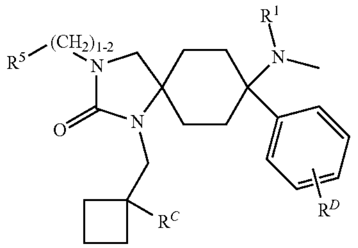
(V-C)
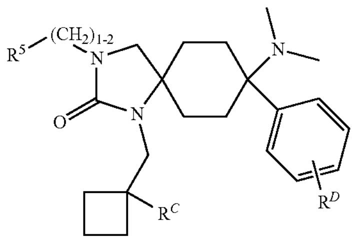
(VI-A)
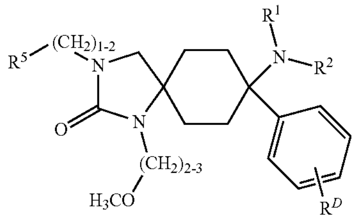
(VI-B)
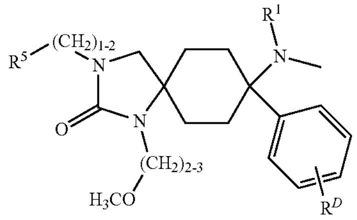
(VI-C)
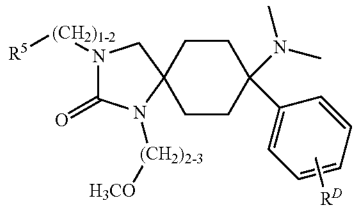

-continued (VII-A)

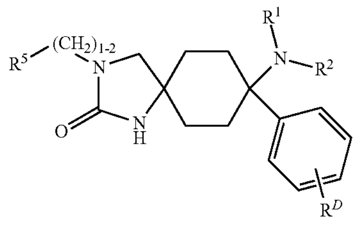

(VII-B)

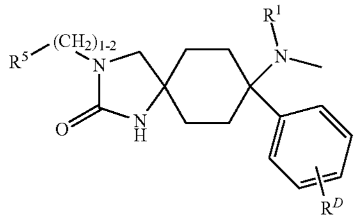

(VII-C)

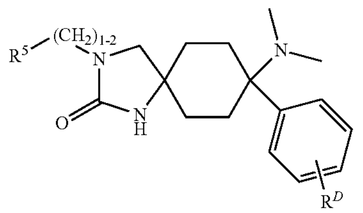

(VIII-A)

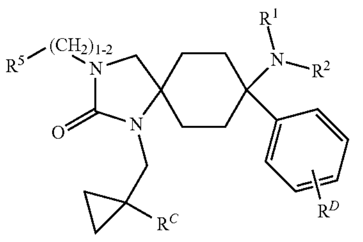

(VIII-B)

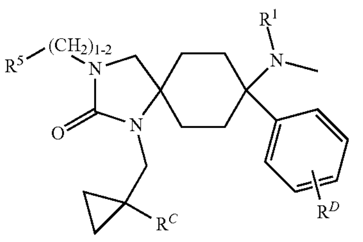

or (VIII-C)

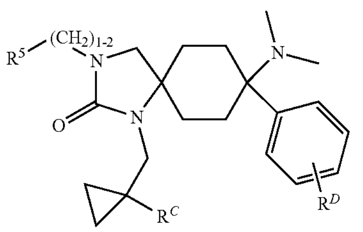

wherein in each case $R^1$, $R^2$, $R^3$, $R^4$, and $R^5$ are defined as in claim 1, $R^C$ means —H, —OH, —F, —CN or —$C_1$-$C_4$-alkyl;

$R^D$ means —H or —F;

or a physiologically acceptable salt thereof.

20. A compound of the general formula (I)

(I)

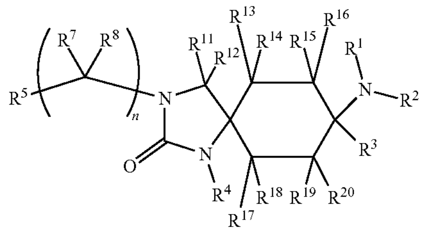

wherein n means 1, 2 or 3;

$R^1$ and $R^2$ independently of one another mean

—H;

—$C_1$-$C_6$-alkyl, linear or branched, saturated or unsaturated, unsubstituted or substituted with one, two, three or four substituents independently of one another selected from the group consisting of —F, —Cl, —Br, —I, —OH, —$OCH_3$, —CN and —$CO_2CH_3$;

a 3-12-membered cycloalkyl moiety, saturated or unsaturated, unsubstituted or substituted with one, two, three or four substituents independently of one another selected from the group consisting of —F, —Cl, —Br, —I, —OH, —$OCH_3$, —CN and —$CO_2CH_3$; wherein said 3-12-membered cycloalkyl moiety is optionally connected through —$C_1$-$C_6$-alkylene-, linear or branched, saturated or unsaturated, unsubstituted; or a 3-12-membered heterocycloalkyl moiety, saturated or unsaturated, unsubstituted or substituted with one, two, three or four substituents independently of one another selected from the group consisting of —F, —Cl, —Br, —I, —OH, —$OCH_3$, —CN and —$CO_2CH_3$; wherein said 3-12-membered heterocycloalkyl moiety is optionally connected through —$C_1$-$C_6$-alkylene-, linear or branched, saturated or unsaturated, unsubstituted;

or $R^1$ and $R^2$ together with the nitrogen atom to which they are attached form a ring and mean —$(CH_2)_{3-6}$—; —$CH_2)_2$—O—$(CH_2)_2$—; or —$CH_2)_2$—$NR^A$—$(CH_2)_2$—, wherein $R^A$ means —H or —$C_1$-$C_6$-alkyl, linear or branched, saturated or unsaturated, unsubstituted or substituted with one, two, three or four substituents independently of one another selected from the group consisting of —F, —Cl, —Br and —I;

$R^3$ means

—$C_1$-$C_6$-alkyl, linear or branched, saturated or unsaturated, unsubstituted, mono- or polysubstituted;

a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted;

a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted;

$R^4$ means

—H;

—$C_1$-$C_6$-alkyl, linear or branched, saturated or unsaturated, unsubstituted, mono- or polysubstituted; wherein said —$C_1$-$C_6$-alkyl is optionally connected through —C(═O)—, —C(═O)O—, or —S(═O)$_2$—;

a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted; or wherein said 3-12-membered cycloalkyl moiety is optionally connected through —C(═O)—, —C(═O)O—, —C(═O)O—$CH_2$—, or —S(═O)$_2$—;

a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted; or wherein said 3-12-membered heterocycloalkyl moiety is optionally connected through —C(═O)—, —C(═O)O—, —C(═O)O—$CH_2$—, or —S(═O)$_2$—;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or wherein said 6-14-membered aryl moiety is optionally connected through —C(═O)—, —C(═O)O—, —C(═O)O—$CH_2$—, or —S(═O)$_2$—; or a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted; or wherein said 5-14-membered heteroaryl moiety is optionally connected through —C(═O)—, —C(═O)O—, —C(═O)O—$CH_2$—, or —S(═O)$_2$—;

$R^5$ is selected from the group consisting of:

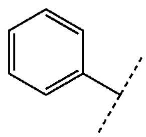 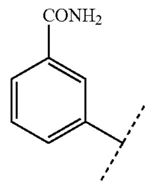 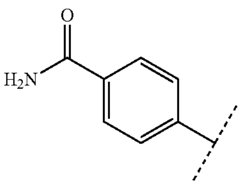

-continued

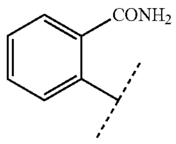 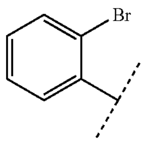 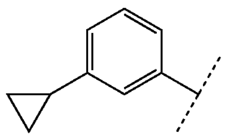

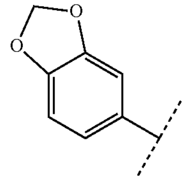 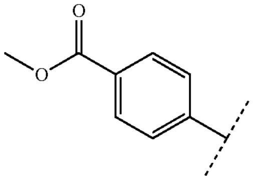

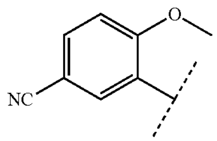 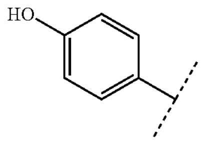

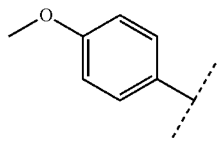 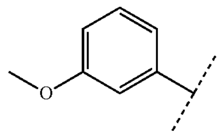

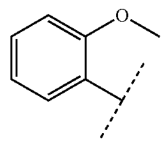 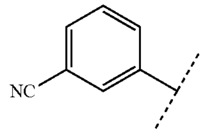

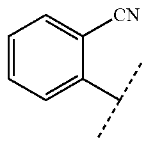 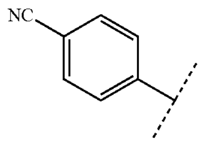

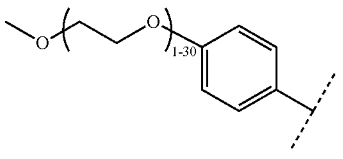

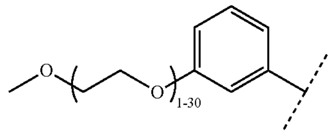 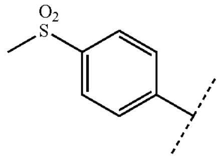

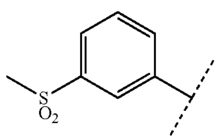 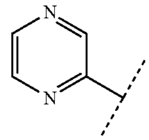 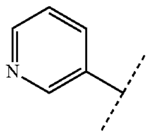

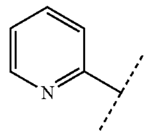 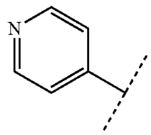 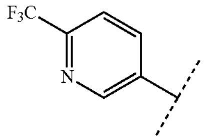

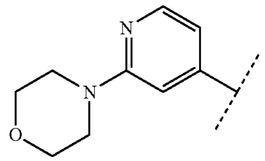 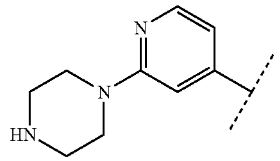

-continued

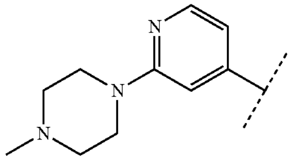 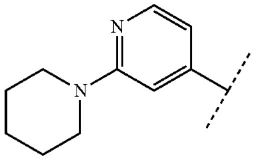

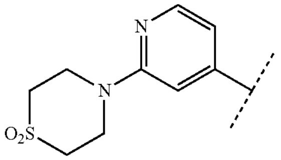 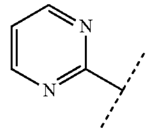

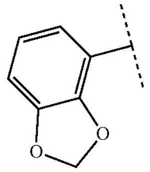 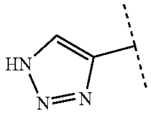

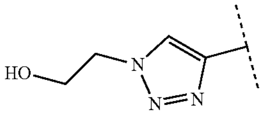 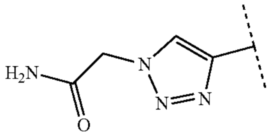

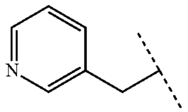 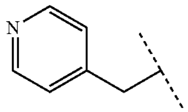 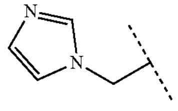

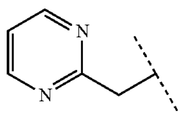 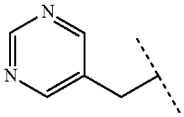

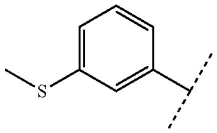 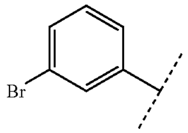

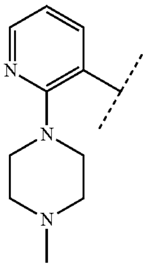 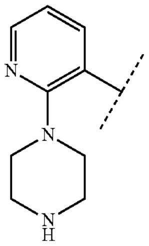 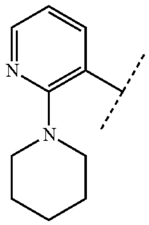

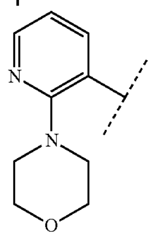

and

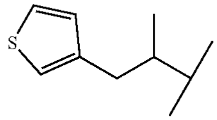

$R^7$, $R^8$, $R^{11}$, $R^{12}$, $R^{13}$, $R^{14}$, $R^{15}$, $R^{16}$, $R^{17}$, $R^{18}$, $R^{19}$, and $R^{20}$ independently of one another mean —H, —F, —Cl, —Br, —I, —OH, or —$C_1$-$C_6$-alkyl, linear or branched, saturated or unsaturated, unsubstituted, mono- or polysubstituted;

or wherein $R^7$ and $R^8$ together with the carbon atom to which they are attached form a ring and mean —$(CH_2)_2$— or —$(CH_2)_3$—;

wherein "mono- or polysubstituted" means that one or more hydrogen atoms are replaced by a substituent independently of one another selected from the group consisting of —F, —Cl, —Br, —I, —CN, —$R^{21}$, —C(=O)$R^{21}$, —C(=O)O$R^{21}$, —C(=O)N$R^{21}R^{22}$, —O—$(CH_2CH_2$—$O)_{1-30}$—H, —O—$(CH_2CH_2$—$O)_{1-30}$—$CH_3$, =O, —O$R^{21}$, —OC(=O)$R^{21}$, —OC(=O)O$R^{21}$, —OC(=O)N$R^{21}R^{22}$, —$NO_2$, —N$R^{21}R^{22}$, —N$R^{21}$—$(CH_2)_{1-6}$—C(=O)$R^{22}$, —N$R^{21}$—$(CH_2)_{1-6}$—C(=O)O$R^{22}$, —N$R^{23}$—$(CH_2)_{1-6}$—C(=O)N$R^{21}R^{22}$, —N$R^{21}$C(=O)$R^{22}$, —N$R^{21}$C(=O)—O$R^{22}$, —N$R^{23}$C(=O)N$R^{21}R^{22}$, —N$R^{21}$S(=$O)_2R^{22}$, —S$R^{21}$, —S(=O)$R^{21}$, —S(=$O)_2R^{21}$, —S(=$O)_2$O$R^{2'}$, and —S(=$O)_2$N$R^{21}R^{22}$;

wherein $R^{21}$, $R^{22}$ and $R^{23}$ independently of one another mean

—H;

—$C_1$-$C_6$-alkyl, linear or branched, saturated or unsaturated, unsubstituted or substituted with one, two, three or four substituents independently of one another selected from the group consisting of —F, —Cl, —Br, —I, —CN, —OH, —$NH_2$, and —O—$C_1$-$C_6$-alkyl;

a 3-12-membered cycloalkyl moiety, saturated or unsaturated, unsubstituted; wherein said 3-12-membered cycloalkyl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl;

a 3-12-membered heterocycloalkyl moiety, saturated or unsaturated, unsubstituted; wherein said 3-12-membered heterocycloalkyl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl;

a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl;

or $R^{21}$ and $R^{22}$ within —C(=O)N$R^{21}R^{22}$, —OC(=O)N$R^{21}R^{22}$, —N$R^{21}R^{22}$, —N$R^{23}$—$(CH_2)_{1-6}$—C(=O)N$R^{21}R^{22}$, —N$R^{23}$C(=O)N$R^{21}R^{22}$, or —S(=$O)_2$N$R^{21}R^{22}$ together with the nitrogen atom to which they are attached form a ring and mean —$(CH_2)_{3-6}$—; —$(CH_2)_2$—O—$(CH_2)_2$—; or $—(CH_2)_2—NR^B—(CH_2)_2—$, wherein $R^B$ means —H or $—C_1-C_6$-alkyl, linear or branched, saturated or unsaturated, unsubstituted or substituted with one, two, three or four substituents independently of one another selected from the group consisting of —F, —Cl, —Br and —I;

or a physiologically acceptable salt thereof.

21. The compound according to claim 1, wherein n means 1 or 2;

$R^1$ means —H or $—CH_3$;

$R^2$ means —H or $—C_1-C_6$-alkyl, linear or branched, saturated or unsaturated, unsubstituted or monosubstituted with —OH, $—OCH_3$, $—C(=O)OCH_3$, or —CN;

$R^3$ means $—C_1-C_4$-alkyl, optionally monosubstituted with $—OCH_3$;

-phenyl, -thienyl or -pyridinyl, in each case unsubstituted or substituted with one, two, three or four substituents independently of one another selected from the group consisting of —F, —Cl, —CN, $—CH_3$, $—CH_2CH_3$, $—CH_2F$, $—CHF_2$, $—CF_3$, —OCF3, —OH, $—OCH_3$, $—O—CH_2—O—CH_3$, $—C(=O)NH_2$, $C(=O)NHCH_3$, $—C(=O)N(CH_3)_2$, $—NH_2$, $—NHCH_3$, $—N(CH_3)_2$, $—NHC(=O)CH_3$, $—CH_2OH$, $SOCH_3$ and $SO_2CH_3$; or $R^4$ means

—H;

$—C_1-C_6$-alkyl, linear or branched, saturated, unsubstituted or substituted with one, two, three or four substituents independently of one another selected from the group consisting of —F, —Cl, —Br, —I, —CN, =O, —OH, $—O—C_1-C_4$-alkyl, $—CO_2H$, $—C(=O)O—C_1-C_4$-alkyl, $—C(=O)NH_2$, $—C(=O)NH—C_1-C_4$-alkyl, $—C(=O)N(C_1-C_4\text{-alkyl})_2$, $—C(=O)NH—C_1-C_4$-alkyl-CN, $—C(=O)NCH_3—C_1-C_4$-alkyl-CN, —C(=O)NH-cyclopropyl-CN, $—C(=O)NCH_3$-cyclopropyl-CN, $—C(=O)NH—C_1-C_4$-alkyl-OH, $—C(=O)NCH_3—C_1-C_4$-alkyl-OH, $—C(=O)NH—C_1-C_4$-alkyl-$OCH_3$, $—C(=O)NCH_3—C1-C_4$-alkyl-$OCH_3$, —C(=O)NRR' wherein R and R' together with the nitrogen atom to which they are attached form a ring and mean $—(CH_2)_{2-4}—$;

3-6-membered cycloalkyl, unsubstituted or substituted with one, two, three or four substituents independently of one another selected from the group consisting of —F, —Cl, —Br, —I, —CN, —OH, and $—O—C_1-C_4$-alkyl, wherein said 3-6-membered cycloalkyl is connected through $—C_1-C_6$-alkylene;

3-6-membered heterocycloalkyl, unsubstituted or substituted with one, two, three or four substituents independently of one another selected from the group consisting of —F, —Cl, —Br, —I, —CN, $—CO_2H$, $—C(=O)O—C_1-C_4$-alkyl, —OH, and $—O—C_1-C_4$-alkyl, wherein said 3-6-membered heterocycloalkyl is connected through $—C_1-C_6$-alkylene;

6-14-membered aryl, unsubstituted or substituted with one, two, three or four substituents independently of one another selected from the group consisting of —F, —Cl, —Br, —I, —CN, $—CO_2H$, $—C(=O)O—C_1-C_4$-alkyl, —OH, and $—O—C_1-C_4$-alkyl; wherein said 6-14-membered aryl is connected through $—C_1-C_6$-alkylene- or $—S(=O)_2—$;

5-14-membered heteroaryl, unsubstituted or substituted with one, two, three or four substituents independently of one another selected from the group consisting of —F, —Cl, —Br, —I, —CN, $—CO_2H$, $—C(=O)O—C_1-C_4$-alkyl, —OH, and $—O—C_1-C_4$-alkyl; wherein said 5-14-membered heteroaryl is connected through $—C_1-C_6$-alkylene- or $—S(=O)_2—$;

$R^5$ means -phenyl, -pyrazinyl, -pyridazinyl, -pyridinyl, -pyrimidinyl, -thienyl, -imidazolyl, triazolyl, or -1,3-benzodioxolyl, in each case unsubstituted or substituted with one, two, three or four substituents independently of one another selected from the group consisting of —F; —Cl; —Br; —I; —CN; —OH; $—CF_3$; $—C_1-C_4$-alkyl-$C(=O)NH_2$; -3-12-membered cycloalkyl, saturated or unsaturated, unsubstituted, mono- or polysubstituted; preferably -cyclopropyl, saturated, unsubstituted; -3-12-membered heterocycloalkyl, saturated or unsaturated, unsubstituted, mono- or polysubstituted; $—O—CH_2—O—$; $—O—C_1-C_4$-alkyl; $—O—(CH_2CH_2—O)_{1-30}—H$; $—O—(CH_2CH_2—O)_{1-30}—CH_3$; —C(=O)OH; —C(=O)OH; $—C(=O)O—C_1-C_4$-alkyl; $—C(=O)NH_2$; $—C(=O)NHC_1-C_4$-alkyl; $—C(=O)N(C_1-C_4\text{-alkyl})_2$; $—SC_1-C_4$-alkyl; $—S(=O)C_1-C_4$-alkyl and $—S(=O)_2C_1-C_4$-alkyl; and $R^7$, $R^8$, $R^{11}$, $R^{12}$, $R^{13}$, $R^{14}$, $R^{15}$, $R^{16}$, $R^{17}$, $R^{18}$, $R^{19}$, and $R^{20}$ mean —H.

22. The compound according to claim 1, which has a structure according to general formula (I')

(I')

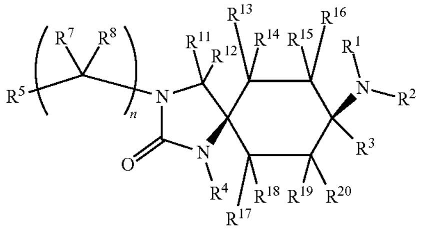

wherein $R^1$ to $R^5$, $R^7$, $R^8$, $R^{11}$ to $R^{20}$ and n are defined as in claim 1, or a physiologically acceptable salt thereof.

23. The compound according to claim 1, which has a structure according to general formula (IX)

(IX)

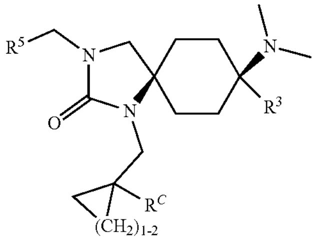

wherein $R^C$ means —H or —OH;

$R^3$ means -phenyl or -3-fluorophenyl; and $R^5$ means 6-14-membered aryl, unsubstituted, mono- or polysubstituted; or 5-14-membered heteroaryl, unsubstituted, mono- or polysubstituted;

or a physiologically acceptable salt thereof.

24. The compound according to claim 23, wherein $R^5$ is selected from -phenyl, -pyridyl, pyrimidinyl, or -triazolyl, in each case unsubstituted, mono- or polysubstituted.

25. A compound selected from the group consisting of

CIS-1-(Cyclobutyl-methyl)-8-dimethylamino-3-[(4-methylsulfonyl-phenyl)-methyl]-8-phenyl-1,3-diazaspiro[4.5]decan-2-one;

CIS-1-(Cyclobutyl-methyl)-8-dimethylamino-3-[(3-methoxyphenyl)-methyl]-8-phenyl-1,3-diazaspiro[4.5]decan-2-one;

CIS-8-Dimethylamino-1-isopropyl-3-[(4-methoxyphenyl)-methyl]-8-phenyl-1,3-diazaspiro[4.5]decan-2-one;

CIS-1-(Cyclopropyl-methyl)-8-dimethylamino-3-[(4-methoxyphenyl)-methyl]-8-phenyl-1,3-diazaspiro[4.5]decan-2-one;

CIS-1-(Cyclobutyl-methyl)-3-[(4-methoxyphenyl)-methyl]-8-[methyl-(2-methyl-propyl)-amino]-8-phenyl-1,3-diazaspiro[4.5]decan-2-one;

CIS-2-[[1-(Cyclobutyl-methyl)-8-dimethylamino-2-oxo-8-phenyl-1,3-diazaspiro[4.5]decan-3-yl]-methyl]-benzamide;

CIS-1-(Cyclobutyl-methyl)-8-dimethylamino-8-phenyl-3-(pyrazin-2-yl-methyl)-1,3-diazaspiro[4.5]decan-2-one;

CIS-8-(Allyl-methyl-amino)-1-(cyclobutyl-methyl)-3-[(4-methoxyphenyl)-methyl]-8-phenyl-1,3-diazaspiro[4.5]decan-2-one;

CIS-4-[[1-(Cyclobutyl-methyl)-8-dimethylamino-2-oxo-8-phenyl-1,3-diazaspiro[4.5]decan-3-yl]-methyl]-benzamide;

CIS-1-(Cyclobutyl-methyl)-8-dimethylamino-8-(3-fluorophenyl)-3-[(4-methoxyphenyl)-methyl]-1,3-diazaspiro[4.5]decan-2-one;

CIS-1-(Cyclobutyl-methyl)-8-dimethylamino-8-(4-fluorophenyl)-3-[(4-methoxyphenyl)-methyl]-1,3-diazaspiro[4.5]decan-2-one;

CIS-1-(Cyclobutyl-methyl)-8-dimethylamino-8-(3-methoxyphenyl)-3-[(4-methoxyphenyl)-methyl]-1,3-diazaspiro[4.5]decan-2-one;

CIS-1-(Cyclobutyl-methyl)-8-dimethylamino-8-(4-methoxyphenyl)-3-[(4-methoxyphenyl)-methyl]-1,3-diaza-spiro [4.5]decan-2-one;

CIS-8-Dimethylamino-3-[(4-methoxyphenyl)-methyl]-1-(2-methyl-propyl)-8-phenyl-1,3-diazaspiro[4.5]decan-2-one;

CIS-1-Butyl-8-dimethylamino-3-[(4-methoxyphenyl)-methyl]—8-phenyl-1,3-diazaspiro[4.5]decan-2-one;

CIS-8-Dimethylamino-8-(4-fluorophenyl)-3-[(4-methoxyphenyl)-methyl]—1,3-diaza-spiro[4.5]decan-2-one;

CIS-8-Dimethylamino-8-(3-fluorophenyl)-3-[(4-methoxyphenyl)-methyl]—1,3-diazaspiro[4.5]decan-2-one;

CIS-1-(Cyclobutyl-methyl)-8-dimethylamino-8-(3-hydroxyphenyl)-3-[(4-methoxyphenyl)-methyl]-1,3-diazaspiro[4.5]decan-2-one;

CIS-1-(Cyclobutyl-methyl)-8-dimethylamino-8-phenyl-3-(pyridin-3-yl-methyl)-1,3-diazaspiro[4.5]decan-2-one;

CIS-1-(Cyclobutyl-methyl)-8-dimethylamino-3-[[3-[2-[2-[2-[2-[2-(2-methoxy-ethoxy)-ethoxy]-ethoxy]-ethoxy]-ethoxy]-ethoxy]-phenyl]-methyl]-8-phenyl-1,3-diazaspiro[4.5]de can-2-one;

CIS-1-(Cyclobutyl-methyl)-8-dimethylamino-8-(4-hydroxyphenyl)-3-[(4-methoxyphenyl)-methyl]-1,3-diazaspiro[4.5]decan-2-one hydrochloride;

CIS-8-Dimethylamino-1-[(1-hydroxy-cyclobutyl)-methyl]-3-[(3-methoxyphenyl)-methyl]-8-phenyl-1,3-diazaspiro[4.5]decan-2-one;

CIS-1-(Cyclopentyl-methyl)-8-dimethylamino-3-[(4-methoxyphenyl)-methyl]-8-phenyl-1,3-diazaspiro[4.5]decan-2-one;

CIS-8-Dimethylamino-1-(2-hydroxy-2-methyl-propyl)-3-[(4-methoxyphenyl)-methyl]-8-phenyl-1,3-diazaspiro[4.5]decan-2-one;

CIS-8-Dimethylamino-1-(2-methoxy-2-methyl-propyl)-3-[(4-methoxyphenyl)-methyl]-8-phenyl-1,3-diazaspiro[4.5]decan-2-one;

CIS-1-(Cyclobutyl-methyl)-3-[(3-methoxyphenyl)-methyl]-8-methylamino-8-phenyl-1,3-diazaspiro[4.5]decan-2-one;

CIS-3-[[1-(Cyclobutyl-methyl)-8-(ethyl-methyl-amino)-2-oxo-8-phenyl-1,3-diazaspiro[4.5]decan-3-yl]-methyl]-benzonitrile;

CIS-1-(Cyclobutyl-methyl)-3-[(3-methoxyphenyl)-methyl]-8-(methyl-propyl-amino)-8-phenyl-1,3-diazaspiro[4.5]decan-2-one;

CIS-1-(Cyclobutyl-methyl)-8-(ethyl-methyl-amino)-3-[(3-methoxyphenyl)-methyl]-8-phenyl-1,3-diazaspiro[4.5]decan-2-one;

CIS-3-[8-Dimethylamino-3-[(4-methoxyphenyl)-methyl]-2-oxo-8-phenyl-1,3-diazaspiro[4.5]decan-1-yl]-propionitrile;

CIS-1-(Cyclobutyl-methyl)-8-methylamino-8-phenyl-3-(pyridin-3-yl-methyl)-1,3-diazaspiro[4.5]decan-2-one;

CIS-8-Dimethylamino-3-[(4-methoxyphenyl)-methyl]—1-(oxetan-3-yl-methyl)-8-phenyl-1,3-diazaspiro[4.5]decan-2-one;

CIS-1-(Cyclobutyl-methyl)-8-(ethyl-methyl-amino)-8-phenyl-3-(pyridin-3-yl-methyl)-1,3-diazaspiro[4.5]decan-2-one;

CIS-8-Dimethylamino-1-(2-hydroxy-ethyl)-3-[(4-methoxyphenyl)-methyl]-8-phenyl-1,3-diazaspiro[4.5]decan-2-one;

CIS-8-Dimethylamino-1-(2,2-dimethyl-propyl)-3-[(4-methoxyphenyl)-methyl]-8-phenyl-1,3-diazaspiro[4.5]decan-2-one;

CIS-8-Dimethylamino-3-[(4-methoxyphenyl)-methyl]-1-(3-methyl-butyl)-8-phenyl-1,3-diazaspiro[4.5]decan-2-one;

CIS-8-Dimethylamino-3-[(4-methoxyphenyl)-methyl]-8-phenyl-1-[3-((trifluoromethyl oxy)-propyl]-1,3-diazaspiro[4.5]decan-2-one;

CIS-1-(2-Cyclobutyl-ethyl)-8-dimethylamino-3-[(4-methoxyphenyl)-methyl]—8-phenyl-1,3-diazaspiro[4.5]decan-2-one;

CIS-1-[(3,3-Difluoro-cyclobutyl)-methyl]-8-dimethylamino-3-[(4-methoxyphenyl)-methyl]-8-phenyl-1,3-diazaspiro[4.5]decan-2-one;

CIS-2-[[1-(Cyclobutyl-methyl)-3-[(4-methoxyphenyl)-methyl]-2-oxo-8-phenyl-1,3-diazaspiro[4.5]decan-8-yl]-methyl-amino]-acetonitrile;

CIS-1-(Cyclobutyl-methyl)-8-[(2-methoxy-ethyl)-methyl-amino]-3-[(4-methoxyphenyl)-methyl]-8-phenyl-1,3-diazaspiro[4.5]decan-2-one;

CIS-2-[8-Dimethylamino-3-[(4-methoxyphenyl)-methyl]-2-oxo-8-phenyl-1,3-diazaspiro[4.5]decan-1-yl]-acetic acid tert-butyl ester;

CIS-2-[8-Dimethylamino-3-[(4-methoxyphenyl)-methyl]-2-oxo-8-phenyl-1,3-diazaspiro[4.5]decan-1-yl]-acetic acid, 2,2,2-trifluoro-acetic acid salt;

CIS-1-(Cyclobutyl-methyl)-3-[(4-methoxyphenyl)-methyl]-8-methylamino-8-phenyl-1,3-diazaspiro[4.5]decan-2-one;

CIS-2-[8-Dimethylamino-3-[(4-methoxyphenyl)-methyl]-2-oxo-8-phenyl-1,3-diazaspiro[4.5]decan-1-yl]-acetic acid methyl ester;
CIS-2-[8-Dimethylamino-3-[(4-methoxyphenyl)-methyl]-2-oxo-8-phenyl-1,3-diazaspiro[4.5]decan-1-yl]-acetamide;
CIS-1-Benzyl-8-dimethylamino-3-[(4-methoxyphenyl)-methyl]-8-phenyl-1,3-diazaspiro[4.5]decan-2-one;
CIS-2-[8-Dimethylamino-3-[(4-methoxyphenyl)-methyl]-2-oxo-8-phenyl-1,3-diazaspiro[4.5]decan-1-yl]-N-methyl-acetamide;
CIS-2-[8-Dimethylamino-3-[(4-methoxyphenyl)-methyl]-2-oxo-8-phenyl-1,3-diazaspiro[4.5]decan-1-yl]-N-propyl-acetamide;
CIS-8-Dimethylamino-3-[(4-methoxyphenyl)-methyl]-1-(3-methoxy-propyl)-8-phenyl-1,3-diazaspiro[4.5]decan-2-one;
CIS-8-Dimethylamino-1-[(1-hydroxy-cyclobutyl)-methyl]-3-[(4-methoxyphenyl)-methyl]-8-phenyl-1,3-diazaspiro[4.5]decan-2-one;
CIS-8-Dimethylamino-1-(2-methoxy-ethyl)-3-[(4-methoxyphenyl)-methyl]-8-phenyl-1,3-diazaspiro[4.5]decan-2-one;
CIS-2-[8-Dimethylamino-3-[(4-methoxyphenyl)-methyl]-2-oxo-8-phenyl-1,3-diazaspiro[4.5]decan-1-yl]-acetonitrile;
CIS-8-Dimethylamino-1-hexyl-3-[(4-methoxyphenyl)-methyl]-8-phenyl-1,3-diazaspiro[4.5]decan-2-one;
CIS-8-Dimethylamino-3-[(4-methoxyphenyl)-methyl]-8-phenyl-1-(tetrahydro-pyran-4-yl-methyl)-1,3-diazaspiro[4.5]decan-2-one;
CIS-1-(Cyclohexyl-methyl)-8-dimethylamino-3-[(4-methoxyphenyl)-methyl]-8-phenyl-1,3-diazaspiro[4.5]decan-2-one;
CIS-N-(Cyano-methyl)-2-[8-dimethylamino-3-[(4-methoxyphenyl)-methyl]-2-oxo-8-phenyl-1,3-diazaspiro[4.5]decan-1-yl]-acetamide;
CIS-8-Dimethylamino-3-[(4-methoxyphenyl)-methyl]-8-phenyl-1-(pyridin-3-yl-methyl)-1,3-diazaspiro[4.5]decan-2-one;
CIS-8-Dimethylamino-3-[(4-methoxyphenyl)-methyl]-8-(3-methoxy-propyl)-1,3-diazaspiro[4.5]decan-2-one;
CIS-2-[8-Dimethylamino-3-[(4-methoxyphenyl)-methyl]-2-oxo-8-phenyl-1,3-diazaspiro[4.5]decan-1-yl]-N-(2-methoxy-ethyl)-acetamide;
CIS-8-Dimethylamino-3-[(4-methoxyphenyl)-methyl]—1-(2-oxo-2-pyrrolidin-1-yl-ethyl)-8-phenyl-1,3-diazaspiro[4.5]decan-2-one;
CIS-2-[8-Dimethylamino-3-[(4-methoxyphenyl)-methyl]-2-oxo-8-phenyl-1,3-diazaspiro[4.5]decan-1-yl]-N,N-dimethyl-acetamide;
CIS-N-(1-Cyano-cyclopropyl)-2-[8-dimethylamino-3-[(4-methoxyphenyl)-methyl]-2-oxo-8-phenyl-1,3-diazaspiro[4.5]decan-1-yl]-acetamide;
CIS-2-[8-Dimethylamino-3-[(4-methoxyphenyl)-methyl]-2-oxo-8-phenyl-1,3-diazaspiro[4.5]decan-1-yl]-N-methyl-N-propyl-acetamide;
CIS-1-(Cyclobutyl-methyl)-8-dimethylamino-3-[(4-methoxyphenyl)-methyl]-8-(3-methoxy-propyl)-1,3-diazaspiro[4.5]decan-2-one;
CIS-8-Dimethylamino-1-(3-hydroxy-propyl)-3-[(4-methoxyphenyl)-methyl]-8-phenyl-1,3-diazaspiro[4.5]decan-2-one;
CIS-8-Dimethylamino-1-(4-methoxy-butyl)-3-[(4-methoxyphenyl)-methyl]-8-phenyl-1,3-diazaspiro[4.5]decan-2-one;
CIS-8-Dimethylamino-3-[(4-methoxyphenyl)-methyl]—1-[(1-methyl-cyclobutyl)-methyl]-8-phenyl-1,3-diazaspiro[4.5]decan-2-one;
CIS-8-Dimethylamino-1-[(1-hydroxy-cyclohexyl)-methyl]-3-[(4-methoxyphenyl)-methyl]-8-phenyl-1,3-diazaspiro[4.5]decan-2-one;
CIS-5-[8-Dimethylamino-3-[(4-methoxyphenyl)-methyl]-2-oxo-8-phenyl-1,3-diazaspiro[4.5]decan-1-yl]-pentanenitrile;
CIS-3-[8-Dimethylamino-3-[(4-methoxyphenyl)-methyl]-2-oxo-8-phenyl-1,3-diazaspiro[4.5]decan-1-yl]-propionamide;
CIS-1-(Cyclobutyl-methyl)-8-[(2-hydroxy-ethyl)-methyl-amino]-3-[(4-methoxyphenyl)-methyl]-8-phenyl-1,3-diazaspiro[4.5]decan-2-one;
CIS-1-[[8-Dimethylamino-3-[(4-methoxyphenyl)-methyl]-2-oxo-8-phenyl-1,3-diazaspiro[4.5]decan-1-yl]-methyl]-cyclobutane-1-carbonitrile;
CIS-8-Dimethylamino-1-[(1-hydroxy-cyclopentyl)-methyl]-3-[(4-methoxyphenyl)-methyl]-8-phenyl-1,3-diazaspiro[4.5]decan-2-one;
CIS-3-[(2-Bromophenyl)-methyl]-1-(cyclobutyl-methyl)-8-dimethylamino-8-phenyl-1,3-diazaspiro[4.5]decan-2-one;
CIS-3-[8-Dimethylamino-3-[(4-methoxyphenyl)-methyl]-2-oxo-8-phenyl-1,3-diazaspiro[4.5]decan-1-yl]-N-methyl-propionamide;
CIS-3-[8-Dimethylamino-3-[(4-methoxyphenyl)-methyl]-2-oxo-8-phenyl-1,3-diazaspiro[4.5]decan-1-yl]-N-propyl-propionamide;
CIS-8-Dimethylamino-1-[(1-fluoro-cyclobutyl)-methyl]-3-[(4-methoxyphenyl)-methyl]-8-phenyl-1,3-diazaspiro[4.5]decan-2-one;
CIS-1-(2-Cyclohexyl-ethyl)-8-dimethylamino-3-[(4-methoxyphenyl)-methyl]-8-phenyl-1,3-diazaspiro[4.5]decan-2-one;
CIS-3-([[1-(Cyclobutyl-methyl)-8-dimethylamino-2-oxo-8-phenyl-1,3-diazaspiro[4.5]decan-3-yl]-methyl]-benzonitrile;
CIS-8-Dimethylamino-3-[(4-methoxyphenyl)-methyl]-1-methyl-8-phenyl-1,3-diazaspiro[4.5]decan-2-one;
CIS-8-Dimethylamino-1-[2-[2-[2-[2-[2-[2-[2-(2-methoxy-ethoxy)-ethoxy]-ethoxy]-ethoxy]-ethoxy]-ethoxy]-ethoxy]-ethyl]-3-[(4-methoxyphenyl)-methyl]-8-phenyl-1,3-diazaspiro[4.5]decan-2-one;
CIS-8-Dimethylamino-3-[(4-methoxyphenyl)-methyl]-8-phenyl-1-(2-tetrahydro-pyran-4-yl-ethyl)-1,3-diazaspiro[4.5]decan-2-one;
CIS-4-[[1-(Cyclobutyl-methyl)-8-dimethylamino-2-oxo-8-phenyl-1,3-diazaspiro[4.5]decan-3-yl]-methyl]-benzonitrile;
CIS-1-(Cyclobutyl-methyl)-8-dimethylamino-8-phenyl-3-[[6-(trifluoromethyl)-pyridin-3-(yl]-methyl]-1,3-diazaspiro[4.5]decan-2-one;
CIS-1-(Cyclobutyl-methyl)-8-dimethylamino-3-[ [4-[2-[2-[2-[2-[2-[2-[2-(2-methoxy-ethoxy)-ethoxy]-ethoxy]-ethoxy]-ethoxy]-ethoxy]-ethoxy]-ethoxy]-phenyl]-methyl]-8-phenyl-1,3-diazaspiro[4.5]decan-2-one;
CIS-3-([[1-(Cyclobutyl-methyl)-8-dimethylamino-2-oxo-8-phenyl-1,3-diazaspiro[4.5]decan-3-yl]-methyl]-benzamide;
CIS-1-(Cyclobutyl-methyl)-8-dimethylamino-3-[(4-hydroxyphenyl)-methyl]-8-phenyl-1,3-diazaspiro[4.5]decan-2-one;

CIS-1-(Cyclobutyl-methyl)-8-(ethyl-methyl-amino)-3-[(4-methoxyphenyl)-methyl]-8-phenyl-1,3-diazaspiro[4.5]decan-2-one;

CIS-8-Dimethylamino-1-[(1-methoxy-cyclobutyl)-methyl]-3-[(4-methoxyphenyl)-methyl]-8-phenyl-1,3-diazaspiro[4.5]decan-2-one;

CIS-2-[[1-(Cyclobutyl-methyl)-8-dimethylamino-2-oxo-8-phenyl-1,3-diazaspiro[4.5]decan-3-yl]-methyl]benzonitrile;

CIS-1-(Cyclobutyl-methyl)-8-dimethylamino-3-[(3-methylsulfonyl-phenyl)-methyl]-8-phenyl-1,3-diazaspiro[4.5]decan-2-one;

CIS-8-Dimethylamino-1-ethyl-3-[(4-methoxyphenyl)-methyl]—8-phenyl-1,3-diazaspiro[4.5]decan-2-one;

CIS-8-Dimethylamino-3-[(4-methoxyphenyl)-methyl]-8-phenyl-1-propyl-1,3-diazaspiro[4.5]decan-2-one;

CIS-3-(Benzyl-1-(cyclobutyl-methyl)-8-dimethylamino-8-phenyl-1,3-diazaspiro[4.5]decan-2-one;

CIS-8-Dimethylamino-3-[(4-methoxyphenyl)-methyl]-8-phenyl-1,3-diazaspiro[4.5]de can-2-one;

CIS-8-Dimethylamino-3-[(4-methoxyphenyl)-methyl]-8-phenyl-1-(pyrimidin-4-yl-methyl)-1,3-diazaspiro[4.5]decan-2-one;

CIS-3-[8-Dimethylamino-3-[(4-methoxyphenyl)-methyl]-2-oxo-8-phenyl-1,3-diazaspiro[4.5]decan-1-yl]-2,2-dimethyl-propionitrile;

CIS-2-[[8-Dimethylamino-3-[(4-methoxyphenyl)-methyl]-2-oxo-8-phenyl-1,3-diazaspiro[4.5]decan-1-yl]-methyl]-benzoic acid methyl ester;

CIS-1-(Cyclobutyl-methyl)-8-dimethylamino-8-phenyl-3-(pyridin-2-yl-methyl)-1,3-diazaspiro[4.5]decan-2-one;

CIS-1-(Cyclobutyl-methyl)-8-dimethylamino-8-phenyl-3-(pyridin-4-yl-methyl)-1,3-diazaspiro[4.5]decan-2-one;

CIS-8-Dimethylamino-3-[(4-methoxyphenyl)-methyl]-8-phenyl-1-(tetrahydro-furan-3-yl-methyl)-1,3-diazaspiro[4.5]decan-2-one;

CIS-1-(Cyclobutyl-methyl)-8-dimethylamino-8-phenyl-3-(pyrimidin-2-yl-methyl)-1,3-diazaspiro[4.5]decan-2-one;

CIS-3-[[1-[(5-Cyano-2-methoxy-phenyl)-methyl]-8-dimethylamino-2-oxo-8-phenyl-1,3-diazaspiro[4.5]decan-3-yl]-methyl]-4-methoxybenzonitrile;

CIS-8-Dimethylamino-1-(3-hydroxy-3-methyl-butyl)-3-[(4-methoxyphenyl)-methyl]-8-phenyl-1,3-diazaspiro[4.5]decan-2-one;

CIS-8-Dimethylamino-1-(3-methoxy-3-methyl-butyl)-3-[(4-methoxyphenyl)-methyl]-8-phenyl-1,3-diazaspiro[4.5]decan-2-one;

CIS-2-[[8-Dimethylamino-1-[(1-hydroxy-cyclobutyl)-methyl]-2-oxo-8-phenyl-1,3-diazaspiro[4.5]decan-3-yl]-methyl]-benzamide;

CIS-3-[[8-Dimethylamino-1-[(1-hydroxy-cyclobutyl)-methyl]-2-oxo-8-phenyl-1,3-diazaspiro[4.5]decan-3-yl]-methyl]-benzamide;

CIS-8-Dimethylamino-3-[(4-methoxyphenyl)-methyl]-1-(2-methylsulfonyl-ethyl)-8-phenyl-1,3-diazaspiro[4.5]decan-2-one;

CIS-1-[(1-Hydroxy-cyclobutyl)-methyl]-3-[(4-methoxy-phenyl)-methyl]-8-methylamino-8-phenyl-1,3-diazaspiro[4.5]decan-2-one;

CIS-8-Dimethylamino-3-[(4-methoxyphenyl)-methyl]-8-phenyl-1-(tetrahydro-furan-2-yl-methyl)-1,3-diazaspiro[4.5]decan-2-one;

CIS-3-(Benzyl-8-dimethylamino-8-phenyl-1,3-diazaspiro[4.5]decan-2-one;

CIS-3-(Benzyl-8-dimethylamino-1-ethyl-8-phenyl-1,3-diazaspiro[4.5]decan-2-one;

CIS-8-Dimethylamino-3-[(4-methoxyphenyl)-methyl]—1-[2-(methylsulfinyl)-ethyl]-8-phenyl-1,3-diazaspiro[4.5]decan-2-one;

CIS-8-Dimethylamino-1-[(2R)-2-hydroxy-propyl]-3-[(4-methoxyphenyl)-methyl]-8-phenyl-1,3-diazaspiro[4.5]decan-2-one;

CIS-8-Dimethylamino-1-[(2 S)-2-hydroxy-propyl]-3-[(4-methoxyphenyl)-methyl]-8-phenyl-1,3-diazaspiro[4.5]decan-2-one;

CIS-8-Dimethylamino-3-[(4-methoxyphenyl)-methyl]-8-phenyl-1-(tetrahydro-furan-3-yl-methyl)-1,3-diazaspiro[4.5]decan-2-one;

CIS-8-Dimethylamino-1-ethyl-3-[(4-methoxyphenyl)-methyl]—8-phenyl-1,3-diazaspiro[4.5]decan-2-one;

CIS-8-Amino-1-[(1-hydroxy-cyclobutyl)-methyl]-3-[(4-methoxyphenyl)-methyl]-8-phenyl-1,3-diazaspiro[4.5]decan-2-one;

CIS-8-Dimethylamino-1-[(1-hydroxy-cyclobutyl)-methyl]-8-phenyl-3-(2-phenyl-ethyl)-1,3-diazaspiro[4.5]decan-2-one;

CIS-1-(Cyclobutyl-methyl)-8-dimethylamino-8-phenyl-3-[(4-methoxyphenyl)-methyl]-1,3-diazaspiro[4.5]decan-2-one;

CIS-3-([[8-Dimethylamino-1-[(1-hydroxycyclobutyl)-methyl]-2-oxo-8-phenyl-1,3-diazaspiro[4.5]decan-3-yl]-methyl]-4-methyl)benzonitrile;

CIS-8-Dimethylamino-1-ethyl-8-phenyl-3-(pyridin-3-yl-methyl)-1,3-diazaspiro[4.5]decan-2-one;

CIS-8-Dimethylamino-1-[2-(1-methoxy-cyclobutyl)-ethyl]-3-[(4-methoxyphenyl)-methyl]-8-phenyl-1,3-diazaspiro[4.5]decan-2-one;

CIS-8-Dimethylamino-8-[3-((4-methoxyphenyl phenyl]-3-[(4-methoxyphenyl)-methyl]—1,3-diazaspiro[4.5]decan-2-one;

CIS-8-Dimethylamino-8-[4-(methoxymethyloxy)-phenyl]-3-[(4-methoxyphenyl)-methyl]-1,3-diazaspiro[4.5]decan-2-one;

CIS-3-[8-Dimethylamino-3-[(4-methoxyphenyl)-methyl]-2-oxo-8-phenyl-1,3-diazaspiro[4.5]decan-1-yl]-propionic acid;

CIS-3-[8-Dimethylamino-3-[(4-methoxyphenyl)-methyl]-2-oxo-8-phenyl-1,3-diazaspiro[4.5]decan-1-yl]-propionic acid tert-butyl ester;

CIS-2-[[1-(Cyclobutyl-methyl)-3-[(4-methoxyphenyl)-methyl]-2-oxo-8-phenyl-1,3-diazaspiro[4.5]decan-8-yl]-methyl-amino]-acetic acid methyl ester;

CIS-8-Dimethylamino-3-[(4-methoxyphenyl)-methyl]-1-(3-methyl-but-2-enyl)-8-phenyl-1,3-diazaspiro[4.5]decan-2-one;

CIS-1-(Cyclobutyl-methyl)-8-dimethylamino-3-[(3-methylsulfanyl-phenyl)-methyl]-8-phenyl-1,3-diazaspiro[4.5]decan-2-one;

CIS-3-([(3-(Bromophenyl)-methyl]—1-(cyclobutyl-methyl)-8-dimethylamino-8-phenyl-1,3-diazaspiro[4.5]decan-2-one;

CIS-2-((8-(dimethylamino)-1-((1-hydroxycyclobutyl)methyl)-2-oxo-8-phenyl-1,3-diazaspiro[4.5]decan-3-yl)methyl)benzonitrile;

CIS-8-Dimethylamino-8-(3-methoxyphenyl)-3-[(4-methoxyphenyl)-methyl]—1,3-diazaspiro[4.5]decan-2-one;

CIS-8-Dimethylamino-8-(4-methoxyphenyl)-3-[(4-methoxyphenyl)-methyl]—1,3-diazaspiro[4.5]decan-2-one;

CIS-3-(((8-(dimethylamino)-1-((1-hydroxycyclobutyl) methyl)-2-oxo-8-phenyl-1,3-diazaspiro[4.5]decan-3-yl)methyl)benzonitrile;
CIS-3-(((8-(dimethylamino)-2-oxo-8-phenyl-1,3-diazaspiro[4.5]decan-3-yl)methyl)-4-methoxybenzonitrile;
CIS-8-Dimethylamino-8-phenyl-3-(1H-[1,2,3]triazol-4-yl-methyl)-1,3-diazaspiro[4.5]decan-2-one;
CIS-8-Dimethylamino-3-[[1-(2-hydroxy-ethyl)-1H-[1,2,3]triazol-4-yl]-methyl]-8-phenyl-1,3-diazaspiro[4.5]decan-2-one;
CIS-2-[4-[(8-Dimethylamino-2-oxo-8-phenyl-1,3-diazaspiro[4.5]decan-3-yl)-methyl]-1H-[1,2,3]triazol-1-yl]-acetamide;
CIS-8-Methylamino-8-phenyl-3-(1H-[1,2,3]triazol-4-yl-methyl)-1,3-diazaspiro[4.5]decan-2-one;
CIS-8-Dimethylamino-3-[(4-methoxyphenyl)-methyl]-8-phenyl-1-(p-tolylsulfonyl)-1,3-diazaspiro[4.5]decan-2-one;
CIS-2-[4-[(8-Methylamino-2-oxo-8-phenyl-1,3-diazaspiro[4.5]decan-3-yl)-methyl]-1H-[1,2,3]triazol-1-yl]-acetamide;
CIS-8-Dimethylamino-3-[(4-methoxyphenyl)-methyl]-2-oxo-8-phenyl-1,3-diazaspiro[4.5]decane-1-carboxylic acid benzyl ester;
CIS-3-([[1-(2-Hydroxy-ethyl)-1H-[1,2,3]triazol-4-yl]-methyl]-8-methylamino-8-phenyl-1,3-diazaspiro[4.5]decan-2-one;
CIS-8-Dimethylamino-8-phenyl-3-(2-pyridin-2-yl-ethyl)-1,3-diazaspiro[4.5]decane-2,4-dione;
CIS-8-Dimethylamino-8-phenyl-3-(2-pyridin-2-yl-ethyl)-1,3-diazaspiro[4.5]decan-2-one;
CIS-8-Dimethylamino-1-[(1-hydroxy-cyclobutyl)-methyl]-3-[[1-(2-hydroxy-ethyl)-1H-[1,2,3]triazol-4-yl]-methyl]-8-phenyl-1,3-diazaspiro[4.5]decan-2-one;
CIS-8-Dimethylamino-3-[2-(1H-imidazol-1-yl)-ethyl]-8-phenyl-1,3-diazaspiro[4.5]decane-2,4-dione;
CIS-2-[4-[[8-Dimethylamino-1-[(1-hydroxy-cyclobutyl)-methyl]-2-oxo-8-phenyl-1,3-diazaspiro[4.5]decan-3-yl]-methyl]-1H-[1,2,3]triazol-1-yl]-acetamide;
CIS-1-[(1-Hydroxy-cyclobutyl)-methyl]-3-[[1-(2-hydroxy-ethyl)-1H-[1,2,3]triazol-4-yl]-methyl]-8-methylamino-8-phenyl-1,3-diazaspiro[4.5]decan-2-one;
CIS-8-Dimethylamino-8-phenyl-3-(2-pyridin-3-yl-ethyl)-1,3-diazaspiro[4.5]decane-2,4-dione;
CIS-8-Dimethylamino-8-phenyl-3-(2-pyridin-4-yl-ethyl)-1,3-diazaspiro[4.5]decane-2,4-dione;
CIS-2-[4-[[1-(Cyclobutyl-methyl)-8-dimethylamino-2-oxo-8-phenyl-1,3-diazaspiro[4.5]decan-3-yl]-methyl]-1H-[1,2,3]triazol-1-yl]-acetamide;
CIS-1-(Cyclobutyl-methyl)-8-dimethylamino-3-[[1-(2-hydroxy-ethyl)-1H-[1,2,3]triazol-4-yl]-methyl]-8-phenyl-1,3-diazaspiro[4.5]decan-2-one;
CIS-2-[4-[[1-[(1-Hydroxy-cyclobutyl)-methyl]-8-methylamino-2-oxo-8-phenyl-1,3-diazaspiro[4.5]decan-3-yl]-methyl]—1H-[1,2,3]triazol-1-yl]-acetamide;
CIS-1-(Cyclobutyl-methyl)-3-([[1-(2-hydroxy-ethyl)-1H-[1,2,3]triazol-4-yl]-methyl]-8-methyl amino-8-phenyl-1,3-diazaspiro[4.5]decan-2-one;
CIS-2-[4-[[1-(Cyclobutyl-methyl)-8-methylamino-2-oxo-8-phenyl-1,3-diazaspiro[4.5]decan-3-yl]-methyl]—1H-[1,2,3]triazol-1-yl]-acetamide;
CIS-8-Dimethylamino-8-phenyl-3-(2-pyridin-3-yl-ethyl)-1,3-diazaspiro[4.5]decan-2-one;
CIS-8-Dimethylamino-3-[2-(1H-imidazol-1-yl)-ethyl]-8-phenyl-1,3-diazaspiro[4.5]decan-2-one;
CIS-8-Dimethylamino-8-phenyl-3-(2-pyridin-4-yl-ethyl)-1,3-diazaspiro[4.5]decan-2-one;
CIS-8-Dimethylamino-8-phenyl-3-(2-pyrimidin-2-yl-ethyl)-1,3-diazaspiro[4.5]decan-2-one;
CIS-8-Dimethylamino-8-phenyl-3-(2-pyrimidin-5-yl-ethyl)-1,3-diazaspiro[4.5]decan-2-one;
CIS-8-Dimethylamino-1-ethyl-3-[(4-methyl sulfonyl-phenyl)-methyl]-8-phenyl-1,3-diazaspiro[4.5]decan-2-one;
CIS-8-Dimethylamino-3-(1-methyl-1-phenyl-ethyl)-8-phenyl-1,3-diazaspiro[4.5]decan-2-one;
CIS-8-Dimethylamino-8-phenyl-3-(1-phenyl-cyclopropyl)-1,3-diazaspiro[4.5]decan-2-one;
CIS-8-Dimethylamino-1,3-bis[(2-methoxyphenyl)-methyl]-8-phenyl-1,3-diazaspiro[4.5]decan-2-one;
CIS-8-Dimethylamino-3-[(3-methylsulfonyl-phenyl)-methyl]-8-phenyl-1,3-diazaspiro[4.5]decan-2-one;
CIS-8-Dimethylamino-1-[(1-hydroxy-cyclobutyl)-methyl]-3-(1-methyl-1-phenyl-ethyl)-8-phenyl-1,3-diazaspiro[4.5]decan-2-one;
CIS-3-[(3-Cyclopropyl-phenyl)-methyl]-8-dimethyl-amino-8-phenyl-1,3-diazaspiro[4.5]decan-2-one;
CIS-3-((1,3-Benzodioxol-4-O-methyl)-8-dimethylamino-8-phenyl-1,3-diazaspiro[4.5]decan-2-one;
CIS-8-Dimethylamino-1-[(1-hydroxy-cyclobutyl)-methyl]-8-phenyl-3-(1-phenyl-cyclopropyl)-1,3-diazaspiro[4.5]decan-2-one;
CIS-4-[[8-Dimethylamino-3-[(2-methoxyphenyl)-methyl]-2-oxo-8-phenyl-1,3-diazaspiro[4.5]decan-1-yl]-methyl]-benzonitrile;
CIS-8-Dimethylamino-3-[(2-methoxyphenyl)-methyl]-8-phenyl-1,3-diazaspiro[4.5]decan-2-one;
CIS-8-Dimethylamino-8-phenyl-3-(pyridin-4-yl -methyl)-1,3-diazaspiro[4.5]decan-2-one;
CIS-8-Dimethylamino-8-phenyl-3-(pyridin-2-yl -methyl)-1,3-diazaspiro[4.5]decan-2-one;
CIS-8-Dimethylamino-8-phenyl-3-(pyridin-3-(yl -methyl)-1,3-diazaspiro[4.5]decan-2-one;
CIS-8-Dimethylamino-3-[[2-(4-methyl-piperazin-1-yl)-pyridin-4-yl]-methyl]-8-phenyl-1,3-diazaspiro[4.5]decan-2-one;
CIS-8-Dimethylamino-8-phenyl-3-[(2-piperidin-1-yl-pyridin-4-yl)-methyl]-1,3-diazaspiro[4.5]decan-2-one;
CIS-8-Dimethylamino-3-[(2-morpholin-4-yl-pyridin-4-yl)-methyl]-8-phenyl-1,3-diazaspiro[4.5]decan-2-one;
CIS-8-Dimethylamino-8-phenyl-3-[(2-piperazin-1-yl-pyridin-4-yl)-methyl]-1,3-diazaspiro[4.5]decan-2-one;
and the physiologically acceptable salts thereof.

26. A medicament comprising a compound according to claim 1.

27. A method of treating pain in a patient in need thereof, said method comprising administering to said patient an effective amount therefor of at least one compound according to claim 1.

* * * * *